United States Patent
Kinoshita et al.

(10) Patent No.: US 10,532,984 B2
(45) Date of Patent: Jan. 14, 2020

(54) PYRIDONECARBOXYLIC ACID DERIVATIVE OR SALT THEREOF

(71) Applicant: WAKUNAGA PHARMACEUTICAL CO., LTD., Osaka-shi (JP)

(72) Inventors: Tomohiko Kinoshita, Akitakata (JP); Yasuhiro Kuramoto, Akitakata (JP); Satoshi Inoue, Akitakata (JP); Kouji Nishimura, Akitakata (JP); Tatsuya Hirano, Akitakata (JP); Mai Arai, Akitakata (JP); Asuka Sakurai, Akitakata (JP); Daichi Kazamori, Akitakata (JP); Ayuka Sasaki, Akitakata (JP)

(73) Assignee: WAKUNAGA PHARMACEUTICAL CO., LTD., Osaka-shi (JP)

( * ) Notice: Subject to any disclaimer, the term of this patent is extended or adjusted under 35 U.S.C. 154(b) by 0 days.

(21) Appl. No.: 16/308,292

(22) PCT Filed: Jun. 14, 2017

(86) PCT No.: PCT/JP2017/021899
§ 371 (c)(1),
(2) Date: Dec. 7, 2018

(87) PCT Pub. No.: WO2017/217441
PCT Pub. Date: Dec. 21, 2017

(65) Prior Publication Data
US 2019/0276407 A1    Sep. 12, 2019

(30) Foreign Application Priority Data

Jun. 15, 2016  (JP) ................................. 2016-118484
Mar. 22, 2017  (JP) ................................. 2017-056474

(51) Int. Cl.
*C07D 215/56*    (2006.01)
*C07D 401/04*    (2006.01)
(Continued)

(52) U.S. Cl.
CPC ............ *C07D 215/56* (2013.01); *A61P 31/04* (2018.01); *C07D 401/04* (2013.01);
(Continued)

(58) Field of Classification Search
CPC .................................................. C07D 215/56
(Continued)

(56) References Cited
U.S. PATENT DOCUMENTS
4,146,719 A    3/1979  Irikura
4,762,845 A    8/1988  Chu et al.
(Continued)

FOREIGN PATENT DOCUMENTS
EP    0 131 839 A1    1/1985
JP    55-34144 B2    9/1980
(Continued)

OTHER PUBLICATIONS

International Search Report dated Aug. 15, 2017 in PCT/JP2017/021899 filed Jun. 14, 2017.
Clinic All-Round, Presented by Medical Online, vol. 44, No. 6, 1995, pp. 1595-1599 (with partial English language translation).
Hirosi Takahashi, et al., "Changes in susceptibity of clinical isolates of *Staphylococcus aureus* to quinolones and other antibacterial agents from 1986 to 1993," Japanese Journal of Chemotherapy. vol. 43, No. 5, May 1995, pp. 547-550.
(Continued)

*Primary Examiner* — Nizal S Chandrakumar
(74) *Attorney, Agent, or Firm* — Oblon, McClelland, Maier & Neustadt, L.L.P.

(57) ABSTRACT

A pyridonecarboxylic acid derivative or a salt thereof is represented by Formula (1), where $R^1$ is hydrogen, a halogen atom, a lower alkyl group, or an amino group; $R^2$ is —NH—$R^6$, where $R^6$ is hydrogen, a lower alkyl group, an amino lower alkyl group, or the like; —O—$R^7$, where $R^7$ is hydrogen, a lower alkyl group, or the like; —$(CH_2)_m$—$R^8$, where $R^8$ is an amino group or the like, m is 1, 2, 3 or 4; or a cyclic amino group of Formula (2), where Y represents NH or C—$R^{9a}R^{9b}$, where $R^{9a}$ and $R^{9b}$ are each independently hydrogen, a lower alkyl group, an amino group, a lower alkyl amino group, or the like; n and p are 1 or 2; $R^3$ is hydrogen, a halogen atom, a lower alkyl group, or the like; $R^4$ is hydrogen or a carboxyl group-protecting group; and $R^5$ is hydrogen or a hydroxyl group-protecting group.

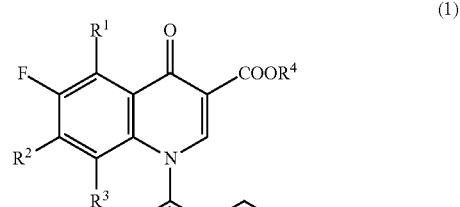

(1)

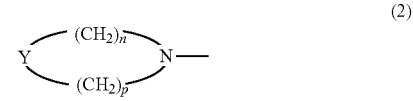

(2)

11 Claims, No Drawings

(51) Int. Cl.
  *A61P 31/04* (2006.01)
  *C07D 401/12* (2006.01)
  *C07D 487/10* (2006.01)
  *C07D 405/14* (2006.01)

(52) U.S. Cl.
  CPC ......... *C07D 401/12* (2013.01); *C07D 405/14* (2013.01); *C07D 487/10* (2013.01)

(58) Field of Classification Search
  USPC .................................................. 546/156
  See application file for complete search history.

(56) References Cited

U.S. PATENT DOCUMENTS

| | | | |
|---|---|---|---|
| 5,153,203 A | 10/1992 | Yatsunami et al. | |
| 5,910,498 A | 6/1999 | Yazaki et al. | |
| 6,211,375 B1 * | 4/2001 | Yazaki | C07D 401/04 546/156 |

FOREIGN PATENT DOCUMENTS

| | | |
|---|---|---|
| JP | 57-10109 B2 | 2/1982 |
| JP | 60-56959 A | 4/1985 |
| JP | 61-11955 B2 | 4/1986 |
| JP | 63-52510 B2 | 10/1988 |
| JP | 63-62510 B2 | 12/1988 |
| JP | 3-7260 A | 1/1991 |
| WO | WO 96/23775 A1 | 8/1996 |
| WO | WO 97/40036 A1 | 10/1997 |

OTHER PUBLICATIONS

Keizo Yamaguchi, et al., "In vitro activities of 23 antimicrobial agents against 4,993 gram-positive and gram-negative bacterial strains isolated from multicenter of Japan during 1994—in vitro susceptibility surveillance," The Japanese Journal of Antibiotics, 52-2, Feb. 1999, pp. 75-92 (with partial English language translation).

Hajime Goto, et al., Field of Chemotherapy, vol. 7, No. 1, 1991, pp. 95-101 (with partial English language translation).

Shigeru Kamiya, "Basic science and clinical aspect of Clostridium difficile infection," Modern Media, vol. 56, No. 10, 2010, pp. 233-241.

Lynne V. McFarland, et al., "Implications of the changing face of Clostridium difficile disease for health care practitioners," Am. J. Infect. Control, vol. 35, No. 4, 2007, pp. 237-253.

Minako Araake, et al., "Antimicrobial activity of NM 394, an active form of prulifloxacin, against clinical isolates of *Pseudomonas aeruginosa* with a type II topoisomerase mutation," Japanese Journal of Chemotherapy, vol. 51, No. 3, Mar. 2003, pp. 132-137 (with partial English language translation).

Kazuki Hoshino, "Research on quinolones and efflux pump inhibitors in the post-genomic era," Japanese Journal of Chemotherapy, vol. 52, No. 7, Jul. 2004, pp. 355-360 (with partial English language translation).

* cited by examiner

PYRIDONECARBOXYLIC ACID DERIVATIVE OR SALT THEREOF

TECHNICAL FIELD

The present invention relates to a novel pyridonecarboxylic acid derivative or a salt thereof having an excellent antimicrobial effect.

BACKGROUND ART

Compounds having pyridonecarboxylic acid as their basic structure include many compounds known to be useful as synthetic antimicrobial agents since they have excellent antimicrobial potency and wide antimicrobial spectra. Among them, norfloxacin (Patent Literature 1), enoxacin (Patent Literature 2), ofloxacin (Patent Literature 3), ciprofloxacin (Patent Literature 4), and tosufloxacin (Patent Literature 5) have been widely used in clinical settings as therapeutic agents for infections. All of these are agents called new quinolone antimicrobial agents and have been used as therapeutic agents for many infections, such as respiratory, gastrointestinal, or urinary tract infections.

Many resistant microorganisms to these quinolone antimicrobial agents have, however, been reported in recent years and also become a clinical problem (Non-Patent Literature 1 to 2). In particular, the numbers of quinolone antimicrobial agent-resistant methicillin-resistant *Staphylococcus aureus* and *Pseudomonas aeruginosa* are tending to increase (Non-Patent Literature 3 to 4).

Furthermore, antibiotic-associated diarrhea caused by quinolone-resistant *Clostridium difficile* due to the disturbance of intestinal bacterial flora by the administration of quinolone antimicrobial agents has become a problem (Non-Patent Literature 5 to 6).

As to the mechanism by which various bacteria acquire the drug resistance to such quinolone antimicrobial agents, it has been reported that the decrease in the affinity due to the mutation in the target molecule, type II topoisomerase (DNA gyrase), or pumping of drugs by drug efflux pumps out of the cells lowers effect of the drugs (Non-Patent Literature 7). Therefore, the development of a derivative effective for mutated DNA gyrases or a drug not susceptible to drug efflux pumps has been desired (Non-Patent Literature 8).

Under such situation, the present inventors found a novel derivative in which a 5-amino-2,4-difluorophenyl group and a 3-aminoazetidine ring are introduced at positions 1 and 7 of pyridonecarboxylic acid, respectively (Non-Patent Literature 6).

However, methicillin-resistant *Staphylococcus aureus* and *Pseudomonas aeruginosa* exhibiting the resistance to the derivative were found and there has been a problem that the derivative fails to provide enough effect.

CITATION LIST

Patent Literature

Patent Literature 1: JP-B-55-34144
Patent Literature 2: JP-B-57-10109
Patent Literature 3: JP-B-61-11955
Patent Literature 4: JP-B-63-52510
Patent Literature 5: JP-B-63-62510
Patent Literature 6: International Publication No. WO 96/23775

Non-Patent Literature

Non-Patent Literature 1: Clinic All-Round 44: 1595-1599, 1995
Non-Patent Literature 2: Japanese Journal of Chemotherapy 43: 547-549, 1995
Non-Patent Literature 3: Jpn. J. Antibiot. 52: 75-92, 1999
Non-Patent Literature 4: Antibiotics & Chemotherapy 7: 95-101, 1991
Non-Patent Literature 5: Modern Media 56 (10): 223-241, 2010
Non-Patent Literature 6: Am. J. Infect. Control 2007, 35, 237-253.
Non-Patent Literature 7: Japanese Journal of Chemotherapy 51 (3): 132-136, 2003
Non-Patent Literature 8: Japanese Journal of Chemotherapy 52 (7): 355-360, 2004

SUMMARY OF INVENTION

Technical Problem

The present invention relates to providing a novel pyridonecarboxylic acid derivative or a salt thereof having an excellent effect against bacteria such as methicillin-resistant *Staphylococcus aureus*, *Pseudomonas aeruginosa*, and *Clostridium difficile*.

Solution to Problem

In view of such situation, the present inventors studied diligently to obtain a compound that can serve as a clinically excellent synthetic antimicrobial agent, and as a result, found that the compound represented by following Formula (1) has an excellent antibacterial activity against bacteria such as methicillin-resistant *Staphylococcus aureus*, *Pseudomonas aeruginosa*, and *Clostridium difficile* and is not susceptible to drug efflux pumps in *Pseudomonas aeruginosa*, thereby completing the present invention.

Accordingly, the present invention relates to the following 1) to 13):

1) A pyridonecarboxylic acid derivative or a salt thereof represented by Formula (1):

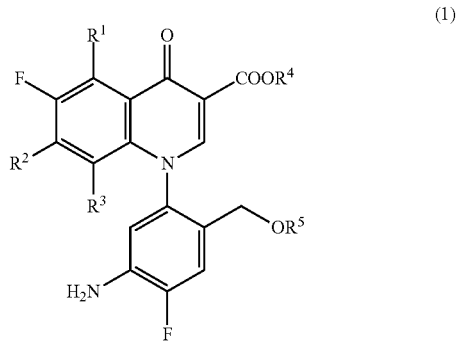

(1)

wherein $R^1$ represents a hydrogen atom, a halogen atom, a lower alkyl group, or an amino group; $R^2$ is a group —NH—$R^6$, wherein $R^6$ represents a hydrogen atom, a lower alkyl group, an amino lower alkyl group, a hydroxy lower alkyl group, a dimethylamino lower alkyl group, a lower alkoxy lower alkyl group, a morpholino lower alkyl group, or an optionally substituted aralkyl group; a group —O—$R^7$, wherein $R^7$ represents a hydrogen atom, a lower alkyl group, an optionally substituted azetidin-3-yl group, or an optionally substituted pyrrolidin-3-yl group; or a group —(CH$_2$)$_m$—$R^8$, wherein $R^8$ represents an amino group, a lower alkyl amino group, a cyclic amino group, a hydroxyl group, or a lower alkoxy group and m represents an integer of 1 to 4; or a cyclic amino group represented by the following Formula (2):

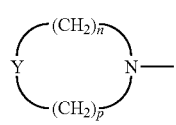

wherein Y represents NH or C—$R^{9a}R^{9b}$, wherein $R^{9a}$ and $R^{9b}$ each independently represent a hydrogen atom, a lower alkyl group, an amino group, a lower alkyl amino group, an N-methyl-N-(5-methyl-2-oxo-1,3-dioxol-4-yl)methylamino group, a hydroxy lower alkyl amino group, a lower alkyl hydrazino group, a tetrahydropyran-4-ylamino group, a pyrazol-1-yl group, a dimethylamino lower alkyl group, or a hydroxyl group or $R^{9a}$ and $R^{9b}$ optionally form a nitrogen-containing saturated heterocyclic ring together with the adjacent carbon atom and n and p represent an integer of 1 or 2; $R^3$ represents a hydrogen atom, a halogen atom, a lower alkyl group, or a lower alkoxy group; $R^4$ represents a hydrogen atom or a carboxyl group-protecting group; and $R^5$ represents a hydrogen atom or a hydroxyl group-protecting group.

2) The pyridonecarboxylic acid derivative or a salt thereof according to 1), wherein a lower alkyl group represented by $R^1$, $R^3$, $R^6$, or $R^7$ is a $C_{1-4}$ alkyl group.

3) The pyridonecarboxylic acid derivative or a salt thereof according to 1) or 2), wherein the lower alkoxy group represented by $R^3$ is a $C_{1-4}$ alkoxy group.

4) The pyridonecarboxylic acid derivative or a salt thereof according to any of 1) to 3), wherein the halogen atom represented by $R^3$ is a fluorine atom, a chlorine atom, or a bromine atom.

5) The pyridonecarboxylic acid derivative or a salt thereof according to any of 1) to 4), wherein $R^1$ is a hydrogen atom, a methyl group, a bromine atom, or an amino group and $R^2$ is a cyclic amino group represented by the Formula (2).

6) The pyridonecarboxylic acid derivative or a salt thereof according to 5), wherein Y is C—$R^{9a}R^{9b}$ and n and p are 1 in the Formula (2).

7) The pyridonecarboxylic acid derivative or a salt thereof according to 6), wherein $R^{9a}$ is a hydrogen atom and $R^{9b}$ is a $C_{1-4}$ alkyl amino group in C—$R^{9a}R^{9b}$.

8) The pyridonecarboxylic acid derivative or a salt thereof according to any of 1) to 7), wherein $R^4$ is a hydrogen atom or a protecting group eliminated easily in a living body and $R^5$ is a hydrogen atom or a protecting group eliminated easily in a living body.

9) An antimicrobial agent comprising the pyridonecarboxylic acid derivative or a salt thereof according to any of 1) to 8) as an active ingredient.

10) An antimicrobial composition comprising the pyridonecarboxylic acid derivative or a salt thereof according to any of 1) to 8) and a pharmaceutically acceptable carrier.

11) Use of the pyridonecarboxylic acid derivative or a salt thereof according to any of 1) to 8) for producing an antimicrobial agent.

12) The pyridonecarboxylic acid derivative or a salt thereof according to any of 1) to 8), used for preventing or treating an infection.

13) A method for treating an infection, comprising administering the pyridonecarboxylic acid derivative or a salt thereof according to any of 1) to 8).

Effects of Invention

The pyridonecarboxylic acid derivative or salt thereof according to the present invention has an excellent effect on bacteria such as methicillin-resistant *Staphylococcus aureus*, *Pseudomonas aeruginosa*, and *Clostridium difficile* and is not susceptible to drug efflux pumps in *Pseudomonas aeruginosa*. Therefore, it can be applied widely to treatment for infections including the bacteria.

DESCRIPTION OF EMBODIMENTS

As used herein, the word "lower" means that the number of carbon atoms in the hydrocarbon moiety of the group designated with the name containing this word is 1 to 7 (abbreviated as "$C_{1-7}$") and the hydrocarbon moiety may be linear or branched.

"Optionally substituted" means that hydrogen atoms in the group of interest may be replaced with the other groups and the number of the substituent(s) may be one or more. When the group of interest has 2 or more substituents, the substituents may be the same or different.

The symbols used in Formula (1) are described below.

Examples of the "halogen atom" represented by $R^1$ include a bromine atom, a chlorine atom, fluorine atom, or an iodine atom and preferably a bromine atom.

The "lower alkyl group" represented by $R^1$ is preferably a $C_{1-4}$ alkyl group such as a methyl group, an ethyl group, a propyl group, an isopropyl group, a butyl group, an isobutyl group, or a tert-butyl group, more preferably a $C_{1-3}$ alkyl group, and even more preferably a methyl group.

The "lower alkyl group" represented by $R^6$ in the group —NH—$R^6$ represented by $R^2$ is preferably a $C_{1-4}$ alkyl group, more preferably a $C_{1-3}$ alkyl group, and even more preferably a methyl group or an ethyl group.

Preferable examples of the "amino lower alkyl group" represented by $R^6$ include amino $C_{1-3}$ alkyl groups such as a 2-aminoethyl group and a 3-aminopropyl group.

Preferable examples of the "hydroxy lower alkyl group" represented by $R^6$ include hydroxy $C_{1-4}$ alkyl groups such as a 2-hydroxyethyl group, a 1-hydroxyisopropyl group, and a 2-hydroxy-2-methylpropyl group.

Preferable examples of the "dimethylamino lower alkyl group" represented by $R^6$ include dimethylamino alkyl groups such as a 3-dimethylamino propyl group and a 2-dimethylaminoethyl group.

Preferable examples of the "lower alkoxy lower alkyl group" represented by $R^6$ include $C_{1-3}$ alkoxy $C_{1-4}$ alkyl groups such as a methoxyethyl group and a 3-methoxypropyl group.

Preferable examples of the "morpholino lower alkyl group" represented by $R^6$ include morpholino $C_{1-4}$ alkyl groups such as a 2-morpholinoethyl group and a 3-morpholinopropyl group.

Examples of the "aralkyl group" in the "optionally substituted aralkyl group" represented by $R^6$ include $C_{7-14}$ aralkyl groups and preferably $C_{6-12}$ aryl-$C_{1-2}$ alkyl groups such as a benzyl group, a phenethyl group, and a benzhydryl group. Examples of the aralkyl group having substituents include aralkyl groups whose aryl moiety are mono-, di-, or tri-substituted with methoxy groups, hydroxy groups, amino groups, carboxy groups, and the like and preferable examples thereof include a 2,4-dimethoxybenzyl group.

More preferable examples of $R^6$ include a $C_{1-4}$ alkyl group and even more preferable examples include a methyl group and an ethyl group.

The "lower alkyl group" represented by $R^7$ in the group —O—$R^7$ represented by $R^2$ is preferably a $C_{1-4}$ alkyl group, more preferably a $C_{1-3}$ alkyl group, and even more preferably a methyl group or an ethyl group.

Examples of the substituents in the "optionally substituted azetidin-3-yl group" and the "optionally substituted pyrrolidin-3-yl group" represented by $R^7$ include a $C_{1-3}$ alkyl group.

Preferable examples of the substituents include an azetidin-3-yl group, a 1-methylazetidin-3-yl group, a pyrrolidin-3-yl group, and a 1-methylpyrrolidin-3-yl group.

Examples of the "lower alkyl amino group" represented by $R^8$ in the group —$(CH_2)_m$—$R^8$ represented by $R^2$ include alkyl amino groups. Among them, $C_{1-3}$ alkyl amino groups are preferred and more preferable examples include an ethylamino group and a methylamino group.

Examples of the "cyclic amino group" represented by $R^8$ include 4 to 6 membered, saturated cyclic amino groups such as an azetidinyl group, a pyrrolidinyl group, a piperidinyl group, a piperazinyl group, and a morpholino group and a preferably an azetidinyl group.

The "lower alkoxy group" represented by $R^8$ is preferably a $C_{1-4}$ alkoxy group such as a methoxy group, an ethoxy group, a propoxy group, or a butoxy group, more preferably a $C_{1-3}$ alkoxy group, and even more preferably a methoxy group.

More preferable examples of $R^8$ include an amino group, a methylamino group, an azetidinyl group, and a hydroxyl group, even more preferable examples include an amino group, and m is preferably 1 to 2.

Examples of the "lower alkyl group" represented by $R^{9a}$ and $R^{9b}$ in the cyclic amino group represented by the Formula (2) where Y is C—$R^{9a}R^{9b}$ include $C_{1-4}$ alkyl groups such as a methyl group, an ethyl group, a propyl group, an isopropyl group, a butyl group, an isobutyl group, and a tert-butyl group. Among them, $C_{1-3}$ alkyl groups are preferred and more preferable examples include a methyl group.

Examples of the "lower alkyl amino group" represented by $R^{9a}$ and $R^{9b}$ include $C_{1-4}$ alkyl amino groups such as a methylamino group, an ethylamino group, a propylamino group, an isopropylamino group, a butylamino group, an isobutylamino group, and a tert-butylamino group. Among them, $C_{1-3}$ alkyl amino groups are preferred and more preferable examples include a methylamino group and an ethyl amino group.

Examples of the "hydroxy lower alkyl amino group" represented by $R^{9a}$ and $R^{9b}$ include a hydroxy $C_{1-4}$ alkyl amino group. Among them, a hydroxy $C_{1-3}$ alkyl amino group is preferable and more preferable examples include a 2-hydroxyethylamino group and a 1-hydroxyisopropylamino group.

Preferable examples of the "dimethylamino lower alkyl group" represented by $R^{9a}$ and $R^{9b}$ include dimethylamino $C_{1-4}$ alkyl groups such as a dimethylaminomethyl group, a 3-dimethylaminopropyl group, and a 2-dimethylaminoethyl group.

Examples of the "lower alkyl hydrazino group" represented by $R^{9a}$ and $R^{9b}$ include $C_{1-3}$ alkyl hydrazino groups such as a methylhydrazino group, an ethylhydrazino group, a propylhydrazino group, and an isopropylhydrazino group. Among them, a 2-methylhydrazino group and a 2-ethylhydrazino group are more preferred.

Preferable examples of the nitrogen-containing saturated heterocyclic ring which $R^{9a}$ and $R^{9b}$ form together with the carbon atom adjacent thereto include 3 to 6 membered, nitrogen-containing, saturated heterocyclic rings containing at least one nitrogen atom and preferable examples include azetidine.

Preferable examples of the cyclic amino group represented by Formula (2) include a 3-aminoazetidin-1-yl group, a 3-hydroxyazetidin-1-yl group, a 3-$C_{1-4}$ alkylaminoazetidin-1-yl group (for example, a 3-methylaminoazetidin-1-yl group, a 3-ethylaminoazetidin-1-yl group, a 3-isopropylaminoazetidin-1-yl group), a 3-(tetrahydropyran-4-yl)amino-azetidin-1-yl group, a 3-amino-3-methylazetidin-1-yl group, a 3-(N—$C_{1-4}$ alkyl-N-(5-methyl-2-oxo-1,3-dioxol-4-yl) methylamino)azetidin-1-yl group (for example, a 3-(N-methyl-N-(5-methyl-2-oxo-1,3-dioxole-4-yl)methylamino) azetidin-1-yl group, a 3-(N-ethyl-N-(5-methyl-2-oxo-1,3-dioxole-4-yl)methylamino)azetidin-1-yl group), a 3-(pyrazol-1-yl)azetidin-1-yl group, a 2-methylhydrazino-azetidin-1-yl group, a 2,6-diazaspiro[3.3]-heptan-2-yl group, a 1,6-diazaspiro[3.3]-heptan-6-yl group, a 3-aminopyrrolidin-1-yl group, and a piperazinyl group. The cyclic amino group is more preferably a 3-$C_{1-4}$ alkylaminoazetidin-1-yl group and even more preferably a 3-methylaminoazetidin-1-yl group or a 3-ethylaminoazetidin-1-yl group.

Examples of the "halogen atom" represented by $R^3$ include a bromine atom, a chlorine atom, a fluorine atom, or iodine and preferably a bromine atom or a chlorine atom.

The "lower alkyl group" represented by $R^3$ is preferably $C_{1-4}$ alkyl groups such as a methyl group, an ethyl group, a propyl group, an isopropyl group, a butyl group, an isobutyl group, and a tert-butyl group, more preferably a $C_{1-3}$ alkyl group, and even more preferably a methyl group.

The "lower alkoxy group" represented by $R^3$ is preferably a $C_{1-4}$ alkoxy group such as a methoxy group, an ethoxy group, a propoxy group, or a butoxy group, more preferably a $C_{1-3}$ alkoxy group, and even more preferably a methoxy group.

More preferable examples of $R^3$ include a chlorine atom, a bromine atom, and a methyl group.

The carboxyl group-protecting group represented by $R^4$ in the formula refers to an ester residue in a carboxylic acid ester and examples thereof include any group which is relatively easily cleaved to produce a corresponding free carboxyl group. Specific examples include groups which are eliminated by a treatment in mild conditions such as hydrolysis or catalytic reduction, such as $C_{1-7}$ alkyl groups such as a methyl group, an ethyl group, an n-propyl group, a 2-propyl group, an n-butyl group, an i-butyl group, a t-butyl group, a pentyl group, a hexyl group, and a heptyl group; $C_{2-7}$ alkenyl groups such as a vinyl group, an allyl group, a 1-propenyl group, a butenyl group, a pentenyl group, a hexenyl group, and a heptenyl group; aralkyl groups such as a benzyl group; and aryl groups such as a phenyl group and a naphthyl group; or groups which are eliminated easily in the living body such as $C_{2-7}$ alkanoyloxy lower alkyl groups such as an acetoxymethyl group and a pivaloyloxymethyl group; $C_{1-4}$ alkoxy carbonyloxy $C_{1-4}$ alkyl groups such as a methoxycarbonyloxy methyl group, a 1-ethoxycarbonyloxy ethyl group; $C_{1-4}$ alkoxy methyl groups such as a methoxymethyl group; lactonyl groups such as a phthalidyl group; and di-$C_{1-4}$ alkyl amino $C_{1-4}$ alkyl groups such as a 1-dimethylaminoethyl group; and a (5-methyl-2-oxo-[1,3] dioxol-4-yl)methyl group.

$R^4$ is preferably a hydrogen atom.

Examples of the hydroxyl group-protecting group represented by $R^5$ include any groups which are relatively easily cleaved to produce a corresponding free hydroxyl group. Specific examples include $C_{1-8}$ alkanoyl groups such as a formyl group, an acetyl group, an n-propanoyl group, an n-butanoyl group, a 2-butanoyl group, a pentanoyl group, a hexanoyl group, and a heptanoyl group; aromatic carbonyl groups such as a benzoyl group and a naphthoyl group; aromatic methylcarbonyl groups such as a benzylcarbonyl group and a naphthylmethylcarbonyl group; $C_{1-7}$ alkyloxy carbonyl groups such as a methoxycarbonyl group, an ethoxycarbonyl group, an n-propoxycarbonyl group, a 2-propoxycarbonyl group, and an n-butoxycarbonyl group; $C_{1-4}$ lower alkoxy methyl groups such as a methoxymethyl group, an ethoxymethyl group, and a propoxymethyl group; as well as $C_{1-7}$ alkyl carbonyloxymethyl groups such as an acetoxymethyl group, a propanoyloxymethyl group, a butanoyloxymethyl group, and a pivaloyloxymethyl group; and groups which are eliminated easily in the living body, such as a phosphate group, a phosphate lower alkyl ester group, a sulfate group, a nitrate group, an oxymethyl phosphate group, and oxymethyl $C_{1-4}$ alkyl phosphate groups.

$R^5$ is preferably a hydrogen atom.

Among the compounds illustrated above, the compounds in which $R^1$ is a hydrogen atom, a halogen atom (preferably a bromine atom), or a $C_{1-4}$ alkyl group (preferably a methyl group); $R^2$ is a cyclic amino group represented by Formula (2) (preferably Y is C—$R^{9a}R^{9b}$ and more preferably $R^{9a}$ is a hydrogen atom and $R^{9b}$ is a $C_{1-4}$ alkyl amino group (preferably a methylamino group or an ethylamino group), and n and p are 1); $R^4$ is a hydrogen atom or a protecting group which is eliminated easily in the living body; and $R^5$ is a hydrogen atom or a protecting group which is eliminated easily in the living body.

The pyridonecarboxylic acid derivative according to the present invention can form both acid addition salts and base addition salts. The salts include chelate salts with boron compounds. Examples of the acid addition salts include (A) salts with mineral acids such as hydrochloric acid and sulfuric acid; (B) salts with organic carboxylic acids such as formic acid, citric acid, trichloroacetic acid, trifluoroacetic acid, fumaric acid, and maleic acid; and (C) salts with sulfonic acids such as methanesulfonic acid, benzenesulfonic acid, p-toluenesulfonic acid, mesitylenesulfonic acid, and naphthalenesulfonic acid. Examples of the base addition salts include (A') salts with alkali metals such as sodium and potassium; (B') salts with alkaline earth metals such as calcium and magnesium; (C') ammonium salts; and (D') salts with nitrogen-containing organic bases such as trimethylamine, triethylamine, tributylamine, pyridine, N,N-dimethylaniline, N-methylpiperidine, N-methylmorpholine, diethylamine, cyclohexylamine, procaine, dibenzylamine, N-benzyl-P-phenethylamine, 1-ephenamine, N,N'-dibenzylethylenediamine, and N-methylglucamine. Examples of the boron compounds include halogenated boron such as boron fluoride and lower acyl oxyboron such as acetoxyboron.

The pyridonecarboxylic acid derivative or salt thereof can be not only in a non-solvate form but also a hydrate or a solvate. Therefore, the compound according to the present invention includes all those in a crystalline form and hydrates or solvates.

The pyridonecarboxylic acid derivative or salt thereof can be an optical isomer. Such optical isomers are also encompassed by the compound according to the present invention. Furthermore, the pyridonecarboxylic acid derivative or salt thereof according the present invention can be a variety of stereoisomers (cis form, trans form). Such stereoisomers are also encompassed by the present invention.

The pyridonecarboxylic acid derivative or salt thereof according to the present invention may be produced by any method suitable therefor depending on the kind of one or more substituents thereof and examples thereof are as follows.

(1) Production Method 1

(Step 1-1)

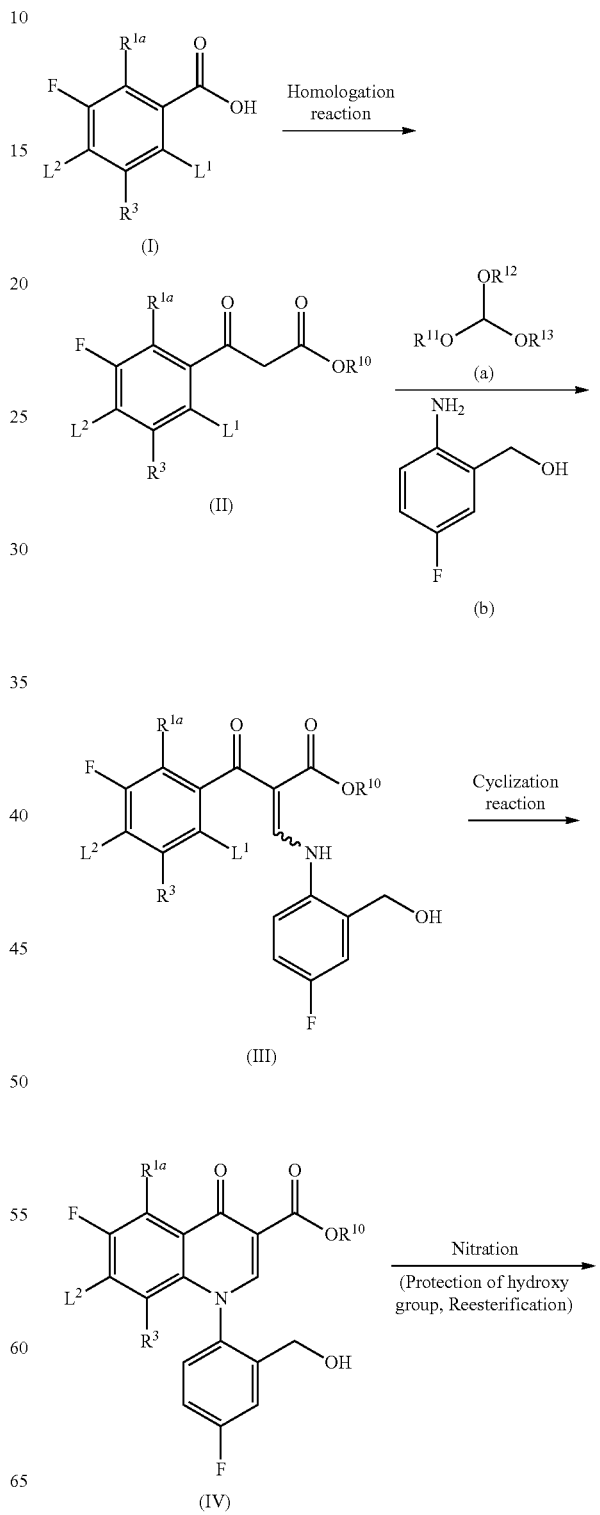

-continued

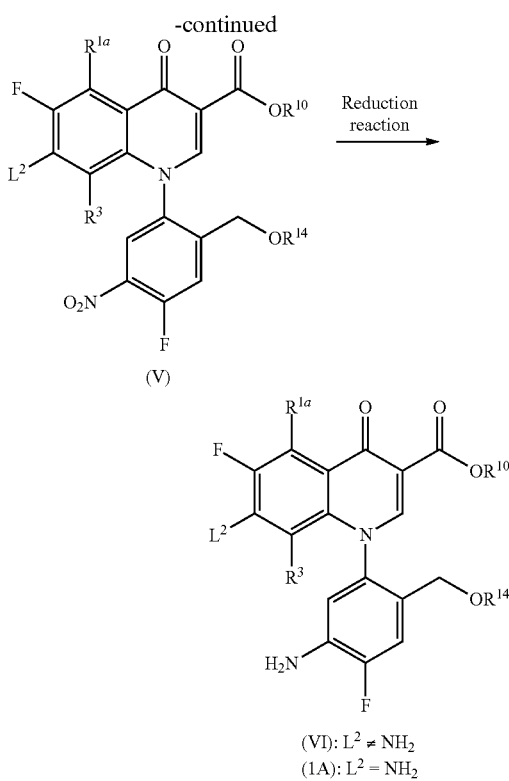

(VI): $L^2 \neq NH_2$
(1A): $L^2 = NH_2$

[In the formula, $R^{1a}$ represents a hydrogen atom, a halogen atom, or a lower alkyl group; $R^{10}$ represents a lower alkyl group, a lower alkenyl group, or an aralkyl group; $R^{11}$, $R^{12}$ and $R^{13}$ each represent a lower alkyl group; $R^{14}$ represents a lower alkanoyl group; $L^1$ represents a halogen atom; $L^2$ represents a halogen atom, a nitro group, or an amino group; and $R^3$ represents the same as that described above.]

More specifically, Compound (I) is converted into Compound (II) by a homologation reaction using a malonic acid ester and then Compound (III) is obtained by the reaction of Compound (II) with an orthoformic acid ester (a) such as ethyl orthoformate or methyl orthoformate and the reaction of the resulting compound with an aniline compound (b). Then, this Compound (III) is subjected to a cyclization reaction. The obtained Compound (IV) is nitrated and reesterified, as needed, to yield Compound (V). This Compound (V) is reduced to obtain Compound (VI) or Compound (1A).

Here, examples of the "lower alkyl group" represented by $R^{10}$ include preferably a $C_{1-4}$ alkyl group and more preferably a methyl group, an ethyl group, and a t-butyl group. Examples of the "Lower alkenyl group" include preferably a $C_{2-4}$ alkenyl group and more preferably a vinyl group, an allyl group, a 1-propenyl group, and the like. The "aralkyl group" is preferably a $C_{7-14}$ aralkyl group and more preferable examples include a benzyl group, a phenethyl group, a benzhydryl group, and the like.

The "lower alkyl group" represented by $R^{11}$, $R^{12}$ and $R^{13}$ is preferably a $C_{1-3}$ alkyl group and further preferably an ethyl group.

Examples of the "lower alkanoyl group" represented by $R^{14}$ include preferably a $C_{1-7}$ alkanoyl group and more preferably an acetyl group, a propionyl group, a butyryl group, a valeryl group, and the like.

Examples of the halogen atom represented by $L^1$ and $L^2$ include preferably a chlorine atom and a fluorine atom.

The homologation reaction of Compound (I) is usually carried out by activation of Compound (I) with oxalyl dichloride or thionyl chloride or carbonyldiimidazole; subsequent addition of a malonic acid diester or a malonic acid monoester such as potassium ethyl malonate in the presence of a base; and subsequent decarboxylation. The reaction in the activation is usually carried out at 0 to 150° C. and preferably 0 to 100° C.; the reaction time of the activation is usually 10 minutes to 48 hours and preferably 1 to 10 hours; the addition reaction is usually carried out at 0 to 150° C. and preferably 0 to 100° C.; and the reaction time of the addition reaction is usually 10 minutes to 48 hours and preferably 1 to 10 hours.

The reaction between Compound (II) and the orthoformic acid ester (a) is usually carried out at 0 to 160° C., preferably 50° C. to 150° C.; and the reaction time thereof is usually 10 minutes to 48 hours and preferably 1 to 10 hours. The amount of the orthoformic acid ester used is preferably equal to or more than, particularly about 1 to 10 times of, the amount of Compound (I) in mol.

The reaction with the aniline compound (b) is carried out in an appropriate reaction solvent. The solvent used here may be any solvent as long as it does not affect the reaction and examples of the solvent include aromatic hydrocarbons such as toluene and xylene; ethers such as diethyl ether, tetrahydrofuran, and dioxane; aliphatic hydrocarbons such as pentane and hexane; halogenated hydrocarbons such as methylene chloride, chloroform, and carbon tetrachloride; aprotic polar solvents such as dimethylformamide, dimethylsulfoxide, and N-methylpyrrolidin-2-one; and alcohols such as methanol, ethanol, and propanol. This reaction is carried out usually at 0 to 150° C. and preferably at 0 to 100° C. and the reaction time thereof is usually 10 minutes to 48 hours and preferably 1 to 10 hours.

The cyclization reaction of Compound (III) is carried out in an appropriate solvent in the presence or absence of a basic compound. The solvent used in this reaction may be any solvent as long as it does not affect the reaction and examples thereof include aromatic hydrocarbons such as toluene and xylene; ethers such as diethyl ether, tetrahydrofuran, and dioxane; aliphatic hydrocarbons such as pentane and hexane; halogenated hydrocarbons such as methylene chloride, chloroform, and carbon tetrachloride; aprotic polar solvents such as dimethylformamide and dimethylsulfoxide; and alcohols such as methanol, ethanol, and propanol. Examples of the basic compound used include alkali metals such as sodium metal and potassium metal; metal hydrides such as sodium hydride and calcium hydride; inorganic bases such as sodium hydroxide, potassium hydroxide, sodium carbonate, and potassium carbonate; alkoxides such as sodium methoxide, sodium ethoxide, and potassium t-butoxide; metal fluorides such as sodium fluoride and potassium fluoride; organic bases such as triethylamine and 1,8-diazabicyclo[5.4.0]undec-7-ene (DBU). This reaction is carried out usually at 0 to 200° C. and preferably at room temperature to 100° C. and the reaction time to complete the reaction is usually 10 minutes to 48 hours.

The method used for the nitration of Compound (IV) is a common method used for aromatic compounds. Examples of nitrating agents include nitrating acids of a combination of nitric acid or a nitrate and sulfuric acid. Preferably, the reaction temperature is −10° C. to 80° C. and the reaction time is 5 minutes to 24 hours. In this reaction, one or more hydroxyl groups may be converted into acid ester by acid used in the reaction. In such cases, subsequent lower alkyl carbonylation is required. This is achieved by the reaction of a common organic acid with the intermediate alcohol acid ester. The acid to be used is formic acid, acetic acid, and propionic acid and preferably acetic acid.

This reaction is carried out usually at 0 to 150° C. and preferably at room temperature to 100° C. and the reaction time to complete the reaction is usually 10 minutes to 48 hours. Furthermore, hydrolysis of $R^{10}$ may result in production of carboxylic acid depending on the reaction conditions. In such a case, the lower alkyl esterification is carried out again. For the esterification, a common method used for aromatic carboxylic acids is used. The esterification is mediated by acid chloride obtained by use of thionyl chloride or oxalyl dichloride and carried out by using a corresponding lower alcohol. The reaction temperature for obtaining the acid chloride is usually −10° C. to 150° C. and preferably 0° C. to 100° C. and the reaction time thereof is usually 10 minutes to 48 hours and preferably 1 to 10 hours. The following reaction with the lower alcohol is usually 0° C. to 150° C. and preferably 0° C. to 100° C. and the reaction time thereof is usually 10 minutes to 48 hours and preferably 1 to 10 hours.

For the reduction reaction of Compound (V), methods commonly used are available and examples thereof include dissolving metal reduction which involves use of zinc, iron, tin, tin chloride, or the like in an acid solution, reduction which involves use of sulfide such as sodium sulfide, sodium hydrosulfide, sodium dithionite, or the like, and catalytic reduction method which involves platinum, Raney nickel, platinum-carbon (Pt—C), palladium-carbon (Pd—C).

(Step 1-2)

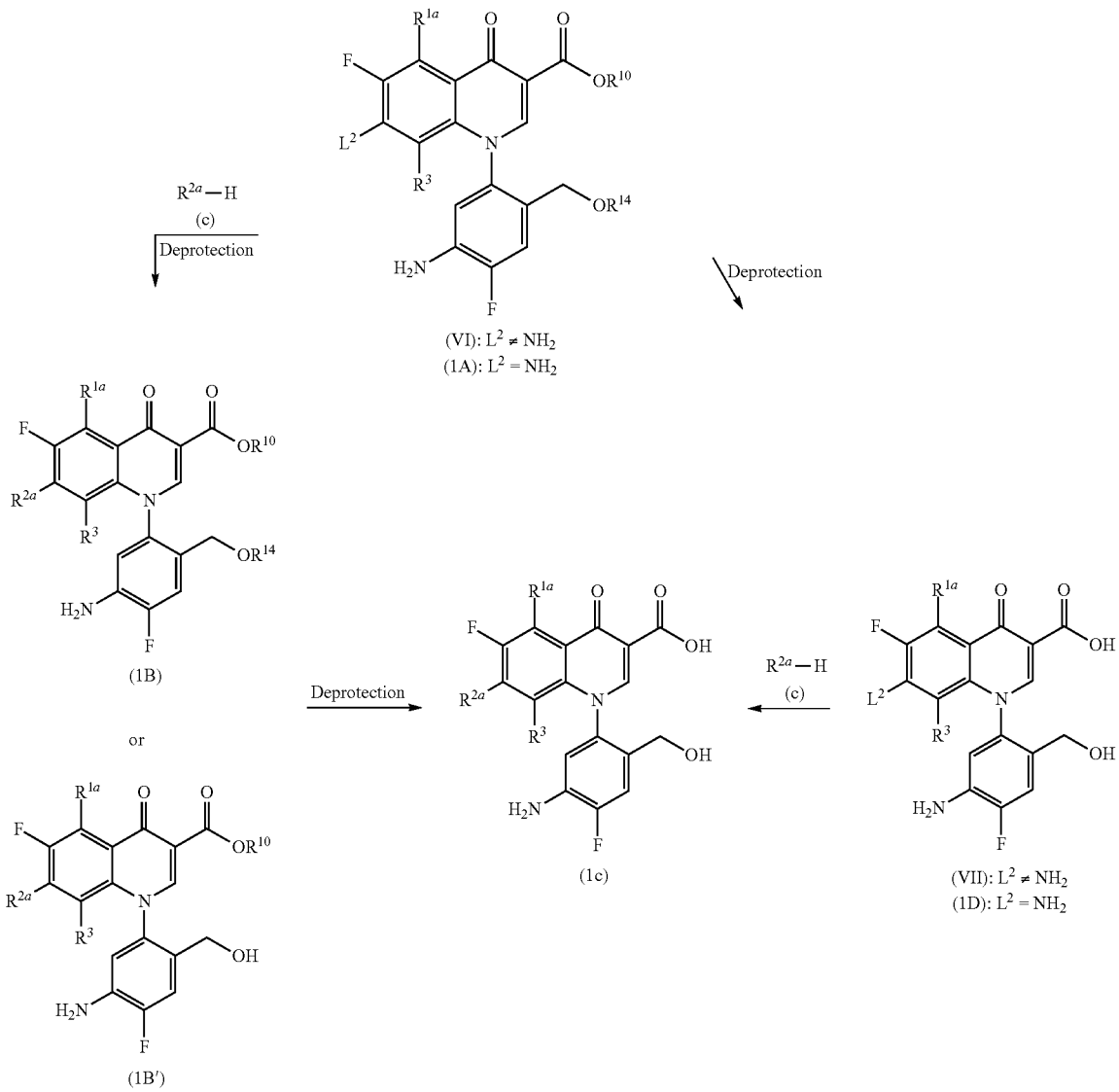

[In the formula, $R^{2a}$ is a group —NH—$R^6$, a group —O—$R^7$ ($R^6$ and $R^7$ represent the same as those described above), or a cyclic amino group represented by the Formula (2); and $R^{1a}$, $R^3$, $R^{10}$, $R^{14}$ and $L^2$ represent the same as those described above.]

More specifically, Compound (1B) or (1B') is obtained by aromatic substitution between Compound (VI) and $R^{2a}$—H (Compound (c)) and subsequent deprotection, if needed, and then Compound (1C) is obtained by elimination of the protecting group on $R^{10}$ and/or $R^{14}$.

Alternatively, Compound (1C) can also be obtained by the elimination of the protecting group of Compound (VI) to produce Compound (VII) and a similar substitution reaction.

Compound (1D), in which $L^2$ is an amino group, can be obtained by the elimination of the protecting group from Compound (1A) by a deprotection reaction such as hydrolysis.

The aromatic substitution is carried out in a solvent which does not affect the reaction, such as aromatic hydrocarbons such as toluene, xylene, and pyridine; ethers such as diethyl ether, tetrahydrofuran, and dioxane; aliphatic hydrocarbons such as pentane and hexane; halogenated hydrocarbons such as methylene chloride, chloroform, and carbon tetrachloride; aprotic polar solvents such as dimethylformamide, N-methylpyrrolidin-2-one, and dimethylsulfoxide; alcohols such as methanol, ethanol, and propanol, in the presence of an acid scavenger, for example, sodium carbonate, calcium carbonate, sodium hydrogen carbonate, potassium carbonate, sodium hydroxide, triethylamine, 1,8-diazabicyclo[5.4.0]undec-7-ene (DBU), tetramethylguanidine, sodium hydride, at room temperature to 100° C. The reaction time to complete the reaction is usually several minutes to 48 hours.

The amount of $R^{2a}$—H (Compound (c)) used is preferably in 1 to 5 times of the amount of Compound (VI) in mol. This reaction may be carried out in the presence of a lithium salt such as lithium chloride as a weak Lewis acid.

Furthermore, when introducing $R^{2a}$, a compound lacking $R^{14}$ (1B') may be obtained depending on the kind of the reagent used and the reaction conditions.

Moreover, when introducing $R^{2a}$, aromatic substitution may be carried out using $R^{2a}$—H having a protecting group (Compound c). For example, when introducing dimethoxybenzylamine or t-butoxycarbonylaminopropylamino group, dimethoxybenzyl group or t-butoxycarbonyl group is eliminated by an acidic compound to obtain a desired compound in which an amino group or an aminopropylamino group is introduced. Examples of the acidic compound which is used include inorganic acids such as hydrochloric acid and organic acids such as trifluoroacetic acid. This reaction is usually carried out at 0 to 80° C. and preferably at 0° C. to room temperature and the reaction time to complete the reaction is usually 5 minutes to 10 hours.

For the deprotection reaction of Compound (1B) or (1B'), for example, the hydrolysis reaction commonly used is available. For example, it can be carried out using an inorganic base such as sodium hydroxide or potassium hydroxide in an alcohol solution. This reaction is carried out usually at 0 to 150° C. and preferably at room temperature to 100° C. and the reaction time thereof is usually 10 minutes to 48 hours.

(Step 1-3)

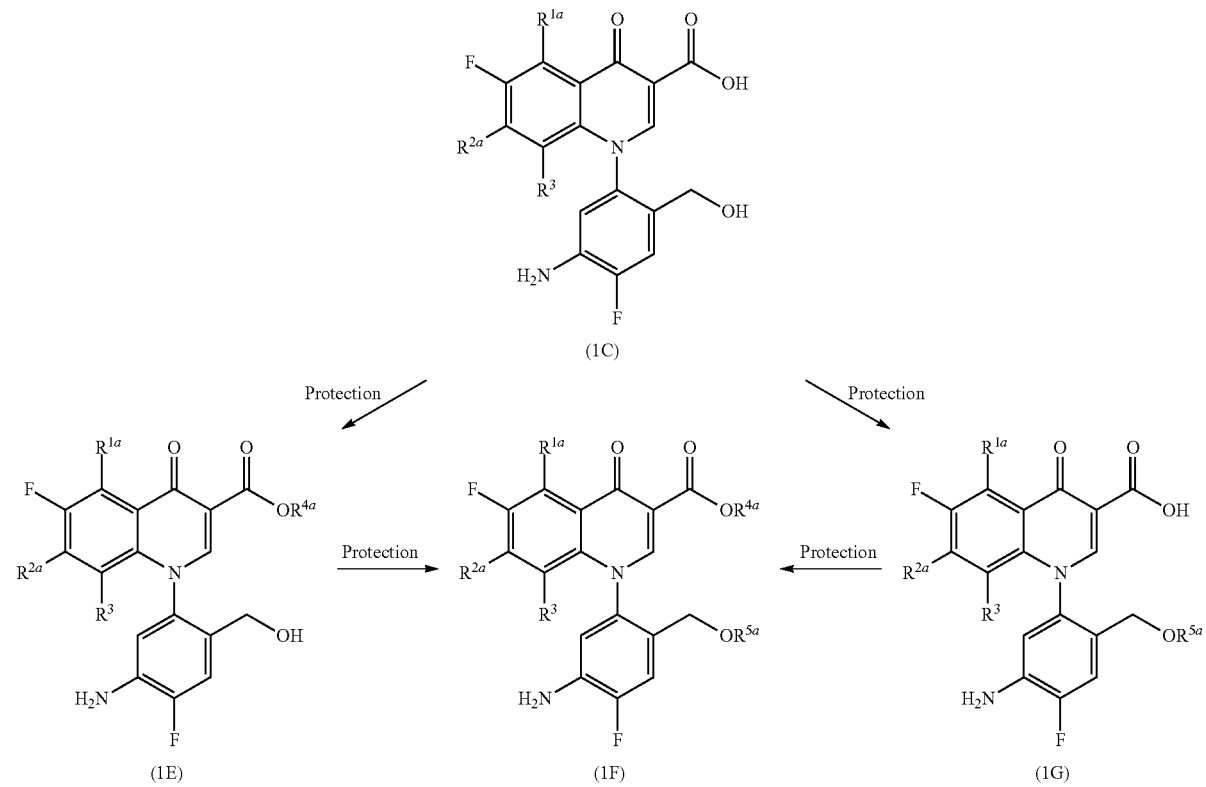

[In the formula, $R^{4a}$ represents a carboxyl group-protecting group, $R^{5a}$ represents a hydroxyl group-protecting group, and $R^{1a}$, $R^{2a}$ and $R^3$ represent the same as those described above.]

Examples of the carboxyl group-protecting group represented by $R^{4a}$ and the hydroxyl group-protecting group represented by $R^{5a}$ include the same as those described for $R^4$ and $R^5$, respectively.

More specifically, Compound (1E) is obtained by the introduction of a carboxyl group-protecting group into Compound (1C) and then Compound (1F) is obtained by the introduction of a hydroxyl group-protecting group. Alternatively, Compound (1F) is derived by the introduction of a hydroxyl group-protecting group to Compound (1C) to yield Compound (1G) and then the introduction of a carboxyl group-protecting group.

The introduction of the carboxyl group-protecting group is carried out by the reaction of an alkyl halide, a 4-halomethyl-5-methyl-2-oxo-1,3-dioxole, acetoxymethyl halide, a pivaloyloxymethyl halide, or the like in a solvent which does not affect the reaction, such as aromatic hydrocarbons such as toluene, xylene, and pyridine; ethers such as diethyl ether, tetrahydrofuran, and dioxane; aliphatic hydrocarbons such as pentane and hexane; halogenated hydrocarbons such as methylene chloride, chloroform, and carbon tetrachloride; aprotic polar solvents such as dimethylformamide, N-methylpyrrolidin-2-one, and dimethylsulfoxide, in the presence of an acid scavenger, for example, sodium carbonate, calcium carbonate, sodium hydrogen carbonate, potassium carbonate, sodium hydroxide, triethylamine, 1,8-diazabicyclo[5.4.0]undec-7-ene (DBU), tetramethylguanidine, sodium hydride, or the like; and an additive, for example, lithium iodide, potassium iodide, or the like, as needed, at room temperature to 100° C. The reaction time to complete the reaction is usually several minutes to 48 hours.

The introduction of the hydroxyl group-protecting group is carried out by the reaction of phosphorus oxychloride, dialkylchloromethylphosphoric acid ester, dibenzylchloromethylphosphoric acid ester, or the like in a solvent which does not affect the reaction, such as ethers such as diethyl ether, tetrahydrofuran, and dioxane; aliphatic hydrocarbons such as pentane and hexane; halogenated hydrocarbons such as methylene chloride, chloroform, and carbon tetrachloride; aprotic polar solvents such as dimethylformamide, N-methylpyrrolidin-2-one, and dimethylsulfoxide, in the presence of an acid scavenger, for example, sodium carbonate, calcium carbonate, sodium hydrogen carbonate, potassium carbonate, sodium hydroxide, triethylamine, 1,8-diazabicyclo[5.4.0]undec-7-ene (DBU), tetramethylguanidine, sodium hydride, or the like, as needed, under cooling conditions to at 100° C. The reaction time to complete the reaction is usually several minutes to 48 hours.

(2) Production Method 2
(Step 2-1)

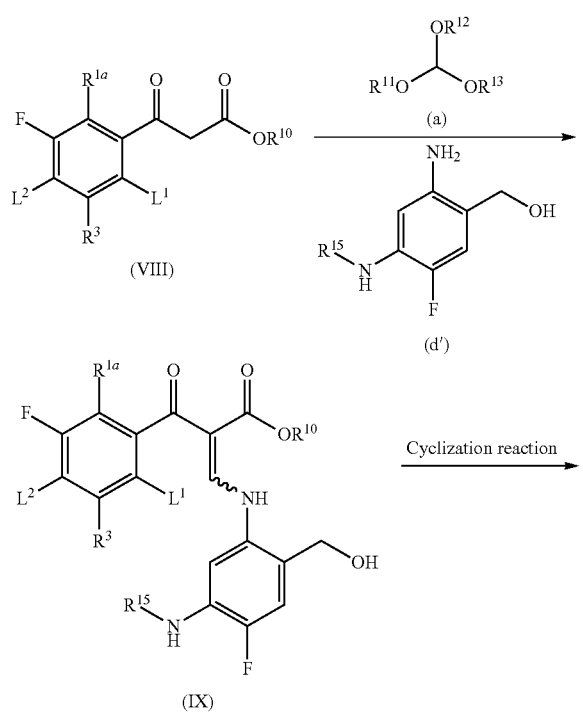

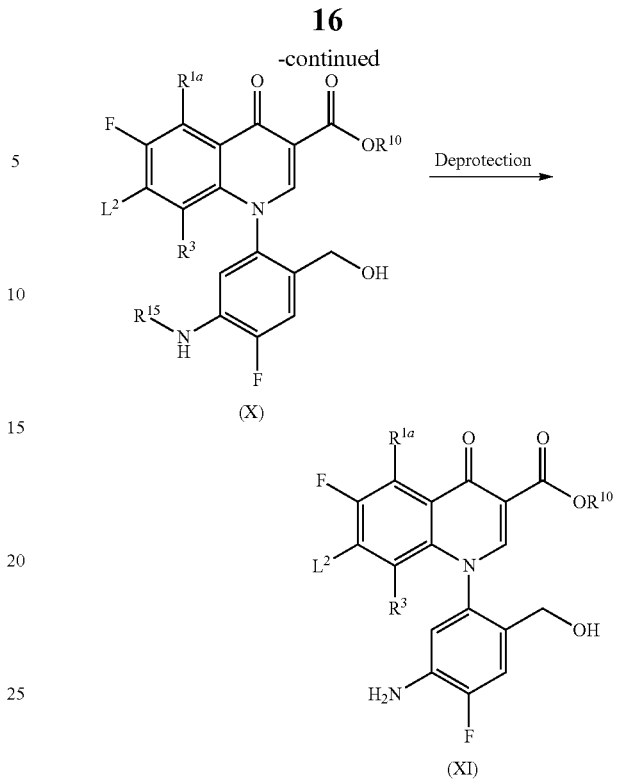

[In the formula, $R^{15}$ represents an amino-protecting group, and $R^{1a}$, $R^3$, $R^{10}$, $R^{11}$, $R^{12}$, $R^{13}$, $L^1$ and $L^2$ represent the same as those described above.]

More specifically, Compound (XI) is obtained by the reaction of orthoformic acid esters (a) with Compound (VIII), the reaction of the obtained compound with an aniline compound (d'), then the cyclization reaction of the obtained compound, and the elimination of the amino-protecting group $R^{15}$ from the obtained compound (X).

Preferable examples of the "amino-protecting group" represented by $R^{15}$ include aralkyl groups such as a benzyl group, a phenethyl group, a benzhydryl group, and a 2,4-dimethoxybenzyl group.

The reaction of Compound (VIII) and an orthoformic acid ester and the reaction with an aniline compound (d') can be carried out in the same way as those in Step 1-1. The cyclization reaction to obtain Compound (X) can also be carried out in the same way as that in Step 1-1.

The elimination of the amino-protecting group $R^{15}$ in Compound (X) is carried out by a common deprotection reaction. For example, it is carried out using an acidic compound in an appropriate solvent in the presence of cation scavengers such as anisole. The solvent used in this reaction may be any solvent as long as it does not affect the reaction and examples thereof include aromatic hydrocarbons such as toluene and xylene; ethers such as diethyl ether, tetrahydrofuran, and dioxane; aliphatic hydrocarbons such as pentane and hexane; halogenated hydrocarbons such as methylene chloride, chloroform, and carbon tetrachloride; aprotic polar solvents such as dimethylformamide and dimethylsulfoxide; and alcohols such as methanol, ethanol, and propanol. Examples of the acidic compound which is used include inorganic acids such as hydrochloric acid and organic acids such as trifluoroacetic acid. This reaction is carried out usually at 0 to 80° C., preferably at 0° C. to room temperature and the reaction time to complete the reaction is usually 5 minutes to 10 hours.

(Step 2-2)

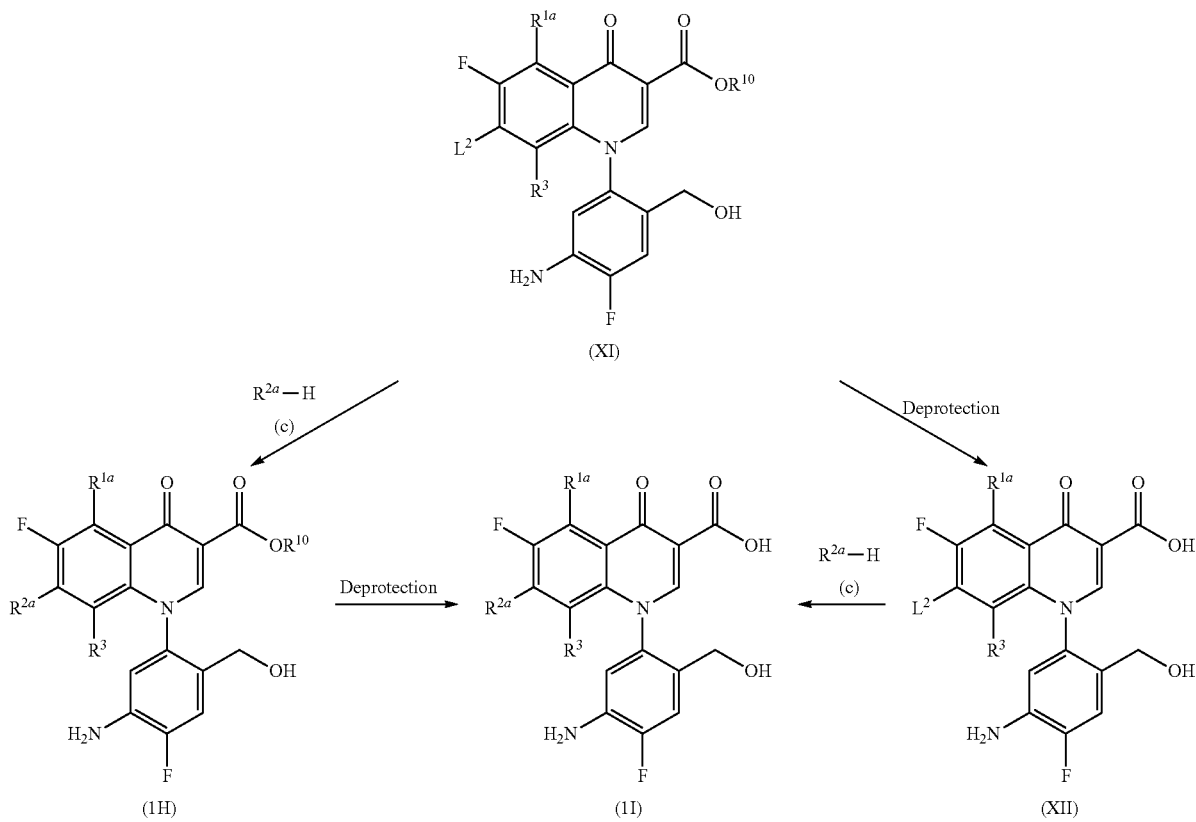

[In the formula, $R^{1a}$, $R^{2a}$, $R^3$, $R^{10}$ and $L^2$ represent the same as those described above.]

More specifically, Compound (1H) is obtained by aromatic substitution between Compound (XI) and $R^{2a}$—H (Compound (c)) and then, Compound (1I) is obtained by the elimination of the protecting group by a deprotection reaction. Alternatively, Compound (1I) is derived by deprotection of Compound (XI) to yield Compound (XII) and the substitution reaction.

The aromatic substitution of Compound (XI) and the deprotection reaction of Compound (1H) can be carried out in the same way as those in Step 1-2.

Compound (1I) can also be derived by the deprotection reaction of Compound (XI) in the same way as that described above to remove the protecting group to yield Compound (XII) and the same substitution reaction as that described above.

(Step 2-3)

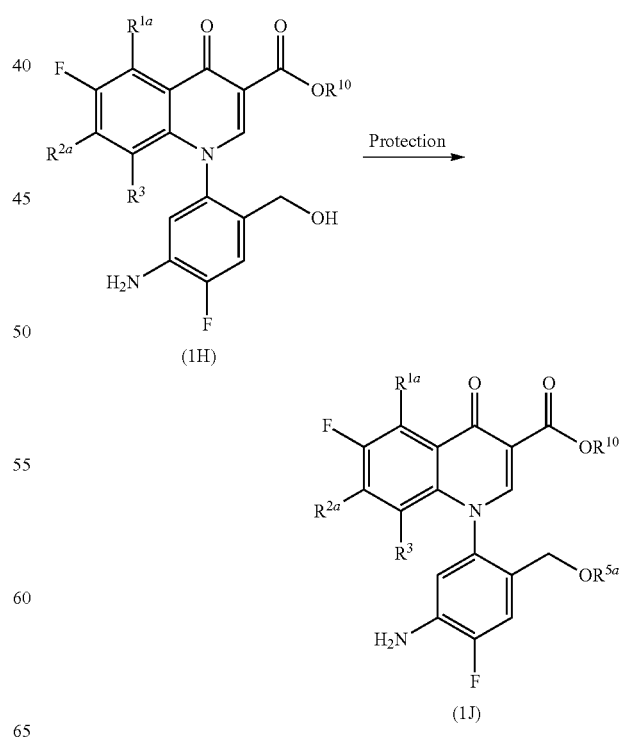

[In the formula, $R^{1a}$, $R^{2a}$, $R^3$, $R^{5a}$ and $R^{10}$ represent the same as those described above.]

More specifically, Compound (1J) is obtained by the introduction of a hydroxyl group-protecting group to Compound (1H) in the same way as that in Step 1-3.

(Step 2-4)

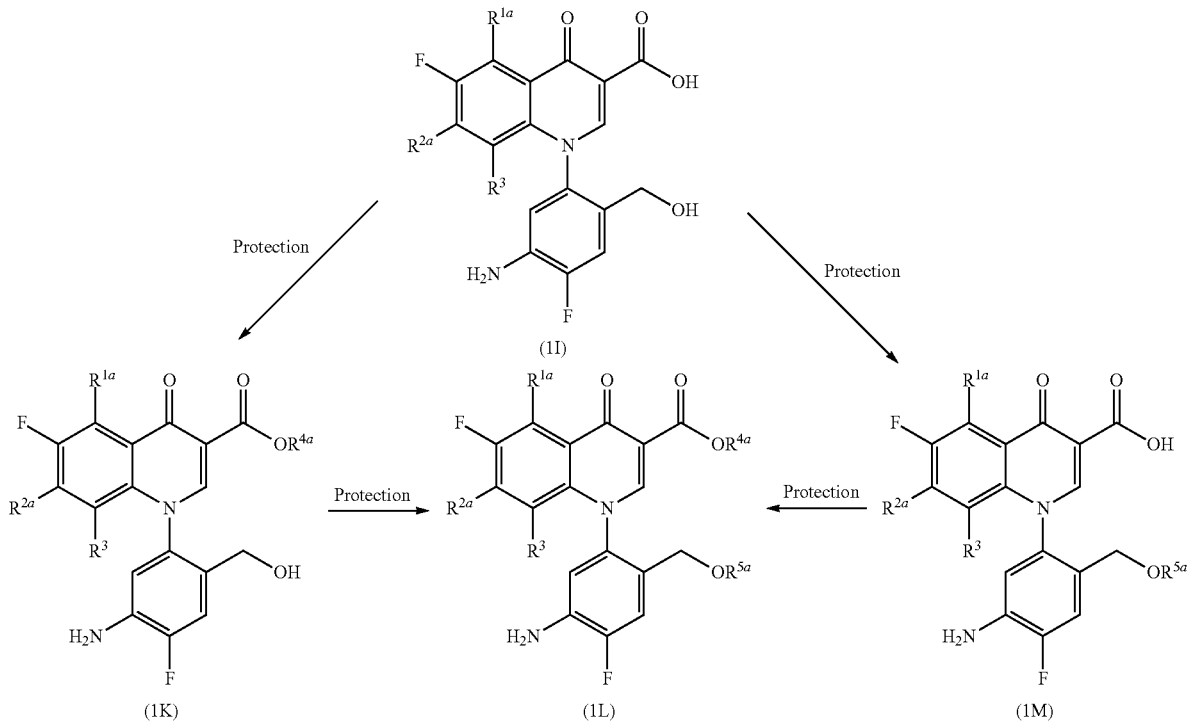

[In the formula, $R^{1a}$, $R^{2a}$, $R^3$, $R^{4a}$ and $R^{5a}$ represent the same as those described above.]

More specifically, Compound (1K) is obtained by the introduction of a carboxyl group-protecting group to Compound (1I) and then Compound (1L) is obtained by the introduction of a hydroxyl group-protecting group to Compound (1K). Alternatively, Compound (1L) can be derived by the introduction of a hydroxyl group-protecting group to Compound (1I) to yield Compound (1M) and subsequent introduction of a carboxyl group-protecting group.

(3) Production Method 3

(Step 3-1)

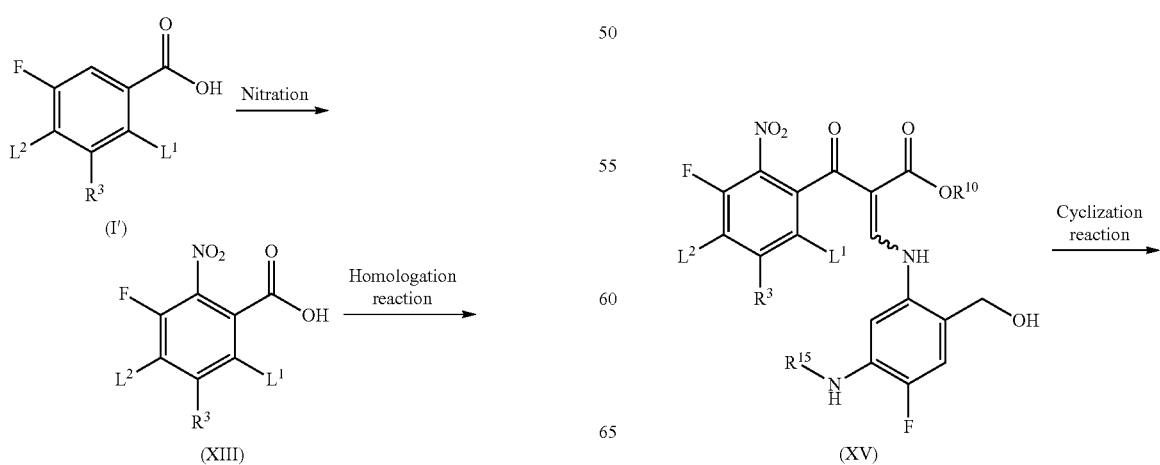

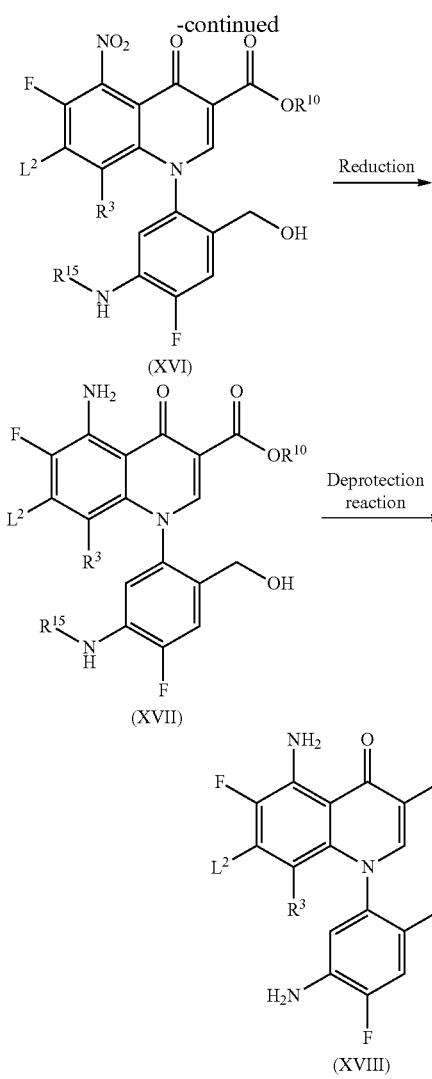

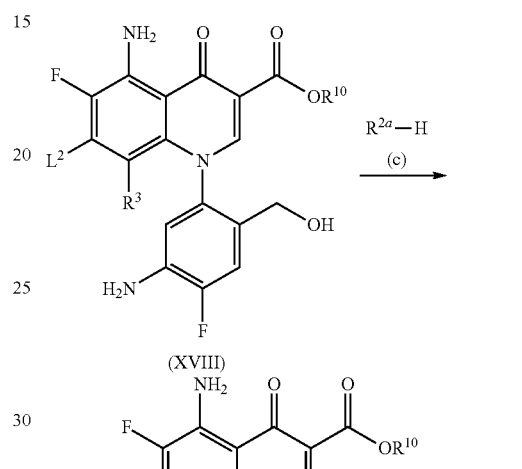

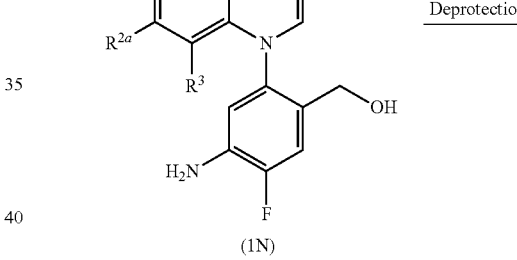

tin, tin chloride, or the like in an acid solution; reduction which involves use of sulfide such as sodium sulfide, sodium hydrosulfide, and sodium dithionite; and catalytic reduction method which involves use of platinum, Raney nickel, platinum-carbon (Pt—C), palladium-carbon (Pd—C), or the like. The reaction with iron is particularly preferred. This reaction is carried out usually at room temperature to 150° C. and preferably at 50 to 100° C. and the reaction time thereof is usually 10 minutes to 48 hours and preferably 1 to 10 hours.

The deprotection reaction to remove $R^{15}$ in Compound (XVII) can be carried out in the same way as that in Step 2-1.

(Step 3-2)

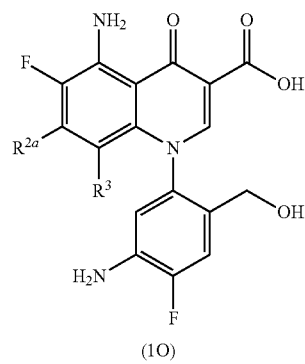

[In the formula, $R^3$, $R^{10}$, $R^{11}$, $R^{12}$, $R_{13}$, $R^{15}$, $L^1$ and $L^2$ represent the same as those described above.]

More specifically, Compound (XV) is obtained by the nitration of Compound (I') to yield Compound (XIII), then a homologation reaction to yield Compound (XIV), the reaction of the resulting compound with an orthoformic acid ester (a), and the reaction of the resulting compound with an aniline compound (d'). Then, Compound (XVIII) is obtained by the cyclization reaction of this Compound (XV), reduction of the nitro group in the resulting Compound (XVI), and then the elimination of the amino-protecting group $R^{15}$.

The nitration of Compound (I') is carried out by using a common method used for aromatic compounds. Examples of nitrating agents include nitrating acids of a combination of nitric acid or a nitrate and sulfuric acid. The reaction temperature is preferably −10° C. to 80° C. and the reaction time is preferably 5 minutes to 24 hours.

All of the homologation reaction of Compound (XIII), the reaction of Compound (XIV) with an orthoformic acid ester, the reaction with an aniline (c), and the cyclization reaction to obtain Compound (XVI) can also be carried out in the same way as those in Step 1-1.

For the reduction reaction of Compound (XVI), methods commonly used are available and examples thereof include dissolving metal reduction which involves use of zinc, iron,

[In the formula, $R^{2a}$, $R^3$, $R^{10}$ and $L^2$ represent the same as those described above.]

More specifically, Compound (1N) is obtained by aromatic substitution between Compound (XVIII) and $R^{2a}$—H (Compound (c)) and then, Compound (1O) is obtained by the elimination of the protecting group by a deprotection reaction.

The aromatic substitution between Compound (XVIII) and Compound (c) and the deprotection reaction of Compound (1N) can be carried out in the same way as those in Step 1-2.

(Step 3-3)

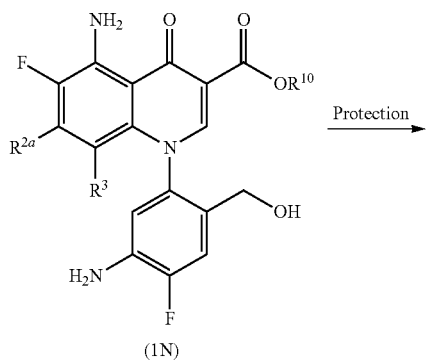

[In the formula, $R^{2a}$, $R^3$, $R^{5a}$ and $R^{10}$ represent the same as those described above.]

More specifically, Compound (1P) is obtained by the introduction of a hydroxyl group-protecting group to Compound (1N) in the same way as that in Step 1-3.

(Step 3-4)

(Step 3-4)

[In the formula, $R^{2a}$, $R^3$, $R^{4a}$ and $R^{5a}$ represent the same as those described above.]

More specifically, Compound (1Q) is obtained by the introduction of a carboxyl group-protecting group to Compound (1O) and then Compound (1R) is obtained by the introduction of a hydroxyl group-protecting group in the same way as that in Step 1-3. Alternatively, Compound (1R) can be derived by the introduction of a hydroxyl group-protecting group to Compound (1O) to yield Compound (1S) and then the introduction of a carboxyl group-protecting group.

(4) Production Method 4

(Step 4-1)

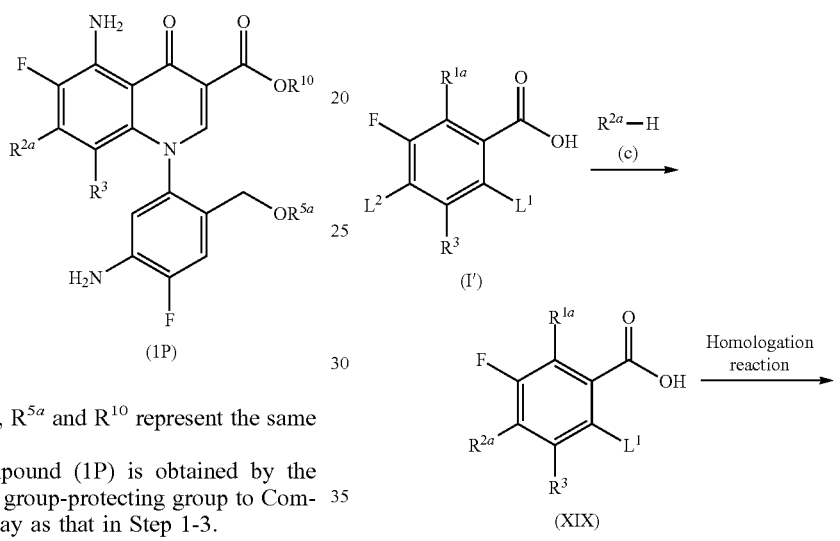

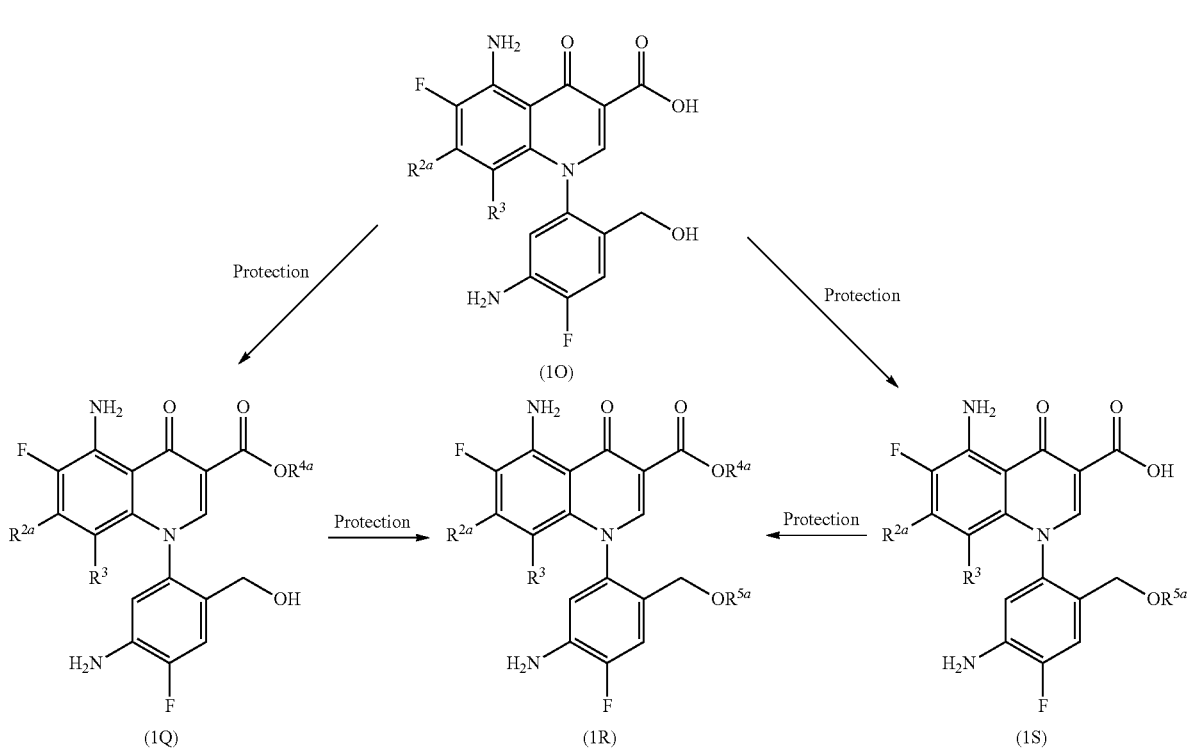

-continued

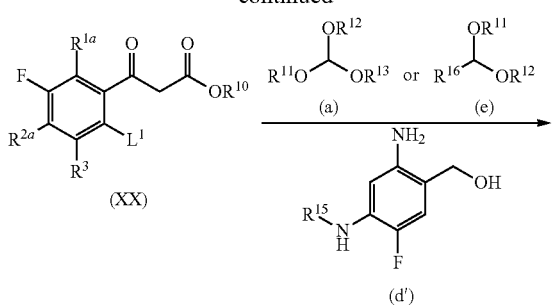

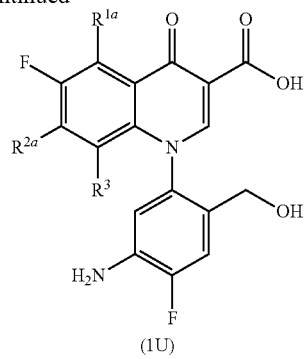

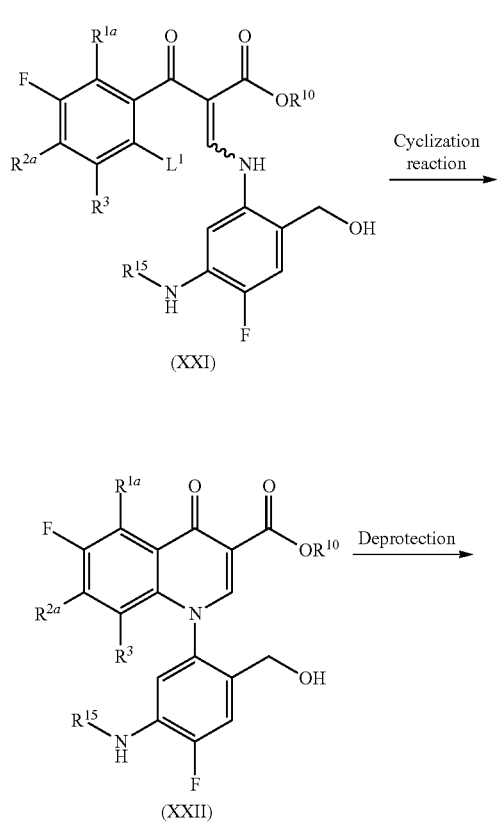

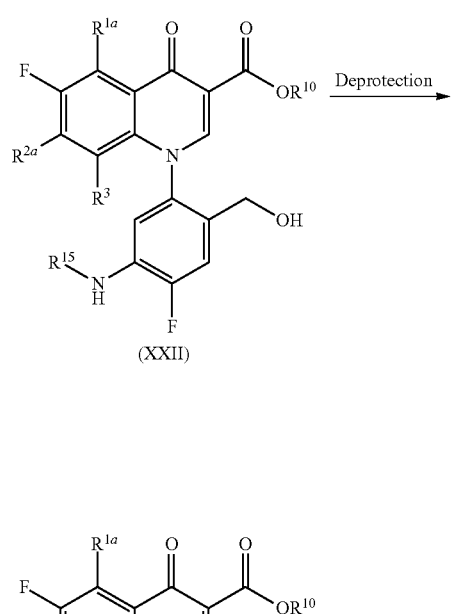

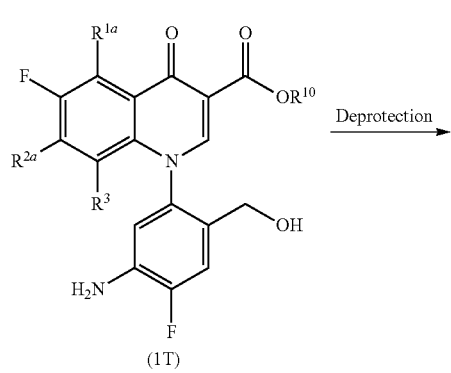

[In the formula, $R^{16}$ represents a lower dialkyl amino group and $R^{1a}$, $R^{2a}$, $R^3$, $R^{10}$, $R^{11}$, $R^{12}$, $R^{13}$, $R^{15}$, $L^1$ and $L^2$ represent the same as those described above.]

More specifically, Compound (1T) is obtained by the aromatic substitution between Compound (I') and $R^{2a}$—H (Compound (c)) to obtain Compound (XIX) and a subsequent homologation reaction to yield Compound (XX); the reaction of Compound (XX) with an orthoformic acid ester (a) or dialkylformamide dialkyl acetal (e) such as dimethylformamide dimethyl acetal; the reaction of the resulting compound with an aniline compound (d'), a subsequent cyclization reaction, and the elimination of the amino-protecting group from the obtained compound (XXII). Compound (1U) can also be obtained by the elimination of the carboxyl group-protecting group in Compound (1T).

The aromatic substitution between Compound (I') and $R^{2a}$—H (Compound (c)) can be carried out in a solvent which does not affect the reaction, such as aromatic hydrocarbons such as toluene, xylene, and pyridine; ethers such as diethyl ether, tetrahydrofuran, and dioxane; aliphatic hydrocarbons such as pentane and hexane; aprotic polar solvents such as dimethylformamide, N-methylpyrrolidin-2-one, and dimethylsulfoxide; in the presence of an acid scavenger, for example, sodium hydride and potassium hydride, as needed, at 0° C. to 100° C. The reaction time to complete the reaction is usually several minutes to 48 hours. The amount of Compound (c) used is preferably 1 to 5 times of the amount of Compound (I') in mol.

The homologation reaction to obtain Compound (XX) and the reaction of Compound (XX) and orthoformic acid esters (a) can be carried out by the same method as the method described in Step 1-1. Alternatively, Compound (XXI) can be derived by the reaction of Compound (XX) with acetals (e) such as N,N-dimethylformamide dimethyl acetal and N,N-dimethylformamide diethyl acetal and a subsequent reaction with Compound (d'). The lower dialkylamino group represented by $R^{16}$ in acetals (e) is a $C_{1-3}$ dialkylamino group and more preferably a dimethylamino group.

The solvent used in the reaction with acetals may be any solvent, as long as it does not affect the reaction and examples thereof include aromatic hydrocarbons such as toluene and xylene; ethers such as diethyl ether, tetrahydrofuran, and dioxane; aliphatic hydrocarbons such as pentane and hexane; halogenated hydrocarbons such as methylene chloride, chloroform, and carbon tetrachloride; aprotic polar solvents such as dimethylformamide and dimethylsulfoxide; and alcohols such as methanol, ethanol, and propanol. This reaction is carried out usually at 0 to 150° C. and preferably at room temperature to 100° C. and the reaction time thereof is usually 10 minutes to 48 hours and preferably 1 to 10 hours.

The cyclization reaction to obtain Compound (XXII) can also be carried out in the same way as that in Step 1-1 and the deprotection reaction of Compound (XXII) and the deprotection reaction of Compound (1T) can be carried out in the same way as those in Step 1-2.

(Step 4-2)

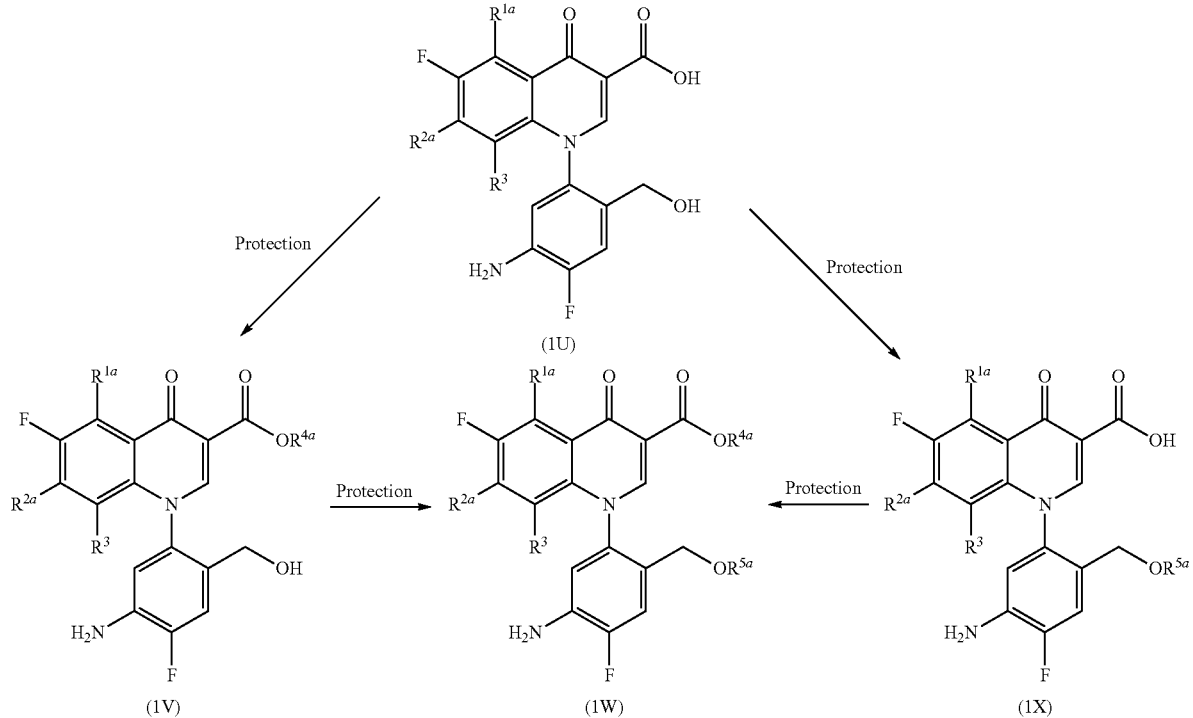

[In the formula, $R^{1a}$, $R^{2a}$, $R^3$, $R^{4a}$ and $R^{5a}$ represent the same as those described above.]

More specifically, Compound (1W) is obtained by the introduction of a carboxyl group-protecting group into Compound (1U) to yield Compound (1V) and subsequent introduction of a hydroxyl group-protecting group in the same way as that in Step 1-3. Alternatively, Compound (1W) can be derived by the introduction of a hydroxyl group-protecting group into Compound (1U) to yield Compound (1X) and subsequent introduction of a carboxyl group-protecting group.

(5) Production Method 5

(Step 5-1)

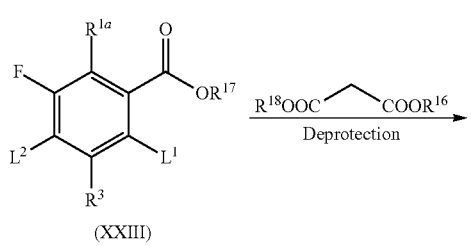

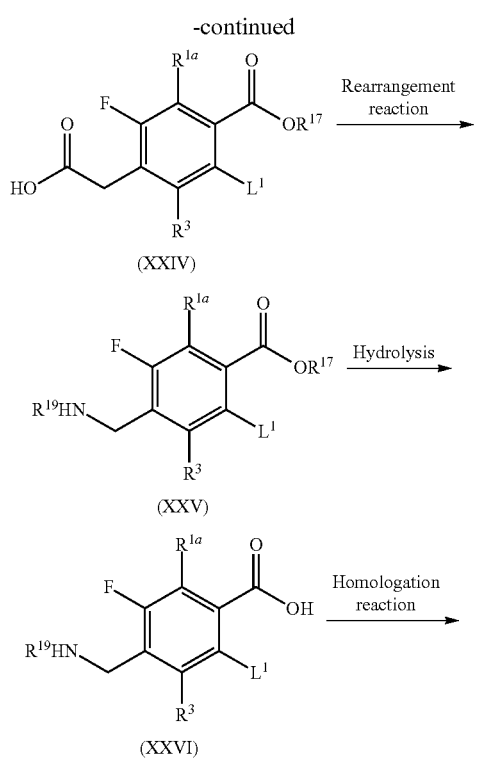

29

-continued

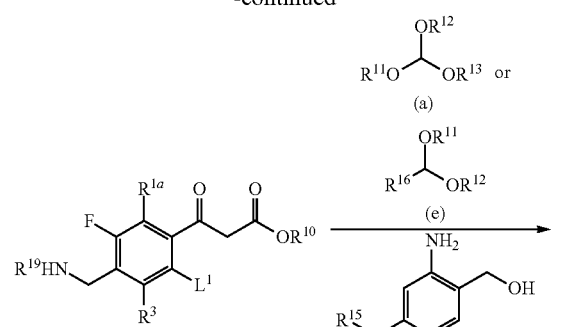

(XXVII)

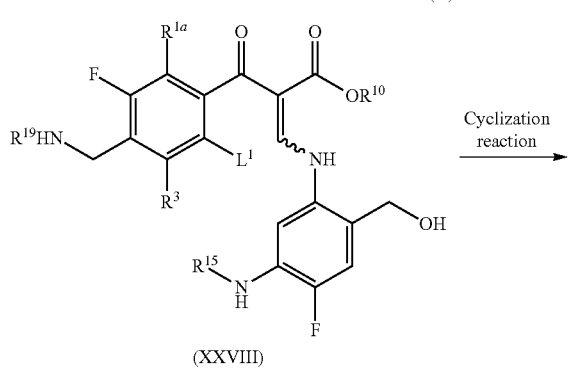

(XXVIII)

Cyclization reaction →

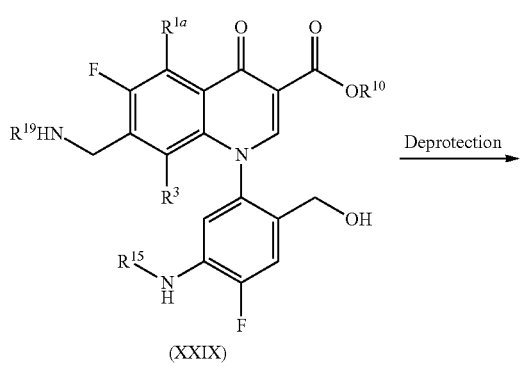

(XXIX)

Deprotection →

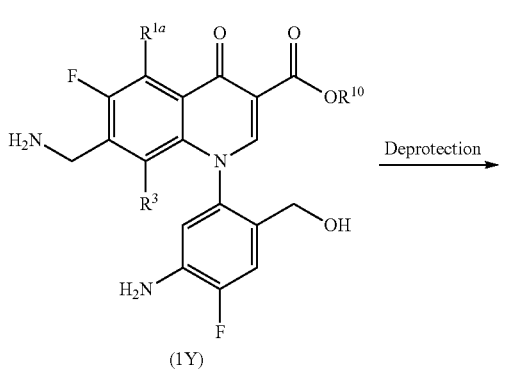

(1Y)

Deprotection →

30

-continued

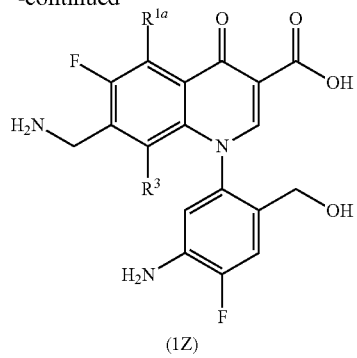

(1Z)

[In the formula, $R^{17}$ represents a lower alkyl group, a lower alkenyl group, or an aralkyl group; $R^{18}$ represents a lower alkyl group; $R^{19}$ represents an amino-protecting group; and $R^{1a}$, $R^3$, $R^{10}$, $R^{11}$, $R^{12}$, $R^{13}$, $R^{15}$, $R^{16}$, $L^1$ and $L^2$ represent the same as those described above.]

More specifically, Compound (XXIV) is obtained by aromatic substitution between Compound (XXIII) and a malonic acid diester and a subsequent deprotection reaction. Then, Compound (XXV) is derived by a rearrangement reaction and then, Compound (XXVI) is obtained by hydrolysis reaction. Then, Compound (XXVII) is derived by a homologation reaction. Compound (1Y) is obtained by the reaction with orthoformic acid esters (a) or dialkylformamide dialkyl acetal (e) such as dimethylformamide dimethyl acetal, the reaction of the resulting compound with an aniline compound (d'), a subsequent cyclization reaction, and the elimination of the amino-protecting group $R^{15}$ and amino-protecting group $R^{19}$ in the resulting compound (XXIX). Furthermore, Compound (1Z) can be obtained by the elimination of the carboxyl group-protecting group in Compound (1Y).

The lower alkyl group, lower alkenyl group, or aralkyl group represented by $R^{17}$ is the same as that indicated for $R^{10}$.

The lower alkyl group represented by $R^{18}$ is preferably a $C_{1-4}$ alkyl group and more preferably a t-butyl group.

Preferable examples of the amino-protecting group represented by $R^{19}$ include a benzyloxycarbonyl group, a t-butoxycarbonyl group, an allyloxycarbonyl group, and a 2,2,2-trichloroethoxycarbonyl group and more preferable example is a t-butoxycarbonyl group.

The aromatic substitution between Compound (XXIII) and a malonic acid diester is carried out usually by the addition of a malonic acid diesters such as di-t-butyl malonate to Compound (XXIII) in the presence of a base and subsequent deprotection and decarboxylation.

The aromatic substitution is carried out in a solvent which does not affect the reaction, such as aromatic hydrocarbons such as toluene, xylene, and pyridine; ethers such as diethyl ether, tetrahydrofuran, and dioxane; aliphatic hydrocarbons such as pentane and hexane; aprotic polar solvents such as dimethylformamide, N-methylpyrrolidin-2-one, and dimethylsulfoxide, in the presence of an acid scavenger, for example, metal hydride such as sodium hydride and calcium hydride; inorganic bases such as sodium hydroxide, potassium hydroxide, and potassium carbonate; alkoxides such as sodium methoxide, sodium ethoxide, and potassium-t-butoxide; 1,8-diazabicyclo[5.4.0]undec-7-ene (DBU), or the like, as needed, at 0° C. to 100° C. The reaction time to complete the reaction is usually several minutes to 48 hours.

The amount of the malonic acid diester used is preferably 1 to 5 times of the amount of Compound (XXIII) in mol.

Compound (XXIV) is obtained by the elimination of $R^{18}$ and decarboxylation following the aromatic substitution. The elimination reaction of $R^{18}$ needs to be carried out in conditions in which $R^{17}$ is not removed. For example, elimination and decarboxylation with acid is usually carried out in a solvent which does not affect the reaction, such as aromatic hydrocarbons such as toluene and xylene; ethers such as diethyl ether, tetrahydrofuran, and dioxane; halogenated hydrocarbons such as methylene chloride, chloroform, and carbon tetrachloride; aliphatic hydrocarbons such as pentane and hexane; aprotic polar solvents such as dimethylformamide, N-methylpyrrolidin-2-one, and dimethylsulfoxide, in the presence of an organic acid such as trifluoroacetic acid or an inorganic acid such as hydrochloric acid, as needed, at 0° C. to 100° C. The reaction time to complete the reaction is usually several minutes to 48 hours.

Compound (XXIV) is converted into Compound (XXV) by synthesis of isocyanate by the Curtius rearrangement and a following additional reaction with alcohol. Usually, Compound (XXIV) is activated with oxalyl dichloride or thionyl chloride, or carbonyldiimidazole and then allowed to react with an azidating agent such as sodium azide and tetra-n-butylammonium azide. The resulting isocyanate can subsequently be converted into a protected amine by an additional reaction with corresponding alcohol. Alternatively, Compound (XXIV) can be directly converted into isocyanate using diphenylphosphoryl azide in a reaction. The reaction in the initial activation is carried out usually at 0 to 150° C. and preferably at 0 to 100° C. and the reaction time thereof is usually 10 minutes to 48 hours and preferably 1 to 10 hours. The following reaction with an azidating agent is usually for 10 minutes to 24 hours and preferably 1 to 10 hours and carried out usually at −20 to 150° C. and preferably at 0 to 100° C. The final additional reaction with alcohol is usually for 10 minutes to 48 hours and preferably 1 to 10 hours and carried out usually at 0 to 150° C. and preferably at room temperature to 100° C.

The hydrolysis of Compound (XXV) can be carried out by the same method as that in Step 1-2 and the homologation reaction to obtain Compound (XXVII) can be carried out in the same way as that in Step 1-1.

The reaction of Compound (XXVII) with the orthoformic acid ester (a) and dimethylformamide dialkyl acetal (e) can be carried out by the same method as that in Step 4-1.

The reaction with Compound (c) and the cyclization reaction to obtain Compound (XXIX) can be carried out by the same method as that in Step 1-1.

The deprotection reaction of the amino-protecting groups $R^{15}$ and $R^{19}$ in Compound (XXIX) is carried out in a common method. For example, for a t-butoxycarbonyl group, the solvent used in this reaction may be any solvent as long as it does not affect the reaction and examples thereof include aromatic hydrocarbons such as toluene and xylene; ethers such as diethyl ether, tetrahydrofuran, and dioxane; aliphatic hydrocarbons such as pentane and hexane; halogenated hydrocarbons such as methylene chloride, chloroform, and carbon tetrachloride; aprotic polar solvents such as dimethylformamide and dimethylsulfoxide; and alcohols such as methanol, ethanol, and propanol. Examples of the acidic compound which is used include inorganic acids such as hydrochloric acid and organic acids such as trifluoroacetic acid. This reaction is carried out usually at 0 to 80° C., preferably at 0° C. to room temperature and the reaction time to complete the reaction is usually 5 minutes to 10 hours.

The deprotection reaction of Compound (1Y) can be carried out by the same method as that in Step 1-2.

Compound (I) and Compound (XXIII) which are used as raw materials may be those which are commercially available.

(6) Production Method 6

(Step 6-1)

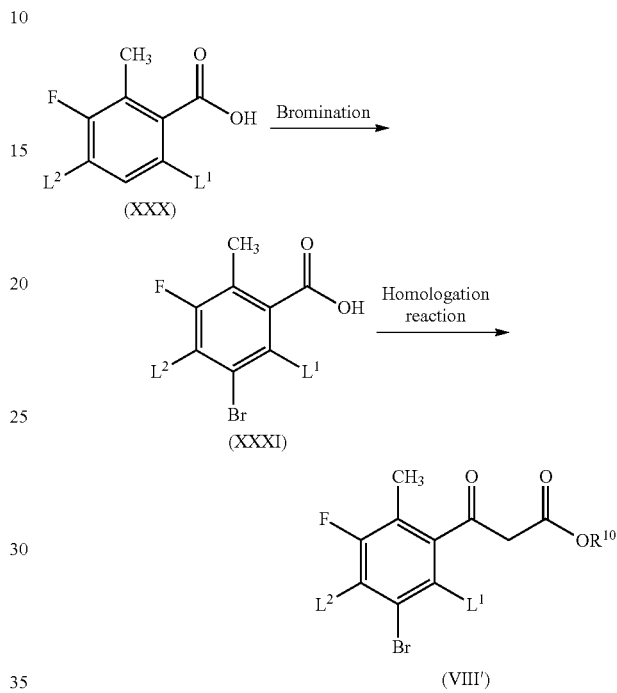

[In the formula, $R^{10}$, $L^1$ and $L^2$ represent the same as those described above.]

More specifically, Compound (VIII') is obtained by the bromination of Compound (XXX) to yield Compound (XXXI) and a subsequent homologation reaction same as that in Step 1-1.

The bromination of Compound (XXX) is carried out by using a brominating agent such as N-bromosuccinimide or 1,3-dibromo-5,5-dimethyl-2,4-imidazolinedione in the presence of strong acid such as concentrated sulfuric acid. The reaction temperature is preferably −10° C. to 80° C. and the reaction time is preferably 72 to 120 hours. The amount of the brominating agent to be used is preferably 1 to 5 times in mol relative to Compound (XXX).

(7) Production Method 7

(Step 7-1)

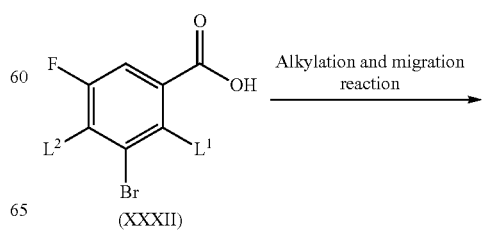

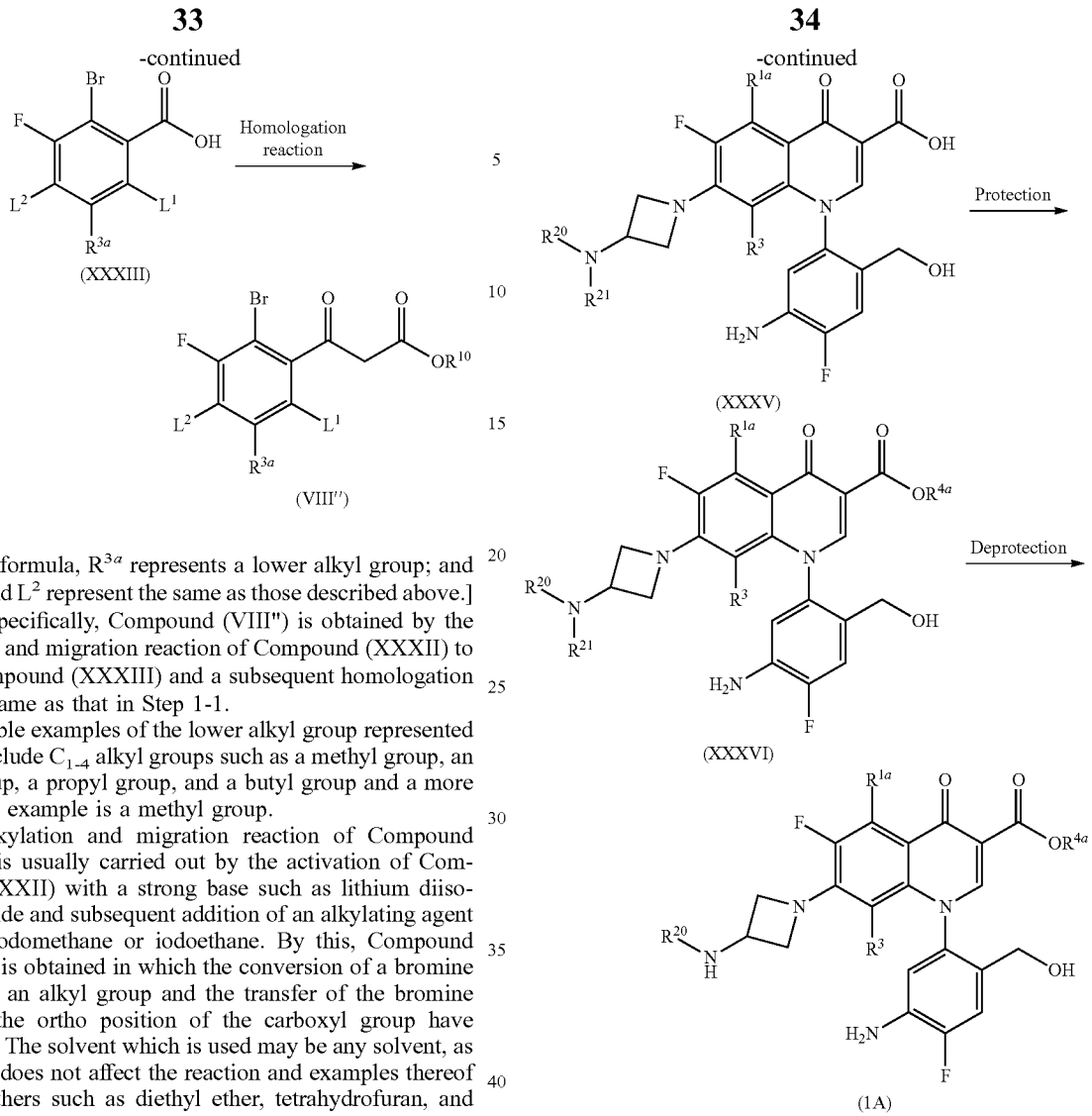

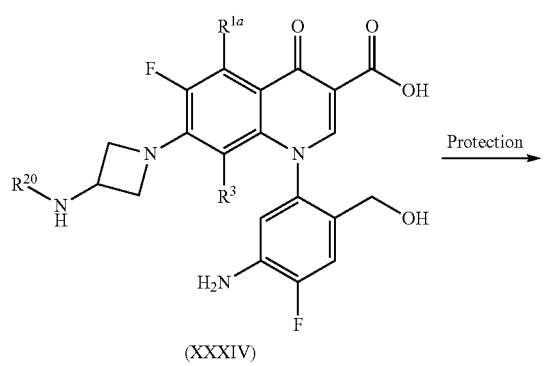

[In the formula, $R^{3a}$ represents a lower alkyl group; and $R^{10}$, $L^1$ and $L^2$ represent the same as those described above.]

More specifically, Compound (VIII″) is obtained by the alkylation and migration reaction of Compound (XXXII) to yield Compound (XXXIII) and a subsequent homologation reaction same as that in Step 1-1.

Preferable examples of the lower alkyl group represented by $R^{3a}$ include $C_{1-4}$ alkyl groups such as a methyl group, an ethyl group, a propyl group, and a butyl group and a more preferable example is a methyl group.

The alkylation and migration reaction of Compound (XXXII) is usually carried out by the activation of Compound (XXXII) with a strong base such as lithium diisopropylamide and subsequent addition of an alkylating agent such as iodomethane or iodoethane. By this, Compound (XXXIII) is obtained in which the conversion of a bromine atom into an alkyl group and the transfer of the bromine atom to the ortho position of the carboxyl group have advanced. The solvent which is used may be any solvent, as long as it does not affect the reaction and examples thereof include ethers such as diethyl ether, tetrahydrofuran, and dioxane; and aliphatic hydrocarbons such as pentane and hexane. The reaction in the activation is carried out usually at −78° C. to 0° C. and preferably −78° C. to −50° C. and the reaction time thereof is usually 10 minutes to 2 hours and preferably 15 minutes to 1 hour. The addition and migration reaction are carried out usually at 0° C. to 100° C. and preferably 0° C. to 50° C. and the reaction time thereof is usually 30 minutes to 24 hours and preferably 1 to 10 hours.

(8) Production Method 8

(Step 8-1)

[In the formula, $R^{20}$ represents a hydrogen atom or a lower alkyl group; $R^{21}$ represents an amino group-protecting group; and $R^{1a}$, $R^3$ and $R^{4a}$ represent the same as those described above.]

More specifically, Compound (1A1) is obtained by the introduction of an amino group-protecting group into Compound (XXXIV) and the following introduction of a carboxyl group-protecting group in the same way as that in Step 1-3 and elimination of the amino group-protecting group $R^{21}$ in the resulting Compound (XXXVI).

Preferable examples of the lower alkyl group represented by $R^{20}$ include $C_{1-4}$ alkyl groups such as a methyl group, an ethyl group, a propyl group, an isopropyl group, a butyl group, an isopropyl group, and a tert-butyl group and more preferable examples thereof are a methyl group and an ethyl group.

Preferable examples of the amino group-protecting group represented by $R^{21}$ include a benzyloxycarbonyl group, a tert-butoxycarbonyl group, an allyloxycarbonyl group, and a 2,2,2-trichloroethoxycarbonyl group and a more preferable example is an allyloxycarbonyl group.

The introduction of the amino group-protecting group into Compound (XXXIV) is carried out by the reaction of benzyl chloroformate, di-tert-butyl dicarbonate, allyl chloroformate, 2,2,2-trichloroethyl chloroformate, or the like in a solvent which does not affect the reaction, such as aromatic hydrocarbons such as toluene and xylene; ethers such as diethyl ether, tetrahydrofuran, and dioxane; aliphatic hydrocarbons such as pentane and hexane; halogenated hydrocarbons such as methylene chloride, chloroform, and carbon tetrachloride; aprotic polar solvents such as dimethylformamide, N-methylpyrrolidin-2-one, and dimethylsulfoxide in the presence of an acid scavenger, for example, sodium carbonate, calcium carbonate, sodium hydrogen carbonate, potassium carbonate, sodium hydroxide, triethylamine, diisopropylethylamine, 1,8-diazabicyclo[5.4.0]undec-7-ene (DBU), tetramethylguanidine, or the like, as needed, at room temperature to 100° C. The reaction time to complete the reaction is usually several minutes to 48 hours.

The elimination of amino group-protecting group $R^{21}$ in Compound (XXXVI) is carried out by a common deprotection reaction. For example, it is carried out using a catalytic amount of palladium such as tetrakis(triphenylphosphine) palladium (0), tris(dibenzylideneacetone)dipalladium (0) in an appropriate solvent in the presence of an additive such as dimedone, trimethylsilyldimethylamine, or 1,3-dimethylbarbituric acid. The solvent used in this reaction may be any solvent as long as it does not affect the reaction and examples thereof include aromatic hydrocarbons such as toluene and xylene; ethers such as diethyl ether, tetrahydrofuran, and dioxane; aliphatic hydrocarbons such as pentane and hexane; halogenated hydrocarbons such as methylene chloride, chloroform, and carbon tetrachloride; aprotic polar solvents such as dimethylformamide, N-methylpyrrolidin-2-one, and dimethylsulfoxide. This reaction is carried out usually at 0 to 50° C. and preferably at 0 to 35° C. and the reaction time to complete the reaction is usually several minutes to 10 hours.

(9) Production Method 9
(Step 9-1)

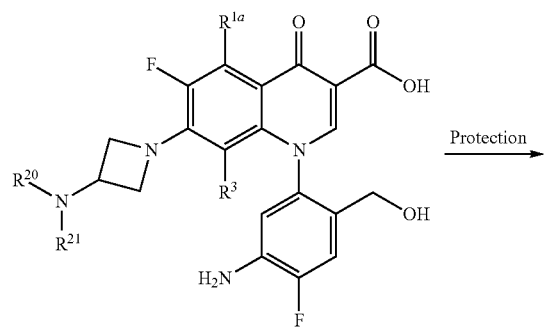

(XXXV)

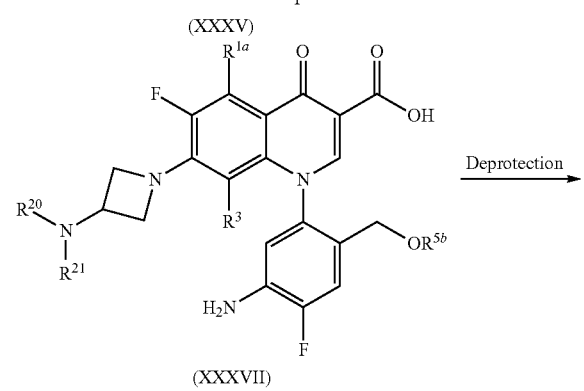

(XXXVII)

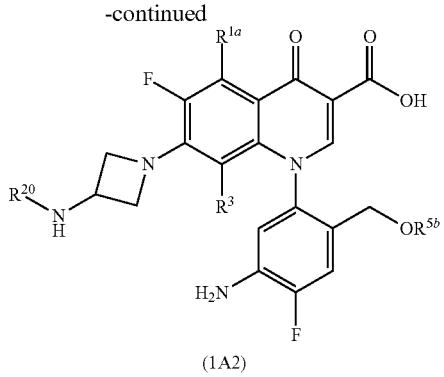

(1A2)

[In the formula, $R^{5b}$ represents a hydroxyl group-protecting group and $R^{1a}$, $R^3$, $R^{20}$ and $R^{21}$ represent the same as those described above.]

More specifically, a hydroxyl group-protecting group is introduced into Compound (XXXV) to yield Compound (XXXVII) and then the elimination of the amino group-protecting group is carried out to obtain Compound (IA2) in the same way as that in Step 8-1, Preferable examples of the hydroxyl group-protecting group represented by $R^{5b}$ include lower alkyl carbonyl groups such as an acetyl group, a propanoyl group, a butanoyl group, a 2-methyl propanoyl group, and a pentanoyl group and a more preferable example is an acetyl group.

The introduction of the hydroxyl group-protecting group to Compound (XXXV) is carried out by a reaction of a symmetric acid anhydride such as acetic anhydride, propionic anhydride, butyric anhydride, or isobutyric anhydride or an unsymmetrical acid anhydride such as acetic pivalic anhydride, propionic pivalic anhydride, butyric pivalic anhydride, or isobutyric pivalic anhydride in a solvent which does not affect the reaction, such as aromatic hydrocarbons such as toluene and xylene; ethers such as diethyl ether, tetrahydrofuran, and dioxane; aliphatic hydrocarbons such as pentane and hexane; halogenated hydrocarbons such as methylene chloride, chloroform, and carbon tetrachloride; aprotic polar solvents such as dimethylformamide, N-methylpyrrolidin-2-one, and dimethylsulfoxide in the presence of 4-dimethylaminopyridine at room temperature to 100° C. The reaction time to complete the reaction is usually several minutes to 48 hours.

(10) Production Method 10
(Step 10-1)

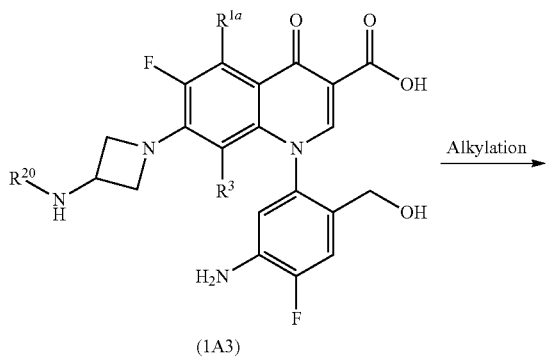

(1A3)

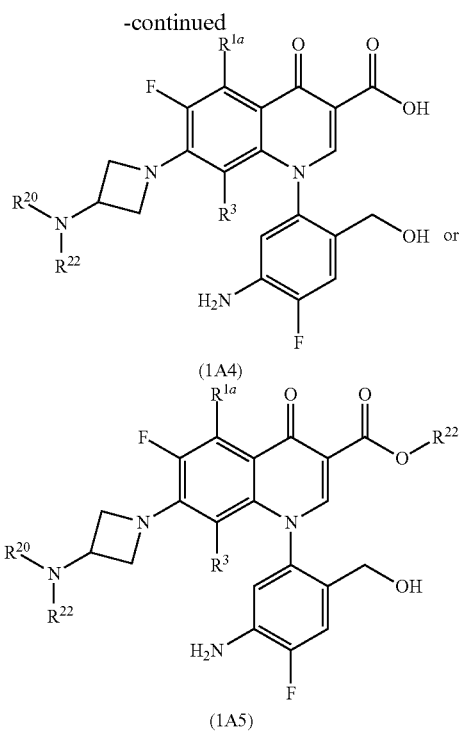

[In the formula, $R^{22}$ represents an alkyl group and $R^{1a}$, $R^3$ and $R^{20}$ represent the same as those described above.]

More specifically, an alkyl group is introduced into Compound (1A3) to obtain Compound (1A4) or Compound (1A5).

Preferable examples of the alkyl group represented by $R^{22}$ include a methyl group, an ethyl group, an isopropyl group, and (5-methyl-2-oxo-1,3-dioxol-4-yl)methyl and a more preferable example is a (5-methyl-2-oxo-1,3-dioxol-4-yl) methyl group.

The introduction of the alkyl group into Compound (1A3) is carried out by the reaction of an alkyl halide such as iodomethane, iodoethane, or 4-halomethyl-5-methyl-2-oxo-1,3-dioxole in a solvent which does not affect the reaction, such as aromatic hydrocarbons such as toluene and xylene; ethers such as diethyl ether, tetrahydrofuran, and dioxane; aliphatic hydrocarbons such as pentane and hexane; halogenated hydrocarbons such as methylene chloride, chloroform, and carbon tetrachloride; aprotic polar solvents such as dimethylformamide, N-methylpyrrolidin-2-one, and dimethylsulfoxide in the presence of an acid scavenger, for example, sodium carbonate, calcium carbonate, sodium hydrogen carbonate, potassium carbonate, sodium hydroxide, triethylamine, diisopropylethylamine, 1,8-diazabicyclo[5.4.0]undec-7-ene (DBU), tetramethylguanidine, or the like and an additive, for example, lithium iodide, a potassium iodide, or the like, as needed, at room temperature to 100° C. The reaction time to complete the reaction is usually several minutes to 48 hours.

The thus obtained pyridonecarboxylic acid derivative of the present invention is isolated and purified according to an ordinary method. It is obtained in the form of salt or the form of free carboxylic acid or free amine depending on the conditions of isolation and purification. Such forms are converted to each other and the compounds of the present invention in desired forms are produced.

The thus obtained pyridonecarboxylic acid derivative or a salt thereof according to the present invention has an excellent antibacterial activity against bacteria such as methicillin-resistant *Staphylococcus aureus*, *Pseudomonas aeruginosa*, and *Clostridium difficile* and is characterized in that it is not susceptible to drug efflux pumps in *Pseudomonas aeruginosa*, as illustrated in Test Examples 1 and 2. Therefore, the pyridonecarboxylic acid derivative or salt thereof according to the present invention can be used as a clinically useful antimicrobial agent.

The antimicrobial agent according to the present invention may be prepared as an antimicrobial composition (pharmaceutical formulation) together with a pharmaceutically acceptable carrier for parenteral administration such as injection, transrectal administration, or instillation or oral administration in a solid or liquid form.

Examples of a formulation for injection include pharmaceutically acceptable aseptic water or non-aqueous solutions, suspensions, or emulsions. Examples of an appropriate non-aqueous carrier, diluent, solvent, or vehicle include propyleneglycol, polyethyleneglycol, vegetable oils, for example, olive oil, and injectable organic esters, for example, ethyl oleate. Such a composition may also contain a pharmaceutic aid, for example, a preservative, a moistening agent, an emulsifier, and a dispersant. These compositions can be sterilized, for example, by filtration with a bacteria retention filter or by adding a sterilization agent just before use or by adding a sterilization agent in the form of an aseptic solid composition which can be dissolved in some other sterilization injectable vehicles.

Formulations for instillation may preferably contain, in addition to the compound of the present invention compound, a solubilizing agent, a preservative, an isotonizing agent, and a thickener.

Examples of the solid formulation for oral administration include capsules, tablets, pills, powder, and granules. In the preparation of this solid formulation, the pyridonecarboxylic acid derivative or a salt thereof according the present invention is mixed with at least one inert diluent, for example, sucrose, lactose, or starch. This formulation may also contain an additional substance other than the inert diluent, for example, a lubricant (for example, magnesium stearate) in usual formulation. For capsules, tablets, and pills, a buffer may also be used. Tablets and pills may be coated with an enterosoluble film.

Examples of the liquid formulation for oral administration include inert diluents commonly used among those skilled in the art, for example, pharmaceutically acceptable emulsions containing water, solutions, suspensions, syrups, and elixirs. In addition to such an inert diluent, the composition may contain a pharmaceutic aid, for example, a moistening agent, an emulsifier, a suspension, and a sweetener, a seasoning, and a flavor agent. The formulation for transrectal administration may preferably contain, in addition to the compound of the present invention a filler, for example, coconut butter or suppository wax.

The dose of the antimicrobial agent according to the present invention depends on the nature of the compound administered, the administration route, the desired treatment period, and other factors, but it is normally preferable to be about 0.1 to 1000 mg/kg per day and particularly about 0.5 to 100 mg/kg in terms of the pyridonecarboxylic acid derivative or a salt thereof according to the present invention for adult. This daily dose may be divided into 2 to 4 doses, if desired.

EXAMPLES

Hereinafter, the present invention will be described in detail in reference with Examples and Reference Examples, but the present invention is not limited thereto.

Reference Example 1

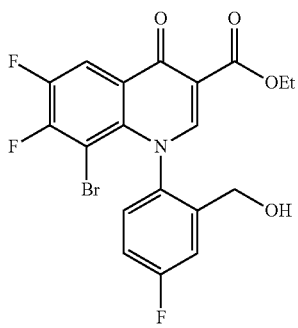

Ethyl 8-bromo-6,7-difluoro-1-[4-fluoro-2-(hydroxymethyl)phenyl]-4-oxo-1,4-dihydroquinoline-3-carboxylate 11.1 g of ethyl orthoformate and 12.8 g of acetic anhydride were added to 16.3 g of ethyl 3-(3-bromo-2,4,5-trifluorophenyl)-3-oxopropanate and the mixture was heated to reflux for 19 hours. The reaction solution was evaporated under reduced pressure and the resulting residue was dissolved in 50 mL of dichloromethane to obtain a crude ethoxyacrylate solution.

7.1 g of 2-amino-5-fluorobenzyl alcohol was suspended in 200 mL of dichloromethane and the ethoxyacrylate solution obtained earlier was added dropwise. The mixture was stirred at room temperature for 1 hour. The reaction solution was washed with water and then dried over anhydrous magnesium sulfate. The solvent was evaporated under reduced pressure and the resulting residue was dispersed in diisopropyl ether, collected by filtration, and dried to obtain 20.3 g of ethyl 2-(3-bromo-2,4,5-trifluorobenzoyl)-3-[[4-fluoro-2-(hydroxymethyl)phenyl]amino]acrylate.

20.0 g of the obtained compound and 3.6 g of lithium chloride were dissolved in 84 mL of N-methylpyrrolidin-2-one and 6.8 g of 1,8-diazabicyclo[5.4.0]undec-7-ene was added. The mixture was stirred at 80° C. for 1 hour. After cooling, the reaction solution was poured into 800 mL of water and precipitated crystals were collected by filtration and dried. The crystals were dissolved in 800 mL of chloroform and washed with water. The organic layer was dried over anhydrous magnesium sulfate and evaporated under reduced pressure. The resulting residue was dispersed in diisopropyl ether, collected by filtration, and dried to obtain 17.5 g of the title compound.

$^1$H-NMR (DMSO-$d_6$); δ 1.25 (3H, t, J=7 Hz), 4.21 (2H, q, J=7 Hz), 4.27 (2H, d, J=5 Hz), 5.42 (1H, t, J=5 Hz), 7.33 (1H, dt, J=13 Hz, 3 Hz), 7.41 (1H, dd, J=10 Hz, 3 Hz), 7.63 (1H, dd, J=9 Hz, 5 Hz), 8.26 (1H, dd, J=10 Hz, 9 Hz), 8.35 (1H, s)

Reference Example 2

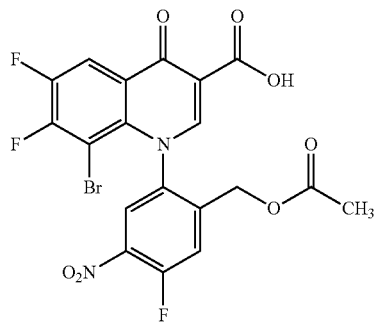

1-(2-Acetoxymethyl-4-fluoro-5-nitrophenyl)-8-bromo-6,7-difluoro-4-oxo-1,4-dihydroquinoline-3-carboxylic acid 4.6 g of ethyl 8-bromo-6,7-difluoro-1-[4-fluoro-2-(hydroxymethyl)phenyl]-4-oxo-1,4-dihydroquinoline-3-carboxylate was dissolved in 40 mL of concentrated sulfuric acid and 2.4 g of potassium nitrate was added.

The mixture was stirred at 50° C. for 4 hours. The reaction solution was poured into 500 mL of iced water and extracted with 500 mL of ethyl acetate. The organic layer was dried over anhydrous magnesium sulfate and then evaporated under reduced pressure to obtain an oily substance. This was dissolved in 50 mL of acetic acid and the solution was stirred at 80° C. for 4 hours. After cooling, acetic acid was evaporated under reduced pressure and the residue was dissolved in chloroform. The solution was washed with water and then a saturated aqueous solution of sodium hydrogen carbonate. The organic layer was dried over anhydrous magnesium sulfate and then evaporated under reduced pressure. The obtained crystals were dispersed in ethyl acetate, collected by filtration, and dried to obtain 3.2 g of the title compound.

$^1$H-NMR (DMSO-$d_6$); δ 1.83 (3H, s), 4.94 (1H, d, J=14 Hz), 4.99 (1H, d, J=14 Hz), 7.95 (1H, d, J=12 Hz), 8.46 (1H, dd, J=10 Hz, 9 Hz), 8.75 (1H, d, J=7 Hz), 8.83 (1H, s)

Reference Example 3

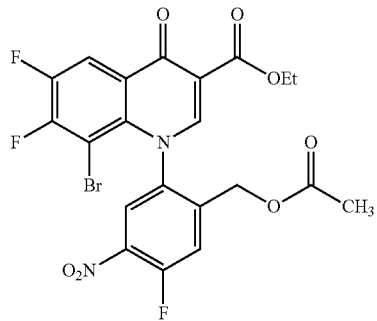

Ethyl 1-(2-acetoxymethyl-4-fluoro-5-nitrophenyl)-8-bromo-6,7-difluoro-4-oxo-1,4-dihydroquinoline-3-carboxylate 2.7 g of 1-(2-acetoxymethyl-4-fluoro-5-nitrophenyl)-8-bromo-6,7-difluoro-4-oxo-1,4-dihydroquinoline-3-carboxylic acid was suspended in 50 mL of dichloromethane and 0.2 mL of N,N-dimethylformamide and 1 mL of oxalyl chloride were added. The mixture was stirred at room temperature for 10 minutes. 20 mL of ethanol was added to this mixture. The reaction solution was washed with water and then a saturated aqueous solution of sodium hydrogen carbonate. The organic layer was dried over anhydrous magnesium sulfate and evaporated under reduced pressure. The resulting residue was dispersed in diethyl ether, collected by filtration, and dried to obtain 1.5 g of the title compound.

$^1$H-NMR (DMSO-d$_6$); δ 1.25 (3H, t, J=7 Hz), 1.89 (3H, s), 4.23 (2H, q, J=7 Hz), 4.93 (1H, d, J=13 Hz), 5.00 (1H, d, J=13 Hz), 7.94 (1H, d, J=12 Hz), 8.28 (1H, dd, J=10 Hz, 9 Hz), 8.51 (1H, s), 8.73 (1H, d, J=7 Hz)

Reference Example 4

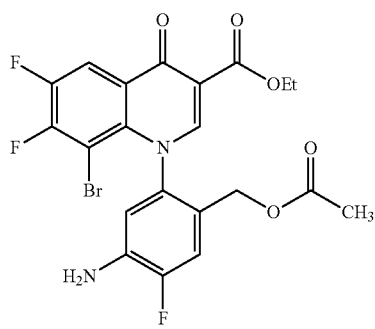

Ethyl 1-(2-acetoxymethyl-5-amino-4-fluorophenyl)-8-bromo-6,7-difluoro-4-oxo-1,4-dihydroquinoline-3-carboxylate 1.9 g of ethyl 1-(2-acetoxymethyl-4-fluoro-5-nitrophenyl)-8-bromo-6,7-difluoro-4-oxo-1,4-dihydroquinoline-3-carboxylate was dissolved in 50 mL of acetic acid and 0.9 g of reduced iron was added. The mixture was stirred at 70° C. for 30 minutes. Insoluble matter was filtered off with celite and the filtrate was evaporated under reduced pressure. The resulting residue was dissolved in 400 mL of chloroform and washed with water and then a saturated aqueous solution of sodium hydrogen carbonate. The organic layer was dried over anhydrous magnesium sulfate and evaporated under reduced pressure. The resulting residue was separated in a silica gel column (0 to 4% methanol/chloroform) to obtain 1.8 g of the title compound.

$^1$H-NMR (DMSO-d$_6$); δ 1.25 (3H, t, J=7 Hz), 1.80 (3H, s), 4.22 (2H, q, J=7 Hz), 4.67 (1H, d, J=13 Hz), 4.74 (1H, d, J=13 Hz), 5.76 (2H, s), 6.88 (1H, d, J=8 Hz), 7.30 (1H, d, J=12 Hz), 8.25 (1H, dd, J=10 Hz, 9 Hz), 8.33 (1H, s)

Example 1

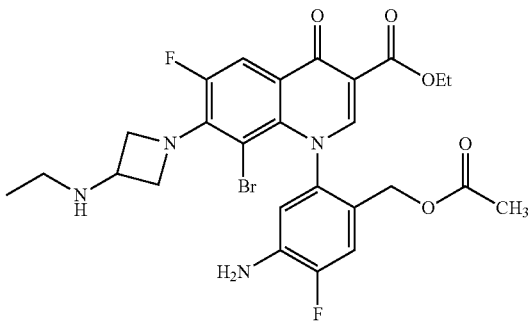

Ethyl 1-(2-acetoxymethyl-5-amino-4-fluorophenyl)-8-bromo-7-[3-(ethylamino)azetidin-1-yl]-6-fluoro-4-oxo-1,4-dihydroquinoline-3-carboxylate 260 mg of ethyl 1-(2-acetoxymethyl-5-amino-4-fluorophenyl)-8-bromo-6,7-difluoro-4-oxo-1,4-dihydroquinoline-3-carboxylate and 260 mg of 3-(ethylamino)azetidine dihydrochloride were suspended in 4 mL of acetonitrile and 350 mg of 1,1,3,3-tetramethylguanidine was added. The mixture was stirred at 35° C. for 3 hours. Precipitated crystals were collected by filtration, then washed with acetonitrile, and dried to obtain 230 mg of the title compound.

$^1$H-NMR (DMSO-d$_6$); δ 0.97 (3H, t, J=7 Hz), 1.23 (3H, t, J=7 Hz), 1.90 (3H, s), 2.45 (2H, q, J=7 Hz), 3.46-3.52 (1H, m), 3.92-3.96 (1H, m), 3.99-4.03 (1H, m), 4.19 (2H, q, J=7 Hz), 4.49-4.54 (1H, m), 4.56-4.60 (1H, m), 4.69 (1H, d, J=13 Hz), 4.78 (1H, d, J=13 Hz), 5.65 (2H, s), 6.71 (1H, d, J=8 Hz), 7.25 (1H, d, J=12 Hz), 7.77 (1H, d, J=14 Hz), 8.22 (1H, s)

Example 2

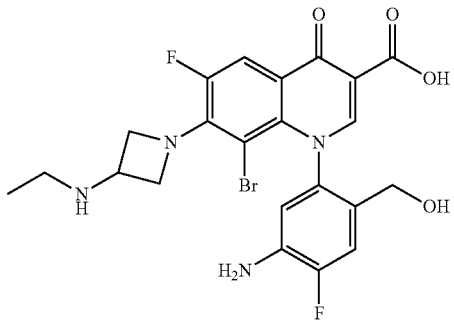 [SMILES: CCNC1CN(c2c(F)cc3c(=O)c(C(=O)O)cn(-c4cc(N)c(F)cc4CO)c3c2Br)C1]

1-[5-Amino-4-fluoro-2-(hydroxymethyl)phenyl]-8-bromo-7-[3-(ethylamino)azetidin-1-yl]-6-fluoro-4-oxo-1,4-dihydroquinoline-3-carboxylic acid 230 mg of ethyl 1-(2-acetoxymethyl-5-amino-4-fluorophenyl)-8-bromo-7-[3-(ethylamino)azetidin-1-yl]-6-fluoro-4-oxo-1,4-dihydroquinoline-3-carboxylate was suspended in 2 mL of ethanol and 2 mL of a 1 mol/L aqueous solution of sodium hydroxide was added. The mixture was stirred at 60° C. for 5 minutes. After cooling, 0.33 mL of 6 mol/L hydrochloric acid was added to neutralize the mixture. The reaction solution was concentrated under reduced pressure and precipitated powder was collected by filtration, washed with water and then acetonitrile, and dried to obtain 12 mg of the title compound.

¹H-NMR (DMSO-d₆); δ 0.98 (3H, t, J=7 Hz), 2.48 (2H, q, J=7 Hz), 3.50-3.56 (1H, m), 3.93-4.15 (4H, m), 4.59-4.64 (2H, m), 5.00 (1H, t, J=5 Hz), 5.47 (2H, s), 6.74 (1H, d, J=8 Hz), 7.16 (1H, d, J=12 Hz), 7.91 (1H, d, J=14 Hz), 8.45 (1H, s)

Example 3

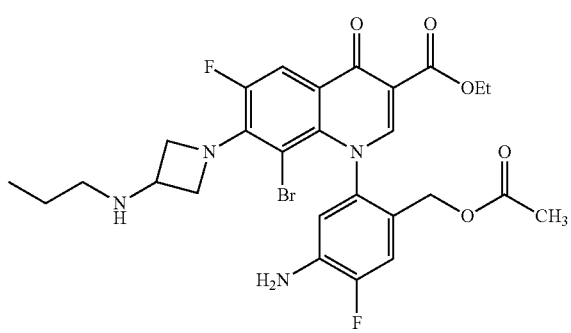 [SMILES: CCCNC1CN(c2c(F)cc3c(=O)c(C(=O)OCC)cn(-c4cc(N)c(F)cc4COC(C)=O)c3c2Br)C1]

Ethyl 1-(2-acetoxymethyl-5-amino-4-fluorophenyl)-8-bromo-6-fluoro-4-oxo-7-[3-(propylamino)azetidin-1-yl]-1,4-dihydroquinoline-3-carboxylate 260 mg of ethyl 1-(2-acetoxymethyl-5-amino-4-fluorophenyl)-8-bromo-6,7-difluoro-4-oxo-1,4-dihydroquinoline-3-carboxylate and 280 mg of 3-(propylamino)azetidine dihydrochloride were suspended in 4 mL of acetonitrile and 350 mg of 1,1,3,3-tetramethylguanidine was added. The mixture was stirred at 35° C. for 2 hours. 50 mL of chloroform was added to the reaction solution and the mixture was washed with a saturated aqueous solution of sodium hydrogen carbonate. The organic layer was dried over anhydrous magnesium sulfate and evaporated under reduced pressure. The resulting residue was crystallized with ethyl acetate to obtain 180 mg of the title compound.

¹H-NMR (DMSO-d₆); δ 0.84 (3H, t, J=7 Hz), 1.23 (3H, t, J=7 Hz), 1.32-1.39 (2H, m), 1.90 (3H, s), 2.38 (2H, t, J=7 Hz), 3.45-3.51 (1H, m), 3.92-3.96 (1H, m), 3.99-4.03 (1H, m), 4.19 (2H, q, J=7 Hz), 4.49-4.53 (1H, m), 4.56-4.60 (1H, m), 4.69 (1H, d, J=13 Hz), 4.77 (1H, d, J=13 Hz), 5.65 (2H, s), 6.71 (1H, d, J=8 Hz), 7.25 (1H, d, J=12 Hz), 7.77 (1H, d, J=14 Hz), 8.22 (1H, s)

Example 4

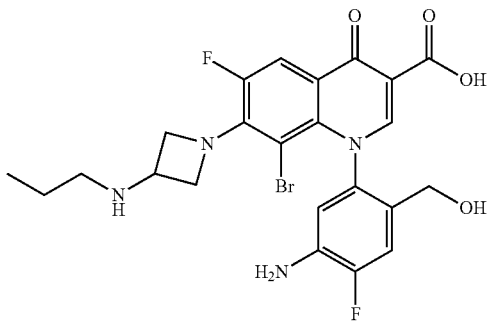 [SMILES: CCCNC1CN(c2c(F)cc3c(=O)c(C(=O)O)cn(-c4cc(N)c(F)cc4CO)c3c2Br)C1]

1-[5-Amino-4-fluoro-2-(hydroxymethyl)phenyl]-8-bromo-6-fluoro-4-oxo-7-[3-(propylamino)azetidin-1-yl]-1,4-dihydroquinoline-3-carboxylic acid 180 mg of ethyl 1-(2-acetoxymethyl-5-amino-4-fluorophenyl)-8-bromo-6-fluoro-4-oxo-7-[3-(propylamino)azetidin-1-yl]-1,4-dihydroquinoline-3-carboxylate was suspended in 2 mL of ethanol and 2 mL of a 1 mol/L aqueous solution of sodium hydroxide was added. The mixture was stirred at 60° C. for 30 minutes. After cooling, 0.33 mL of 6 mol/L hydrochloric acid was added to neutralize the mixture and precipitated crystals were collected by filtration, washed with water and then acetonitrile, and then dried to obtain 110 mg of the title compound.

¹H-NMR (DMSO-d₆); δ 0.85 (3H, t, J=7 Hz), 1.33-1.40 (2H, m), 2.39 (2H, t, J=7 Hz), 3.48-3.54 (1H, m), 4.03-4.15 (4H, m), 4.59-4.63 (2H, m), 5.05 (1H, t, J=5 Hz), 5.47 (2H, s), 6.74 (1H, d, J=8 Hz), 7.16 (1H, d, J=12 Hz), 7.90 (1H, d, J=14 Hz), 8.45 (1H, s)

Example 5

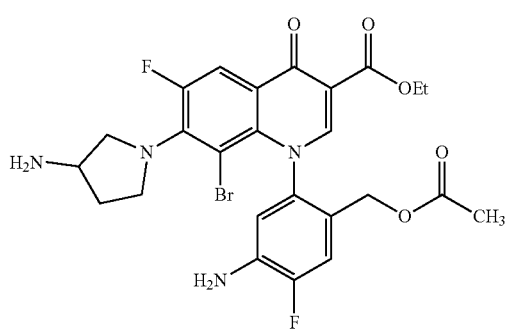 [SMILES: CCOC(=O)c1cn(-c2cc(N)c(F)cc2COC(C)=O)c2c(Br)c(N3CCC(N)C3)c(F)cc2c1=O]

Ethyl 1-(2-acetoxymethyl-5-amino-4-fluorophenyl)-7-[3-aminopyrrolidin-1-yl]-8-bromo-6-fluoro-4-oxo-1,4-dihydroquinoline-3-carboxylate 260 mg of ethyl 1-(2-acetoxymethyl-5-amino-4-fluorophenyl)-8-bromo-6,7-difluoro-4-oxo-1,4-dihydroquinoline-3-carboxylate and 130 mg of 3-aminopyrrolidine were suspended in 4 mL of acetonitrile and the suspension was stirred at 35° C. for 16 hours. 50 mL of chloroform was added to the reaction solution and the mixture was washed with a saturated aqueous solution of sodium hydrogen carbonate. The organic layer was dried over anhydrous magnesium sulfate and evaporated under reduced pressure. The resulting residue was crystallized with ethyl acetate to obtain 170 mg of the title compound.

$^1$H-NMR (DMSO-d$_6$); δ 1.24 (3H, t, J=7 Hz), 1.58-1.65 (1H, m), 1.87 (3H, s), 1.98-2.04 (1H, m), 2.94-2.97 (1H, m), 3.40-3.61 (4H, m), 4.21 (2H, q, J=7 Hz), 4.67 (1H, d, J=12 Hz), 4.75 (1H, d, J=12 Hz), 5.66 (2H, s), 6.74 (1H, d, J=8 Hz), 7.26 (1H, d, J=13 Hz), 7.91 (1H, d, J=13 Hz), 8.30 (1H, s)

Example 6

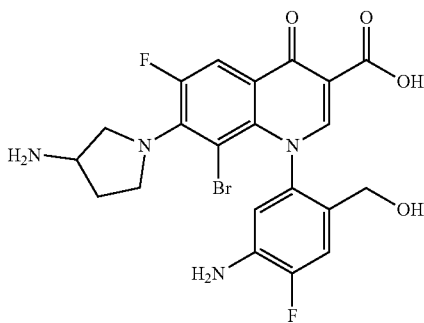

1-[5-Amino-4-fluoro-2-(hydroxymethyl)phenyl]-7-(3-aminopyrrolidin-1-yl)-8-bromo-6-fluoro-4-oxo-1,4-dihydroquinoline-3-carboxylic acid 170 mg of ethyl 1-(2-acetoxymethyl-5-amino-4-fluorophenyl)-7-[3-aminopyrrolidin-1-yl]-8-bromo-6-fluoro-4-oxo-1,4-dihydroquinoline-3-carboxylate was suspended in 2 mL of ethanol and 2 mL of a 1 mol/L aqueous solution of sodium hydroxide was added. The mixture was stirred at 60° C. for 20 minutes. After cooling, 0.33 mL of 6 mol/L hydrochloric acid was added to neutralize the mixture. Precipitated powder was collected by filtration, washed with water and then ethanol, and dried to obtain 75 mg of the title compound.

$^1$H-NMR (DMSO-d$_6$); δ 1.60-1.68 (1H, m), 1.99-2.07 (1H, m), 3.08-3.69 (5H, m), 4.03-4.13 (2H, m), 5.06 (1H, m), 5.46 (2H, s), 6.74 (1H, d, J=8 Hz), 7.17 (1H, d, J=12 Hz), 8.01 (1H, d, J=13 Hz), 8.54 (1H, s)

Example 7

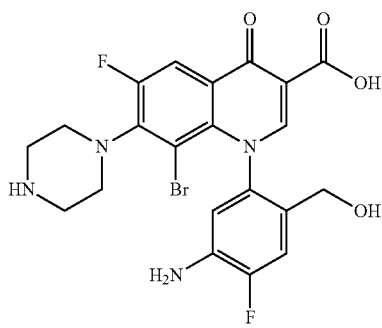

1-[5-Amino-4-fluoro-2-(hydroxymethyl)phenyl]-8-bromo-6-fluoro-4-oxo-7-(piperazin-1-yl)-1,4-dihydroquinoline-3-carboxylic acid 250 mg of ethyl 1-(2-acetoxymethyl-5-amino-4-fluorophenyl)-8-bromo-6,7-difluoro-4-oxo-1,4-dihydroquinoline-3-carboxylate and 130 mg of piperazine were suspended in 4 mL of acetonitrile and 350 mg of 1,1,3,3-tetramethylguanidine was added. The mixture was stirred at 50° C. for 3 days. 50 mL of chloroform was added to the reaction solution and the mixture was washed with a saturated aqueous solution of sodium hydrogen carbonate. The organic layer was dried over anhydrous magnesium sulfate and evaporated under reduced pressure. The obtained oily substance was dissolved in 30 mL of chloroform and 100 mg of triethylamine and 300 mg of di-t-butyl dicarbonate. The mixture was stirred at room temperature for 2 hours. The reaction solution was washed with a 10% aqueous solution of citric acid, brine, and then a saturated aqueous solution of sodium hydrogen carbonate and then dried over anhydrous magnesium sulfate. The organic layer was evaporated under reduced pressure and the resulting residue was separated by a silica gel column (0 to 1% methanol/chloroform).

The obtained compound was dissolved in 2 mL of methanol and 3 mL of 4 mol/L hydrogen chloride/1,4-dioxane was added. The mixture was stirred at room temperature for 1 hour. The solvent was evaporated under reduced pressure to obtain a crude hydrochloride salt. This hydrochloride salt was suspended in 2 mL of ethanol and 2 mL of a 1 mol/L aqueous solution of sodium hydroxide was added. The mixture was stirred at 50° C. for 15 minutes. After cooling, 0.33 mL of 6 M hydrochloric acid was added to neutralize the mixture and the mixture was evaporated under reduced pressure. The resulting residue was dissolved in 20% methanol/chloroform, dried over anhydrous magnesium sulfate, and then evaporated under reduced pressure. The residue was crystallized with ethanol to obtain 5 mg of the title compound.

$^1$H-NMR (DMSO-d$_6$) δ 2.90-3.40 (8H, br), 3.99 (1H, d, J=13 Hz), 4.04 (1H, d, J=13 Hz), 5.52 (2H, br), 6.79 (1H, d, J=8 Hz), 7.16 (1H, d, J=12 Hz), 8.20 (1H, d, J=12 Hz), 8.58 (1H, s)

Example 8

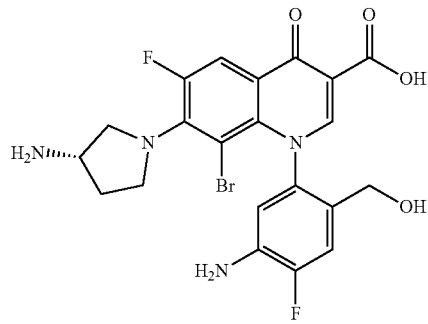 [SMILES: Nc1cc(-n2cc(C(=O)O)c(=O)c3cc(F)c(N4CC[C@H](N)C4)c(Br)c32)c(CO)cc1F]

(S)-1-[5-Amino-4-fluoro-2-(hydroxymethyl)phenyl]-7-(3-aminopyrrolidin-1-yl)-8-bromo-6-fluoro-4-oxo-1,4-dihydroquinoline-3-carboxylic acid 260 mg of ethyl 1-(2-acetoxymethyl-5-amino-4-fluorophenyl)-8-bromo-6,7-difluoro-4-oxo-1,4-dihydroquinoline- 3-carboxylate and 300 mg of (S)-3-aminopyrrolidine were suspended in 4 mL of acetonitrile and the suspension was stirred at 40° C. overnight. 50 mL of chloroform was added to the reaction solution and the mixture was washed with a saturated aqueous solution of sodium hydrogen carbonate. The organic layer was dried over anhydrous magnesium sulfate and evaporated under reduced pressure. The resulting residue was crystallized with ethyl acetate to obtain 130 mg of ethyl (S)-1-(2-acetoxymethyl-5-amino-4-fluorophenyl)-7-(3-aminopyrrolidin-1-yl)-8-bromo-6-fluoro-4-oxo-1,4-dihydroquinoline-3-carboxylate. 130 mg of the obtained compound was suspended in 2 mL of ethanol and 2 mL of a 1 mol/L aqueous solution of sodium hydroxide was added. The mixture was stirred at 60° C. for 20 minutes. After cooling, 0.33 mL of 6 mol/L hydrochloric acid was added to neutralize the mixture. The reaction solution was concentrated under reduced pressure and precipitated powder was collected by filtration, washed with water and then acetonitrile, and dried to obtain 93 mg of the title compound.

$^1$H-NMR (DMSO-$d_6$) δ 1.60-1.68 (1H, m), 1.99-2.07 (1H, m), 3.08-3.69 (5H, m), 4.03-4.13 (2H, m), 5.07 (1H, brs), 5.46 (1H, s), 5.47 (1H, s), 6.74 (1H, d, J=8 Hz), 7.16 (1H, d, J=12 Hz), 8.00 (1H, d, J=13 Hz), 8.53 (0.5H, s), 8.53 (0.5H, s)

Reference Example 5

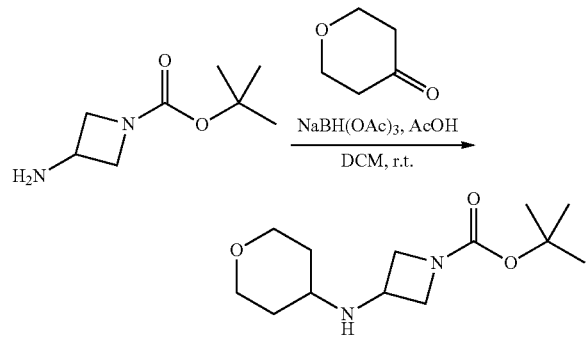

tert-Butyl 3-(tetrahydropyran-4-yl)aminoazetidine-1-carboxylate 50 mL of dichloromethane and 0.50 g of tetrahydropyran-4-one were added to 0.86 g of tert-butyl 3-aminoazetidine-1-carboxylate and the mixture was stirred at room temperature for 2 hours. 1.5 g of sodium triacetoxyhydroborate and 1 mL of acetic acid were added to the reaction solution under ice cooling and the mixture was stirred at room temperature overnight. The reaction solution was filtered and the filtrate was washed three times with 50 mL of saturated sodium bicarbonate water and once with 50 mL of saturated brine. The solution was dried over sodium sulfate and then the solvent was evaporated under reduced pressure to obtain 1.3 g of the title compound.

$^1$H-NMR (CDCl$_3$): δ 1.38-1.42 (11H, m), 1.45-1.62 (1H, m), 1.71-1.74 (2H, m), 2.65-2.71 (1H, m), 3.40 (2H, dt, J=2.2 Hz, 11.8 Hz), 3.60-3.71 (3H, m), 3.95-3.97 (2H, m), 4.12 (2H, t, J=8.1 Hz).

Example 9

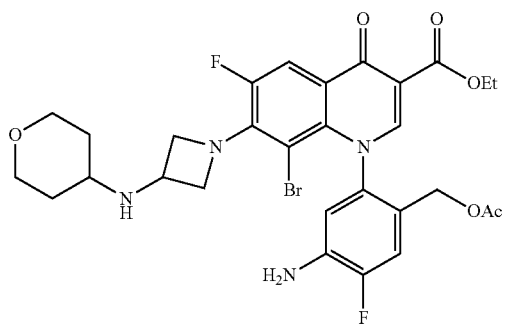 [SMILES: CCOC(=O)c1cn(-c2cc(N)c(F)cc2COC(C)=O)c2c(Br)c(N3CC(NC4CCOCC4)C3)c(F)cc2c1=O]

Ethyl 1-(2-acetoxymethyl-5-amino-4-fluorophenyl)-8-bromo-6-fluoro-4-oxo-7-[3-(tetrahydropyran-4-yl) aminoazetidin-1-yl]-1,4-dihydroquinoline-3-carboxylate 1.0 mL of ethyl acetate and 1.0 mL of 4 mol/L hydrogen chloride/ethyl acetate were added to 0.15 g of tert-butyl 3-(tetrahydropyran-4-yl)aminoazetidine-1-carboxylate and the mixture was stirred at room temperature for 1 hour. The reaction solution was concentrated to obtain 3-(tetrahydropyran-4-yl)aminoazetidine hydrochloride.

1.0 mL of acetonitrile, 0.15 g of ethyl 1-(2-acetoxymethyl-5-amino-4-fluorophenyl)-8-bromo-6,7-difluoro-4-oxo-1,4-dihydroquinoline-3-carboxylate, and 0.13 mL of 1,1,3,3-tetramethylguanidine were added to the obtained compound and the mixture was stirred at room temperature overnight. The reaction solution was concentrated and suspended in 0.50 mL of acetonitrile. The resulting precipitates were collected by filtration to obtain 0.13 g of the title compound.

$^1$H-NMR (DMSO-$d_6$): δ 1.18-1.24 (5H, m), 1.60-1.67 (2H, m), 1.89 (3H, s), 2.48-2.50 (1H, m), 3.24 (2H, dt, J=2.2 Hz, 6.5 Hz), 3.60-3.67 (1H, m), 3.76-3.82 (2H, m), 3.90-4.20 (2H, m), 4.21 (2H, q, J=7.1 Hz), 4.55-4.66 (2H, m), 4.71 (1H, d, J=12.3 Hz), 4.79 (1H, d, J=12.3 Hz), 5.65 (2H, brs), 6.71 (1H, d, J=8.1 Hz), 7.26 (1H, d, J=11.8 Hz), 7.79 (1H, d, J=14.2 Hz), 8.22 (1H, s).

Example 10

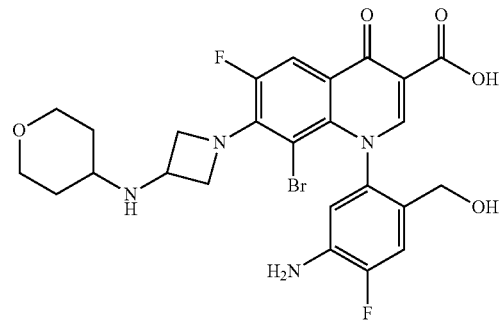

1-[5-Amino-4-fluoro-2-(hydroxymethyl)phenyl]-8-bromo-6-fluoro-4-oxo-7-[3-(tetrahydropyran-4-yl)aminoazetidin-1-yl]-1,4-dihydroquinoline-3-carboxylic acid 1.0 mL of ethanol, 0.20 mL of a 3 mol/L aqueous solution of sodium hydroxide, and 0.80 mL of water were added to 0.13 g of ethyl 1-(2-acetoxymethyl-5-amino-4-fluoro)phenyl-8-bromo-6-fluoro-4-oxo-7-[3-(tetrahydropyran-4-yl)aminoazetidin-1-yl]-1,4-dihydroquinoline-3-carboxylate and the mixture was stirred at room temperature for 4 days. A 5% aqueous solution of citric acid was added to make the solution acidic (pH 5 to 6). The resulting precipitates were collected by filtration to obtain 0.11 g of the title compound.

$^1$H-NMR (DMSO-$d_6$): δ 1.24 (2H, dq, J=4.35 Hz, 11.3 Hz), 1.65 (2H, d, J=12.8 Hz), 2.55-2.59 (1H, m), 3.27 (2H, dt, J=2.3 Hz, 11.8 Hz), 3.68 (1H, q, J=6.5 Hz), 3.77-3.81 (2H, m), 4.15-4.01 (4H, m), 4.63-4.68 (2H, m), 5.06 (1H, t, J=5.4 Hz), 5.46 (2H, brs), 6.74 (1H, d, J=8.1 Hz), 7.17 (1H, d, J=12.0 Hz), 7.92 (1H, d, J=14.0 Hz), 8.45 (1H, s).

Example 11

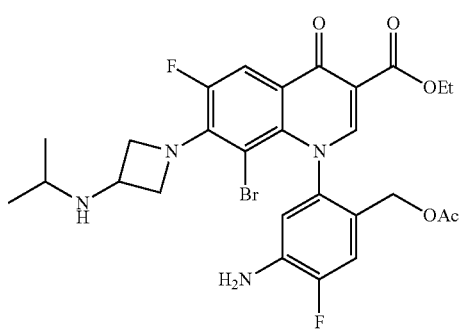

Ethyl 1-(2-acetoxymethyl-5-amino-4-fluorophenyl)-8-bromo-6-fluoro-4-oxo-7-[3-(propan-2-yl)aminoazetidin-1-yl]-1,4-dihydroquinoline-3-carboxylate 1.0 mL of acetonitrile, 0.11 g of 3-(propan-2-yl)aminoazetidine hydrochloride, and 0.25 mL of triethylamine were added to 0.21 g of ethyl 1-(2-acetoxymethyl-5-amino-4-fluorophenyl)-8-bromo-6,7-difluoro-4-oxo-1,4-dihydroquinoline-3-carboxylate and the mixture was stirred at room temperature overnight. The resulting precipitates were collected by filtration to obtain 0.14 g of the title compound.

$^1$H-NMR (DMSO-$d_6$): δ 0.93 (6H, d, J=6.2 Hz), 1.24 (3H, t, J=7.1 Hz), 1.89 (3H, s), 2.69-2.75 (1H, m), 3.55-3.62 (1H, m), 4.05-3.89 (4H, m), 4.20 (2H, q, J=7.1 Hz), 4.54-4.66 (2H, m), 4.70 (1H, d, J=12.4 Hz), 4.79 (1H, d, J=12.4 Hz), 5.65 (2H, brs), 6.72 (1H, d, J=8.2 Hz), 7.26 (1H, d, J=11.8 Hz), 7.79 (1H, d, J=14.3 Hz), 8.22 (1H, s).

Example 12

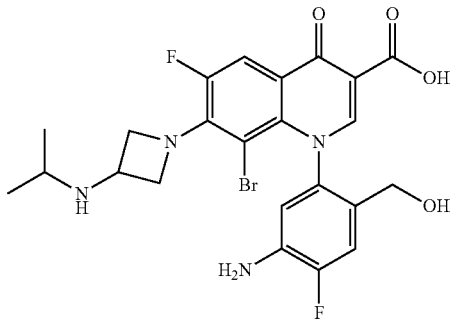 [SMILES: CC(C)NC1CN(c2c(F)cc3c(=O)c(C(=O)O)cn(-c4cc(N)c(F)cc4CO)c3c2Br)C1]

1-[5-Amino-4-fluoro-2-(hydroxymethyl)phenyl]-8-bromo-6-fluoro-4-oxo-7-[3-(propan-2-yl)aminoazetidin-1-yl]-1,4-dihydroquinoline-3-carboxylic acid 1.0 mL of ethanol, 0.20 mL of a 10 mol/L aqueous solution of sodium hydroxide, and 0.80 mL of water were added to 0.14 g of ethyl 1-(2-acetoxymethyl-5-amino-4-fluorophenyl)-8-bromo-6-fluoro-4-oxo-7-[3-(propan-2-yl)aminoazetidin-1-yl]-1,4-dihydroquinoline-3-carboxylate and the mixture was stirred at 50° C. for 1 hour. A 5% citric acid aqueous solution was added to the mixture to make the solution acidic (pH 5 to 6). The resulting precipitates were collected by filtration to obtain 0.11 g of the title compound.

$^1$H-NMR (DMSO-$d_6$): δ 0.96 (6H, d, J=6.3 Hz), 2.74-2.82 (1H, m), 3.63-3.70 (1H, m), 4.03-4.15 (4H, m), 4.65-4.69 (2H, m), 5.06 (1H, t, J=5.3 Hz), 5.47 (2H, brs), 6.75 (1H, d, J=8.1 Hz), 7.17 (1H, d, J=12.0 Hz), 7.93 (1H, d, J=14.0 Hz), 8.45 (1H, s).

Example 13

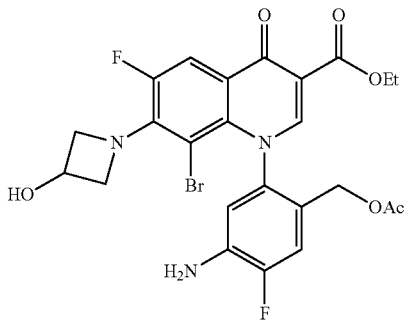 [SMILES: CCOC(=O)c1cn(-c2cc(N)c(F)cc2COC(C)=O)c2c(Br)c(N3CC(O)C3)c(F)cc2c1=O]

Ethyl 1-(2-acetoxymethyl-5-amino-4-fluorophenyl)-8-bromo-6-fluoro-7-(3-hydroxyazetidin-1-yl)-4-oxo-1,4-dihydroquinoline-3-carboxylate 1.0 mL of acetonitrile, 52 mg of 3-hydroxyazetidine tartrate, 98 μL of triethylamine were added to 50 mg of ethyl 1-(2-acetoxymethyl-5-amino-4-fluorophenyl)-8-bromo-6,7-difluoro-4-oxo-1,4-dihydroquinoline-3-carboxylate and the mixture was stirred at room temperature for 15 hours. 88 μL of 1,1,3,3-tetramethylguanidine was added to the reaction solution and the mixture was stirred at room temperature for 4 hours. The resulting precipitates were collected by filtration to obtain 37 mg of the title compound.

$^1$H-NMR (CDCl$_3$): δ 1.24 (3H, t, J=7.1 Hz), 3.98-4.03 (1H, m), 4.05-4.10 (1H, m), 4.17-4.23 (2H, m), 4.38-4.45 (1H, m), 4.54-4.60 (1H, m), 4.61-4.68 (1H, m), 4.71 (1H, d, J=12.4 Hz), 4.78 (1H, d, J=12.4 Hz), 5.66 (2H, brs), 6.72 (1H, d, J=8.13 Hz), 7.26 (1H, d, J=11.7 Hz), 7.78 (1H, d, J=14.2 Hz), 8.23 (1H, s).

Example 14

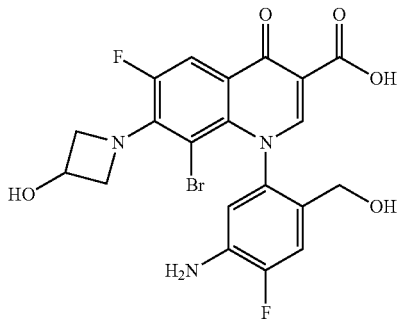

1-[5-Amino-4-fluoro-2-(hydroxymethyl)phenyl]-8-bromo-6-fluoro-7-(3-hydroxyazetidin-1-yl)-4-oxo-1,4-dihydroquinoline-3-carboxylic acid 3.0 mL of ethanol and 0.17 mL of a 2 mol/L lithium hydroxide aqueous solution were added to 37 mg of ethyl 1-(2-acetoxymethyl-5-amino-4-fluorophenyl)-8-bromo-6-fluoro-7-(3-hydroxyazetidin-1-yl)-4-oxo-1,4-dihydroquinoline-3-carboxylate and the mixture was stirred at 40° C. for 1 hour. Ethanol was evaporated under reduced pressure and then 1 mol/L hydrochloric acid was added to neutralize the solution. The resulting precipitates were collected by filtration. 1.0 mL of ethanol was added to the obtained solid and the mixture was heated to reflux for 1 hour. The resulting precipitates were collected by filtration to obtain 14 mg of the title compound.

$^1$H-NMR (DMSO-d$_6$): δ 4.05-4.17 (4H, m), 4.40-4.47 (1H, m), 4.63-4.71 (2H, m), 5.07 (1H, t, J=5.3 Hz), 5.47 (2H, brs), 5.71 (1H, d, J=5.6 Hz), 6.74 (1H, d, J=8.13 Hz), 7.17 (1H, d, J=12.0 Hz), 7.92 (1H, d, J=13.9 Hz), 8.47 (1H, s).

Example 15

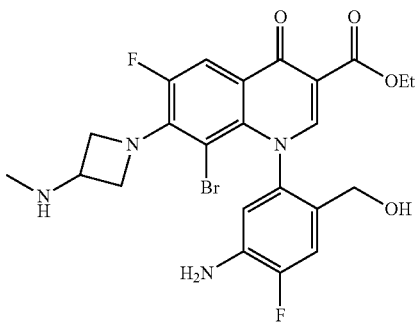 [SMILES: CCOC(=O)c1cn(-c2cc(N)c(F)cc2CO)c2c(Br)c(N3CC(NC)C3)c(F)cc2c1=O]

Ethyl 1-[5-amino-4-fluoro-2-(hydroxymethyl)phenyl]-8-bromo-6-fluoro-7-(3-methylaminoazetidin-1-yl)-4-oxo-1,4-dihydroquinoline-3-carboxylate 1.5 mL of dimethylsulfoxide, 0.13 g of 3-methylaminoazetidine hydrochloride, 0.30 mL of 1,1,3,3-tetramethylguanidine were added to 0.15 g of ethyl 1-(2-acetoxymethyl-5-amino-4-fluorophenyl)-8-bromo-6,7-difluoro-4-oxo-1,4-dihydroquinoline-3-carboxylate and the mixture was stirred at 40° C. for 3 days. 3.0 mL of acetonitrile and 50 mL of water were added to the reaction solution and extracted with 20 mL of chloroform three times. The extract was dried over anhydrous sodium sulfate and then the solvent was evaporated under reduced pressure. 5.0 mL of acetonitrile was added to the obtained crystalline residue. The resulting precipitates were collected by filtration to obtain 0.11 g of the title compound.

$^1$H-NMR (DMSO-d$_6$): δ 1.23 (3H, t, J=7.09 Hz), 2.19 (3H, s), 3.38-3.41 (1H, m), 3.92-3.97 (1H, m), 3.97-4.03 (1H, m), 4.09-4.22 (4H, m), 4.46-4.52 (1H, m), 4.52-4.58 (1H, m), 5.09-5.12 (1H, m), 5.40 (2H, brs), 6.64 (1H, d, J=8.1 Hz), 7.16 (1H, d, J=12.0 Hz), 7.78 (1H, d, J=14.3 Hz), 8.29 (1H, s).

Example 16

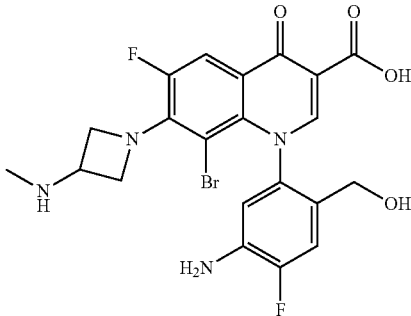 [SMILES: CNC1CN(c2c(F)cc3c(=O)c(C(=O)O)cn(-c4cc(N)c(F)cc4CO)c3c2Br)C1]

1-[5-Amino-4-fluoro-2-(hydroxymethyl)phenyl]-8-bromo-6-fluoro-7-(3-methylaminoazetidin-1-yl)-4-oxo-1,4-dihydroquinoline-3-carboxylic acid 2.0 mL of ethanol and 0.51 mL of a 2 mol/L lithium hydroxide aqueous solution were added to 0.11 g of ethyl 1-[5-amino-4-fluoro-2-(hydroxymethyl)phenyl]-8-bromo-6-fluoro-7-(3-methylaminoazetidin-1-yl)-4-oxo-1,4-dihydroquinoline-3-carboxylate and the mixture was stirred at 50° C. for 2 hours. 1 mol/L hydrochloric acid was added to neutralize the solution. The resulting precipitates were collected by filtration to obtain 42 mg of the title compound.

$^1$H-NMR (DMSO-d$_6$): δ 2.55 (3H, s), 3.93-4.00 (1H, m), 4.00-4.06 (1H, m), 4.12 (1H, dd, J=13.0, 4.5 Hz), 4.43-4.49 (1H, m), 4.50-4.56 (1H, m), 4.63-4.74 (2H, m), 5.02-5.06 (1H, m), 5.51 (2H, brs), 7.17 (1H, d, J=11.9 Hz), 7.99 (1H, d, J=13.9 Hz), 8.48 (1H, s).

Example 17

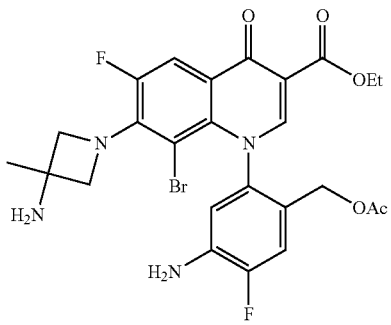 [SMILES: CCOC(=O)c1cn(-c2cc(N)c(F)cc2COC(C)=O)c2c(Br)c(N3CC(C)(N)C3)c(F)cc2c1=O]

Ethyl 1-(2-acetoxymethyl-5-amino-4-fluorophenyl)-7-(3-amino-3-methylazetidin-1-yl)-8-bromo-6-fluoro-4-oxo-1,4-dihydroquinoline-3-carboxylate 100 mg of ethyl 1-(2-acetoxymethyl-5-amino-4-fluorophenyl)-8-bromo-6,7-difluoro-4-oxo-1,4-dihydroquinoline-3-carboxylate was suspended to 1.0 mL of acetonitrile and 0.24 mL of triethylamine and 77 mg of 3-amino-3-methylazetidine diacetate were added at room temperature. The mixture was stirred at room temperature for 5 days. The resulting precipitates were collected by filtration with acetonitrile to obtain 99 mg of the title compound.

$^1$H-NMR (DMSO-$d_6$): δ 1.23 (3H, t, J=7.1 Hz), 1.34 (3H, s), 1.89 (3H, s), 4.01 (2H, dd, J=8.3, 3.0 Hz), 4.19-4.27 (4H, m), 4.70 (1H, d, J=12.4 Hz), 4.78 (1H, d, J=12.4 Hz), 5.65 (2H, s), 6.71 (1H, d, J=8.1 Hz), 7.26 (1H, d, J=11.8 Hz), 7.78 (1H, d, J=14.3 Hz), 8.22 (1H, s).

Example 18

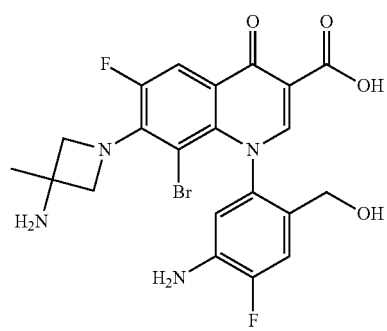 [SMILES: CC1(N)CN(c2c(F)cc3c(=O)c(C(=O)O)cn(-c4cc(N)c(F)cc4CO)c3c2Br)C1]

1-[5-Amino-4-fluoro-2-(hydroxymethyl)phenyl]-7-(3-amino-3-methylazetidin-1-yl)-8-bromo-6-fluoro-4-oxo-1,4-dihydroquinoline-3-carboxylic acid 54 mg of ethyl 1-(2-acetoxymethyl-5-amino-4-fluorophenyl)-7-(3-amino-3-methylazetidin-1-yl)-8-bromo-6-fluoro-4-oxo-1,4-dihydroquinoline-3-carboxylate was suspended in 0.5 mL of ethanol and 0.19 mL of a 3 mol/L aqueous solution of sodium hydroxide was added at room temperature. The mixture was stirred at room temperature for 1 day. Ethanol was evaporated under reduced pressure and then the residue was neutralized with 1 mol/L hydrochloric acid. The resulting precipitates were collected by filtration with water to obtain 39 mg of the title compound.

$^1$H-NMR (DMSO-$d_6$): δ 1.34 (3H, s), 4.05 (1H, dd, J=13.0, 6.0 Hz), 4.11-4.15 (3H, m), 4.29 (2H, dd, J=9.1, 3.2 Hz), 5.04 (1H, t, J=6.0 Hz), 5.47 (2H, s), 6.75 (1H, d, J=8.1 Hz), 7.16 (1H, d, J=12.0 Hz), 7.92 (1H, d, J=14.0 Hz)

Example 19

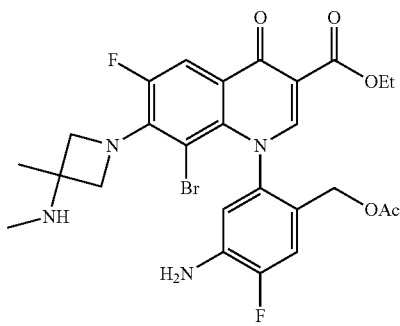 [SMILES: CCOC(=O)c1cn(-c2cc(N)c(F)cc2COC(C)=O)c2c(Br)c(N3CC(C)(NC)C3)c(F)cc2c1=O]

Ethyl 1-(2-acetoxymethyl-5-amino-4-fluorophenyl)-8-bromo-6-fluoro-7-(3-methyl-3-methylaminoazetidin-1-yl)-4-oxo-1,4-dihydroquinoline-3-carboxylate 100 mg of ethyl 1-(2-acetoxymethyl-5-amino-4-fluorophenyl)-8-bromo-6,7-difluoro-4-oxo-1,4-dihydroquinoline-3-carboxylate was suspended in 1.0 mL of acetonitrile and 0.24 mL of triethylamine and 56 mg of 3-methyl-3-methylaminoazetidine dihydrochloride were added at room temperature. The mixture was stirred at room temperature for 4 days. The resulting precipitates were collected by filtration with acetonitrile to obtain 85 mg of the title compound.

$^1$H-NMR (DMSO-$d_6$): δ 1.14 (3H, t, J=7.2 Hz), 1.34 (3H, s), 1.90 (3H, s), 2.25 (3H, s), 4.11-4.22 (6H, m), 4.69 (1H, d, J=12.4 Hz), 4.79 (1H, d, J=12.4 Hz), 5.66 (2H, s), 6.73 (1H, d, J=8.2 Hz), 7.26 (1H, d, J=11.8 Hz), 7.79 (1H, d, J=14.3 Hz), 8.23 (1H, s).

Example 20

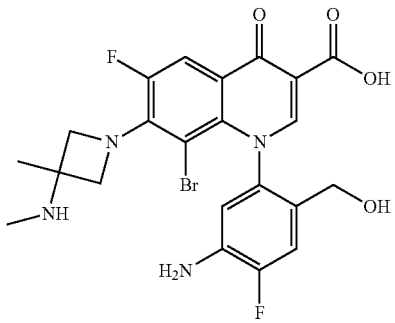 [SMILES: CNC1(C)CN(c2c(F)cc3c(=O)c(C(=O)O)cn(-c4cc(N)c(F)cc4CO)c3c2Br)C1]

1-[5-Amino-4-fluoro-2-(hydroxymethyl)phenyl]-8-bromo-6-fluoro-7-(3-methyl-3-methylaminoazetidin-1-yl)-4-oxo-1,4-dihydroquinoline-3-carboxylic acid 85 mg of ethyl 1-(2-acetoxymethyl-5-amino-4-fluoro)phenyl-8-bromo-6-fluoro-7-(3-methyl-3-methylaminoazetidin-1-yl)-4-oxo-1,4-dihydroquinoline-3-carboxylate was suspended to 1.0 mL of ethanol and 0.37 mL of a 3 mol/L aqueous solution of sodium hydroxide was added at room temperature. The mixture was stirred at room temperature for 2 days. Ethanol was evaporated under reduced pressure and then the residue was neutralized with 1 mol/L hydrochloric acid. The resulting precipitates were collected by filtration with water to obtain 69 mg of the title compound.

$^1$H-NMR (DMSO-$d_6$): δ 1.33 (3H, s), 2.24 (3H, brs), 4.07 (1H, dd, J=13.0, 5.5 Hz), 4.12 (1H, dd, J=13.0, 5.5 Hz), 4.22 (4H, brs), 5.05 (1H, t, J=5.5 Hz), 5.48 (2H, s), 6.75 (1H, d, J=8.1 Hz), 7.16 (1H, d, J=11.9 Hz), 7.93 (1H, d, J=14.0 Hz), 8.46 (1H, s).

Example 21

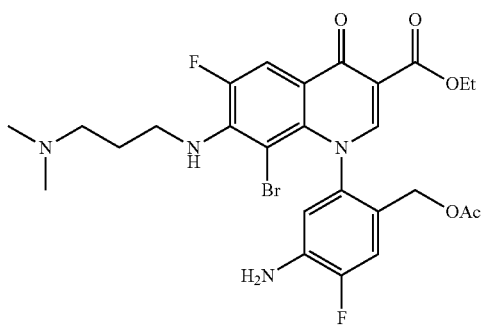

Ethyl 1-(2-acetoxymethyl-5-amino-4-fluorophenyl)-8-bromo-7-[3-(dimethylamino)propylamino]-6-fluoro-4-oxo-1,4-dihydroquinoline-3-carboxylate 100 mg of ethyl 1-(2-acetoxymethyl-5-amino-4-fluorophenyl)-8-bromo-6,7-difluoro-4-oxo-1,4-dihydroquinoline-3-carboxylate was suspended in 1.0 mL of acetonitrile and 0.24 mL of triethylamine and 36 μL of dimethylaminopropylamine were added at room temperature. The mixture was stirred at 50° C. for 4 hours. The reaction solution was diluted in 100 mL of ethyl acetate and then washed with 50 mL of water and then 50 mL of saturated brine. The obtained solution was dried over anhydrous sodium sulfate. The solvent was evaporated under reduced pressure to obtain 90 mg of the title compound.

$^1$H-NMR (DMSO-$d_6$): δ 1.24 (3H, t, J=7.1 Hz), 1.64-1.69 (2H, m), 1.85 (3H, s), 2.12 (6H, s), 2.30 (1H, t, J=6.5 Hz), 3.51-3.55 (2H, m), 4.20 (2H, q, J=7.1 Hz), 4.67 (1H, d, J=12.4 Hz), 4.73 (1H, d, J=12.4 Hz), 5.68 (2H, s), 6.61 (1H, brs), 6.74 (1H, d, J=8.1 Hz), 7.27 (1H, d, J=11.8 Hz), 7.87 (1H, d, J=14.2 Hz), 8.20 (1H, s).

Example 22

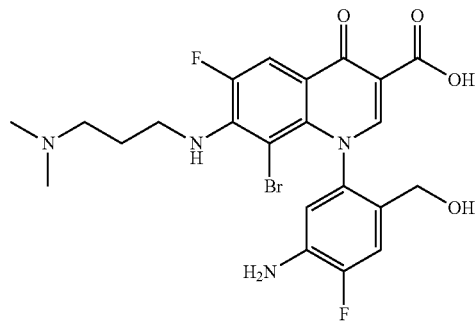 [SMILES: CN(C)CCCNc1c(F)cc2c(=O)c(C(=O)O)cn(-c3cc(N)c(F)cc3CO)c2c1Br]

1-[5-amino-4-fluoro-2-(hydroxymethyl)phenyl]-8-bromo-7-[3-(dimethylamino)propylamino]-6-fluoro-4-oxo-1,4-dihydroquinoline-3-carboxylic acid 90 mg of ethyl 1-(2-acetoxymethyl-5-amino-4-fluorophenyl)-8-bromo-7-[3-(dimethylamino)propylamino]-6-fluoro-4-oxo-1,4-dihydroquinoline-3-carboxylate was suspended in 1.0 mL of ethanol and 0.30 mL of a 3 mol/L aqueous solution of sodium hydroxide was added. The mixture was heated to reflux for 5 hours. Ethanol was evaporated under reduced pressure and then the residue was neutralized with hydrochloric acid. The obtained precipitates were collected by filtration with water to obtain 29 mg of the title compound.

$^1$H-NMR (DMSO-$d_6$): δ 1.84-1.90 (2H, m), 2.72 (6H, s), 3.02 (2H, brs), 3.43-3.45 (2H, m), 5.28 (2H, s), 5.73 (2H, s), 6.22 (1H, t, J=5.9 Hz), 6.83 (1H, d, J=7.7 Hz), 7.35 (1H, d, J=10.8 Hz), 7.70 (1H, d, J=13.3 Hz), 8.55 (1H, s).

Example 23

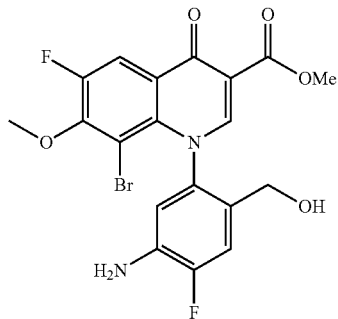 [SMILES: COC(=O)c1cn(-c2cc(N)c(F)cc2CO)c2c(Br)c(OC)c(F)cc2c1=O]

Methyl 1-[5-amino-4-fluoro-2-(hydroxymethyl)phenyl]-8-bromo-6-fluoro-7-methoxy-4-oxo-1,4-dihydroquinoline-3-carboxylate 0.10 mg of ethyl 1-(2-acetoxymethyl-5-amino-4-fluorophenyl)-8-bromo-6,7-difluoro-4-oxo-1,4-dihydroquinoline-3-carboxylate was suspended in 2.0 mL of methanol and 55 mg of potassium carbonate was added. The mixture was stirred at room temperature overnight. The resulting precipitates were collected by filtration and then washed with 2.0 mL of water to obtain 56 mg of the title compound.

¹H-NMR (DMSO-d₆): δ 3.74 (3H, s), 3.92 (3H, d, J=1.8 Hz), 4.14-4.05 (2H, m), 5.06 (1H, t, J=5.8 Hz), 5.44 (2H, brs), 6.75 (1H, d, J=8.2 Hz), 7.16 (1H, d, J=11.9 Hz), 8.13 (1H, d, J=11.2 Hz), 8.36 (1H, s).

Example 24

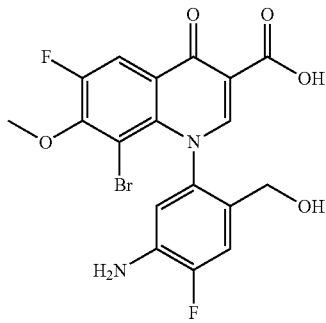 [SMILES: COc1c(F)cc2c(=O)c(C(=O)O)cn(-c3cc(N)c(F)cc3CO)c2c1Br]

1-[5-Amino-4-fluoro-2-(hydroxymethyl)phenyl]-8-bromo-6-fluoro-7-methoxy-4-oxo-1,4-dihydroquinoline-3-carboxylic acid 1.0 mL of ethanol, 0.10 mL of a 10 mol/L aqueous solution of sodium hydroxide and 0.90 mL of water were added to 56 mg of methyl 1-[5-amino-4-fluoro-2-(hydroxymethyl)phenyl]-8-bromo-6-fluoro-7-methoxy-4-oxo-1,4-dihydroquinoline-3-carboxylate and the mixture was stirred at room temperature overnight. A 5% aqueous solution of citric acid was added to make the solution acidic (pH 5 to 6). The resulting precipitates were collected by filtration to obtain 44 mg of the title compound.

¹H-NMR (DMSO-d₆): δ 3.98 (3H, d, J=2.1 Hz), 4.09-4.12 (2H, m), 5.03 (1H, t, J=5.2 Hz), 5.52 (2H, brs), 6.82 (1H, d, J=8.1 Hz), 7.17 (1H, d, J=12.0 Hz), 8.30 (1H, d, J=11.0 Hz), 8.54 (1H, s).

Reference Example 6

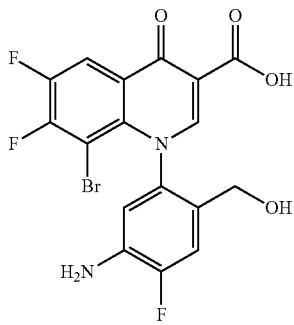 [SMILES: Nc1cc(-n2cc(C(=O)O)c(=O)c3cc(F)c(F)c(Br)c32)c(CO)cc1F]

1-[5-Amino-4-fluoro-2-(hydroxymethyl)phenyl]-8-bromo-6,7-difluoro-4-oxo-1,4-dihydroquinoline-3-carboxylic acid 1.0 mL of acetic acid and 2.0 mL of 6 mol/L hydrochloric acid were added to 0.14 g of ethyl 1-(2-acetoxymethyl-5-amino-4-fluorophenyl)-8-bromo-6,7-difluoro-4-oxo-1,4-dihydroquinoline-3-carboxylate and the mixture was stirred at 80° C. for 2 hours. The reaction solution was poured into 10 mL of water and a 10% aqueous solution of sodium hydroxide was added to adjust pH to approximately 6. The resulting precipitates were collected by filtration. The filtrate was extracted with 30 mL of chloroform twice. The precipitates obtained earlier were dissolved in the extract and chloroform was evaporated under reduced pressure. The residue was subjected to silica gel column chromatography (methanol: 1% acetic acid/chloroform=0 to 6% gradient) to obtain 36 mg of the title compound.

¹H-NMR (DMSO-d₆): δ 4.03 (1H, d, J=12.4 Hz), 4.10 (1H, d, J=12.4 Hz), 5.03 (1H, brm), 5.65 (2H, brs), 6.86 (1H, d, J=7.8 Hz), 7.17 (1H, d, J=11.9 Hz), 8.44 (1H, t, J=9.2 Hz), 8.55 (1H, s).

Example 25

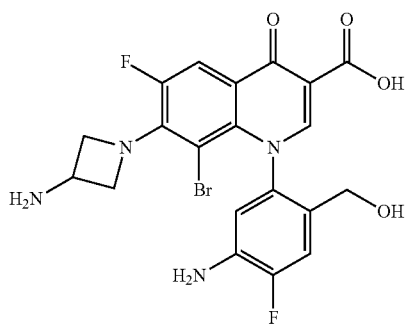 [SMILES: Nc1cc(-n2cc(C(=O)O)c(=O)c3cc(F)c(N4CC(N)C4)c(Br)c32)c(CO)cc1F]

7-(3-Aminoazetidin-1-yl)-1-[5-amino-4-fluoro-2-(hydroxymethyl)phenyl]-8-bromo-6-fluoro-4-oxo-1,4-dihydroquinoline-3-carboxylic acid 0.18 mL of dimethylsulfoxide, 11 mg of 3-aminoazetidine hydrochloride, 18 mg of lithium chloride, and 36 μL of N-methylpyrrolidine were added to 20 mg of 1-[5-amino-4-fluoro-2-(hydroxymethyl)phenyl]-8-bromo-6,7-difluoro-4-oxo-1,4-dihydroquinoline-3-carboxylic acid and the mixture was stirred at 40° C. for 20 minutes. 1.5 mL of diethyl ether was added to the reaction solution. The mixture was stirred and then the supernatant was removed by decantation. This procedure was repeated five times. 0.20 mL of water was added to the residue and then a 10% aqueous solution of citric acid was added to make the solution acidic (pH 6). The resulting precipitates were collected by filtration to obtain 14 mg of the title compound.

¹H-NMR (DMSO-d₆): δ 3.94-4.21 (4H, m), 4.52-4.75 (2H, m), 5.05 (1H, brm), 5.47 (2H, brs), 6.75 (1H, d, J=8.2 Hz), 7.16 (1H, d, J=11.0 Hz), 7.93 (1H, d, J=14.0 Hz), 8.44 (1H, s).

Reference Example 7

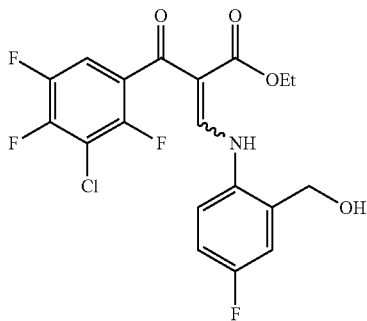 [SMILES: CCOC(=O)C(=CNc1ccc(F)cc1CO)C(=O)c1cc(F)c(F)c(Cl)c1F]

Ethyl 2-(3-chloro-2,4,5-trifluorobenzoyl)-3-[[4-fluoro-2-(hydroxymethyl)phenyl]amino]acrylate 18.0 g of ethyl orthoformate and 21.0 g of acetic anhydride were added to 21.0 g of ethyl 3-(3-chloro-2,4,5-trifluorophenyl)-3-oxopropionate and the mixture was heated to reflux for 4 hours. The reaction solution was evaporated under reduced pressure and the resulting residue was dissolve in 50 mL of dichloromethane to obtain a crude ethoxyacrylate solution. 11.6 g of 2-amino-5-fluorobenzyl alcohol was suspended into 150 mL of dichloromethane and the ethoxyacrylate solution obtained earlier was added dropwise. The mixture was stirred at room temperature overnight. The reaction solution was washed with water and then dried over anhydrous magnesium sulfate. The solvent was evaporated under reduced pressure and the resulting residue was dispersed in n-hexane, collected by filtration, and dried to obtain 29.3 g of the title compound.

$^1$H-NMR (DMSO-$d_6$); δ 1.03 (3H, t, J=7 Hz), 4.01 (2H, q, J=7 Hz), 4.60 (2H, d, J=5 Hz), 5.81 (1H, t, J=5 Hz), 7.23-7.29 (2H, m), 7.59-7.68 (2H, m), 8.41 (0.3H, d, J=14 Hz), 8.50 (0.7H, d, J=14 Hz), 11.56 (0.3H, d, J=14 Hz), 12.73 (0.7H, d, J=14 Hz)

Reference Example 8

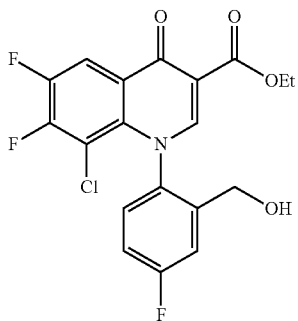 [SMILES: CCOC(=O)c1cn(-c2ccc(F)cc2CO)c2c(Cl)c(F)c(F)cc2c1=O]

Ethyl 8-chloro-6,7-difluoro-1-[4-fluoro-2-(hydroxymethyl)phenyl]-4-oxo-1,4-dihydroquinoline-3-carboxylate 29.3 g of ethyl 2-(3-chloro-2,4,5-trifluorobenzoyl)-3-[[4-fluoro-2-(hydroxymethyl)phenyl]amino]acrylate and 3.4 g of lithium chloride were dissolved in 150 mL of N,N-dimethylformamide and 11.5 g of 1,8-diazabicyclo[5.4.0]undec-7-ene was added. The mixture was stirred at room temperature overnight. The reaction solution was poured into 1 L of iced water and precipitated crystals were collected by filtration and dried. The crystals were dissolved in 1 L of chloroform and washed with water, then dried over anhydrous magnesium sulfate, and evaporated under reduced pressure. The resulting residue was dispersed in diisopropyl ether, collected by filtration, and dried to obtain 20.0 g of the title compound.

$^1$H-NMR (DMSO-$d_6$); δ 1.25 (3H, t, J=7 Hz), 4.21 (2H, q, J=7 Hz), 4.30 (2H, d, J=5 Hz), 5.41 (1H, t, J=5 Hz), 7.32 (1H, dt, J=8 Hz, 3 Hz), 7.41 (1H, dd, J=9 Hz, 3 Hz), 7.65 (1H, dd, J=9 Hz, 5 Hz), 8.23 (1H, dd, J=10 Hz, 9 Hz), 8.33 (1H, s)

Reference Example 9

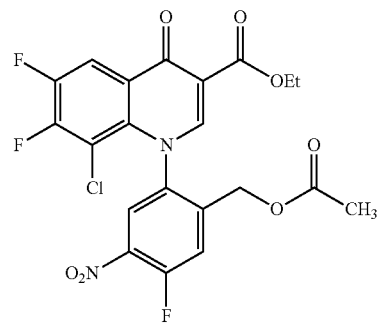

Ethyl 1-(2-acetoxymethyl-4-fluoro-5-nitrophenyl)-8-chloro-6,7-difluoro-4-oxo-1,4-dihydroquinolinp-3-carboxylate 20.0 g of ethyl 8-chloro-6,7-difluoro-1-[4-fluoro-2-(hydroxymethyl)phenyl]-4-oxo-1,4-dihydroquinoline-3-carboxylate was dissolved in 200 mL of concentrated sulfuric acid and 11.7 g of potassium nitrate was added. The mixture was stirred at 50° C. for 5 hours. The reaction solution was poured into 2 L of iced water and extracted with 2 L of ethyl acetate. The organic layer was dried over anhydrous magnesium sulfate and then evaporated under reduced pressure to obtain an oily substance. This was dissolved in 200 mL of acetic acid and the solution was stirred at 80° C. for 3 hours. After cooling, acetic acid was evaporated under reduced pressure and the residue was dissolved in chloroform. The solution was washed with water and then a saturated aqueous solution of sodium hydrogen carbonate. The organic layer was dried over anhydrous magnesium sulfate and then evaporated under reduced pressure. The obtained crystals were dispersed in ethyl acetate and collected by filtration. The obtained solid was suspended in 200 mL of dichloromethane and 0.3 mL of N,N-dimethylformamide and then 4 mL of oxalyl chloride were added. The mixture was stirred for 10 minutes. 30 mL of ethanol was added to this mixture. The reaction solution was washed with water and then a saturated aqueous solution of sodium hydrogen carbonate, then dried over anhydrous magnesium sulfate, and evaporated under reduced pressure. The resulting residue was dispersed in diisopropyl ether, collected by filtration, and dried to obtain 10.6 g of the title compound.

¹H-NMR (DMSO-d₆); δ 1.25 (3H, t, J=7 Hz), 1.89 (3H, s), 4.23 (2H, q, J=7 Hz), 5.01 (2H, d, J=13 Hz), 7.92 (1H, d, J=12 Hz), 8.24 (1H, dd, J=10 Hz, 9 Hz), 8.49 (1H, s), 8.72 (1H, d, J=7 Hz)

Reference Example 10

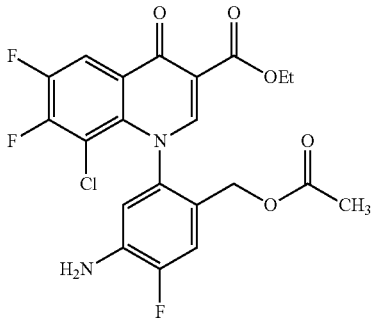 [SMILES: CCOC(=O)c1cn(-c2cc([N+](=O)[O-])c(F)cc2COC(C)=O)c2c(Cl)c(F)c(F)cc2c1=O]

Ethyl 1-(2-acetoxymethyl-5-amino-4-fluorophenyl)-8-chloro-6,7-difluoro-4-oxo-1,4-dihydroquinoline-3-carboxylate 15.8 g of ethyl 1-(2-acetoxymethyl-4-fluoro-5-nitrophenyl)-8-chloro-6,7-difluoro-4-oxo-1,4-dihydroquinoline-3-carboxylate was dissolved in 300 mL of acetic acid and 8.0 g of reduced iron was added. The mixture was stirred at 80° C. for 90 minutes. Insoluble matter was filtered off with celite and the filtrate was evaporated under reduced pressure. The resulting residue was dissolved in 500 mL of chloroform and washed with water and then a saturated aqueous solution of sodium hydrogen carbonate. The organic layer was dried over anhydrous magnesium sulfate and evaporated under reduced pressure. The resulting residue was crystallized with diethyl ether. The crystals were separated in a silica gel column (0 to 3% methanol/chloroform) to obtain 11.5 g of the title compound.

¹H-NMR (DMSO-d₆); δ 1.25 (3H, t, J=7 Hz), 1.78 (3H, s), 4.22 (2H, q, J=7 Hz), 4.69 (1H, d, J=12 Hz), 4.75 (1H, d, J=12 Hz), 5.76 (2H, s), 6.91 (1H, d, J=8 Hz), 7.29 (1H, d, J=12 Hz), 8.22 (1H, dd, J=10 Hz, 9 Hz), 8.31 (1H, s)

Example 26

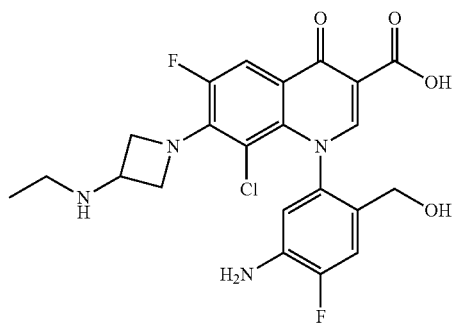 [SMILES: CCNC1CN(c2c(F)cc3c(=O)c(C(=O)O)cn(-c4cc(N)c(F)cc4CO)c3c2Cl)C1]

1-[5-Amino-4-fluoro-2-(hydroxymethyl)phenyl]-8-chloro-7-[3-(ethylamino)azetidin-1-yl]-6-fluoro-4-oxo-1,4-dihydroquinoline-3-carboxylic acid 230 mg of ethyl 1-(2-acetoxymethyl-5-amino-4-fluorophenyl)-8-chloro-6,7-difluoro-4-oxo-1,4-dihydroquinoline-3-carboxylate, 260 mg of 3-ethylaminoazetidine dihydrochloride were suspended in 4 mL of acetonitrile and 350 mg of 1,1,3,3-tetramethylguanidine was added. The mixture was stirred at room temperature overnight. 50 mL of chloroform was added to the reaction solution and the mixture was washed with a saturated aqueous solution of sodium hydrogen carbonate. The organic layer was dried over anhydrous magnesium sulfate and evaporated under reduced pressure. The resulting residue was dispersed in ethyl acetate, collected by filtration, and dried to obtain 230 mg of ethyl 1-(2-acetoxymethyl-5-amino-4-fluorophenyl)-8-chloro-7-[3-(ethylamino)azetidin-1-yl]-6-fluoro-4-oxo-1,4-dihydroquinoline-3-carboxylate.

230 mg of the obtained compound was suspended in 2 mL of ethanol and 2 mL of a 1 mol/L aqueous solution of sodium hydroxide was added. The mixture was stirred at 80° C. for 30 minutes. After cooling, 0.33 mL of 6 mol/L hydrochloric acid was added to neutralize the mixture. The reaction solution was concentrated under reduced pressure and precipitated powder was collected by filtration, washed with water and then acetonitrile, and dried to obtain 160 mg of the title compound.

¹H-NMR (DMSO-d₆); δ 1.17 (3H, t, J=7 Hz), 2.91 (2H, q, J=7 Hz), 4.00-4.13 (3H, m), 4.53-4.59 (2H, m), 4.68-4.74 (2H, m), 5.04 (1H, t, J=5 Hz), 5.51 (2H, s), 6.82 (1H, d, J=8 Hz), 7.15 (1H, d, J=12 Hz), 7.95 (1H, d, J=14 Hz), 8.39 (1H, s)

Example 27

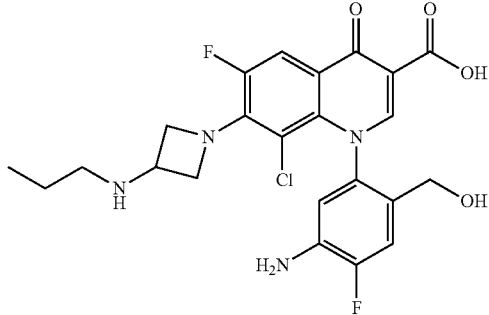

1-[5-Amino-4-fluoro-2-(hydroxymethyl)phenyl]-8-chloro-6-fluoro-4-oxo-7-[3-(propylamino)azetidin-1-yl]-1,4-dihydroquinoline-3-carboxylic acid 230 mg of ethyl 1-(2-acetoxymethyl-5-amino-4-fluoro)phenyl-8-chloro-6,7-difluoro-4-oxo-1,4-dihydroquinoline-3-carboxylate and 280 mg of 3-propylaminoazetidine dihydrochloride were suspended in 4 mL of acetonitrile and 350 mg of 1,1,3,3-tetramethylguanidine was added. The mixture was stirred at room temperature overnight. 50 mL of chloroform was added to the reaction solution and the mixture was washed with a saturated aqueous solution of sodium hydrogen carbonate. The organic layer was dried over anhydrous magnesium sulfate and evaporated under reduced pressure. The resulting residue was crystallized with ethyl acetate/diethyl ether to obtain 220 mg of ethyl 1-(2-acetoxymethyl-5-amino-4-fluorophenyl)-8-chloro-6-fluoro-4-oxo-7-[3-(propylamino)azetidin-1-yl]-1,4-dihydroquinoline-3-carboxylate.

The obtained compound was suspended in 2 mL of ethanol and 2 mL of a 1 mol/L aqueous solution of sodium hydroxide was added. The mixture was stirred at 60° C. for 30 minutes. After cooling, 0.33 mL of 6 mol/L hydrochloric acid was added to neutralize the mixture and precipitated crystals were collected by filtration, washed with water and then acetonitrile, and then dried to obtain 160 mg of the title compound.

$^1$H-NMR (DMSO-$d_6$); δ 0.84 (3H, t, J=7 Hz), 1.32-1.39 (2H, m), 2.38 (2H, t, J=7 Hz), 3.41-3.54 (1H, m), 4.03-4.13 (4H, m), 4.59-4.64 (2H, m), 5.03 (1H, t, J=5 Hz), 5.48 (2H, s), 6.78 (1H, d, J=8 Hz), 7.14 (1H, d, J=12 Hz), 7.87 (1H, d, J=14 Hz), 8.37 (1H, s)

Example 28

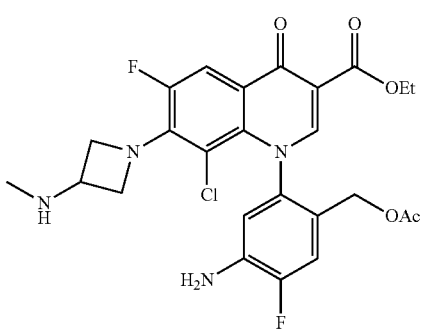 [SMILES: CCOC(=O)c1cn(-c2cc(N)c(F)cc2COC(C)=O)c2c(Cl)c(N3CC(NC)C3)c(F)cc2c1=O]

Ethyl 1-(2-acetoxymethyl-5-amino-4-fluorophenyl)-8-chloro-6-fluoro-7-(3-methylaminoazetidin-1-yl)-4-oxo-1,4-dihydroquinoline-3-carboxylate 6.0 mL of acetonitrile, 0.28 g of 3-methylaminoazetidine hydrochloride, and 0.76 mL of triethylamine were added to 0.35 g of ethyl 1-(2-acetoxymethyl-5-amino-4-fluorophenyl)-8-chloro-6,7-difluoro-4-oxo-1,4-dihydroquinoline-3-carboxylate and the mixture was stirred at room temperature for 4 days. The resulting precipitates were collected by filtration to obtain 0.37 g of the title compound.

$^1$H-NMR (CDCl$_3$): δ 1.36 (3H, t, J=7.1 Hz), 1.96 (3H, s), 2.54 (3H, s), 3.68-3.76 (1H, m), 4.31-4.48 (4H, m), 4.60-4.70 (3H, m), 4.86 (1H, d, J=7.8 Hz), 6.67 (1H, d, J=7.8 Hz), 7.12 (1H, d, J=11.0 Hz), 7.88 (1H, d, J=13.9 Hz), 8.30 (1H, s).

Example 29

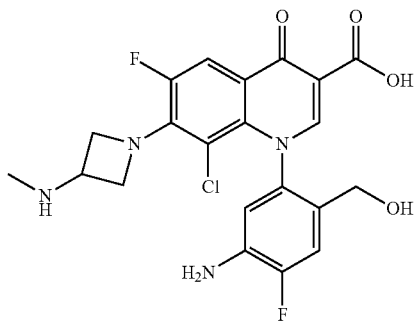 [SMILES: CNC1CN(c2c(F)cc3c(=O)c(C(=O)O)cn(-c4cc(N)c(F)cc4CO)c3c2Cl)C1]

1-[5-Amino-4-fluoro-2-(hydroxymethyl)phenyl]-8-chloro-6-fluoro-7-(3-methylaminoazetidin-1-yl)-4-oxo-1,4-dihydroquinoline-3-carboxylic acid 3.0 mL of ethanol and 1.0 mL of a 3 mol/L aqueous solution of sodium hydroxide were added to 0.37 g of etnyl 1-(2-acetoxymethyl-5-amino-4-fluorophenyl)-8-chloro-6-fluoro-7-(3-methylaminoazetidin-1-yl)-4-oxo-1,4-dihydroquinoline-3-carboxylate. The mixture was stirred at room temperature overnight. A 5% aqueous solution of citric acid was added to make the solution acidic (pH 5 to 6) and then ethanol was evaporated under reduced pressure. The resulting precipitates were collected by filtration to obtain 0.22 g of the title compound.

$^1$H-NMR (DMSO-$d_6$): δ 2.18 (3H, s), 3.39-3.45 (1H, m), 4.03-4.13 (4H, m), 4.54-4.62 (2H, m), 5.05 (1H, t, J=5.4 Hz), 5.46 (2H, s), 6.74 (1H, d, J=8.6 Hz), 7.13 (1H, d, J=11.9 Hz), 7.84 (1H, d, J=13.9 Hz), 8.37 (1H, s).

Example 30

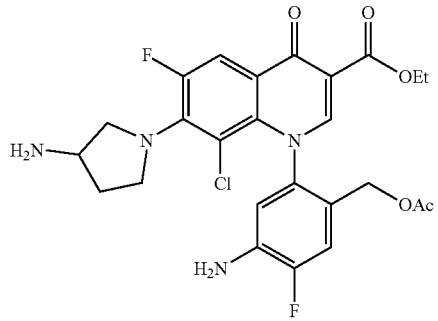 [SMILES: CCOC(=O)c1cn(-c2cc(N)c(F)cc2COC(C)=O)c2c(Cl)c(N3CCC(N)C3)c(F)cc2c1=O]

Ethyl 1-(2-acetoxymethyl-5-amino-4-fluorophenyl)-7-(3-aminopyrrolidin-1-yl)-8-chloro-6-fluoro-4-oxo-1,4-dihydroquinoline-3-carboxylate 1.0 mL of acetonitrile and 0.40 g of 3-aminopyrrolidine were added to 0.10 g of ethyl 1-(2-acetoxymethyl-5-amino-4-fluorophenyl)-8-chloro-6,7-difluoro-4-oxo-1,4-dihydroquinoline-3-carboxylate and the mixture was stirred at room temperature for 3 days. The resulting precipitates were collected by filtration to obtain 96 mg of the title compound.

¹H-NMR (DMSO-d₆): δ 1.24 (3H, t, J=7.1 Hz), 1.56-1.64 (1H, m), 1.84 (3H, s), 1.94-2.20 (1H, m), 2.76-2.80 (1H, m), 3.40-3.62 (4H, m), 4.22 (2H, q, J=7.1 Hz), 4.65 (1H, d, J=12.3 Hz), 4.72 (1H, d, J=12.3 Hz), 5.68 (2H, brs), 6.79 (1H, d, J=8.3 Hz), 7.24 (1H, d, J=11.7 Hz), 7.82 (1H, d, J=13.7 Hz), 8.24 (1H, s).

Example 31

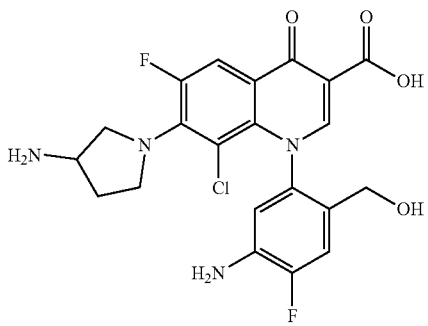 [SMILES: Nc1cc(-n2cc(C(=O)O)c(=O)c3cc(F)c(N4CCC(N)C4)c(Cl)c32)c(CO)cc1F]

1-[5-Amino-4-fluoro-2-(hydroxymethyl)phenyl]-7-(3-aminopyrrolidin-1-yl)-8-chloro-6-fluoro-4-oxo-1,4-dihydroquinoline-3-carboxylic acid 1.0 mL of ethanol and 1.0 mL of an a 1 mol/L aqueous solution of sodium hydroxide were added to 96 mg of ethyl 1-(2-acetoxymethyl-5-amino-4-fluorophenyl)-7-(3-aminopyrrolidin-1-yl)-8-chloro-6-fluoro-4-oxo-1,4-dihydroquinoline-3-carboxylate. The mixture was stirred at room temperature overnight. Hydrochloric acid was added to make the solution acidic (pH 5 to 6). The resulting precipitates were collected by filtration to obtain 70 mg of the title compound.

¹H-NMR (DMSO-d₆): δ 1.74-1.89 (1H, m), 2.15-2.22 (1H, m), 3.56-3.68 (5H, m), 4.02-4.12 (2H, m), 5.00 (0.5H, t, J=5.4 Hz), 5.06 (0.5H, t, J=5.4 Hz), 5.50 (1H, s), 5.52 (1H, s), 6.80 (0.5H, d, J=8.1 Hz), 6.84 (1H, d, J=8.1 Hz), 7.14 (0.5H, d, J=12.0 Hz), 7.18 (0.5H, d, J=12.0 Hz), 8.02 (1H, d, J=13.2 Hz), 8.48 (0.5H, s), 8.50 (0.5H, s).

Example 32

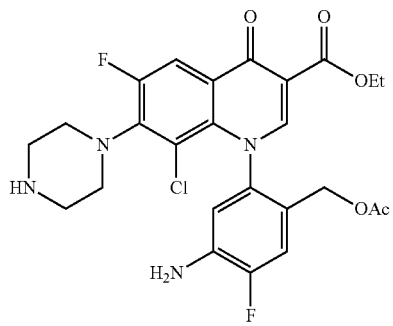 [SMILES: CCOC(=O)c1cn(-c2cc(N)c(F)cc2COC(C)=O)c2c(Cl)c(N3CCNCC3)c(F)cc2c1=O]

Ethyl 1-(2-acetoxymethyl-5-amino-4-fluorophenyl)-8-chloro-6-fluoro-4-oxo-7-(piperazin-1-yl)-1,4-dihydroquinoline-3-carboxylate 3.0 mL of acetonitrile, 0.19 g of piperazine hexahydrate, and 0.25 mL of triethylamine were added to 0.14 g of ethyl 1-(2-acetoxymethyl-5-amino-4-fluorophenyl)-8-chloro-6,7-difluoro-4-oxo-1,4-dihydroquinoline-3-carboxylate and the mixture was stirred at room temperature for 3 days. The resulting precipitates were collected by filtration to obtain 93 mg of the title compound.

¹H-NMR (DMSO-d₆): δ 1.33 (3H, t, J=7.1 Hz), 1.93 (3H, s), 2.82-3.10 (8H, m), 4.26 (2H, q, J=7.1 Hz), 4.70 (1H, d, J=12.4 Hz), 4.83 (1H, d, J=12.4 Hz), 5.53 (2H, brs), 6.86 (1H, d, J=8.1 Hz), 7.16 (1H, d, J=11.6 Hz), 8.25 (1H, d, J=12.0 Hz), 8.50 (1H, s).

Example 33

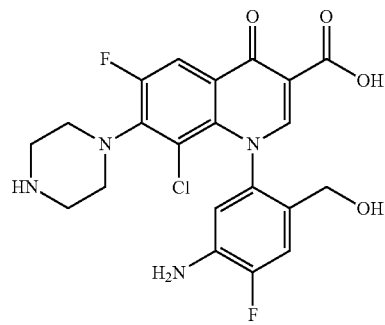 [SMILES: Nc1cc(-n2cc(C(=O)O)c(=O)c3cc(F)c(N4CCNCC4)c(Cl)c32)c(CO)cc1F]

1-[5-amino-4-fluoro-2-(hydroxymethyl)phenyl]-8-chloro-6-fluoro-4-oxo-7-(piperazin-1-yl)-1,4-dihydroquinoline-3-carboxylic acid 1.0 mL of ethanol and 0.4 mL of a 3 mol/L aqueous solution of sodium hydroxide were added to 93 mg of ethyl 1-(2-acetoxymethyl-5-amino-4-fluorophenyl)-8-chloro-6-fluoro-4-oxo-7-(piperazin-1-yl)-1,4-dihydroquinoline-3-carboxylate. The mixture was stirred at room temperature overnight. Hydrochloric acid was added to make the solution acidic (pH 5 to 6). The resulting precipitates were collected by filtration to obtain 77 mg of the title compound.

¹H-NMR (DMSO-d₆): δ 2.67-3.08 (8H, m), 4.00-4.16 (2H, m), 5.04 (1H, t, J=5.3 Hz), 5.55 (2H, brs), 6.87 (1H, d, J=8.1 Hz), 7.14 (1H, d, J=11.6 Hz), 8.23 (1H, d, J=10.8 Hz), 8.48 (1H, s).

Example 34

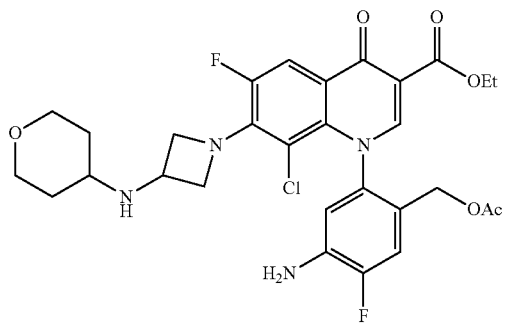

Ethyl 1-(2-acetoxymethyl-5-amino-4-fluorophenyl)-8-chloro-6-fluoro-4-oxo-7-[3-(tetrahydropyran-4-ylamino)azetidin-1-yl]-1,4-dihydroquinoline-3-carboxylate 1.0 mL of ethyl acetate and 1.0 mL of 4 mol/L hydrogen chloride/ethyl acetate were added to 0.15 g of tert-Butyl 3-(tetrahydropyran-4-yl)aminoazetidine-1-carboxylate and the mixture was stirred at room temperature for 1 hour. The reaction solution was concentrated to obtain a 3-(tetrahydropyran-4-yl)aminoazetidine hydrochloride.

To 3-(tetrahydropyran-4-yl)aminoazetidine hydrochloride obtained as described above, 1.0 mL of acetonitrile, 0.14 g of ethyl 1-(2-acetoxymethyl-5-amino-4-fluorophenyl)-8-chloro-6,7-difluoro-4-oxo-1,4-dihydroquinoline-3-carboxylate, and 0.13 mL of 1,1,3,3-tetramethylguanidine were added and the mixture was stirred at room temperature overnight. The reaction solution was concentrated and suspended in 0.50 mL of acetonitrile. The resulting precipitates were collected by filtration to obtain 0.12 g of the title compound.

$^1$H-NMR (DMSO-$d_6$): δ 1.14-1.23 (5H, m), 1.60-1.66 (2H, m), 1.85 (3H, s), 2.52-2.60 (1H, m), 3.26 (2H, dt, J=2.1 Hz, 11.5 Hz), 3.60-3.66 (1H, m), 3.75-3.82 (2H, m), 3.84-4.03 (2H, m), 4.21 (2H, q, J=7.1 Hz), 4.55-4.62 (2H, m), 4.68 (1H, d, J=12.4 Hz), 4.75 (1H, d, J=12.4 Hz), 5.67 (2H, brs), 6.78 (1H, d, J=8.2 Hz), 7.26 (1H, d, J=11.7 Hz), 7.75 (1H, d, J=14.2 Hz), 8.14 (1H, s).

Example 35

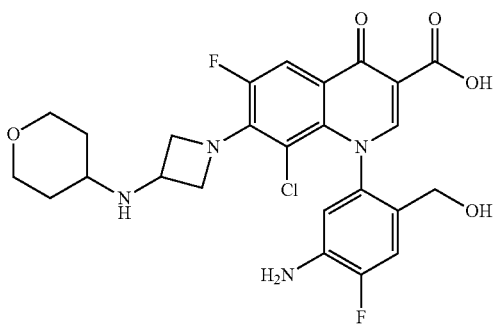

1-[5-Amino-4-fluoro-2-(hydroxymethyl)phenyl]-8-chloro-6-fluoro-4-oxo-7-[3-(tetrahydropyran-4-yl)aminoazetidin-1-yl]-1,4-dihydroquinoline-3-carboxylic acid 1.0 mL of ethanol, 0.20 mL of a 3 mol/L aqueous solution of sodium hydroxide and 0.80 mL of water were added to 0.12 g of ethyl 1-(2-acetoxymethyl-5-amino-4-fluorophenyl)-8-chloro-6-fluoro-4-oxo-7-[3-(tetrahydropyran-4-yl)aminoazetidin-1-yl]-1,4-dihydroquinoline-3-carboxylate and the mixture was stirred at room temperature for 4 days. A 5% aqueous solution of citric acid was added to make the solution acidic (pH 5 to 6). The resulting precipitates were collected by filtration to obtain 0.10 g of the title compound.

$^1$H-NMR (DMSO-$d_6$): δ 1.23 (2H, dq, J=4.4 Hz, 11.4 Hz), 1.64 (2H, d, J=12.1 Hz), 2.542.59 (1H, m), 3.27 (2H, dt, J=2.0 Hz, 11.6 Hz), 3.62-3.70 (1H, m), 3.77-3.80 (2H, m), 4.13-4.02 (4H, m), 4.61-4.66 (2H, m), 5.05 (1H, t, J=5.1 Hz), 5.46 (2H, brs), 6.76 (1H, d, J=8.2 Hz), 7.15 (1H, d, J=11.9 Hz), 7.87 (1H, d, J=14.0 Hz), 8.33 (1H, s).

Example 36

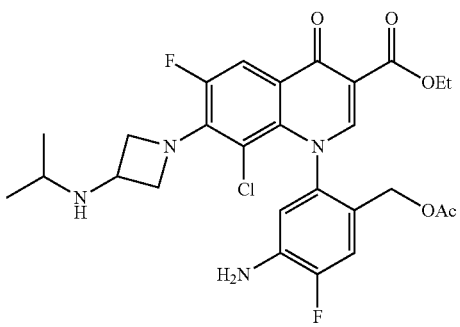 [SMILES: CCOC(=O)c1cn(-c2cc(N)c(F)cc2COC(C)=O)c2c(Cl)c(N3CC(NC(C)C)C3)c(F)cc2c1=O]

Ethyl 1-(2-acetoxymethyl-5-amino-4-fluorophenyl)-8-chloro-6-fluoro-4-oxo-7-[3-(propan-2-yl)aminoazetidin-1-yl]-1,4-dihydroquinoline-3-carboxylate 1.0 mL of acetonitrile, 0.11 g of 3-(propan-2-yl)aminoazetidine hydrochloride, and 0.25 mL of triethylamine were added to 0.19 g of ethyl 1-(2-acetoxymethyl-5-amino-4-fluorophenyl)-8-chloro-6,7-difluoro-4-oxo-1,4-dihydroquinoline-3-carboxylate and the mixture was stirred at room temperature overnight. The resulting precipitates were collected by filtration to obtain 0.19 g of the title compound.

$^1$-H-NMR (DMSO-$d_6$): δ 0.97 (6H, brm), 1.24 (3H, t, J=7.1 Hz), 1.85 (3H, s), 2.78-2.83 (1H, m), 3.60-3.75 (1H, m), 3.98-4.11 (2H, m), 4.21 (2H, q, J=7.1 Hz), 4.56-4.64 (2H, m), 4.68 (1H, d, J=12.4 Hz), 4.75 (1H, d, J=12.4 Hz), 5.68 (2H, brs), 6.78 (1H, d, J=8.1 Hz), 7.26 (1H, d, J=11.8 Hz), 7.77 (1H, d, J=14.2 Hz), 8.15 (1H, s).

Example 37

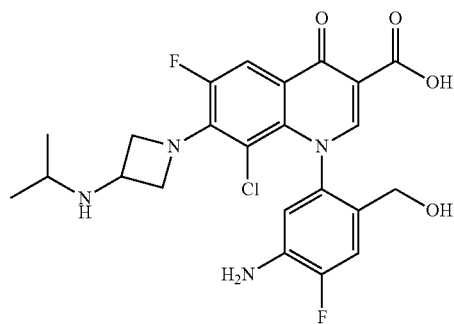

1-[5-Amino-4-fluoro-2-(hydroxymethyl)phenyl]-8-chloro-6-fluoro-4-oxo-7-[3-(propan-2-yl)aminoazetidin-1-yl]-1,4-dihydroquinoline-3-carboxylic acid 1.0 mL of ethanol, 0.20 mL of a 10 mol/L aqueous solution of sodium hydroxide and 0.80 mL of water were added to 0.19 g of ethyl 1-(2-acetoxymethyl-5-amino-4-fluorophenyl)-8-chloro-6-fluoro-4-oxo-7-[3-(propan-2-yl)aminoazetidin-1-yl]-1,4-dihydroquinoline-3-carboxylate and the mixture was stirred at 50° C. for 1 hour. A 5 aqueous solution of citric acid was added to make the solution acidic (pH 5 to 6). The resulting precipitates were collected by filtration to obtain 0.16 g of the title compound.

$^1$H-NMR (DMSO-d$_6$): δ 0.93 (6H, d, J=6.3 Hz), 2.65-2.72 (1H, m), 3.58-3.63 (1H, m), 4.03-4.13 (4H, m), 4.62-4.67 (2H, m), 5.04 (1H, t, J=5.4 Hz), 5.48 (2H, brs), 6.79 (1H, d, J=8.2 Hz), 7.15 (1H, d, J=11.9 Hz), 7.89 (1H, d, J=13.9 Hz), 8.37 (1H, s)

Example 38

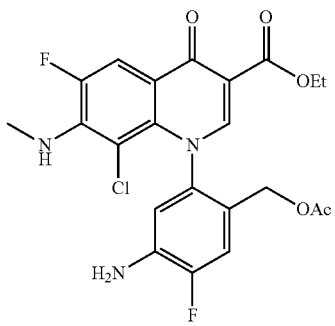 [SMILES: CCOC(=O)c1cn(-c2cc(N)c(F)cc2COC(C)=O)c2c(Cl)c(NC)c(F)cc2c1=O]

Ethyl 1-(2-acetoxymethyl-5-amino-4-fluorophenyl)-8-chloro-6-fluoro-7-methylamino-4-oxo-1,4-dihydroquinoline-3-carboxylate 1.0 mL of acetonitrile, 0.69 mg of methylamine hydrochloride, and 0.25 mL of triethylamine were added to 91 mg of ethyl 1-(2-acetoxymethyl-5-amino-4-fluorophenyl)-8-chloro-6,7-difluoro-4-oxo-1,4-dihydroquinoline-3-carboxylate and the mixture was stirred at room temperature for 3 days. The resulting precipitates were collected by filtration to obtain 60 mg of the title compound.

$^1$H-NMR (DMSO-d$_6$): δ 1.24 (3H, t, J=7.1 Hz), 1.81 (3H, s), 3.97 (3H, dd, J=5.2 Hz, 7.1 Hz), 4.21 (2H, q, J=7.1 Hz), 4.67 (1H, d, J=12.3 Hz), 4.72 (1H, d, J=12.3 Hz), 5.68 (2H, brs), 6.15 (1H, brm), 6.80 (1H, d, J=8.2 Hz), 7.27 (1H, d, J=11.8 Hz), 7.82 (1H, d, J=14.2 Hz), 8.14 (1H, s).

Example 39

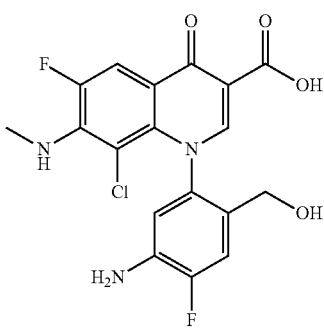 [SMILES: CNc1c(F)cc2c(=O)c(C(=O)O)cn(-c3cc(N)c(F)cc3CO)c2c1Cl]

1-[5-Amino-4-fluoro-2-(hydroxymethyl)phenyl]-8-chloro-6-fluoro-7-methylamino-4-oxo-1,4-dihydroquinoline-3-carboxylic acid 1.0 mL of ethanol, 0.20 mL of a 10 mol/L aqueous solution of sodium hydroxide and 0.80 mL of water were added to 60 mg of ethyl 1-(2-acetoxymethyl-5-amino-4-fluorophenyl)-8-chloro-6-fluoro-7-methylamino-4-oxo-1,4-dihydroquinoline-3-carboxylate and the mixture was stirred at room temperature overnight. A 5' aqueous solution of citric acid was added to make the solution acidic (pH 5 to 6). The resulting precipitates were collected by filtration to obtain 37 mg of the title compound.

$^1$H-NMR (DMSO-d$_6$): δ 3.12 (3H, dt, J=5.2 Hz, 7.5 Hz), 4.05 (2H, dq, J=4.7 Hz, 8.3 Hz), 5.04 (1H, t, J=5.9 Hz), 5.48 (2H, brs), 6.52 (1H, brs), 6.78 (1H, d, J=8.2 Hz), 7.16 (1H, d, J=11.9 Hz), 7.97 (1H, d, J=13.9 Hz), 8.36 (1H, s).

Example 40

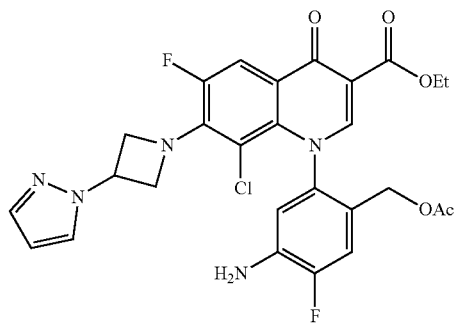 [SMILES: CCOC(=O)c1cn(-c2cc(N)c(F)cc2COC(C)=O)c2c(Cl)c(N3CC(n4cccn4)C3)c(F)cc2c1=O]

Ethyl 1-(2-acetoxymethyl-5-amino-4-fluorophenyl)-8-chloro-6-fluoro-4-oxo-7-[3-(1H-pyrazol-1-yl)azetidin-1-yl]-1,4-dihydroquinoline-3-carboxylate 1.0 mL of acetonitrile, 95 mg of 3-(1H-pyrazol-1-yl)azetidine hydrochloride, and 0.34 mL of triethylamine were added to 94 mg of ethyl 1-(2-acetoxymethyl-5-amino-4-fluorophenyl)-8-chloro-6,7-difluoro-4-oxo-1,4-dihydroquinoline-3-carboxylate and the mixture was stirred at room temperature overnight. The resulting precipitates were collected by filtration to obtain 42 mg of the title compound.

$^1$H-NMR (DMSO-d$_6$): δ 1.25 (3H, t, J=7.1 Hz), 1.87 (3H, s), 4.22 (2H, q, J=7.1 Hz), 4.58-4.65 (2H, m), 4.71 (1H, d, J=12.4 Hz), 4.77 (1H, d, J=12.4 Hz), 4.83-4.93 (2H, m), 5.24-5.30 (1H, m), 5.67 (2H, brs), 6.29 (1H, t, J=2.0 Hz), 6.80 (1H, d, J=8.2 Hz), 7.26 (1H, d, J=11.8 Hz), 7.54 (1H, d, J=1.3 Hz), 7.81 (1H, d, J=14.1 Hz), 7.89 (1H, d, J=2.3 Hz), 8.17 (1H, s), 8.30 (1H, s).

Example 41

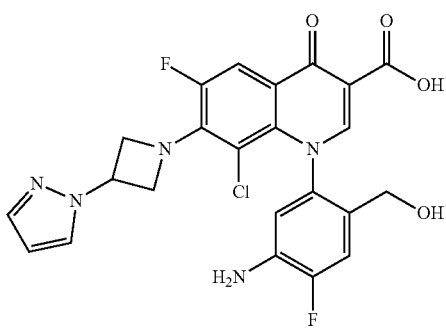 [SMILES: Nc1cc(-n2cc(C(=O)O)c(=O)c3cc(F)c(N4CC(n5cccn5)C4)c(Cl)c32)c(CO)cc1F]

1-[5-Amino-4-fluoro-2-(hydroxymethyl)phenyl]-8-chloro-6-fluoro-4-oxo-7-[3-(1H-pyrazol-1-yl) azetidin-1-yl]-1,4-dihydroquinoline-3-carboxylic acid 0.50 mL of ethanol, 0.10 mL of a 10 mol/L aqueous solution of sodium hydroxide and 0.50 mL of water were added to 42 mg of ethyl 1-(2-acetoxymethyl-5-amino-4-fluorophenyl)-8-chloro-6-fluoro-4-oxo-7-[3-(1H-pyrazol-1-yl)azetidin-1-yl]-1,4-dihydroquinoline-3-carboxylate and the mixture was stirred at 50° C. for 2 hours. 1 mol/L hydrochloric acid was added to make the solution acidic (pH 6 to 7). The resulting precipitates were collected by filtration to obtain 32 mg of the title compound.

$^1$H-NMR (DMSO-d$_6$): δ 4.06-4.12 (2H, m), 4.66-4.69 (2H, m), 4.91-4.95 (2H, m), 5.07 (1H, t, J=5.4 Hz), 5.27-5.30 (1H, m), 5.46 (2H, brs), 6.30 (1H, t, J=2.0 Hz), 6.79 (1H, d, J=8.1 Hz), 7.15 (1H, d, J=12.0 Hz), 7.55 (1H, d, J=1.6 Hz), 7.90 (1H, d, J=2.4 Hz), 7.94 (1H, d, J=13.9 Hz), 8.35 (1H, s).

Example 42

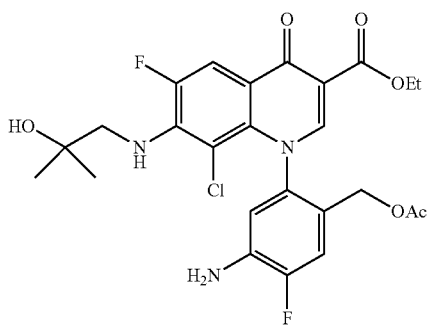 [SMILES: CCOC(=O)c1cn(-c2cc(N)c(F)cc2COC(C)=O)c2c(Cl)c(NCC(C)(C)O)c(F)cc2c1=O]

Ethyl 1-(2-acetoxymethyl-5-amino-4-fluorophenyl)-8-chloro-6-fluoro-7-(2-hydroxy-2-methylpropylamino)-4-oxo-1,4-dihydroquinoline-3-carboxylate 1.0 mL of acetonitrile, 89 μL of 3-amino-2-methylpropan-2-ol, and 0.25 mL of triethylamine were added to 93 mg of ethyl 1-(2-acetoxymethyl-5-amino-4-fluorophenyl)-8-chloro-6,7-difluoro-4-oxo-1,4-dihydroquinoline-3-carboxylate and the mixture was stirred at room temperature overnight. The resulting precipitates were collected by filtration to obtain 66 mg of the title compound.

$^1$H-NMR (CDCl$_3$): δ 1.28 (6H, s), 1.39 (3H, t, J=7.1 Hz), 1.94 (3H, s), 3.50 (2H, d, J=5.8 Hz), 3.99 (2H, brs), 4.38 (2H, q, J=7.1 Hz), 4.74 (1H, d, J=12.7 Hz), 4.84 (1H, d, J=12.7 Hz), 5.15 (1H, brm), 6.68 (1H, d, J=7.8 Hz), 7.16 (1H, d, J=11.0 Hz), 8.13 (1H, d, J=13.9 Hz), 8.28 (1H, s).

Example 43

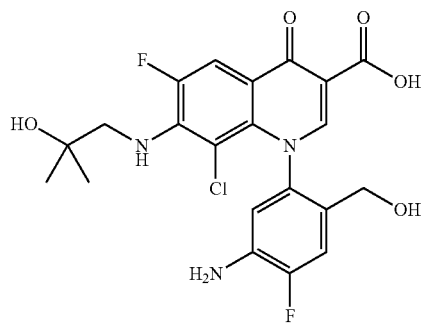 [SMILES: CC(C)(O)CNc1c(F)cc2c(=O)c(C(=O)O)cn(-c3cc(N)c(F)cc3CO)c2c1Cl]

1-[5-Amino-4-fluoro-2-(hydroxymethyl)phenyl]-8-chloro-6-fluoro-7-(2-hydroxy-2-methylpropylamino)-4-oxo-1,4-dihydroquinoline-3-carboxylic acid 0.50 mL of ethanol, 0.10 mL of a 10 mol/L aqueous solution of sodium hydroxide and 0.50 mL of water were added to 66 mg of ethyl 1-(2-acetoxymethyl-5-amino-4-fluorophenyl)-8-chloro-6-fluoro-7-(2-hydroxy-2-methylpropylamino)-4-oxo-1,4-dihydroquinoline-3-carboxylate and the mixture was stirred at 50° C. for 2 hours. 1 mol/L hydrochloric acid was added to make the solution acidic (pH 6 to 7). The resulting precipitates were collected by filtration to obtain 51 mg of the title compound.

$^1$H-NMR (DMSO-d$_6$): δ 1.11 (6H, s), 3.42 (2H, d, J=3.6 Hz), 4.02-4.11 (2H, m), 4.74 (1H, s), 5.04 (1H, t, J=5.3 Hz), 5.50 (2H, brs), 5.86 (1H, brs), 6.81 (1H, d, J=8.0 Hz), 7.17 (1H, d, J=11.8 Hz), 7.99 (1H, d, J=13.6 Hz), 8.38 (1H, s).

Example 44

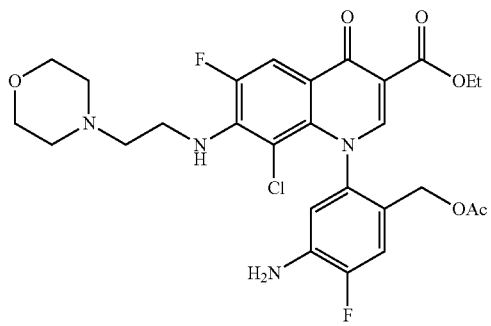 [SMILES: CCOC(=O)c1cn(-c2cc(N)c(F)cc2COC(C)=O)c2c(Cl)c(NCCN3CCOCC3)c(F)cc2c1=O]

Ethyl 1-(2-acetoxymethyl-5-amino-4-fluorophenyl)-8-chloro-6-fluoro-7-[(2-morpholin-4-yl)ethylamino]-4-oxo-1,4-dihydroquinoline-3-carboxylate 1.0 mL of acetonitrile, 78 mg of 2-(morpholin-4-yl) ethylamine, and 0.25 mL of triethylamine were added to 93 mg of ethyl 1-(2-acetoxymethyl-5-amino-4-fluorophenyl)-8-chloro-6,7-difluoro-4-oxo-1,4-dihydroquinoline-3-carboxylate and the mixture was stirred at room temperature overnight. The resulting precipitates were collected by filtration to obtain 50 mg of the title compound.

$^1$H-NMR (CDCl$_3$): δ 1.39 (3H, t, J=7.1 Hz), 1.95 (3H, s), 2.44-2.50 (2H, m), 2.62 (2H, t, J=5.8 Hz), 3.60 (2H, t, J=4.3 Hz), 3.68 (4H, t, J=4.3 Hz), 4.00 (2H, brs), 4.39 (2H, q, J=7.1 Hz), 4.75 (1H, d, J=12.6 Hz), 4.84 (1H, d, J=12.6 Hz), 5.72 (1H, brm), 6.69 (1H, d, J=7.9 Hz), 7.18 (1H, d, J=11.0 Hz), 8.14 (1H, d, J=13.5 Hz), 8.28 (1H, s).

Example 45

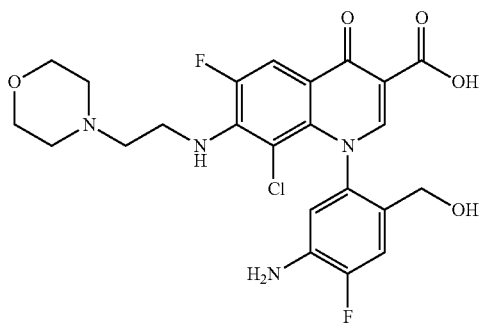 [SMILES: Nc1cc(-n2cc(C(=O)O)c(=O)c3cc(F)c(NCCN4CCOCC4)c(Cl)c32)c(CO)cc1F]

1-[5-Amino-4-fluoro-2-(hydroxymethyl)phenyl]-8-chloro-6-fluoro-7-[(2-morpholin-4-yl)ethylamino]-4-oxo-1,4-dihydroquinoline-3-carboxylic acid 0.5 mL of ethanol, 0.10 mL of a 10 mol/L aqueous solution of sodium hydroxide and 0.50 mL of water were added to 50 mg of ethyl 1-(2-acetoxymethyl-5-amino-4-fluorophenyl)-8-chloro-6-fluoro-7-[(2-morpholin-4-yl)ethylamino]-4-oxo-1,4-dihydroquinoline-3-carboxylate and the mixture was stirred at 50° C. for 2 hours. 1 mol/L hydrochloric acid was added to make the solution acidic (pH 6 to 7). The resulting precipitates were collected by filtration to obtain 43 mg of the title compound.

$^1$H-NMR (DMSO-d$_5$): δ 2.33-2.40 (4H, m), 3.48-3.52 (4H, m), 3.57-3.62 (2H, m), 4.02-4.11 (2H, m), 5.05 (1H, t, J=5.3 Hz), 5.50 (2H, brs), 6.33 (1H, brs), 6.79 (1H, d, J=8.1 Hz), 7.17 (1H, d, J=11.9 Hz), 8.01 (1H, d, J=13.6 Hz), 8.38 (1H, s).

Example 46

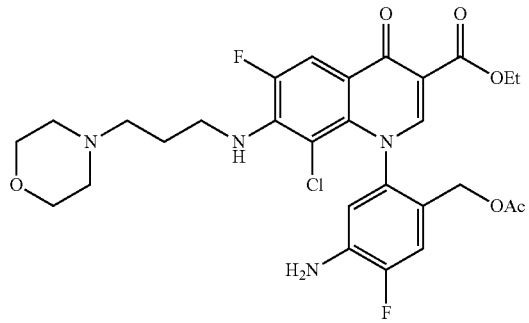 [SMILES: CCOC(=O)c1cn(-c2cc(N)c(F)cc2COC(C)=O)c2c(Cl)c(NCCCN3CCOCC3)c(F)cc2c1=O]

Ethyl 1-(2-acetoxymethyl-5-amino-4-fluorophenyl)-8-chloro-6-fluoro-7-[(3-morpholin-4-yl)propylamino]-4-oxo-1,4-dihydroquinoline-3-carboxylate 1.0 mL of acetonitrile, 84 mg of 3-(morpholin-4-yl) propylamine, and 0.25 mL of triethylamine were added to 93 mg of ethyl 1-(2-acetoxymethyl-5-amino-4-fluorophenyl)-8-chloro-6,7-difluoro-4-oxo-1,4-dihydroquinoline-3-carboxylate and the mixture was stirred at room temperature overnight. The resulting precipitates were collected by filtration to obtain 34 mg of the title compound.

$^1$H-NMR (CDCl$_3$): δ 1.39 (3H, t, J=7.1 Hz), 1.77-1.81 (2H, m), 1.95 (3H, s), 2.40-2.50 (6H, m), 3.60-3.72 (6H, m), 4.02 (2H, brs), 4.39 (2H, q, J=7.1 Hz), 4.75 (1H, d, J=12.6 Hz), 4.85 (1H, d, J=12.6 Hz), 5.55 (1H, brm), 6.68 (1H, d, J=7.9 Hz), 7.17 (1H, d, J=11.0 Hz), 8.12 (1H, d, J=13.9 Hz), 8.27 (1H, s).

Example 47

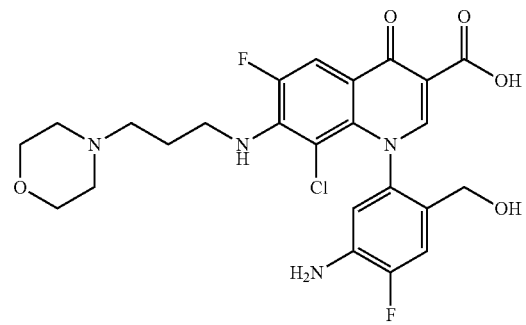 [SMILES: Nc1cc(-n2cc(C(=O)O)c(=O)c3cc(F)c(NCCCN4CCOCC4)c(Cl)c32)c(CO)cc1F]

1-[5-Amino-4-fluoro-2-(hydroxymethyl)phenyl]-8-chloro-6-fluoro-7-[(3-morpholin-4-yl)propylamino]-4-oxo-1,4-dihydroquinoline-3-carboxylic acid 0.50 mL of ethanol, 0.10 mL of a 10 mol/L aqueous solution of sodium hydroxide and 0.50 mL of water were added to 34 mg of ethyl 1-(2-acetoxymethyl-5-amino-4-fluorophenyl)-8-chloro-6-fluoro-7-[(3-morpholin-4-yl)propylamino]-4-oxo-1,4-dihydroquinoline-3-carboxylate and the mixture was stirred at room temperature overnight. 1 mol/L hydrochloric acid was added to make the solution acidic (pH 6 to 7). The resulting precipitates were collected by filtration to obtain 25 mg of the title compound.

$^1$H-NMR (DMSO-d$_6$): δ 1.63-1.71 (2H, m), 2.22-2.36 (6H, m), 3.47-3.54 (4H, m), 4.02-4.11 (2H, m), 5.14 (1H, brs), 5.41 (2H, brs), 6.25 (1H, b rs), 6.69 (1H, d, J=8.1 Hz), 7.15 (1H, d, J=12.0 Hz), 7.90 (1H, d, J=14.2 Hz), 8.20 (1H, s).

Example 48

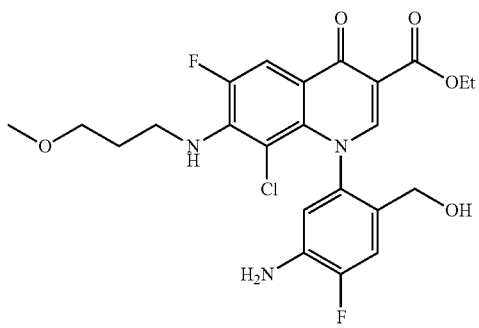 [SMILES: CCOC(=O)c1cn(-c2cc(N)c(F)cc2CO)c2c(Cl)c(NCCCOC)c(F)cc2c1=O]

Ethyl 1-[5-amino-4-fluoro-2-(hydroxymethyl)phenyl]-8-chloro-6-fluoro-7-(3-methoxypropyl)amino-4-oxo-1,4-dihydroquinoline-3-carboxylate 1.0 mL of acetonitrile, 92 μL of 3-methoxypropylamine, and 0.25 mL of triethylamine were added to 93 mg of ethyl 1-(2-acetoxymethyl-5-amino-4-fluorophenyl)-8-chloro-6,7-difluoro-4-oxo-1,4-dihydroquinoline-3-carboxylate and the mixture was stirred at room temperature overnight. The resulting precipitates were collected by filtration to obtain 30 mg of the title compound.

$^1$H-NMR (DMSO-d$_6$): δ 1.24 (3H, t, J=7.1 Hz), 1.81 (2H, brm), 3.19 (3H, s), 3.16-3.20 (2H, m), 3.4-3.52 (2H, m), 4.20 (2H, q, J=7.1 Hz), 4.68 (1H, dd, J=5.8 Hz, 12.6 Hz), 4.73 (1H, dd, J=4.7 Hz, 12.6 Hz), 4.80 (1H, t, J=5.1 Hz), 5.69 (2H, brs), 5.86 (1H, brs), 6.80 (1H, d, J=8.3 Hz), 7.28 (1H, d, J=11.8 Hz), 7.84 (1H, d, J=14.1 Hz), 8.15 (1H, s).

Example 49

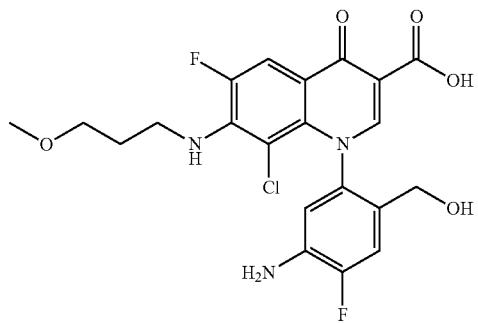 [SMILES: COCCCNc1c(F)cc2c(=O)c(C(=O)O)cn(-c3cc(N)c(F)cc3CO)c2c1Cl]

1-[5-Amino-4-fluoro-2-(hydroxymethyl)phenyl]-8-chloro-6-fluoro-7-(3-methoxypropyl)amino-4-oxo-1,4-dihydroquinoline-3-carboxylic acid 0.50 mL of ethanol, 0.10 mL of a 10 mol/L aqueous solution of sodium hydroxide and 0.50 mL of water were added to 30 mg of ethyl 1-[5-amino-4-fluoro-2-(hydroxymethyl)phenyl]-8-chloro-6-fluoro-7-(3-methoxypropyl) amino-4-oxo-1,4-dihydroquinoline-3-carboxylate and the mixture was stirred at 50° C. for 2 hours. 1 mol/L hydrochloric acid was added to make the solution acidic (pH 6 to 7). The resulting precipitates were collected by filtration to obtain 21 mg of the title compound.

$^1$H-NMR (DMSO-d$_6$): δ 1.74-1.81 (2H, m), 3.19 (3H, s), 3.37 (2H, t, J=5.9 Hz), 3.55-3.58 (2H, m), 4.06 (1H, dd, J=5.8 Hz, 12.9 Hz), 4.12 (1H, dd, J=4.7 Hz, 12.9 Hz), 5.05 (1H, t, J=5.3 Hz), 5.46 (2H, br s), 6.47 (1H, brs), 6.79 (1H, d, J=8.2 Hz), 7.17 (1H, d, J=11.9 Hz), 7.99 (1H, d, J=14.0 Hz), 8.37 (1H, s).

Example 50

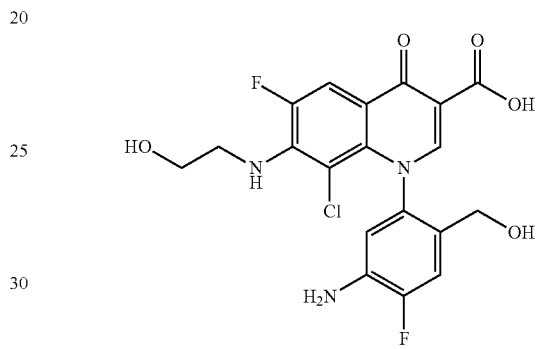

1-[5-Amino-4-fluoro-2-(hydroxymethyl)phenyl]-8-chloro-6-fluoro-7-(2-hydroxyethyl)amino-4-oxo-1,4-dihydroquinoline-3-carboxylic acid 1.0 mL of acetonitrile, 27 μL of 2-aminoethanol, and 0.50 mL of triethylamine were added to 0.19 g of ethyl 1-(2-acetoxymethyl-5-amino-4-fluorophenyl)-8-chloro-6,7-difluoro-4-oxo-1,4-dihydroquinoline-3-carboxylate and the mixture was stirred at room temperature overnight. 27 μL of 2-aminoethanol was added to the reaction solution and the mixture was stirred at room temperature overnight. The reaction solution was subjected to silica gel column chromatography (dichloromethane:methanol=0 to 7% gradient) to obtain 24 mg of a 1:1 mixture of ethyl 1-(2-acetoxymethyl-5-amino-4-fluorophenyl)-8-chloro-6-fluoro-7-(2-hydroxyethyl)amino-4-oxo-1,4-dihydroquinoline-3-carboxylate and the deacetylated derivative thereof. 0.50 mL of ethanol, 0.10 mL of a 10 mol/L aqueous solution of sodium hydroxide and 0.50 mL of water were added to the mixture and the mixture was stirred at 50° C. for 2 hours. 1 mol/L hydrochloric acid was added to make the solution acidic (pH 6 to 7). The resulting precipitates were collected by filtration to obtain 19 mg of the title compound.

$^1$H-NMR (DMSO-d$_6$): δ 3.35-3.40 (2H, m), 3.48-3.56 (6H, m), 4.00-4.10 (2H, m), 4.80 (2H, brs), 5.06 (1H, t, J=5.2 Hz), 5.94 (1H, brs), 5.44 (2H, brs), 6.73 (1H, d, J=8.2 Hz), 7.16 (1H, d, J=12.0 Hz), 7.94 (1H, d, J=14.0 Hz), 8.30 (1H, s), 9.87 (1H, t, J=5.5 Hz).

Example 51

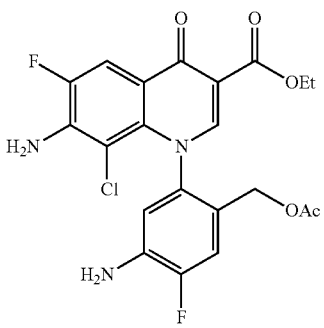 [SMILES: CCOC(=O)c1cn(-c2cc(N)c(F)cc2COC(C)=O)c2c(Cl)c(N)c(F)cc2c1=O]

Ethyl 1-(2-acetoxymethyl-5-amino-4-fluorophenyl)-7-amino-8-chloro-6-fluoro-4-oxo-1,4-dihydroquinoline-3-carboxylate 2.0 mL of acetonitrile, 0.40 mL of 2,4-dimethoxybenzylamine, and 0.40 mL of diisopropylethylamine were added to 0.20 g of ethyl 1-(2-acetoxymethyl-5-amino-4-fluorophenyl)-8-chloro-6,7-difluoro-4-oxo-1,4-dihydroquinoline-3-carboxylate and the mixture was stirred at 80° C. for 2 hours. The reaction solution was cooled to room temperature and diluted with 20 mL of ethyl acetate. The solution was washed twice with 20 mL of a 5% aqueous solution of citric acid, 20 mL of a saturated aqueous solution of sodium bicarbonate, and 20 mL of saturated brine and then dried over anhydrous sodium sulfate. The solvent was evaporated under reduced pressure.

1.0 mL of dichloromethane and 0.50 mL of 4 mol/L hydrochloric acid/1,4-dioxane were added to the residue under ice cooling and the mixture was stirred at room temperature for 1 hour. The reaction solution was diluted with 10 mL of dichloromethane, then washed with 10 mL of a saturated aqueous solution of sodium bicarbonate and 10 mL of saturated brine, and then dried over anhydrous sodium sulfate. The solvent was evaporated under reduced pressure. The residue was subjected to silica gel column chromatography (dichloromethane:methanol=0 to 10% gradient) to obtain 40 mg of the title compound.

$^1$H-NMR (DMSO-$d_6$): δ 1.25 (3H, t, J=7.1 Hz), 1.79 (3H, s), 4.24 (2H, q, J=7.1 Hz), 4.66 (1H, d, J=12.6 Hz), 4.79 (1H, d, J=12.6 Hz), 5.56 (2H, brs), 6.92 (1H, d, J=8.3 Hz), 7.00 (2H, brs), 7.20 (1H, d, J=11.8 Hz), 7.89 (1H, d, J=11.4 Hz), 8.17 (1H, s).

Example 52

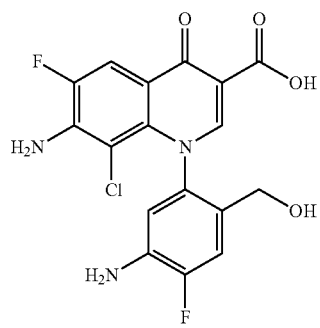 [SMILES: Nc1cc(-n2cc(C(=O)O)c(=O)c3cc(F)c(N)c(Cl)c32)c(CO)cc1F]

7-Amino-1-[5-amino-4-fluoro-2-(hydroxymethyl)phenyl]-8-chloro-6-fluoro-4-oxo-1,4-dihydroquinoline-3-carboxylic acid 0.50 mL of ethanol, 80 μL of a 10 mol/L aqueous solution of sodium hydroxide and 0.50 mL of water were added to 40 mg of ethyl 1-(2-acetoxymethyl-5-amino-4-fluorophenyl)-7-amino-8-chloro-6-fluoro-4-oxo-1,4-dihydroquinoline-3-carboxylate and the mixture was stirred at 50° C. for 4 hours. 1 mol/L hydrochloric acid was added to make the solution acidic (pH 6 to 7). The resulting precipitates were collected by filtration to obtain 27 mg of the title compound.

$^1$H-NMR (DMSO-$d_6$): δ 4.11 (1H, dd, J=4.6 Hz, 12.9 Hz), 5.04 (1H, t, J=5.3 Hz), 5.48 (2H, brs), 6.80 (1H, d, J=8.1 Hz), 6.88 (2H, brs), 7.16 (1H, d, J=11.9 Hz), 7:96 (1H, d, J=11.1 Hz), 8.35 (1H, s).

Example 53

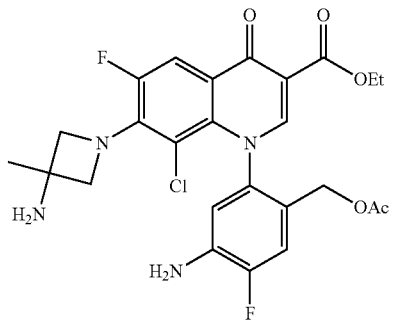 [SMILES: CCOC(=O)c1cn(-c2cc(N)c(F)cc2COC(C)=O)c2c(Cl)c(N3CC(C)(N)C3)c(F)cc2c1=O]

Ethyl 1-(2-acetoxymethyl-5-amino-4-fluorophenyl)-7-(3-amino-3-methylazetidin-1-yl)-8-chloro-6-fluoro-4-oxo-1,4-dihydroquinoline-3-carboxylate 94 mg of ethyl 1-(2-acetoxymethyl-5-amino-4-fluorophenyl)-8-chloro-6,7-difluoro-4-oxo-1,4-dihydroquinoline-3-carboxylate was suspended in 1.0 mL of acetonitrile and 0.21 mL of triethylamine and 66 mg of 3-amino-3-methylazetidine dihydrochloride were added at room temperature. The mixture was stirred at room temperature for 4 days. The resulting precipitates were collected by filtration with acetonitrile to obtain 44 mg of the title compound.

$^1$H-NMR (DMSO-$d_6$): δ 1.23 (3H, t, J=7.0 Hz), 1.33 (3H, s) 1.86 (3H, s), 4.06-4.10 (2H, m), 4.17-4.23 (4H, m), 4.68 (1H, d, J=12.4 Hz), 4.75 (1H, d, J=12.4 Hz), 5.68 (2H, s), 6.76 (1H, d, J=8.2 Hz), 7.25 (1H, d, J=11.8 Hz), 7.75 (1H, d, J=14.1 Hz), 8.15 (1H, s).

Example 54

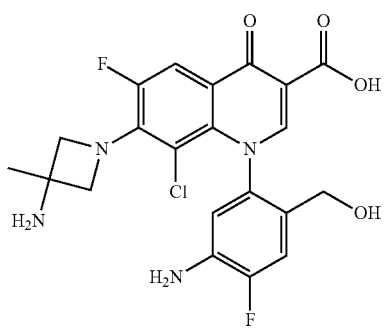 [SMILES: CC1(N)CN(c2c(F)cc3c(=O)c(C(=O)O)cn(-c4cc(N)c(F)cc4CO)c3c2Cl)C1]

1-[5-Amino-4-fluoro-2-(hydroxymethyl)phenyl]-7-(3-amino-3-methylazetidin-1-yl)-8-chloro-6-fluoro-4-oxo-1,4-dihydroquinoline-3-carboxylic acid 44 mg of ethyl 1-(2-acetoxymethyl-5-amino-4-fluorophenyl)-7-(3-amino-3-methylazetidin-1-yl)-8-chloro-6-fluoro-4-oxo-1,4-dihydroquinoline-3-carboxylate was suspended in 0.5 mL of ethanol and 0.16 mL of a 3 mol/L aqueous solution of sodium hydroxide was added at room temperature. The mixture was stirred at 50° C. for 1 day. Ethanol was evaporated under reduced pressure and then the residue was neutralized with hydrochloric acid. The resulting precipitates were collected by filtration with water to obtain 13 mg of the title compound.

$^1$H-NMR (DMSO-$d_6$): δ 1.32 (3H, s), 4.05 (1H, dd, J=13.0, 5.5 Hz), 4.10-4.15 (3H, m), 4.25-4.28 (2H, m), 5.04 (1H, t, J=5.5 Hz), 5.49 (2H, s), 6.78 (1H, d, J=8.1 Hz), 7.15 (1H, d, J=11.9 Hz), 7.88 (1H, d, J=13.9 Hz), 8.37 (1H, s).

Example 55

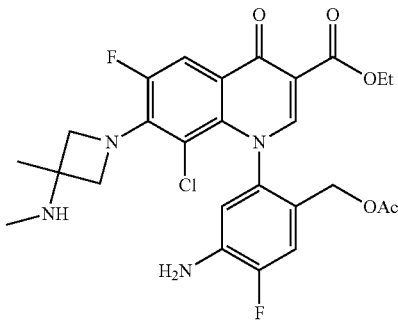 [SMILES: CCOC(=O)c1cn(-c2cc(N)c(F)cc2COC(C)=O)c2c(Cl)c(N3CC(C)(NC)C3)c(F)cc2c1=O]

Ethyl 1-(2-acetoxymethyl-5-amino-4-fluorophenyl)-8-chloro-6-fluoro-7-(3-methyl-3-methylaminoazetidin-1-yl)-4-oxo-1,4-dihydroquinoline-3-carboxylate 94 mg of ethyl 1-(2-acetoxymethyl-5-amino-4-fluorophenyl)-8-chloro-6,7-difluoro-4-oxo-1,4-dihydroquinoline-3-carboxylate was suspended in 1.0 mL of acetonitrile and 0.21 mL of triethylamine and 38 mg of 3-methyl-3-methylaminoazetidine dihydrochloride were added at room temperature. The mixture was stirred at room temperature for 4 days. The resulting precipitates were collected by filtration with acetonitrile to obtain 62 mg of the title compound.

$^1$H-NMR (DMSO-$d_6$): δ 1.23 (3H, t, J=7.1 Hz), 1.29 (3H, s), 1.86 (3H, s), 2.17 (3H, s), 4.09-4.17 (4H, m), 4.19 (2H, d, J=7.1 Hz), 4.68 (1H, d, J=12.4 Hz), 4.75 (1H, d, J=12.4 Hz), 5.68 (2H, s), 6.77 (1H, d, J=8.2 Hz), 7.25 (1H, d, J=11.7 Hz), 7.74 (1H, d, J=14.3 Hz), 8.15 (1H, s).

Example 56

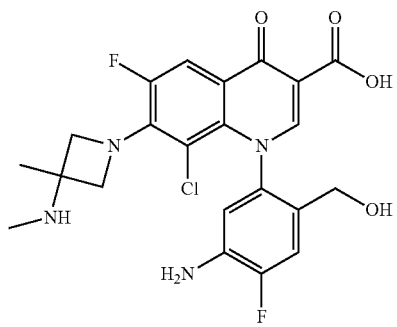 [SMILES: CNC1(C)CN(c2c(F)cc3c(=O)c(C(=O)O)cn(-c4cc(N)c(F)cc4CO)c3c2Cl)C1]

1-[5-Amino-4-fluoro-2-(hydroxymethyl)phenyl]-8-chloro-6-fluoro-7-(3-methyl-3-methylaminoazetidin-1-yl)-4-oxo-1,4-dihydroquinoline-3-carboxylic acid 62 mg of ethyl 1-(2-acetoxymethyl-5-amino-4-fluorophenyl)-8-chloro-6-fluoro-7-(3-methyl-3-methylaminoazetidin-1-yl)-4-oxo-1,4-dihydroquinoline-3-carboxylate was suspended in 0.5 mL of ethanol and 0.22 mL of a 3 mol/L aqueous solution of sodium hydroxide was added at room temperature. The mixture was stirred at 50° C. for 4 days. Ethanol was evaporated under reduced pressure and then the residue was neutralized with hydrochloric acid. The resulting precipitates were collected by filtration with water to obtain 47 mg of the title compound.

$^1$H-NMR (DMSO-$d_6$): δ 1.31 (3H, s), 2.19 (3H, s), 4.06 (1H, dd, J=13.0, 5.0 Hz), 4.12 (1H, dd, J=13.0, 5.0 Hz), 4.18-4.24 (4H, m), 5.05 (1H, t, J=5.0 Hz), 5.49 (2H, s), 6.78 (1H, d, J=8.1 Hz), 7.15 (1H, d, J=11.9 Hz), 7.89 (1H, d, J=13.9 Hz), 8.38 (1H, s).

Example 57

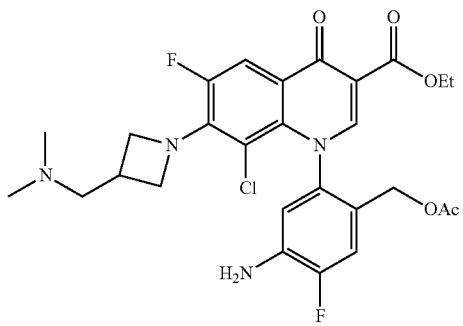 [SMILES: CCOC(=O)c1cn(-c2cc(N)c(F)cc2COC(C)=O)c2c(Cl)c(N3CC(CN(C)C)C3)c(F)cc2c1=O]

Ethyl 1-(2-acetoxymethyl-5-amino-4-fluorophenyl)-8-chloro-7-[3-(dimethylamino)azetidin-1-yl]-6-fluoro-4-oxo-1,4-dihydroquinoline-3-carboxylate 94 mg of ethyl 1-(2-acetoxymethyl-5-amino-4-fluorophenyl)-8-chloro-6,7-difluoro-4-oxo-1,4-dihydroquinoline-3-carboxylate was suspended in 1.0 mL of acetonitrile and 0.16 mL of triethylamine and 45 mg of 3-(dimethylaminomethyl)azetidine dihydrochloride were added at room temperature. The mixture was stirred at room temperature for 4 days. The resulting precipitates were collected by filtration with acetonitrile to obtain 96 mg of the title compound.

$^1$H-NMR (DMSO-$d_6$): δ 1.23 (3H, t, J=7.1 Hz), 1.86 (3H, s), 2.09 (6H, s), 2.43 (1H, d, J=7.6 Hz), 2.73-2.78 (1H, m), 3.97-4.04 (2H, m), 4.19 (2H, q, J=7.1 Hz), 4.44-4.50 (2H, m), 4.68 (1H, d, J=12.4 Hz), 4.74 (1H, d, J=12.4 Hz), 5.67 (2H, s), 6.77 (1H, d, J=8.2 Hz), 7.25 (1H, d, J=11.8 Hz), 7.74 (1H, d, J=14.2 Hz), 8.15 (1H, s).

Example 58

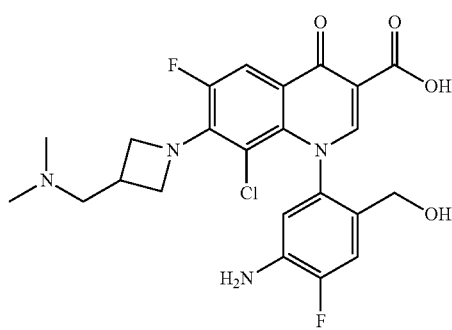 [SMILES: CN(C)CC1CN(c2c(F)cc3c(=O)c(C(=O)O)cn(-c4cc(N)c(F)cc4CO)c3c2Cl)C1]

1-[5-Amino-4-fluoro-2-(hydroxymethyl)phenyl]-8-chloro-7-[3-(dimethylaminomethyl)azetidin-1-yl]-6-fluoro-4-oxo-1,4-dihydroquinoline-3-carboxylic acid 96 mg of ethyl 1-(2-acetoxymethyl-5-amino-4-fluorophenyl)-8-chloro-7-[3-(dimethylaminomethyl)azetidin-1-yl]-6-fluoro-4-oxo-1,4-dihydroquinoline-3-carboxylate was suspended in 1.0 mL of ethanol and 0.34 mL of a 3 mol/L aqueous solution of sodium hydroxide was added at room temperature. The mixture was stirred at room temperature for 7 hours. Ethanol was evaporated under reduced pressure and then the residue was neutralized with hydrochloric acid. The resulting precipitates were collected by filtration with water to obtain 67 mg of the title compound.

$^1$H-NMR (CD$_3$OD): δ 2.78 (6H, s), 3.06-3.12 (1H, m), 4.22 (2H, brs), 4.30 (2H, brs), 4.57 (1H, brs), 4.72 (2H, brs), 6.80 (1H, d, J=8.0 Hz), 7.15 (1H, d, J=11.6 Hz), 7.96 (1H, d, J=13.9 Hz), 8.55 (1H, s).

Example 59

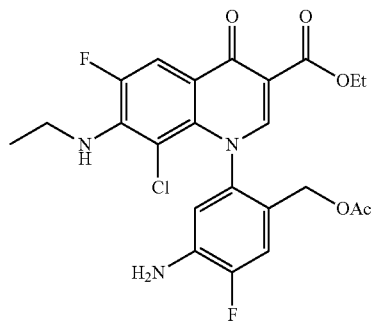 [SMILES: CCNc1c(F)cc2c(=O)c(C(=O)OCC)cn(-c3cc(N)c(F)cc3COC(C)=O)c2c1Cl]

Ethyl 1-(2-acetoxymethyl-5-amino-4-fluorophenyl)-8-chloro-7-ethylamino-6-fluoro-4-oxo-1,4-dihydroquinoline-3-carboxylate 94 mg of ethyl 1-(2-acetoxymethyl-5-amino-4-fluorophenyl)-8-chloro-6,7-difluoro-4-oxo-1,4-dihydroquinoline-3-carboxylate was suspended in 1.0 mL of acetonitrile and 0.20 mL of triethylamine and 24 mg of ethylamine hydrochloride were added at room temperature. The mixture was stirred in a sealed tube at 50° C. for 3 days. The reaction solution was diluted in 50 mL of ethyl acetate and then the diluted solution was washed with 30 mL of a saturated aqueous solution of ammonium chloride and then 30 mL of saturated brine. The obtained solution was dried over anhydrous sodium sulfate. The residue was subjected to silica gel column chromatography (methanol:chloroform=0 to 5' gradient) to obtain 44 mg of the title compound.

$^1$H-NMR (DMSO-$d_6$): δ 1.12 (3H, t, J=7.2 Hz), 1.45 (3H, t, J=7.1 Hz), 1.81 (3H, s), 3.43-3.47 (2H, m), 4.19 (2H, q, J=7.1 Hz), 4.67 (1H, d, J=12.4 Hz), 4.72 (1H, d, J=12.4 Hz), 5.68 (2H, s), 6.04 (1H, t, J=6.3 Hz), 6.80 (1H, d, J=8.2 Hz), 7.27 (1H, d, J=11.8 Hz), 7.83 (1H, d, J=14.3 Hz), 8.15 (1H, s).

Example 60

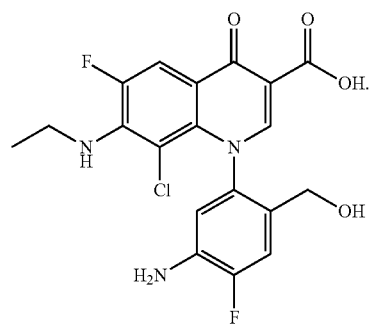 [SMILES: CCNc1c(F)cc2c(=O)c(C(=O)O)cn(-c3cc(N)c(F)cc3CO)c2c1Cl]

1-[5-Amino-4-fluoro-2-(hydroxymethyl)phenyl]-8-chloro-7-ethylamino-6-fluoro-4-oxo-1,4-dihydroquinoline-3-carboxylic acid 44 mg of ethyl 1-(2-acetoxymethyl-5-amino-4-fluorophenyl)-8-chloro-7-ethylamino-6-fluoro-4-oxo-1,4-dihydroquinoline-3-carboxylate was suspended in 0.5 mL of ethanol and 0.18 mL of a 3 mol/L aqueous solution of sodium hydroxide was added at room temperature. The mixture was heated to reflux for 30 minutes. Ethanol was evaporated under reduced pressure and then the residue was neutralized with hydrochloric acid. The resulting precipitates were collected by filtration with water to obtain 32 mg of the title compound.

$^{1}$H-NMR (DMSO-$d_{6}$): δ 0.84 (3H, t, J=7.4 Hz), 3.49-3.52 (2H, m), 4.06 (1H, dd, J=12.8, 5.0 Hz), 4.11 (1H, dd, J=12.8, 5.0 Hz), 5.06 (1H, t, J=5.0 Hz), 5.49 (2H, s), 6.46 (1H, brs), 6.78 (1H, d, J=8.0 Hz), 7.16 (1H, d, J=12.0 Hz), 7.98 (1H, d, J=13.9 Hz), 8.38 (1H, s).

Example 61

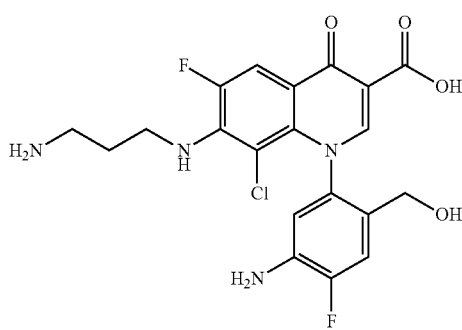 [SMILES: NCCCNc1c(F)cc2c(=O)c(C(=O)O)cn(-c3cc(N)c(F)cc3CO)c2c1Cl]

1-[5-Amino-4-fluoro-2-(hydroxymethyl)phenyl]-7-(3-aminopropylamino)-8-chloro-6-fluoro-4-oxo-1,4-dihydroquinoline-3-carboxylic acid 94 mg of ethyl 1-(2-acetoxymethyl-5-amino-4-fluorophenyl)-8-chloro-6,7-difluoro-4-oxo-1,4-dihydroquinoline-3-carboxylate was suspended in 1.0 mL of acetonitrile and 84 µL of tert-butyl N-(3-aminopropyl)carbamate was added at room temperature. The mixture was stirred at 50° C. for 7 hours. The reaction solution was diluted in 100 mL of ethyl acetate and then the diluted solution was washed with 60 mL of a saturated aqueous solution of ammonium chloride, 60 mL of water and then 60 mL of saturated brine. The obtained solution was dried over anhydrous sodium sulfate. The solvent was evaporated under reduced pressure. The resulting residue was dissolved in 2.0 mL of chloroform and a dioxane solution of 4 mol/L hydrogen chloride was added at room temperature. The mixture was stirred at room temperature for 3 hours. The reaction solution was evaporated under reduced pressure. The resulting residue was dissolved in 1.0 mL of ethanol and 0.40 mL of a 3 mol/L aqueous solution of sodium hydroxide was added at room temperature. The mixture was stirred at room temperature overnight. Ethanol was evaporated under reduced pressure and then the residue was neutralized with hydrochloric acid. The resulting precipitates were collected by filtration with water to obtain 40 mg of the title compound.

$^{1}$H-NMR (DMSO-$d_{6}$): δ 1.65-1.68 (2H, m), 2.67 (2H, t, J=6.6 Hz), 3.54-3.58 (2H, m), 4.05 (1H, d, J=12.0 Hz), 4.10 (1H, d, J=12.0 Hz), 5.06 (1H, brs), 5.50 (2H, s), 6.78 (1H, d, J=8.1 Hz), 7.16 (1H, d, J=11.9 Hz), 7.98 (1H, d, J=14.0 Hz), 8.37 (1H, s).

Example 62

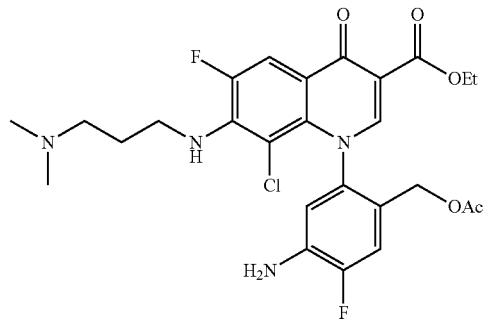 [SMILES: CCOC(=O)c1cn(-c2cc(N)c(F)cc2COC(C)=O)c2c(Cl)c(NCCCN(C)C)c(F)cc2c1=O]

Ethyl 1-(2-acetoxymethyl-5-amino-4-fluorophenyl)-8-chloro-7-[3-(dimethylamino)propylamino]-6-fluoro-4-oxo-1,4-dihydroquinoline-3-carboxylate 94 mg of ethyl 1-(2-acetoxymethyl-5-amino-4-fluorophenyl)-8-chloro-6,7-difluoro-4-oxo-1,4-dihydroquinoline-3-carboxylate was suspended in 1.0 mL of acetonitrile and 60 µL of 3-dimethylaminopropylamine was added at room temperature. The mixture was stirred at room temperature for 4 days. The reaction solution was diluted in 100 mL of ethyl acetate and then washed with 50 mL of water and then 50 mL of saturated brine. The obtained solution was dried over anhydrous sodium sulfate. The solvent was evaporated under reduced pressure to obtain 120 mg of the title compound.

$^{1}$H-NMR (DMSO-$d_{6}$): δ 1.24 (3H, t, J=7.1 Hz), 1.62-1.68 (2H, m), 1.81 (3H, s), 2.09 (9H, s), 2.27 (2H, t, J=6.5 Hz), 3.48-3.52 (2H, m), 4.19 (2H, q, J=7.1 Hz), 4.66 (1H, d, J=12.3 Hz), 4.72 (1H, d, J=12.3 Hz), 5.69 (2H, s), 6.63 (1H, t, J=6.3 Hz), 6.80 (1H, d, J=8.2 Hz), 7.27 (1H, d, J=11.7 Hz), 7.82 (1H, d, J=14.2 Hz), 8.14 (1H, s).

Example 63

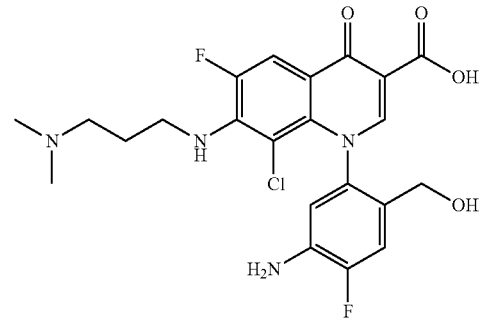 [SMILES: CN(C)CCCNc1c(F)cc2c(=O)c(C(=O)O)cn(-c3cc(N)c(F)cc3CO)c2c1Cl]

1-[5-Amino-4-fluoro-2-(hydroxymethyl)phenyl]-8-chloro-7-[3-(dimethylaminopropyl)amino]-6-fluoro-4-oxo-1,4-dihydroquinoline-3-carboxylic acid 120 mg of ethyl 1-(2-acetoxymethyl-5-amino-4-fluorophenyl)-8-chloro-7-[3-(dimethylaminopropyl)amino]-6-fluoro-4-oxo-1,4-dihydroquinoline-3-carboxylate was suspended in 1.0 mL of ethanol and 0.40 mL of a 3 mol/L aqueous solution of sodium hydroxide was added at room temperature. The mixture was stirred at 50° C. for 3 hours. Ethanol was evaporated under reduced pressure and then the residue was neutralized with hydrochloric acid. The resulting precipitates were collected by filtration with water to obtain 55 mg of the title compound.

$^1$H-NMR (DMSO-$d_6$): δ 1.87-1.91 (2H, m), 2.72 (6H, brs), 3.03 (2H, brs), 3.51-3.53 (2H, m), 4.06 (1H, dd, J=12.9, 5.0 Hz), 4.11 (1H, dd, J=12.9, 5.0 Hz), 5.06 (1H, t, J=5.0 Hz), 5.52 (2H, s), 6.57 (1H, br s), 6.78 (1H, d, J=8.1 Hz), 7.17 (1H, d, J=11.9 Hz), 8.02 (1H, d, J=14.0 Hz), 8.40 (1H, s).

Example 64

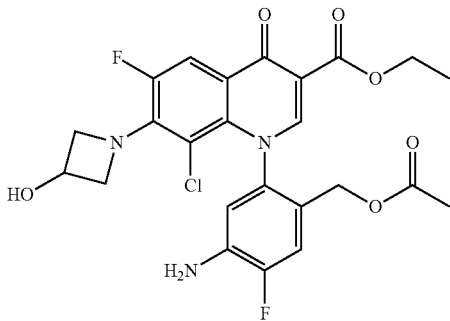 [SMILES: CCOC(=O)c1cn(-c2cc(N)c(F)cc2COC(C)=O)c2c(Cl)c(N3CC(O)C3)c(F)cc2c1=O]

Ethyl 1-(2-acetoxymethyl-5-amino-4-fluorophenyl)-8-chloro-6-fluoro-7-(3-hydroxyazetidin-1-yl)-4-oxo-1,4-dihydroquinoline-3-carboxylate 94 mg of ethyl 1-(2-acetoxymethyl-5-amino-4-fluorophenyl)-8-chloro-6,7-difluoro-4-oxo-1,4-dihydroquinoline-3-carboxylate was suspended in 1.0 mL of acetonitrile and 0.240 mL of triethylamine and 88 mg of 3-hydroxyazetidine tartrate were added. The mixture was stirred at 50° C. for 20 hours. The resulting precipitates were collected by filtration with acetonitrile to obtain 76 mg of the title compound.

$^1$H-NMR (DMSO-$d_6$) δ 1.23 (3H, t, J=7.1 Hz), 1.86 (3H, s), 4.00-4.09 (2H, m), 4.19 (2H, q, J=7.1 Hz), 4.37-4.46 (1H, m), 4.56-4.64 (2H, m), 4.68 (1H, d, J=12.3 Hz), 4.74 (1H, d, J=12.3 Hz), 5.69 (2H, br s), 6.79 (1H, d, J=8.1 Hz), 7.25 (1H, d, J=11.8 Hz), 7.75 (1H, d, J=14.1 Hz), 8.16 (1H, s).

Example 65

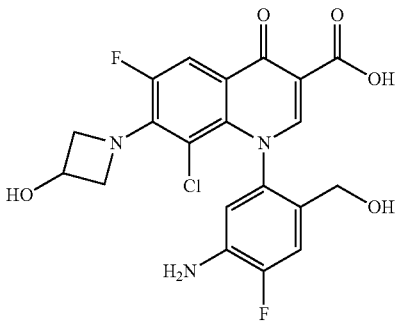 [SMILES: Nc1cc(-n2cc(C(=O)O)c(=O)c3cc(F)c(N4CC(O)C4)c(Cl)c32)c(CO)cc1F]

1-[5-Amino-4-fluoro-2-(hydroxymethyl)phenyl]-8-chloro-6-fluoro-7-[3-hydroxyazetidin-1-yl]-4-oxo-1,4-dihydroquinoline-3-carboxylic acid 76 mg of ethyl 1-(2-acetoxymethyl-5-amino-4-fluorophenyl)-8-chloro-6-fluoro-7-(3-hydroxyazetidin-1-yl)-4-oxo-1,4-dihydroquinoline-3-carboxylate was suspended in 1.0 mL of ethanol and 0.5 mL of a 3 mol/L aqueous solution of sodium hydroxide was added. The mixture was stirred at 50° C. for 10 minutes. 1 mol/l hydrochloric acid was added to the reaction solution to neutralize the solution. The resulting precipitates were collected by filtration with water to obtain 48 mg of the title compound.

$^1$H-NMR (DMSO-$d_6$) δ 4.06 (1H, d, J=12.8 Hz), 4.10-4.16 (3H, m), 4.40-4.47 (1H, m), 4.65-4.71 (2H, m), 5.50 (2H, brs), 6.79 (1H, d, J=8.1 Hz), 7.15 (1H, d, J=12.0 Hz), 7.89 (1H, d, J=13.8 Hz), 8.38 (1H, s).

Example 66

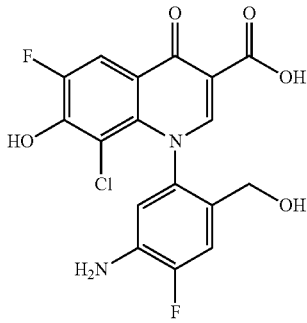 [SMILES: Nc1cc(-n2cc(C(=O)O)c(=O)c3cc(F)c(O)c(Cl)c32)c(CO)cc1F]

1-[5-Amino-4-fluoro-2-(hydroxymethyl)phenyl]-8-chloro-6-fluoro-7-hydroxy-4-oxo-1,4-dihydroquinoline-3-carboxylic acid 1.0 mL of water and 0.50 mL of a 10 mol/L aqueous solution of sodium hydroxide were added to 0.30 g of ethyl 1-(2-acetoxymethyl-5-amino-4-fluorophenyl)-8-chloro-6,7-difluoro-4-oxo-1,4-dihydroquinoline-3-carboxylate and the mixture was heated to reflux for 1 hour. The reaction solution was cooled to room temperature and 1 mol/L hydrochloric acid was added to make the solution acidic (pH 6 to 7). The resulting precipitates were collected by filtration to obtain 0.23 g of the title compound.

$^1$H-NMR (CDCl$_3$): δ 4.04 (1H, d, J=12.9 Hz), 4.11 (1H, d, J=13 Hz), 5.04 (1H, brs), 5.49 (2H, brs), 6.82 (1H, d, J=8.1 Hz), 7.51 (1H, d, J=11.9 Hz), 8.06 (1H, d, J=10.4 Hz), 8.39 (1H, s).

Example 67

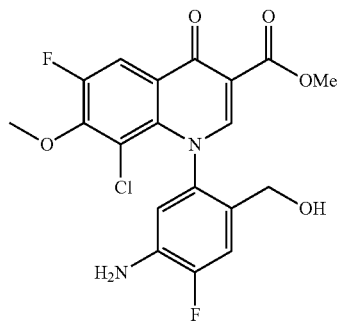 [SMILES: COC(=O)c1cn(-c2cc(N)c(F)cc2CO)c2c(Cl)c(OC)c(F)cc2c1=O]

Methyl 1-[5-amino-4-fluoro-2-(hydroxymethyl)phenyl]-8-chloro-6-fluoro-7-methoxy-4-oxo-1,4-dihydroquinoline-3-carboxylate 2.0 mL of methanol and 55 mg of potassium carbonate were added to 91 mg of ethyl 1-(2-acetoxymethyl-5-amino-4-fluorophenyl)-8-chloro-6,7-difluoro-4-oxo-1,4-dihydroquinoline-3-carboxylate and the mixture was stirred at room temperature overnight. The resulting precipitates were collected by filtration and then washed with 2.0 mL of water to obtain 60 mg of the title compound.

$^1$H-NMR (DMSO-$d_6$): δ 3.73 (3H, s), 3.95 (3H, d, J=1.9 Hz), 4.13-4.07 (2H, m), 5.04 (1H, t, J=5.6 Hz), 5.45 (2H, brs), 6.79 (1H, d, J=8.1 Hz), 7.15 (1H, d, J=11.9 Hz), 8.08 (1H, d, J=11.3 Hz), 8.31 (1H, s).

Example 68

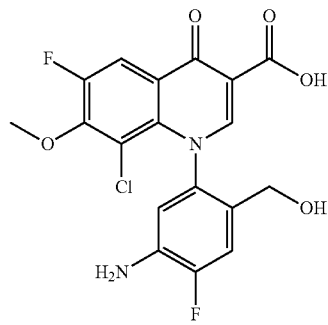 [SMILES: COc1c(F)cc2c(=O)c(C(=O)O)cn(-c3cc(N)c(F)cc3CO)c2c1Cl]

1-[5-Amino-4-fluoro-2-(hydroxymethyl)phenyl]-8-chloro-6-fluoro-7-methoxy-4-oxo-1,4-dihydroquinoline-3-carboxylic acid 1.0 mL of ethanol, 0.10 mL of a 10 mol/L aqueous solution of sodium hydroxide, and 0.90 mL of water were added to 60 mg of methyl 1-[5-amino-4-fluoro-2-(hydroxymethyl)phenyl]-8-chloro-6-fluoro-7-methoxy-4-oxo-1,4-dihydroquinoline-3-carboxylate and the mixture was stirred at room temperature overnight. A 5% aqueous solution of citric acid was added to make the solution acidic (pH 5 to 6). The resulting precipitates were collected by filtration to obtain 48 mg of the title compound.

$^1$H-NMR (DMSO-$d_6$): δ 4.01 (3H, d, J=2.3 Hz), 4.04-4.12 (2H, m), 5.02 (1H, t, J=5.4 Hz), 5.52 (2H, brs), 6.86 (1H, d, J=8.2 Hz), 7.17 (1H, d, J=12.0 Hz), 8.25 (1H, d, J=11.1 Hz), 8.50 (1H, s).

Reference Example 11

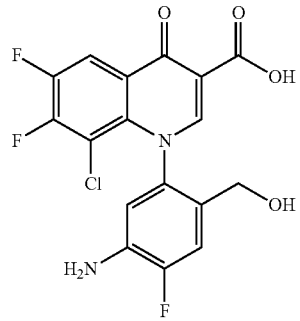 [SMILES: Nc1cc(-n2cc(C(=O)O)c(=O)c3cc(F)c(F)c(Cl)c32)c(CO)cc1F]

1-[5-Amino-4-fluoro-2-(hydroxymethyl)phenyl]-8-chloro-6,7-difluoro-4-oxo-1,4-dihydroquinoline-3-carboxylic acid 1.0 mL of acetic acid and 2.0 mL of 6 mol/L hydrochloric acid were added to 85 mg of ethyl 1-(2-acetoxymethyl-5-amino-4-fluorophenyl)-8-chloro-6,7-difluoro-4-oxo-1,4-dihydroquinoline-3-carboxylate and the mixture was stirred at 80° C. for 2 hours. The reaction solution was poured into 8.0 mL of water and a 10% aqueous solution of sodium hydroxide was added to adjust pH to 6. The resulting precipitates were collected by filtration. The collected precipitates were subjected to silica gel column chromatography (methanol: 1% acetic acid/chloroform=0 to 5% gradient) to obtain 33 mg of the title compound.

$^1$H-NMR (DMSO-$d_6$): δ 4.08 (1H, dd, J=5.5 Hz, 12.7 Hz), 4.13 (1H, dd, J=5.5 Hz, 12.7 Hz), 5.02 (1H, t, J=5.1 Hz), 5.58 (2H, brs), 6.90 (1H, d, J=8.3 Hz), 7.18 (1H, d, J=11.9 Hz), 8.42 (1H, t, J=9.6 Hz), 8.53 (1H, s).

Example 69

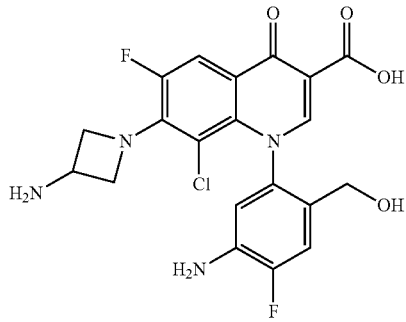 [SMILES: Nc1cc(-n2cc(C(=O)O)c(=O)c3cc(F)c(N4CC(N)C4)c(Cl)c32)c(CO)cc1F]

7-(3-Aminoazetidin-1-yl)-1-[5-amino-4-fluoro-2-(hydroxymethyl)phenyl]-8-chloro-6-fluoro-4-oxo-1,4-dihydroquinoline-3-carboxylic acid 0.18 mL of dimethylsulfoxide, 11 mg of 3-aminoazetidine dihydrochloride, 18 mg of lithium chloride, and 36 µL of N-methylpyrrolidine were added to 18 mg of 1-[5-amino-4-fluoro-2-(hydroxymethyl)phenyl]-8-chloro-6,7-difluoro-4-oxo-1,4-dihydroquinoline-3-carboxylic acid and the mixture was stirred at 50° C. for 20 minutes. 1.5 mL of diethyl ether was added to the reaction solution. The mixture was stirred and then the supernatant was removed by decantation. This procedure was repeated five times. 0.20 mL of water was added to the residue and then a 10% aqueous solution of citric acid was added to make the solution acidic (pH 6). The resulting precipitates were collected by filtration to obtain 18 mg of the title compound.

$^1$H-NMR (DMSO-d$_6$): δ 3.63-3.72 (1H, m), 3.97-4.04 (3H, m), 4.11 (1H, d, J=13.3 Hz), 4.56-4.69 (2H, m), 5.04 (1H, brm), 5.48 (2H, brs), 6.77 (1H, d, J=8.3 Hz), 7.15 (1H, d, J=12.0 Hz), 7.88 (1H, d, J=13.7 Hz), 8.35 (1H, s).

Reference Example 12

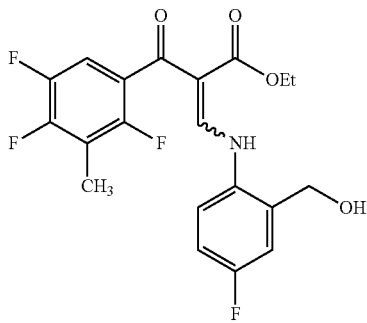 [SMILES: CCOC(=O)C(=CNc1ccc(F)cc1CO)C(=O)c1cc(F)c(F)c(C)c1F]

Ethyl 3-[4-fluoro-2-(hydroxymethyl)phenyl]amino-2-(3-methyl-2,4,5-trifluorobenzoyl)acrylate 14.5 g of potassium monoethyl malonate was added to 20 mL of 6 mol/L cold hydrochloric acid and then the mixture was extracted with diethyl ether. The extract was washed with saturated brine and then dried over anhydrous sodium sulfate. The solvent was evaporated under reduced pressure and then 20 mL of acetonitrile, 1.9 g of magnesium chloride, and 4.1 g of triethylamine were added to the resulting residue under ice cooling. The mixture was stirred at room temperature for 4 hours to obtain a suspension. 15 mL of acetonitrile and 2.8 g of carbonyldiimidazole were added to 3.5 g of 3-methyl-2,4,5-trifluorobenzoic acid and the mixture was stirred at room temperature for 4 hours. The reaction solution was added to the aforementioned suspension at room temperature and the mixture was stirred at 80° C. for 3 hours. 100 mL of 1 mol/L hydrochloric acid was added and then the mixture was extracted with ethyl acetate. The extract was dried over anhydrous sodium sulfate. The solvent was evaporated under reduced pressure and the residue was subjected to silica gel column chromatography (n-hexane/ethyl acetate=200) to obtain 3.9 g of ethyl 2-(3-methyl-2,4,5-trifluoro)benzoylacetate.

3 mL of the acetic anhydride and 3 mL of ethyl orthoformate were added to the obtained compound and the mixture was stirred at 130° C. for 6 hours. The solvent was evaporated under reduced pressure. The residue was subjected to azeotropic distillation twice with toluene and the resulting residue was dissolved in dichloromethane to prepare a 1 mol/L solution for use in the following reaction.

29.7 mL of N,N-dimethylformamide and 29.7 mL of the dichloromethane solution of ethoxyacrylate prepared earlier were added to 4.19 g of 2-amino-5-fluorophenylmethanol and the mixture was stirred at room temperature for 1 hour. The solvent was evaporated under reduced pressure and ethyl acetate was added to the residue. The mixture was washed with water. The organic layer was dried using anhydrous sodium sulfate and the solvent was evaporated under reduced pressure. The resulting residue was dispersed in hexane, collected by filtration, and dried under reduced pressure to obtain 10.4 g of the title compound.

$^1$H-NMR (DMSO-d$_6$): δ 0.91 (0.9H, t, J=7.1 Hz), 1.00 (2.1H, t, J=7.2 Hz), 2.21 (3H, brs), 3.97-4.03 (2H, m), 4.60 (2H, d, J=4.6 Hz), 5.79-5.83 (1H, m), 7.20-7.29 (2H, m), 7.36-7.45 (1H, m), 7.58 (0.3H, dd, J=4.5, 8.6 Hz), 7.65 (0.7H, dd, J=4.8, 8.7 Hz), 8.36 (0.3H, d, J=14.3 Hz), 8.46 (0.7H, d, J=13.8 Hz).

Reference Example 13

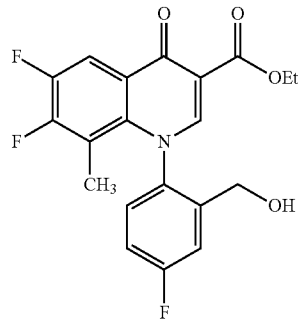 [SMILES: CCOC(=O)c1cn(-c2ccc(F)cc2CO)c2c(C)c(F)c(F)cc2c1=O]

Ethyl 6,7-difluoro-1-[4-fluoro-2-(hydroxymethyl)phenyl]-8-methyl-4-oxo-1,4-dihydroquinoline-3-carboxylate 29.3 g of ethyl 3-[4-fluoro-2-(hydroxymethyl)phenylamino]-2-(3-methyl-2,4,5-trifluorobenzoyl)acrylate and 3.4 g of lithium chloride were dissolved in 150 mL of N,N-dimethylformamide and 11.5 g of 1,8-diazabicyclo[5.4.0]undec-7-ene was added. The mixture was stirred at room temperature overnight. The reaction solution was poured into 1 L of iced water and precipitated crystals were collected by filtration and dried. The crystals were dissolved in 1 L of chloroform, washed with water, then dried over anhydrous magnesium sulfate, and evaporated under reduced pressure. The resulting residue was dispersed in diisopropyl ether, collected by filtration, and dried to obtain 20.0 g of the title compound.

$^1$H NMR (DMSO-d$_6$): δ 1.25 (3H, t, J=7.0 Hz), 1.58 (3H, t, J=2.8 Hz), 4.21 (2H, q, J=7.0 Hz), 4.26 (2H, d, J=5.5 Hz), 5.43 (1H, t, J=5.5 Hz), 7.37 (1H, dt, J=2.8, 8.5 Hz), 7.45 (1H, dd, J=2.8, 9.2 Hz), 7.71 (1H, dd, J=5.0, 8.5 Hz), 8.09 (1H, t, J=9.2 Hz), 8.33 (1H, s).

Reference Example 14

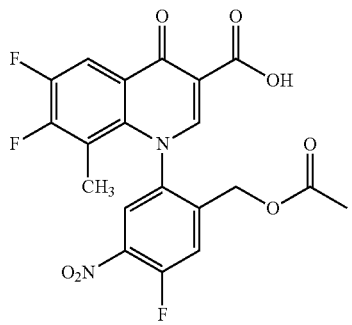 [SMILES: CC(=O)OCc1cc(F)c([N+](=O)[O-])cc1-n1cc(C(=O)O)c(=O)c2cc(F)c(F)c(C)c21]

1-(2-Acetoxymethyl-4-fluoro-5-nitrophenyl)-6,7-difluoro-8-methyl-4-oxo-1,4-dihydroquinoline-3-carboxylic acid 3.9 g of ethyl 6,7-difluoro-1-[4-fluoro-2-(hydroxymethyl)phenyl]-8-methyl-4-oxo-1,4-dihydroquinoline-3-carboxylate was dissolved in 40 mL of concentrated sulfuric acid and 2.4 g of potassium nitrate was added. The mixture was stirred at 60° C. for 4.5 hours. The reaction solution was poured into 500 mL of iced water and extracted with 500 mL of ethyl acetate. The organic layer was dried over anhydrous magnesium sulfate and evaporated under reduced pressure to obtain an oily substance. This was dissolved in 50 mL of acetic acid and the solution was stirred at 80° C. for 3 hours. The solvent was evaporated under reduced pressure and the residue was dissolved in 200 mL of chloroform. The organic layer was washed with water and then a saturated aqueous solution of sodium hydrogen carbonate, then dried over anhydrous magnesium sulfate, and evaporated under reduced pressure. The obtained residue was dispersed in ethyl acetate, collected by filtration, and dried to obtain 1.40 g of the title compound.

$^1$H-NMR (DMSO-$d_6$): δ 1.72 (3H, d, J=3 Hz), 1.88 (3H, s), 4.91 (1H, d, J=14 Hz), 5.00 (1H, d, J=14 Hz), 7.92 (1H, d, J=12 Hz), 8.28 (1H, dd, J=10 Hz, 9 Hz), 8.76 (1H, d, J=7 Hz), 8.80 (1H, s)

Reference Example 15

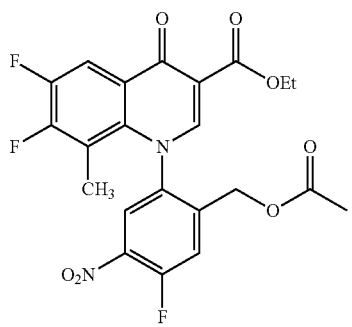 [SMILES: CCOC(=O)c1cn(-c2cc([N+](=O)[O-])c(F)cc2COC(C)=O)c2c(C)c(F)c(F)cc2c1=O]

Ethyl 1-(2-acetoxymethyl-4-fluoro-5-nitrophenyl)-6,7-difluoro-8-methyl-4-oxo-1,4-dihydroquinoline-3-carboxylate 1.40 g of 1-(2-acetoxymethyl-4-fluoro-5-nitrophenyl)-6,7-difluoro-8-methyl-4-oxo-1,4-dihydroquinoline-3-carboxylic acid was suspended in 40 mL of dichloromethane, and 40 μL of N,N-dimethylformamide and then 540 μL of oxalyl chloride were added. The mixture was stirred for 10 minutes. 20 mL of ethanol was further added to this mixture. The reaction solution was washed with a saturated aqueous solution of sodium hydrogen carbonate, then dried over anhydrous magnesium sulfate, and evaporated under reduced pressure. The resulting residue was separated by using a silica gel column chromatography (0 to 2% methanol/chloroform) to obtain 800 mg of the title compound.

$^1$H-NMR (DMSO-$d_6$): δ 1.25 (3H, t, J=7 Hz), 1.66 (3H, d, J=3 Hz), 1.89 (3H, s), 4.22 (2H, q, J=7 Hz), 4.87 (1H, d, J=14 Hz), 4.99 (1H, d, J=14 Hz), 7.90 (1H, d, J=12 Hz), 8.09 (1H, dd, J=10 Hz, 9 Hz), 8.45 (1H, s), 8.72 (1H, d, J=7 Hz)

Reference Example 16

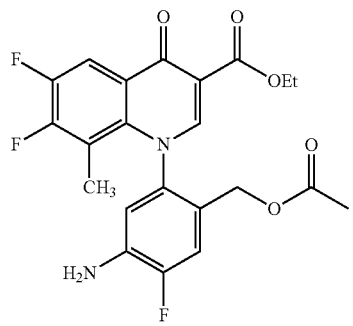 [SMILES: CCOC(=O)c1cn(-c2cc(N)c(F)cc2COC(C)=O)c2c(C)c(F)c(F)cc2c1=O]

Ethyl 1-(2-acetoxymethyl-5-amino-4-fluorophenyl)-6,7-difluoro-8-methyl-4-oxo-1,4-dihydroquinoline-3-carboxylate 1.44 g of ethyl 1-(2-acetoxymethyl-4-fluoro-5-nitrophenyl)-6,7-difluoro-8-methyl-4-oxo-1,4-dihydroquinoline-3-carboxylate was dissolved in 30 mL of acetic acid, and 800 mg of reduced iron was added and the mixture was stirred at 70° C. for 1 hour. Insoluble matter was filtered off with celite and the filtrate was evaporated under reduced pressure. The resulting residue was dissolved in 200 mL of chloroform and washed with water and then a saturated aqueous solution of sodium hydrogen carbonate. The organic layer was dried over anhydrous magnesium sulfate and evaporated under reduced pressure. The resulting residue was separated by using a silica gel column chromatography (0 to 2% methanol/chloroform) to obtain 0.82 g of the title compound.

$^1$H-NMR (DMSO-$d_6$): δ 1.25 (3H, t, J=7 Hz), 1.73 (3H, d, J=3 Hz), 1.76 (3H, s), 4.21 (2H, q, J=7 Hz), 4.61 (1H, d, J=13 Hz), 4.71 (1H, d, J=13 Hz), 5.82 (2H, s), 6.96 (1H, d, J=8 Hz), 7.31 (1H, d, J=12 Hz), 8.07 (1H, dd, J=10 Hz, 9 Hz), 8.29 (1H, s)

Reference Example 17

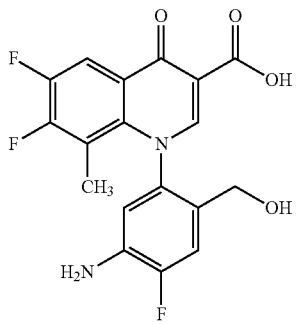 [SMILES: Cc1c(F)c(F)cc2c(=O)c(C(=O)O)cn(-c3cc(N)c(F)cc3CO)c12]

1-[5-Amino-4-fluoro-2-(hydroxymethyl)phenyl]-6,7-difluoro-8-methyl-4-oxo-1,4-dihydroquinoline-3-carboxylic acid 590 mg of ethyl 1-(2-acetoxymethyl-5-amino-4-fluorophenyl)-6,7-difluoro-8-methyl-4-oxo-1,4-dihydroquinoline-3-carboxylate was suspended in 4 mL of ethanol and 4 mL of a 1 mol/L aqueous solution of sodium hydroxide was added. The mixture was stirred at 80° C. for 10 minutes and then at room temperature for 1 hour. To the reaction solution, 10 mL of water was added and 0.7 mL of 6 mol/L hydrochloric acid was further added to make the solution acidic. Precipitated crystals were collected by filtration. The obtained crystals were washed with water and then ethanol and then dried to obtain 470 mg of the title compound.

$^1$H-NMR (DMSO-d$_6$): δ 1.79 (3H, d, J=3 Hz), 4.02-4.11 (2H, m), 5.02 (1H, t, J=5 Hz), 5.64 (2H, s), 6.93 (1H, d, J=8 Hz), 7.21 (1H, d, J=12 Hz), 8.25 (1H, dd, J=10 Hz, 9 Hz), 8.54 (1H, s)

Example 70

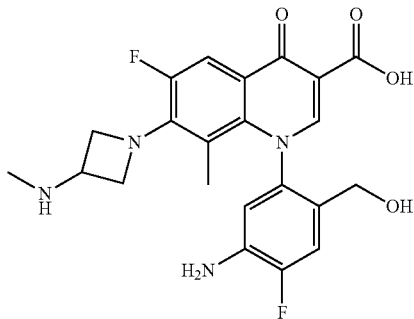 [SMILES: CNC1CN(c2c(F)cc3c(=O)c(C(=O)O)cn(-c4cc(N)c(F)cc4CO)c3c2C)C1]

1-[5-Amino-4-fluoro-2-(hydroxymethyl)phenyl]-6-fluoro-8-methyl-7-(3-methylamino)azetidin-1-yl)-4-oxo-1,4-dihydroquinoline-3-carboxylic acid 132 mg of 1-[5-amino-4-fluoro-2-(hydroxymethyl)phenyl]-6,7-difluoro-8-methyl-4-oxo-1,4-dihydroquinoline-3-carboxylic acid, 80 mg of 3-methylaminoazetidine dihydrochloride, 42 mg of lithium hydroxide monohydrate, and 42 mg of lithium chloride were suspended in 0.5 mL of dimethylsulfoxide. 75 mg of 1,1,3,3-tetramethylguanidine was added to the suspension and the mixture was stirred at room temperature for 5 days. Addition of diethyl ether to the reaction solution and decantation were repeated five times. Then 3 mL of water was added to the resultant to dissolve the solution and hydrochloric acid was added to make the solution acidic. Precipitated crystals were collected by filtration and dried to obtain 120 mg of a crude form of the title compound. This was added to and dissolved in 16 mL of 0.5 mol/L hydrochloric acid and insoluble matter was filtered off. A saturated aqueous solution of sodium hydrogen carbonate was added to the filtrate for neutralization and precipitated crystals were collected by filtration. The crystals were washed with water and then ethanol and then dried to obtain 55 mg of the title compound.

$^1$H-NMR (DMSO-d$_6$): δ 1.58 (3H, s), 2.19 (3H, s), 3.42-3.47 (1H, m), 3.82-3.93 (2H, m), 3.95-4.11 (2H, m), 4.33-4.40 (2H, m), 5.04 (1H, t, J=5 Hz), 5.55 (2H, s), 6.88 (1H, d, J=8 Hz), 7.19 (1H, d, J=12 Hz), 7.78 (1H, d, J=14 Hz), 8.44 (1H, s)

Example 71

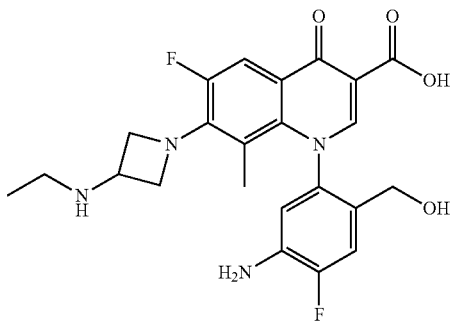 [SMILES: CCNC1CN(c2c(F)cc3c(=O)c(C(=O)O)cn(-c4cc(N)c(F)cc4CO)c3c2C)C1]

1-[5-Amino-4-fluoro-2-(hydroxymethyl)phenyl]-7-[3-(ethylamino)azetidin-1-yl]-6-fluoro-8-methyl-4-oxo-1,4-dihydroquinoline-3-carboxylic acid 132 mg of 1-[5-amino-4-fluoro-2-(hydroxymethyl)phenyl]-6,7-difluoro-8-methyl-4-oxo-1,4-dihydroquinoline-3-carboxylic acid, 87 mg of 3-ethylaminoazetidine dihydrochloride, 42 mg of lithium hydroxide monohydrate and 42 mg of lithium chloride were suspended in 0.5 mL of dimethylsulfoxide. 75 mg of 1,1,3,3-tetramethylguanidine was added to the suspension and the mixture was stirred at room temperature for 3 days. Addition of diethyl ether to the reaction solution and decantation were repeated five times. Then 3 mL of water was added to the solution for dissolution and hydrochloric acid was added to make the solution acidic. Precipitated crystals were collected by filtration, washed with water and then ethanol, and then dried to obtain 120 mg of the title compound.

$^1$H-NMR (DMSO-d$_6$): δ 0.93 (3H, t, J=7 Hz), 1.57 (3H, s), 2.46 (2H, q, J=7 Hz), 3.51-3.56 (1H, m), 3.80-3.84 (1H, m), 3.89-3.92 (1H, m), 3.95-3.98 (1H, m), 4.07-4.11 (1H, m), 4.36-4.42 (2H, m), 5.03 (1H, t, J=5 Hz), 5.55 (2H, s), 6.88 (1H, d, J=8 Hz), 7.18 (1H, d, J=12 Hz), 7.78 (1H, d, J=14 Hz), 8.43 (1H, s)

Example 72

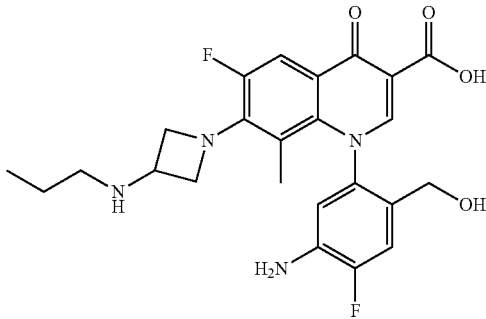

1-[5-Amino-4-fluoro-2-(hydroxymethyl)phenyl]-6-fluoro-8-methyl-4-oxo-7-[3-(propylamino)azetidin-1-yl]-1,4-dihydroquinoline-3-carboxylic acid 132 mg of 1-[5-amino-4-fluoro-2-(hydroxymethyl)phenyl]-6,7-difluoro-8-methyl-4-oxo-1,4-dihydroquinoline-3-carboxylic acid, 92 mg of 3-propylaminoazetidine dihydrochloride, 42 mg of lithium hydroxide monohydrate, 42 mg of lithium chloride were suspended in 0.5 mL of dimethylsulfoxide. 75 mg of 1,1,3,3-tetramethylguanidine was added to the suspension and the mixture was stirred at room temperature for 6 days. Addition of diethyl ether to the reaction solution and decantation were repeated five times. Then, 10 mL of water was added to dissolve the solution and hydrochloric acid was added to neutralize the solution. Precipitated crystals were collected by filtration, washed with water and then ethanol, and then dried to obtain 110 mg of a crude form of the title compound. This is suspended in 12 mL of 1.0 mol/L hydrochloric acid. The suspension was stirred at room temperature for 30 minutes and then 4 mol/L aqueous solution of sodium hydroxide was added to neutralize the suspension. The obtained crystals were collected by filtration. The crystals were washed with water and then washed with ethanol, and then dried to obtain 68 mg of the title compound.

$^1$H-NMR (DMSO-$d_6$): δ 0.88 (3H, t, J=7 Hz), 1.43-1.50 (2H, m), 1.59 (3H, s), 2.59-2.62 (2H, m), 3.77 (1H, br), 3.93-4.15 (4H, m), 4.40-4.47 (2H, m), 5.03 (1H, t, J=5 Hz), 5.57 (2H, s), 6.91 (1H, d, J=8 Hz), 7.19 (1H, d, J=12 Hz), 7.82 (1H, d, J=14 Hz), 8.44 (1H, s)

Example 73

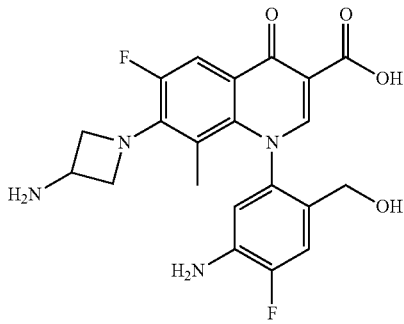 [SMILES: Cc1c(N2CC(N)C2)c(F)cc2c(=O)c(C(=O)O)cn(-c3cc(N)c(F)cc3CO)c12]

7-(3-Aminoazetidin-1-yl)-1-[5-amino-4-fluoro-2-(hydroxymethyl)phenyl]-6-fluoro-8-methyl-4-oxo-1,4-dihydroquinoline-3-carboxylic acid 50 μL of dimethylsulfoxide, 7 mg of 3-aminoazetidine dihydrochloride, 4 mg of lithium chloride, 7.5 μL of 1,1,3,3-tetramethylguanidine were added to 11 mg of 1-(5-amino-4-fluoro-2-hydroxymethyl)phenyl-6,7-difluoro-8-methyl-4-oxo-1,4-dihydroquinoline-3-carboxylic acid and the mixture was stirred at 65° C. for 22 hours. 1.5 mL of diethyl ether was added to the reaction solution. The mixture was stirred and then the supernatant was removed by decantation. This procedure was repeated five times. 0.20 mL of water was added to the residue and then a 10% aqueous solution of citric acid was added to make the solution acidic (pH 6). The resulting precipitates were collected by filtration to obtain 6 mg of the title compound.

$^1$H-NMR (DMSO-$d_6$): δ 1.56 (3H, s), 3.68-3.77 (2H, m), 3.82-3.88 (1H, m), 3.97 (1H, d, J=13.5 Hz), 4.10 (1H, d, J=13.5 Hz), 4.36-4.43 (2H, m), 5.04 (1H, brm), 5.57 (2H, brs), 6.89 (1H, d, J=8.3 Hz), 7.20 (1H, d, J=11.5 Hz), 7.80 (1H, d, J=13.8 Hz), 8.43 (1H, s)

Reference Example 18

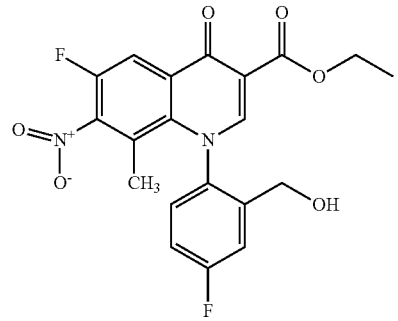 [SMILES: CCOC(=O)c1cn(-c2ccc(F)cc2CO)c2c(C)c([N+](=O)[O-])c(F)cc2c1=O]

Ethyl 6-fluoro-1-[4-fluoro-2-(hydroxymethyl)phenyl]-8-methyl-7-nitro-4-oxo-1,4-dihydroquinoline-3-carboxylate 1.02 g of ethyl 2-(2,5-difluoro-3-methyl-4-nitrobenzoyl)-3-ethoxyacrylate was dissolved in 20 mL of dichloromethane and 282 mg of (2-amino-5-fluorophenyl)methanol was added thereto. The mixture was stirred at room temperature for 50 minutes. The solvent was evaporated under reduced pressure. 550 mg of potassium carbonate and 10 mL of N,N-dimethylformamide were added to the residue and the mixture was stirred at 75° C. for 0.5 hours. 200 mL of a 5% aqueous solution of citric acid was added and the mixture was extracted with 200 mL of ethyl acetate. The organic layer was washed with 200 mL of water and 100 mL of saturated brine. The organic layer was dried and then concentrated under reduced pressure. Diethyl ether was added and the resulting precipitates were collected by filtration to obtain 540 mg of the title compound as a colorless powder.

$^1$H-NMR (DMSO-$d_6$): δ 1.25 (3H, t, J=7.0 Hz), 1.61 (3H, s), 4.22 (2H, q, J=7.0 Hz), 4.32 (2H, dd, J=2.5, 5.0 Hz), 5.46 (1H, t, J=5.0 Hz), 7.36-7.40 (1H, m), 7.46 (1H, dd, J=2.5, 4.0 Hz), 7.72 (1H, dd, J=7.0, 9.0 Hz), 8.23 (1H, d, J=9.5 Hz), 8.42 (1H, s).

Reference Example 19

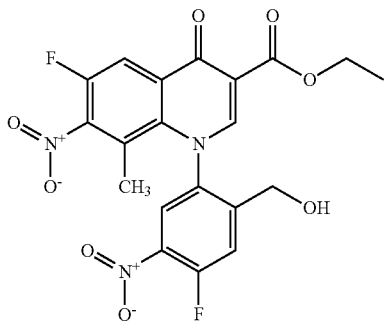 [SMILES: CCOC(=O)c1cn(-c2cc([N+](=O)[O-])c(F)cc2CO)c2c(C)c([N+](=O)[O-])c(F)cc2c1=O]

Ethyl 6-fluoro-1-[4-fluoro-2-(hydroxymethyl)-5-nitrophenyl]-8-methyl-7-nitro-4-oxo-1,4-dihydroquinoline-3-carboxylate 100 mg of ethyl 6-fluoro-1-[4-fluoro-2-(hydroxymethyl)phenyl]-8-methyl-7-nitro-4-oxo-1,4-dihydroquinoline-3-carboxylate was dissolved in 1.5 mL of sulfuric acid and 140 mg of potassium nitrate was added. The mixture was stirred at 40° C. for 19 hours. The mixture was added to 20 mL of iced water and extracted with 30 mL of ethyl acetate. The organic layer was washed with 200 mL of water and 100 mL of saturated brine. The organic layer was dried and then concentrated under reduced pressure. The residue was subjected to silica gel column chromatography (dichloromethane:ethyl acetate=0 to 40% gradient) to obtain 50 mg of the title compound.

$^1$H-NMR (CDCl3): δ 1.38 (3H, t, J=7.0 Hz), 1.73 (s, 3H), 4.30-4.42 (m, 4H), 5.47 (1H, t, J=5.5 Hz), 7.79 (1H, d, J=11.0 Hz), 8.20 (1H, d, J=6.5 Hz), 8.34 (1H, s), 8.35 (1H, d, J=6.5 Hz).

Example 74

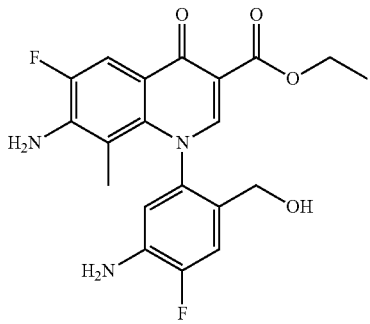 [SMILES: CCOC(=O)c1cn(-c2cc(N)c(F)cc2CO)c2c(C)c(N)c(F)cc2c1=O]

Ethyl 7-amino-1-[5-amino-4-fluoro-2-(hydroxymethyl)phenyl]-6-fluoro-8-methyl-4-oxo-1,4-dihydroquinoline-3-carboxylate 1.0 g of iron powder was added to 3 mL of ethanol and 2 mL of water and 0.5 mL of concentrated hydrochloric acid was added thereto. The mixture was stirred at 80° C. for 20 minutes. 3 mL of a solution of 50 mg of ethyl 6-fluoro-1-[4-fluoro-2-(hydroxymethyl)-5-nitrophenyl]-8-methyl-7-nitro-4-oxo-1,4-dihydroquinoline-3-carboxylate in tetrahydrofuran was added and the mixture was stirred at 80° C. for 50 minutes. The reaction solution was filtered through Celite and Celite was washed four times with 20 mL of tetrahydrofuran, four times with 20 mL of ethanol, and three times with 20 mL of dichloromethane. The filtrates were combined and concentrated. 10 mL of water was added and a solid was collected by filtration. The solid was washed with 3 mL of ethanol to obtain 22 mg of the title compound.

$^1$H-NMR (DMSO-$d_6$): δ 1.23 (3H, t, J=7.0 Hz), 1.53 (3H, s), 4.05-4.25 (4H, m), 5.13 (1H, s), 5.49 (2H, s), 5.91 (2H, s), 6.69 (1H, s), 7.18 (1H, d, J=12.0 Hz), 7.71 (1H, brs), 8.21 (1H, s).

Example 75

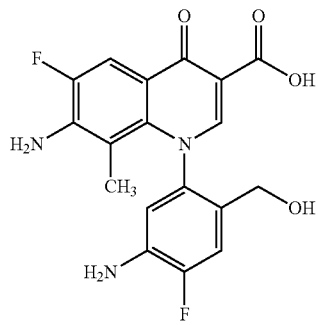 [SMILES: Cc1c(N)c(F)cc2c(=O)c(C(=O)O)cn(-c3cc(N)c(F)cc3CO)c12]

7-Amino-1-[5-amino-4-fluoro-2-(hydroxymethyl)phenyl]-6-fluoro-8-methyl-4-oxo-1,4-dihydroquinoline-3-carboxylic acid 22 mg of ethyl 7-amino-1-[5-amino-4-fluoro-2-(hydroxymethyl)phenyl]-6-fluoro-8-methyl-4-oxo-1,4-dihydroquinoline-3-carboxylate was suspended in 2 mL of tetrahydrofuran, 2 mL of ethanol, and 1 mL of water and 0.2 mL of a 1 mol/L aqueous solution of sodium hydroxide was added. The mixture was stirred at 70° C. for 30 minutes. The solvent was evaporated under reduced pressure and 1 mL of water was added to the residue and a solid was filtered. The solid was dried to obtain 18 mg of the title compound.

$^1$H-NMR (DMSO-$d_6$): δ 1.57 (3H, s), 3.95-4.20 (2H, m), 5.08 (1H, s), 5.56 (2H, s), 6.36 (2H, s), 6.77 (1H, s), 7.21 (1H, brs), 7.85 (1H, brs), 8.38 (1H, s).

Reference Example 20

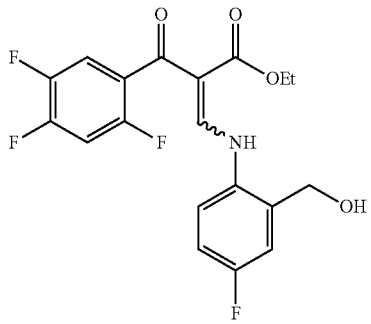 [SMILES: CCOC(=O)C(=CNc1ccc(F)cc1CO)C(=O)c1cc(F)c(F)cc1F]

Ethyl 3-[4-fluoro-2-(hydroxymethyl)phenyl]amino-2-(2,4,5-trifluorobenzoyl)acrylate 9.0 g of ethyl orthoformate and 10.4 g of acetic anhydride were added to 10.0 g of ethyl 3-oxo-3-(2,4,5-trifluorophenyl)propionate and the mixture was heated to reflux for 17 hours. The solvent was evaporated under reduced pressure and the obtained residue was dissolved in 50 mL of dichloromethane to obtain a crude ethoxyacrylate solution. 5.8 g of 2-amino-5-fluorobenzyl alcohol was suspended in 150 mL of dichloromethane and the ethoxyacrylate solution obtained earlier was added dropwise. The mixture was stirred at room temperature for 1 hour and then evaporated under reduced pressure. The resulting residue was dispersed in diisopropyl ether, collected by filtration, and dried to obtain 13.8 g of the title compound.

$^1$H-NMR (DMSO-$d_6$); δ 0.93 (0.9H, t, J=7 Hz), 1.02 (2.1H, t, J=7 Hz), 4.00 (1.4H, q, J=7 Hz), 4.02 (0.6H, q, J=7 Hz), 4.59 (1.4H, s), 4.60 (0.6H, s), 5.78-5.82 (1H, m), 7.20-7.29 (2H, m), 7.53-7.66 (3H, m), 8.36 (0.3H, d, J=14 Hz), 8.46 (0.7H, d, J=14 Hz), 11.44 (0.3H, d, J=14 Hz), 12.66 (0.7H, d, J=14 Hz)

Reference Example 21

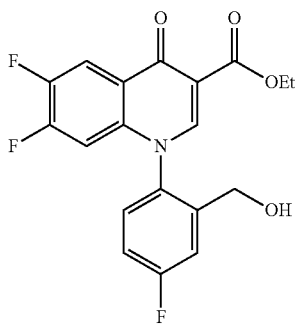 [SMILES: CCOC(=O)c1cn(-c2ccc(F)cc2CO)c2cc(F)c(F)cc2c1=O]

Ethyl 6,7-difluoro-1-[4-fluoro-2-(hydroxymethyl)phenyl]-4-oxo-1,4-dihydroquinoline-3-carboxylate 13.8 g of ethyl 3-[4-fluoro-2-(hydroxymethyl)phenyl]amino-2-(2,4,5-trifluorobenzoyl)acrylate and 3.0 g of lithium chloride were dissolved in 70 mL of N-methylpyrrolidin-2-one and 5.6 g of 1,8-diazabicyclo[5.4.0]undec-7-ene was added. The mixture was stirred at 80° C. for 90 minutes. After cooling, the reaction solution was poured into 700 mL of iced water and precipitated crystals were collected by filtration and dried. The crystals were dissolved in 800 mL of chloroform and washed with water. The organic layer was dried over anhydrous magnesium sulfate and evaporated under reduced pressure. The resulting residue was dispersed in diisopropyl ether, collected by filtration, and dried to obtain 12.7 g of the title compound.

$^1$H-NMR (DMSO-$d_6$); δ 1.25 (3H, t, J=7 Hz), 4.16-4.27 (4H, m), 5.36 (1H, t, J=5 Hz), 6.84 (1H, dd, J=12 Hz, 7 Hz), 7.41 (1H, dt, J=9 Hz, 3 Hz), 7.51 (1H, dd, J=10 Hz, 3 Hz), 7.67 (1H, dd, J=9 Hz, 5 Hz), 8.14 (1H, dd, J=10 Hz, 9 Hz), 8.45 (1H, s)

Reference Example 22

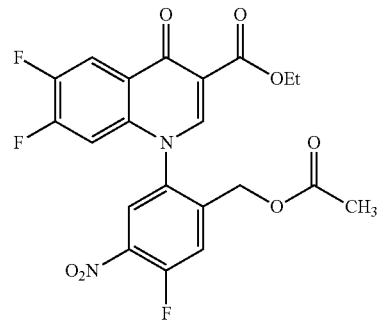

Ethyl 1-(2-acetoxymethyl-4-fluoro-5-nitrophenyl)-6,7-difluoro-4-oxo-1,4-dihydroquinoline-3-carboxylate 3.8 g of ethyl 6,7-difluoro-1-[4-fluoro-2-(hydroxymethyl)phenyl]-4-oxo-1,4-dihydroquinoline-3-carboxylate was dissolved in 50 mL of concentrated sulfuric acid and 2.4 g of potassium nitrate was added. The mixture was stirred at 60° C. for 4 hours. The reaction solution was poured into 500 mL of iced water and extracted with 500 mL of ethyl acetate. The organic layer was dried over anhydrous magnesium sulfate and then evaporated under reduced pressure to obtain an oily substance. This was dissolved in 50 mL of acetic acid and the solution was stirred at 80° C. for 2 hours. The solvent was evaporated under reduced pressure and the residue was dissolved in 300 mL of chloroform. The organic layer was washed with water and then a saturated aqueous solution of sodium hydrogen carbonate, then dried over anhydrous magnesium sulfate, and evaporated under reduced pressure. The resulting residue was separated through a silica gel column (0 to 2% methanol/chloroform) to obtain 660 mg of the title compound.

$^1$H-NMR (DMSO-$d_6$); δ 1.25 (3H, t, J=7 Hz), 1.82 (3H, s), 4.22 (2H, q, J=7 Hz), 4.88 (1H, d, J=13 Hz), 4.94 (1H, d, J=13 Hz), 7.18 (1H, dd, J=12 Hz, 7 Hz), 7.99 (1H, d, J=12 Hz), 8.14 (1H, dd, J=11 Hz, 9 Hz), 8.59 (1H, s), 8.68 (1H, d, J=7 Hz)

Reference Example 23

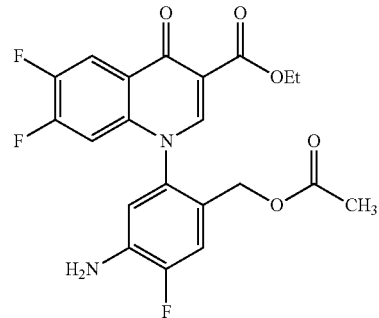 [SMILES: CCOC(=O)c1cn(-c2cc([N+](=O)[O-])c(F)cc2COC(C)=O)c2cc(F)c(F)cc2c1=O]

Ethyl 1-(2-acetoxymethyl-5-amino-4-fluorophenyl)-6,7-difluoro-4-oxo-1,4-dihydroquinoline-3-carboxylate 6.3 g of ethyl 1-(2-acetoxymethyl-4-fluoro-5-nitrophenyl)-6,7-difluoro-4-oxo-1,4-dihydroquinoline-3-carboxylate was dissolved in 150 mL of acetic acid and 3.5 g of reduced iron was added. The mixture was stirred at 70° C. for 1 hour. Insoluble matter was filtered off with Celite and the filtrate was evaporated under reduced pressure. The resulting residue was dissolved in 400 mL of chloroform and washed with water and then a saturated aqueous solution of sodium hydrogen carbonate. The organic layer was dried over anhydrous magnesium sulfate and then evaporated under reduced pressure. The resulting residue was crystallized using ethyl acetate to obtain 4.1 g of the title compound.

$^1$H-NMR (DMSO-$d_6$); δ 1.25 (3H, t, J=7 Hz), 1.74 (3H, s), 4.20 (2H, q, J=7 Hz), 4.55 (1H, d, J=12 Hz), 4.71 (1H, d, J=12 Hz), 5.84 (2H, b r), 6.89 (1H, d, J=8 Hz), 6.92 (1H, dd, J=12 Hz, 7 Hz), 7.39 (1H, d, J=12 Hz), 8.12 (1H, dd, J=10 Hz, 9 Hz), 8.42 (1H, s)

Example 76

Ethyl 1-(2-acetoxymethyl-5-amino-4-fluorophenyl)-6-fluoro-7-[3-(methylamino)azetidin-1-yl]-4-oxo-1,4-dihydroquinoline-3-carboxylate

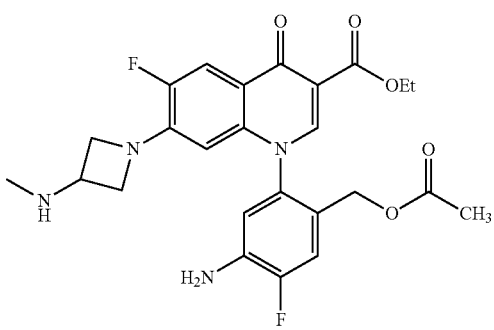 [SMILES: CCOC(=O)c1cn(-c2cc(N)c(F)cc2COC(C)=O)c2cc(N3CC(NC)C3)c(F)cc2c1=O]

220 mg of ethyl 1-(2-acetoxymethyl-5-amino-4-fluorophenyl)-6,7-difluoro-4-oxo-1,4-dihydroquinoline-3-carboxylate and 240 mg of 3-methylaminoazetidine dihydrochloride were suspended in 4 mL of acetonitrile. 350 mg of 1,1,3,3-tetramethylguanidine was added to the suspension and the mixture was stirred at 35° C. overnight. 50 mL of chloroform was added to the reaction solution and the mixture was washed with a saturated aqueous solution of sodium hydrogen carbonate. The organic layer was dried over anhydrous magnesium sulfate and then evaporated under reduced pressure. The resulting residue was dispersed in ethanol, collected by filtration, and dried to obtain 200 mg of the title compound.

$^1$H-NMR (DMSO-$d_6$); δ 1.23 (3H, t, J=7 Hz), 1.78 (3H, s), 2.18 (3H, s), 3.49-3.58 (3H, m), 4.04-4.07 (2H, m), 4.17 (2H, q, J=7 Hz), 4.53 (1H, d, J=12 Hz), 4.68 (1H, d, J=12 Hz), 5.52 (1H, d, J=8 Hz), 5.80 (2H, s), 6.83 (1H, d, J=8 Hz), 7.37 (1H, d, J=12 Hz), 7.70 (1H, d, J=13 Hz), 8.21 (1H, s)

Example 77

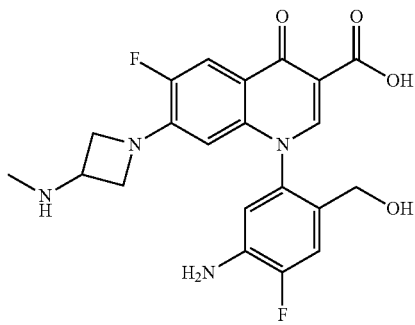 [SMILES: CNC1CN(c2cc3c(cc2F)c(=O)c(C(=O)O)cn3-c2cc(N)c(F)cc2CO)C1]

1-[5-Amino-4-fluoro-2-(hydroxymethyl)phenyl]-6-fluoro-7-[3-(methylamino)azetidin-1-yl]-4-oxo-1,4-dihydroquinoline-3-carboxylic acid 200 mg of ethyl 1-(2-acetoxymethyl-5-amino-4-fluorophenyl)-6-fluoro-7-[3-(methylamino)azetidin-1-yl]-4-oxo-1,4-dihydroquinoline-3-carboxylate was suspended in 2 mL of ethanol and 2 mL of a 1 mol/L aqueous solution of sodium hydroxide was added. The mixture was stirred at 60° C. for 30 minutes. After cooling, 0.33 mL of 6 mol/L hydrochloric acid was added to neutralize the mixture. Precipitated powder was collected by filtration, washed with water and then acetonitrile, and dried to obtain 56 mg of the title compound.

$^1$H-NMR (DMSO-$d_6$); 2.18 (3H, s), 3.51-3.55 (1H, m), 3.63-3.67 (2H, m), 3.93-4.04 (2H, m), 4.09-4.14 (2H, m), 5.02 (1H, t, J=5 Hz), 5.61 (2H, s), 5.63 (1H, d, J=8 Hz), 6.81 (1H, d, J=8 Hz), 7.27 (1H, d, J=12 Hz), 7.84 (1H, d, J=13 Hz), 8.44 (1H, s)

Example 78

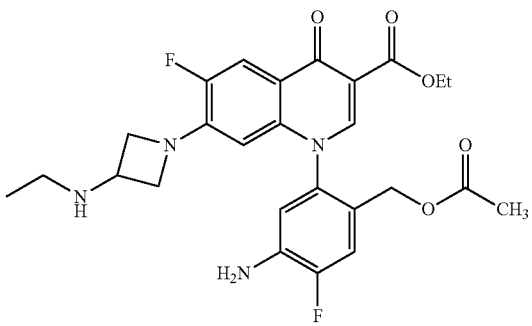 [SMILES: CCNC1CN(c2cc3c(cc2F)c(=O)c(C(=O)OCC)cn3-c2cc(N)c(F)cc2COC(C)=O)C1]

Ethyl 1-(2-acetoxymethyl-5-amino-4-fluoropilenyl)-7-[3-(ethylamino)azetidin-1-yl]-6-fluoro-4-oxo-1,4-dihydroquinoline-3-carboxylate 220 mg of ethyl 1-(2-acetoxymethyl-5-amino-4-fluorophenyl)-6,7-difluoro-4-oxo-1,4-dihydroquinoline-3-carboxylate and 260 mg of 3-ethylaminoazetidine dihydrochloride were suspended in 4 mL of acetonitrile. 350 mg of 1,1,3,3-tetramethylguanidine was added to the suspension and the mixture was stirred at 35° C. overnight. 50 mL of chloroform was added to the reaction solution and the mixture was washed with a saturated aqueous solution of sodium hydrogen carbonate. The organic layer was dried over anhydrous magnesium sulfate and then evaporated under reduced pressure. The obtained residue was dispersed in ethyl acetate, collected by filtration, and dried to obtain 200 mg of the title compound.

$^1$H-NMR (DMSO-$d_6$); δ 0.95 (3H, t, J=7 Hz), 1.23 (3H, t, J=7 Hz), 1.78 (3H, s), 2.44 (2H, q, J=7 Hz), 3.54-3.62 (3H, m), 4.05-4.09 (2H, m), 4.17 (2H, q, J=7 Hz), 4.53 (1H, d, J=12 Hz), 4.68 (1H, d, J=12 Hz), 5.52 (1H, d, J=8 Hz), 5.80 (2H, s), 6.83 (1H, d, J=8 Hz), 6.37 (1H, d, J=12 Hz), 7.69 (1H, d, J=13 Hz), 8.21 (1H, s)

Example 79

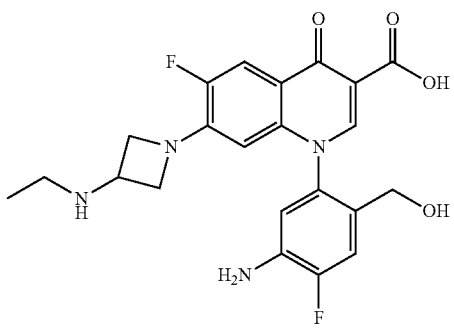 [SMILES: CCNC1CN(c2cc3c(cc2F)c(=O)c(C(=O)O)cn3-c2cc(N)c(F)cc2CO)C1]

1-[5-Amino-4-fluoro-2-(hydroxymethyl)phenyl]-7-[3-(ethylamino)azetidin-1-yl]-6-fluoro-4-oxo-1,4-dihydroquinoline-3-carboxylic acid 200 mg of ethyl 1-(2-acetoxymethyl-5-amino-4-fluorophenyl)-7-[3-(ethylamino)azetidin-1-yl]-6-fluoro-4-oxo-1,4-dihydroquinoline-3-carboxylate was suspended in 2 mL of ethanol and 2 mL of a 1 mol/L aqueous solution of sodium hydroxide was added. The mixture was stirred at 60° C. for 30 minutes. After cooling, 0.33 mL of 6 mol/L hydrochloric acid was added to neutralize the mixture. The reaction solution was concentrated under reduced pressure and precipitated powder was collected by filtration, washed with water and then acetonitrile, and dried to obtain 72 mg of the title compound.

$^1$H-NMR (DMSO-$d_6$); δ 1.15 (3H, t, J=7 Hz), 2.89 (2H, q, J=7 Hz), 3.94-4.13 (5H, m), 4.25-4.29 (2H, m), 5.04 (1H, t, J=5 Hz), 5.64 (2H, s), 5.71 (1H, d, J=8 Hz), 6.83 (1H, d, J=8 Hz), 7.29 (1H, d, J=12 Hz), 7.92 (1H, d, J=13 Hz), 8.47 (1H, s)

Example 80

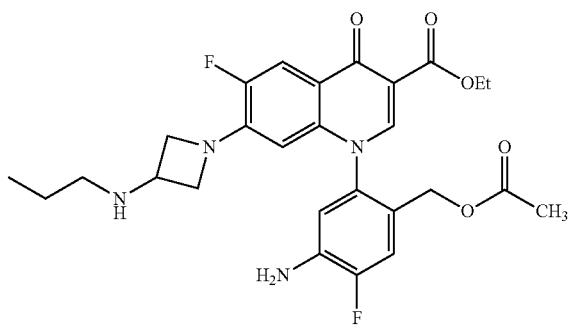 [SMILES: CCCNC1CN(c2cc3c(cc2F)c(=O)c(C(=O)OCC)cn3-c2cc(N)c(F)cc2COC(C)=O)C1]

Ethyl 1-(2-acetoxymethyl-5-amino-4-fluorophenyl)-6-fluoro-4-oxo-7-[3-(propylamino)azetidin-1-yl]-1,4-dihydroquinoline-3-carboxylate 220 mg of ethyl 1-(2-acetoxymethyl-5-amino-4-fluorophenyl)-6,7-difluoro-4-oxo-1,4-dihydroquinoline-3-carboxylate and 280 mg of 3-propylaminoazetidine dihydrochloride were suspended in 4 mL of acetonitrile. 350 mg of 1,1,3,3-tetramethylguanidine was added to the suspension and the mixture was stirred at 35° C. overnight. 50 mL of chloroform was added to the reaction solution and the mixture was washed with a saturated aqueous solution of sodium hydrogen carbonate. The organic layer was dried over anhydrous magnesium sulfate and then evaporated under reduced pressure. The resulting residue was crystallized using diethyl ether to obtain 210 mg of the title compound.

$^1$H-NMR (DMSO-$d_6$); δ 0.83 (3H, t, J=7 Hz), 1.23 (3H, t, J=7 Hz), 1.30-1.37 (2H, m), 1.78 (3H, s), 2.35-2.38 (2H, m), 3.53-3.61 (3H, m), 4.04-4.09 (2H, m), 4.17 (2H, q, J=7 Hz), 4.53 (1H, d, J=12 Hz), 4.68 (1H, d, J=12 Hz), 5.52 (1H, d, J=8 Hz), 5.80 (2H, s), 6.83 (1H, d, J=8 Hz), 7.37 (1H, d, J=12 Hz), 7.70 (1H, d, J=13 Hz), 8.21 (1H, s)

Example 81

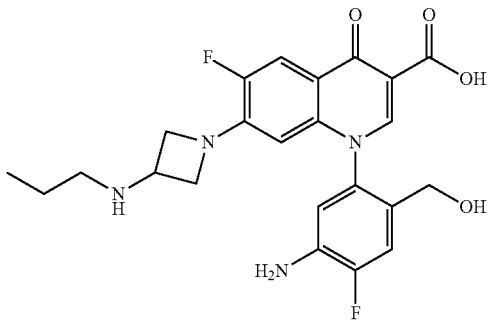 [SMILES: CCCNC1CN(c2cc3c(cc2F)c(=O)c(C(=O)O)cn3-c2cc(N)c(F)cc2CO)C1]

1-[5-Amino-4-fluoro-2-(hydroxymethyl)phenyl]-6-fluoro-4-oxo-7-[3-(propylamino)azetidin-1-yl]-1,4-dihydroquinoline-3-carboxylic acid 210 mg of ethyl 1-(2-acetoxymethyl-5-amino-4-fluorophenyl)-6-fluoro-4-oxo-7-[3-(propylamino)azetidin-1-yl]-1,4-dihydroquinoline-3-carboxylate was suspended in 2 mL of ethanol and 2 mL of a 1 mol/L aqueous solution of sodium hydroxide was added. The mixture was stirred at 60° C. for 30 minutes. After cooling, 0.33 mL of 6 mol/L hydrochloric acid was added to neutralize the mixture. Precipitated crystals were collected by filtration, washed with water and then acetonitrile, and then dried to obtain 120 mg of the title compound.

$^1$H-NMR (DMSO-$d_6$); δ 0.83 (3H, t, J=7 Hz), 1.31-1.38 (2H, m), 2.36-2.39 (2H, m), 3.59-3.67 (3H, m), 3.93-4.04 (2H, m), 4.13 (2H, br), 5.01 (1H, t, J=5 Hz), 5.61 (2H, s), 5.62 (1H, d, J=8 Hz), 6.81 (1H, d, J=8 Hz), 7.27 (1H, d, J=12 Hz), 7.85 (1H, d, J=13 Hz), 8.44 (1H, s)

Example 82

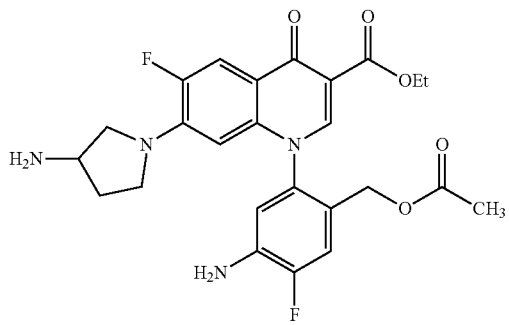

Ethyl 1-(2-acetoxymethyl-5-amino-4-fluorophenyl)-7-(3-aminopyrrolidin-1-yl)-6-fluoro-4-oxo-1,4-dihydroquinoline-3-carboxylate 220 mg of ethyl 1-(2-acetoxymethyl-5-amino-4-fluorophenyl)-6,7-difluoro-4-oxo-1,4-dihydroquinoline-3-carboxylate and 300 mg of 3-aminopyrrolidine were suspended in 4 mL of acetonitrile and the mixture was stirred at 35° C. overnight. 50 mL of chloroform was added to the reaction solution and the mixture was washed with a saturated aqueous solution of sodium hydrogen carbonate. The organic layer was dried over anhydrous magnesium sulfate and then evaporated under reduced pressure. The resulting residue was crystallized using ethyl acetate to obtain 128 mg of the title compound.

$^1$H-NMR (DMSO-$d_6$); δ 1.23 (3H, t, J=7 Hz), 1.58-1.70 (2H, m), 1.77 (3H, s), 1.89-1.96 (1H, m), 2.91-2.96 (1H, m), 3.23-3.49 (3H, m), 4.17 (2H, q, J=7 Hz), 4.54 (1H, d, J=12 Hz), 4.69 (1H, d, J=12 Hz), 5.68 (1H, d, J=8 Hz), 5.79 (2H, s), 6.84 (1H, d, J=8 Hz), 7.37 (1H, d, J=12 Hz), 7.69 (1H, d, J=13 Hz), 8.21 (1H, s)

Example 83

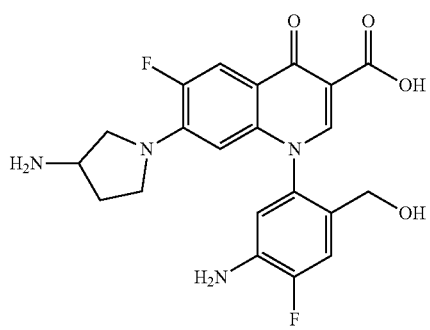 [SMILES: Nc1cc(-n2cc(C(=O)O)c(=O)c3cc(F)c(N4CCC(N)C4)cc32)c(CO)cc1F]

1-[5-Amino-4-fluoro-2-(hydroxymethyl)phenyl]-7-(3-aminopyrrolidin-1-yl)-6-fluoro-4-oxo-1,4-dihydroquinoline-3-carboxylic acid 128 mg of ethyl 1-(2-acetoxymethyl-5-amino-4-fluorophenyl)-7-(3-aminopyrrolidin-1-yl)-6-fluoro-4-oxo-1,4-dihydroquinoline-3-carboxylate was suspended in 2 mL of ethanol and 2 mL of a 1 mol/L aqueous solution of sodium hydroxide was added. The mixture was stirred at 60° C. for 20 minutes. After cooling, 0.33 mL of 6 mol/L hydrochloric acid was added to neutralize the mixture. Precipitated powder was collected by filtration, washed with water and then acetonitrile, and dried to obtain 95 mg of the title compound.

$^1$H-NMR (DMSO-$d_6$); δ 1.78-1.85 (1H, m), 2.03-2.11 (1H, m), 3.17-3.69 (5H, m), 3.97 (1H, d, J=12 Hz), 4.03 (1H, d, J=12 Hz), 5.04 (2H, s), 5.62 (2H, s), 5.83 (0.4H, d, J=8 Hz), 5.84 (0.6H, d, J=8 Hz), 6.83 (0.6H, d, J=8 Hz), 6.83 (0.4H, d, J=8 Hz), 7.28 (1H, d, J=12 Hz), 7.87 (1H, d, J=14 Hz), 8.45 (0.4H, s), 8.46 (0.6H, s)

Example 84

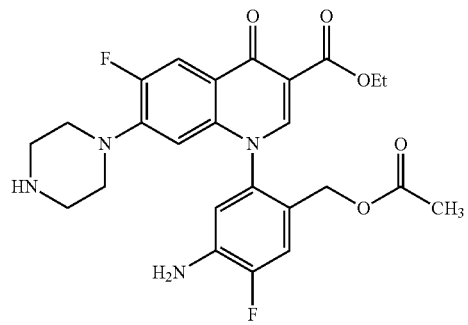 [SMILES: CCOC(=O)c1cn(-c2cc(N)c(F)cc2COC(C)=O)c2cc(N3CCNCC3)c(F)cc2c1=O]

Ethyl 1-(2-acetoxymethyl-5-amino-4-fluorophenyl)-6-fluoro-4-oxo-7-(piperazin-1-yl)-1,4-dihydroquinoline-3-carboxylate 220 mg of ethyl 1-(2-acetoxymethyl-5-amino-4-fluorophenyl)-6,7-difluoro-4-oxo-1,4-dihydroquinoline-3-carboxylate and 300 mg of piperazine were suspended in 4 mL of acetonitrile and the mixture was stirred at 40° C. overnight. Precipitated crystals were collected by filtration, washed with acetonitrile, and then dried to obtain 300 mg of the title compound.

$^1$H-NMR (DMSO-$d_6$); δ 1.24 (3H, t, J=7 Hz), 1.72 (3H, s), 2.76-2.78 (4H, m), 2.85-2.88 (4H, m), 4.19 (2H, q, J=7 Hz), 4.55 (1H, d, J=12 Hz), 4.69 (1H, d, J=12 Hz), 5.81 (2H, s), 6.15 (1H, d, J=8 Hz), 6.89 (1H, d, J=8 Hz), 7.39 (1H, d, J=12 Hz), 7.79 (1H, d, J=13 Hz), 8.31 (1H, s)

Example 85

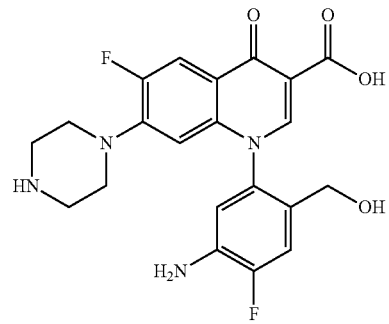 [SMILES: Nc1cc(-n2cc(C(=O)O)c(=O)c3cc(F)c(N4CCNCC4)cc32)c(CO)cc1F]

1-[5-Amino-4-fluoro-2-(hydroxymethyl)phenyl]-6-fluoro-4-oxo-7-(piperazin-1-yl)-1,4-dihydroquinoline-3-carboxylic acid 300 mg of ethyl 1-(2-acetoxymethyl-5-amino-4-fluorophenyl)-6-fluoro-4-oxo-7-(piperazin-1-yl)-1,4-dihydroquinoline-3-carboxylate was suspended in 2 mL of ethanol and 2 mL of a 1 mol/L aqueous solution of sodium hydroxide was added. The mixture was stirred at 60° C. for 20 minutes. After cooling, 0.33 mL of 6 mol/L hydrochloric acid was added to neutralize the mixture. Precipitated powder was collected by filtration, washed with water and then acetonitrile, and dried to obtain 190 mg of the title compound.

$^1$H-NMR (DMSO-$d_6$); δ 2.87-2.89 (4H, m), 2.96-3.05 (4H, m), 3.95-4.03 (2H, m), 5.00 (1H, t, J=5 Hz), 5.63 (2H, br), 6.32 (1H, d, J=7 Hz), 6.87 (1H, d, J=8 Hz), 7.28 (1H, d, J=12 Hz), 7.96 (1H, d, J=14 Hz), 8.55 (1H, s)

Example 86

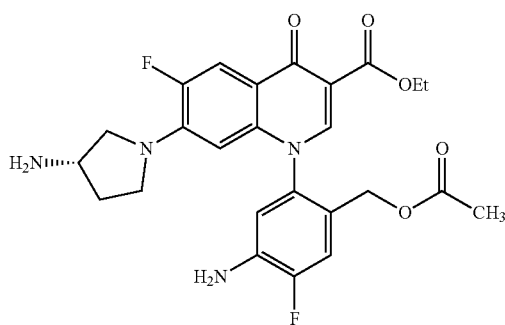 [SMILES: CCOC(=O)c1cn(-c2cc(N)c(F)cc2COC(C)=O)c2cc(N3CC[C@H](N)C3)c(F)cc2c1=O]

Ethyl (S)-1-(2-acetoxymethyl-5-amino-4-fluorophenyl)-7-(3-aminopyrrolidin-1-yl)-6-fluoro-4-oxo-1,4-dihydroquinoline-3-carboxylate 220 mg of ethyl 1-(2-acetoxymethyl-5-amino-4-fluorophenyl)-6,7-difluoro-4-oxo-1,4-dihydroquinoline-3-carboxylate and 300 mg of (S)-3-aminopyrrolidine were suspended in 4 mL of acetonitrile and the mixture was stirred at 40° C. overnight. 50 mL of chloroform was added to the reaction solution and the mixture was washed with a saturated aqueous solution of sodium hydrogen carbonate. The organic layer was dried over anhydrous magnesium sulfate and then evaporated under reduced pressure. The resulting residue was crystallized with ethyl acetate to obtain 192 mg of the title compound.

Example 87

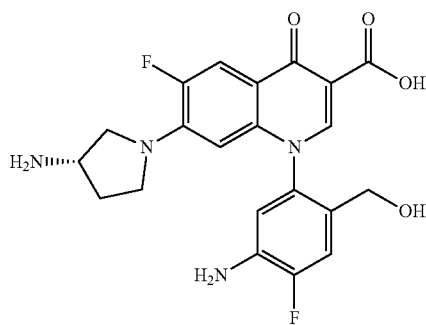 [SMILES: Nc1cc(-n2cc(C(=O)O)c(=O)c3cc(F)c(N4CC[C@H](N)C4)cc32)c(CO)cc1F]

(S)-1-[5-Amino-4-fluoro-2-(hydroxymethyl)phenyl]-7-(3-aminopyrrolidin-1-yl)-6-fluoro-4-oxo-1,4-dihydroquinoline-3-carboxylic acid 192 mg of ethyl (S)-1-(2-acetoxymethyl-5-amino-4-fluorophenyl)-7-(3-aminopyrrolidin-1-yl)-6-fluoro-4-oxo-1,4-dihydroquinoline-3-carboxylate was suspended in 2 mL of ethanol and 2 mL of a 1 mol/L aqueous solution of sodium hydroxide was added. The mixture was stirred at 60° C. for 20 minutes. After cooling, 0.33 mL of 6 M hydrochloric acid was added to neutralize the mixture. Precipitated powder was collected by filtration, washed with water and then acetonitrile, and dried to obtain 145 mg of the title compound.

$^1$H-NMR (DMSO-$d_6$); δ 1.78-1.86 (1H, m), 2.03-2.11 (1H, m), 3.17-3.69 (5H, m), 3.97 (1H, d, J=13 Hz), 4.03 (1H, d, J=13 Hz), 5.04 (1H, s), 5.62 (2H, s), 5.83 (0.5H, d, J=8 Hz), 5.84 (0.5H, d, J=8 Hz), 6.83 (0.5H, d, J=8 Hz), 6.83 (0.5H, d, J=8 Hz), 7.28 (1H, d, J=12 Hz), 7.87 (1H, d, J=14 Hz), 8.45 (0.5H, s), 8.46 (0.5H, s)

Reference Example 24

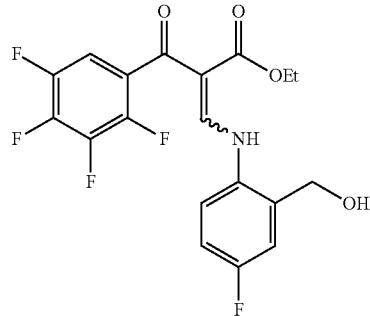

Ethyl 3-[4-fluoro-2-(hydroxymethyl)phenyl]amino-2-(2,3,4,5-tetrafluorobenzoyl)acrylate 8.5 g of ethyl orthoformate and 9.7 g of acetic anhydride were added to 10.0 g of ethyl 3-oxo-3-(2,3,4,5-tetrafluorophenyl)propionate and the mixture was heated to reflux for 4 hours. The reaction solution was evaporated under reduced pressure and the resulting residue was dissolve in 30 mL of dichloromethane to obtain a crude ethoxyacrylate solution. 5.4 g of 2-amino-5-fluorobenzyl alcohol was suspended in 80 mL of dichloromethane and the ethoxyacrylate solution obtained earlier was added dropwise. The mixture was stirred at room temperature overnight. The solvent was evaporated under reduced pressure and the resulting residue was dispersed in diisopropyl ether, collected by filtration, and dried to obtain 13.31 g of the title compound.

$^1$H-NMR (DMSO-$d_6$); δ 0.97 (0.9H, t, J=7 Hz), 1.06 (2.1H, t, J=7 Hz), 4.00-4.08 (2H, m), 4.59 (1.4H, s), 4.60 (0.6H, s), 5.80-5.84 (1H, m), 7.21-7.68 (4H, m), 8.39 (0.3H, d, J=14 Hz), 8.50 (0.7H, d, J=14 Hz), 11.54 (0.3H, d, J=14 Hz), 12.72 (0.7H, d, J=14 Hz)

Reference Example 25

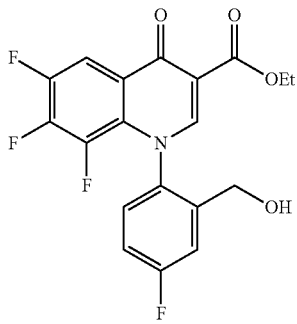

Ethyl 1-(4-fluoro-2-hydroxymethylphenyl)-4-oxo-6,7,8-trifluoro-1,4-dihydroquinoline-3-carboxylate 12.9 g of ethyl 3-[4-fluoro-2-(hydroxymethyl)phenyl]amino-2-(2,3,4,5-tetrafluorobenzoyl)acrylate and 2.6 g of lithium chloride were dissolved in 62 mL of N-methylpyrrolidin-2-one and 5.0 g of 1,8-diazabicyclo[5.4.0]undec-7-ene was added. The mixture was stirred at 80° C. for 2 hours. After cooling, the reaction solution was poured into 620 mL of water and precipitated crystals were collected by filtration and dried. The crystals were dissolved in 1 L of 10% methanol/chloroform, dried over anhydrous magnesium sulfate, and then evaporated under reduced pressure. The resulting residue was dispersed in diisopropyl ether, collected by filtration, and dried to obtain 10.8 g of the title compound.

$^1$H-NMR (DMSO-$d_6$); δ 1.25 (3H, t, J=7 Hz), 4.21 (2H, q, J=7 Hz), 4.34 (2H, d, J=5 Hz), 5.37 (1H, t, J=5 Hz), 7.34 (1H, dt, J=8 Hz, 3 Hz), 7.42 (1H, dd, J=9 Hz, 3 Hz), 7.74 (1H, dd, J=9 Hz, 5 Hz), 8.02-8.06 (1H, m), 8.33 (1H, s)

Reference Example 26

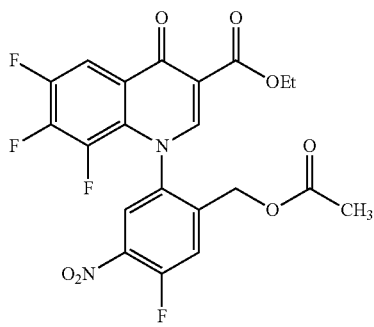 [SMILES: CCOC(=O)c1cn(-c2cc([N+](=O)[O-])c(F)cc2COC(C)=O)c2c(F)c(F)c(F)cc2c1=O]

Ethyl 1-(2-acetoxymethyl-4-fluoro-5-nitrophenyl)-4-oxo-6,7,8-trifluoro-1,4-dihydroquinoline-3-carboxylate 4.0 g of ethyl 1-(4-fluoro-2-hydroxymethylphenyl)-4-oxo-6,7,8-trifluoro-1,4-dihydroquinoline-3-carboxylate was dissolved in 50 mL of sulfuric acid and 2.4 g of potassium nitrate was added. The mixture was stirred at 60° C. for 4 hours. The reaction solution was poured into 1 L of iced water and extracted with 1 L of ethyl acetate. The organic layer was dried over anhydrous magnesium sulfate and then evaporated under reduced pressure to obtain 6.0 g of an oily substance. This was dissolved in acetic acid (60 mL) and the solution was stirred at 60° C. for 3 hours. Acetic acid was evaporated under reduced pressure and the residue was dissolved in chloroform (300 mL). The organic layer was washed with water and then a saturated aqueous solution of sodium hydrogen carbonate, then dried over anhydrous magnesium sulfate, and evaporated under reduced pressure. The resulting residue was separated through a silica gel column (0 to 2% methanol/chloroform) to obtain 630 mg of the title compound.

$^1$H-NMR (DMSO-$d_6$); δ 1.25 (3H, t, J=7 Hz), 1.85 (3H, s), 4.22 (2H, q, J=7 Hz), 5.07 (2H, d, J=2 Hz), 7.95 (1H, d, J=11 Hz), 8.05-8.09 (1H, m), 8.50 (1H, s), 8.78 (1H, d, J=7 Hz)

Reference Example 27

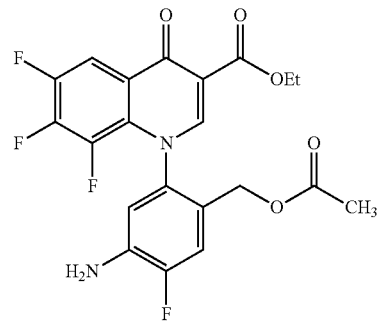

Ethyl 1-(2-acetoxymethyl-5-amino-4-fluorophenyl)-4-oxo-6,7,8-trifluoro-1,4-dihydroquinoline-3-carboxylate 2.5 g of ethyl 1-(2-acetoxymethyl-4-fluoro-5-nitrophenyl)-4-oxo-6,7,8-trifluoro-1,4-dihydroquinoline-3-carboxylate was dissolved in 70 mL of acetic acid and 1.3 g of reduced iron was added. The mixture was stirred at 80° C. for 90 minutes. Insoluble matter was filtered off with Celite and the filtrate was evaporated under reduced pressure. The resulting residue was dissolved in 400 mL of chloroform and washed with water and then a saturated aqueous solution of sodium hydrogen carbonate. The organic layer was dried over anhydrous magnesium sulfate and then evaporated under reduced pressure. The resulting residue was crystallized using diisopropyl ether to obtain 1.9 g of the title compound.

$^1$H-NMR (DMSO-$d_6$); δ 1.25 (3H, t, J=7 Hz), 1.74 (3H, s), 4.21 (2H, q, J=7 Hz), 4.74 (2H, d, J=4 Hz), 5.77 (2H, s), 6.99 (1H, d, J=8 Hz), 7.31 (1H, d, J=12 Hz), 8.02-8.05 (1H, m), 8.30 (1H, s)

Example 88

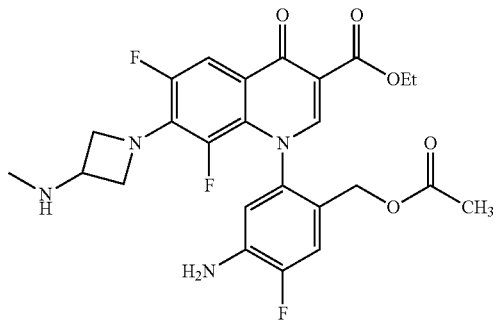

Ethyl 1-(2-acetoxymethyl-5-amino-4-fluorophenyl)-
6,8-difluoro-7-[3-(methylamino)azetidin-1-yl]-4-
oxo-1,4-dihydroquinoline-3-carboxylate 230 mg of ethyl 1-(2-acetoxymethyl-5-amino-4-fluorophenyl)-4-oxo-6,7,8-trifluoro-1,4-dihydroquinoline-3-carboxylate and 240 mg of 3-(methylamino)azetidine dihydrochloride were suspended in 4 mL of acetonitrile and 350 mg of 1,1,3,3-tetramethylguanidine was added. The mixture was stirred at room temperature for 90 minutes. Precipitated crystals were collected by filtration, then washed with acetonitrile, and dried to obtain 150 mg of the title compound.
$^1$H-NMR (DMSO-$d_6$); δ 1.22 (3H, t, J=7 Hz), 1.78 (3H, s), 2.17 (3H, s), 3.43-3.48 (1H, m), 3.86 (2H, brs), 4.17 (2H, q, J=7 Hz), 4.30 (2H, brs), 4.70 (2H, dd, J=25 Hz, 12 Hz), 5.71 (2H, s), 6.89 (1H, d, J=8 Hz), 7.27 (1H, d, J=12 Hz), 7.61 (1H, dd, J=13 Hz, 1 Hz), 8.06 (1H, s)

Example 89

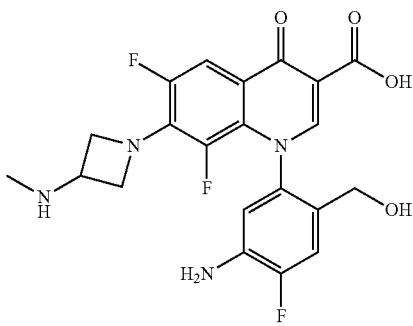

1-[5-Amino-4-fluoro-2-(hydroxymethyl)phenyl]-6,8-
difluoro-7-[3-(methylamino)azetidin-1-yl]-4-oxo-1,
4-dihydroquinoline-3-carboxylic acid 150 mg of ethyl 1-(2-acetoxymethyl-5-amino-4-fluorophenyl)-6,8-difluoro-7-[3-(methylamino)azetidin-1-yl]-4-oxo-1,4-dihydroquinoline-3-carboxylate was suspended in 2 mL of ethanol and 2 mL of a 1 mol/L aqueous solution of sodium hydroxide was added. The mixture was stirred at 60° C. for 5 minutes. After cooling, 0.33 mL of 6 mol/L hydrochloric acid was added to neutralize the mixture. The reaction solution was concentrated under reduced pressure and precipitated powder was collected by filtration, washed with water and then acetonitrile, and dried to obtain 40 mg of the title compound.
$^1$H-NMR (DMSO-$d_6$); δ 2.51 (3H, s), 3.97-4.04 (1H, m), 4.05-4.13 (2H, m), 4.37 (2H, brs), 4.50 (2H, brs), 5.03 (1H, t, J=5 Hz), 5.54 (2H, s), 6.91 (1H, d, J=8 Hz), 7.16 (1H, d, J=12 Hz), 7.83 (1H, d, J=13 Hz), 8.31 (1H, s)

Example 90

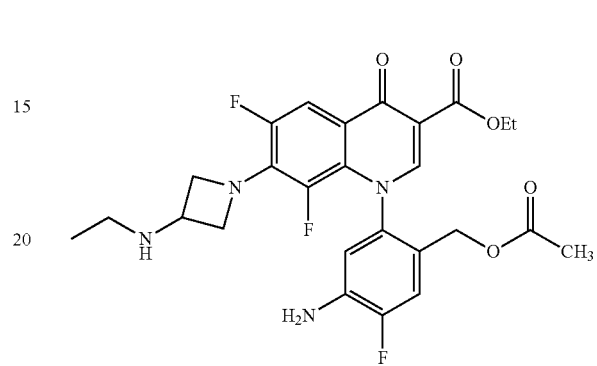

Ethyl 1-(2-acetoxymethyl-5-amino-4-fluorophenyl)-
6,8-difluoro-7-[3-(ethylamino)azetidin-1-yl]-4-oxo-
1,4-dihydroquinoline-3-carboxylate 230 mg of ethyl 1-(2-acetoxymethyl-5-amino-4-fluorophenyl)-4-oxo-6,7,8-trifluoro-1,4-dihydroquinoline-3-carboxylate and 260 mg of 3-(ethylamino)azetidine dihydrochloride were suspended in 4 mL of acetonitrile and 350 mg of 1,1,3,3-tetramethylguanidine was added. The mixture was stirred at 25° C. for 90 minutes. 50 mL of chloroform was added to the reaction solution and the mixture was washed with a saturated aqueous solution of sodium hydrogen carbonate. The organic layer was dried over anhydrous magnesium sulfate and then evaporated under reduced pressure. The resulting residue was crystallized using ethyl acetate to obtain 200 mg of the title compound.
$^1$H-NMR (DMSO-$d_6$); δ 0.94 (3H, t, J=7 Hz), 1.22 (3H, t, J=7 Hz), 1.78 (3H, s), 2.44 (2H, q, J=7 Hz), 3.52-3.57 (1H, m), 3.83-3.89 (2H, m), 4.17 (2H, q, J=7 Hz), 4.30-4.33 (2H, m), 4.70 (2H, q, J=12 Hz), 5.70 (2H, s), 6.89 (1H, d, J=8 Hz), 7.27 (1H, d, J=12 Hz), 7.61 (1H, dd, J=13 Hz, 1 Hz), 8.06 (1H, s)

Example 91

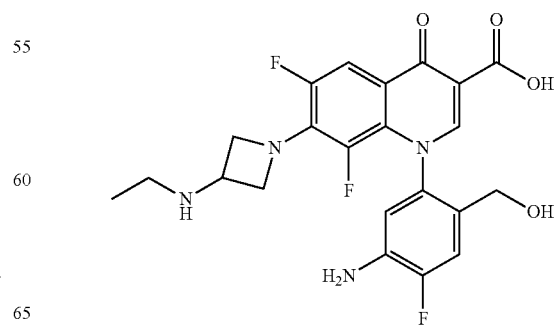

1-[5-Amino-4-fluoro-2-(hydroxymethyl)phenyl]-6,8-difluoro-7-[3-(ethylamino)azetidin-1-yl]-4-oxo-1,4-dihydroquinoline-3-carboxylic acid 200 mg of ethyl 1-(2-acetoxymethyl-5-amino-4-fluoro)phenyl-6,8-difluoro-7-[3-(ethylamino)azetidin-1-yl]-4-oxo-1,4-dihydroquinoline-3-carboxylate was suspended in 2 mL of ethanol and 2 mL of a 1 mol/L aqueous solution of sodium hydroxide was added. The mixture was stirred at 60° C. for 5 minutes. After cooling, 0.33 mL of 6 mol/L hydrochloric acid was added to neutralize the mixture. The reaction solution was concentrated under reduced pressure and precipitated powder was collected by filtration, washed with water and then acetonitrile, and dried to obtain 140 mg of the title compound.

$^1$H-NMR (DMSO-$d_6$); δ 0.95 (3H, t, J=7 Hz), 2.44 (2H, q, J=7 Hz), 3.55-3.60 (1H, m), 3.92-3.97 (2H, m), 4.04-4.13 (2H, m), 4.36-4.42 (2H, m), 5.00 (1H, t, J=5 Hz), 5.51 (2H, s), 6.88 (1H, d, J=8 Hz), 7.15 (1H, d, J=12 Hz), 7.77 (1H, dd, J=13 Hz, 1 Hz), 8.28 (1H, s)

Example 92

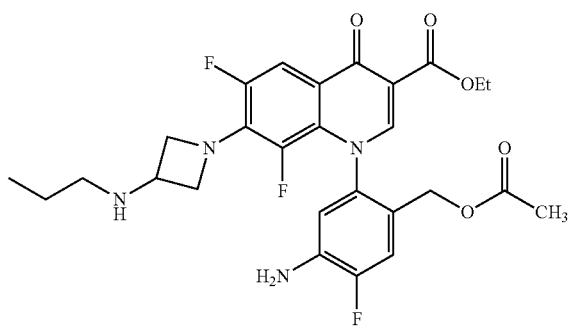 [SMILES: CCCNC1CN(c2c(F)cc3c(=O)c(C(=O)OCC)cn(-c4cc(N)c(F)cc4COC(C)=O)c3c2F)C1]

Ethyl 1-(2-acetoxymethyl-5-amino-4-fluorophenyl)-6,8-difluoro-4-oxo-7-[3-(propylamino)azetidin-1-yl]-1,4-dihydroquinoline-3-carboxylate 230 mg of ethyl 1-(2-acetoxymethyl-5-amino-4-fluorophenyl)-4-oxo-6,7,8-trifluoro-1,4-dihydroquinoline-3-carboxylate and 280 mg of 3-(propylamino)azetidine dihydrochloride were suspended in 4 mL of acetonitrile and 350 mg of 1,1,3,3-tetramethylguanidine was added. The mixture was stirred at 35° C. for 2 hours. 50 mL of chloroform was added to the reaction solution and the mixture was washed with a saturated aqueous solution of sodium hydrogen carbonate. The organic layer was dried over anhydrous magnesium sulfate and then evaporated under reduced pressure. The resulting residue was crystallized using ethyl acetate to obtain 200 mg of the title compound.

$^1$H-NMR (DMSO-$d_5$); δ 0.83 (3H, t, J=7 Hz), 1.22 (3H, t, J=7 Hz), 1.30-1.37 (2H, m), 1.78 (3H, s), 2.36 (2H, t, J=7 Hz), 3.51-3.57 (1H, m), 3.84-3.90 (2H, m), 4.17 (2H, q, J=7 Hz), 4.28-4.33. (2H, m), 4.68 (1H, d, J=12 Hz), 4.73 (1H, d, J=12 Hz), 5.70 (2H, s), 6.89 (1H, d, J=8 Hz), 7.27 (1H, d, J=11 Hz), 7.61 (1H, dd, J=13 Hz, 1 Hz), 8.06 (1H, s)

Example 93

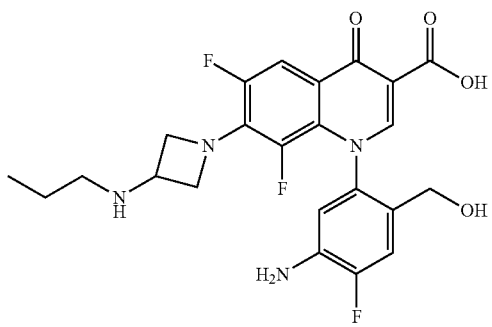 [SMILES: CCCNC1CN(c2c(F)cc3c(=O)c(C(=O)O)cn(-c4cc(N)c(F)cc4CO)c3c2F)C1]

1-[5-Amino-4-fluoro-2-(hydroxymethyl)phenyl]-6,8-difluoro-4-oxo-7-[3-(propylamino)azetidin-1-yl]-1,4-dihydroquinoline-3-carboxylic acid 200 mg of ethyl 1-(2-acetoxymethyl-5-amino-4-fluorophenyl)-6,8-difluoro-4-oxo-7-[3-(propylamino)azetidin-1-yl]-1,4-dihydroquinoline-3-carboxylate was suspended in 2 mL of ethanol and 2 mL of a 1 mol/L aqueous solution of sodium hydroxide was added. The mixture was stirred at 60° C. for 5 minutes. After cooling, 0.33 mL of 6 mol/L hydrochloric acid was added to neutralize the reaction solution. The reaction solution was concentrated under reduced pressure. The residue was dissolved in 20% methanol/chloroform, dried over anhydrous magnesium sulfate, and then evaporated under reduced pressure. The residue was crystallized using ethanol to obtain 45 mg of the title compound.

$^1$H-NMR (DMSO-$d_6$); δ 0.89 (3H, t, J=7 Hz), 1.54-1.62 (2H, m), 2.78-2.81 (2H, m), 4.02-4.13 (3H, m), 4.39-4.44 (2H, m), 4.49-4.53 (2H, m), 5.03 (1H, t, J=5 Hz), 5.54 (2H, s), 6.91 (1H, d, J=8 Hz), 7.16 (1H, d, J=12 Hz), 7.83 (1H, dd, J=13 Hz, 1 Hz), 8.31 (1H, s)

Example 94

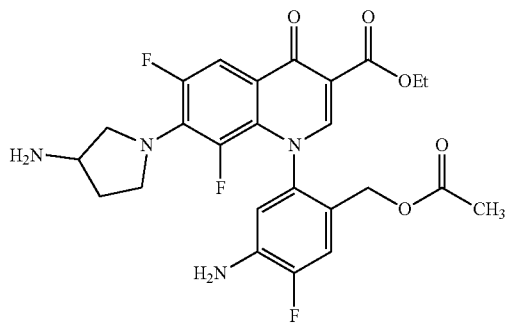 [SMILES: CCOC(=O)c1cn(-c2cc(N)c(F)cc2COC(C)=O)c2c(F)c(N3CCC(N)C3)c(F)cc2c1=O]

Ethyl 1-(2-acetoxymethyl-5-amino-4-fluorophenyl)-7-(3-aminopyrrolidin-1-yl)-6,8-difluoro-4-oxo-1,4-dihydroquinoline-3-carboxylate 230 mg of ethyl 1-(2-acetoxymethyl-5-amino-4-fluorophenyl)-4-oxo-6,7,8-trifluoro-1,4-dihydroquinoline-3-carboxylate and 130 mg of 3-aminopyrrolidine were suspended in 4 mL of acetonitrile and 350 mg of 1,1,3,3-tetramethylguanidine was added. The mixture was stirred at 35° C. for 17 hours. Precipitated crystals were collected by filtration, then washed with acetonitrile, and dried to obtain 210 mg of the title compound.

$^1$H-NMR (DMSO-d$_6$); δ 1.23 (3H, t, J=7 Hz), 1.51-1.58 (1H, m), 1.76 (3H, s), 1.84-1.90 (1H, m), 3.10-3.15 (1H, m), 3.36-3.42 (1H, m), 3.48-3.66 (3H, m), 4.18 (2H, q, J=7 Hz), 4.67-4.74 (2H, m), 5.69 (2H, s), 6.91 (1H, d, J=8 Hz), 7.27 (1H, d, J=11 Hz), 7.62 (1H, dd, J=14 Hz, 1 Hz), 8.08 (1H, s)

Example 95

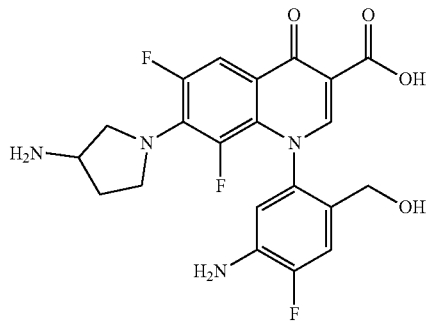

1-[5-Amino-4-fluoro-2-(hydroxymethyl)phenyl]-7-(3-aminopyrrolidin-1-yl)-6,8-difluoro-4-oxo-1,4-dihydroquinoline-3-carboxylic acid 210 mg of ethyl 1-(2-acetoxymethyl-5-amino-4-fluorophenyl)-7-(3-aminopyrrolidin-1-yl)-6,8-difluoro-4-oxo-1,4-dihydroquinoline-3-carboxylate was suspended in 2 mL of ethanol and 2 mL of a 1 mol/L aqueous solution of sodium hydroxide was added. The mixture was stirred at 60° C. for 20 minutes. After cooling, 0.33 mL of 6 mol/L hydrochloric acid was added to neutralize the mixture. Precipitated powder was collected by filtration, washed with water and then ethanol, and dried to obtain 180 mg of the title compound.

$^1$H-NMR (DMSO-d$_6$); δ 1.67-1.76 (1H, m), 1.95-2.03 (1H, m), 3.37-3.75 (5H, m), 4.06-4.13 (2H, m), 5.00 (1H, t, J=5 Hz), 5.51 (2H, s), 6.89 (1H, d, J=8 Hz), 7.15 (1H, d, J=12 Hz), 7.80 (1H, d, J=14 Hz), 8.31 (1H, s)

Example 96

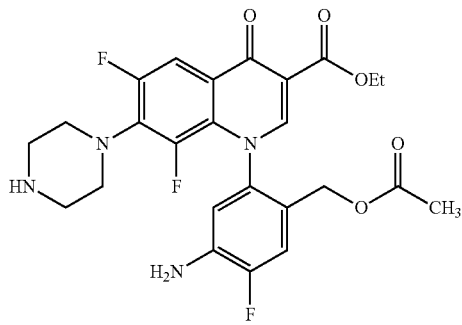 [SMILES: CCOC(=O)c1cn(-c2cc(N)c(F)cc2COC(C)=O)c2c(F)c(N3CCNCC3)c(F)cc2c1=O]

Ethyl 1-(2-acetoxymethyl-5-amino-4-fluorophenyl)-6,8-difluoro-4-oxo-7-(piperazin-1-yl)-1,4-dihydroquinoline-3-carboxylate 230 mg of ethyl 1-(2-acetoxymethyl-5-amino-4-fluorophenyl)-4-oxo-6,7,8-trifluoro-1,4-dihydroquinoline-3-carboxylate and 130 mg of piperazine were suspended in 4 mL of acetonitrile and 350 mg of 1,1,3,3-tetramethylguanidine was added. The mixture was stirred at 35° C. for 20 hours. 50 mL of chloroform was added to the reaction solution and the mixture was washed with a saturated aqueous solution of sodium hydrogen carbonate. The organic layer was dried over anhydrous magnesium sulfate and then evaporated under reduced pressure. The resulting residue was dispersed in ethanol, collected by filtration, and dried to obtain 170 mg of the title compound.

$^1$H-NMR (DMSO-d$_6$); δ 1.23 (3H, t, J=7 Hz), 1.72 (3H, s), 2.71-2.73 (4H, m), 3.04 (4H, brs), 4.19 (2H, q, J=7 Hz), 4.71 (2H, q, J=13 Hz), 5.72 (2H, s), 6.93 (1H, d, J=8 Hz), 7.28 (1H, d, J=12 Hz), 7.72 (1H, dd, J=12 Hz, 1 Hz), 8.16 (1H, s)

Example 97

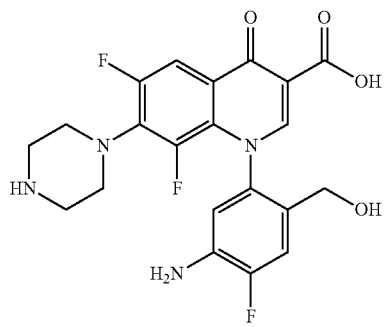 [SMILES: Nc1cc(-n2cc(C(=O)O)c(=O)c3cc(F)c(N4CCNCC4)c(F)c32)c(CO)cc1F]

1-[5-Amino-4-fluoro-2-(hydroxymethyl)phenyl]-6,8-difluoro-4-oxo-7-(piperazin-1-yl)-1,4-dihydroquinoline-3-carboxylic acid 170 mg of ethyl 1-(2-acetoxymethyl-5-amino-4-fluorophenyl)-6,8-difluoro-4-oxo-7-(piperazin-1-yl)-1,4-dihydroquinoline-3-carboxylate was suspended in 2 mL of ethanol and 2 mL of a 1 mol/L aqueous solution of sodium hydroxide was added. The mixture was stirred at 50° C. for 15 minutes. After cooling, 0.33 mL of 6 mol/L hydrochloric acid was added to neutralize the mixture. The reaction solution was concentrated under reduced pressure and precipitated powder was collected by filtration, washed with water, and dried to obtain 80 mg of the title compound.

$^1$H-NMR (DMSO-d$_6$); δ 3.03-3.05 (4H, m), 3.28-3.31 (4H, m), 4.08 (2H, d, J=5 Hz), 4.97 (1H, t, J=5 Hz), 5.55 (2H, s), 6.93 (1H, d, J=8 Hz), 7.17 (1H, d, J=12 Hz), 7.92 (1H, dd, J=12 Hz, 1 Hz), 8.40 (1H, s)

Reference Example 28

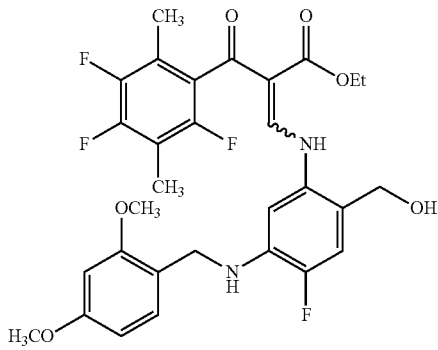

Ethyl 3-[5-(2,4-dimethoxybenzyl)amino-4-fluoro-2-(hydroxymethyl)phenyl]amino-2-(3,6-dimethyl-2,4,5-trifluoro)benzoylacrylate 0.563 g of ethyl 2-(3,6-dimethyl-2,4,5-trifluoro)benzoylacetate was dissolved in 0.58 mL of acetic anhydride and 0.51 mL of ethyl orthoformate and the mixture was stirred at 130° C. for 1 hour. The solvent was evaporated under reduced pressure and then the residue was subjected to azeotropic distillation with toluene. The resulting residue was dissolved in 5 mL of dichloromethane for use in the following reaction. 0.684 g of methyl 2-amino-4-(2,4-dimethoxybenzyl)amino-5-fluorobenzoate was suspended in 20 mL of toluene and 5 mL of tetrahydrofuran and 89 mg of lithium borohydride was added. The mixture was stirred by heating to reflux for 1.5 hours. The reaction solution was cooled to room temperature and then water was added. The mixture was extracted with ethyl acetate and the extract was dried over anhydrous sodium sulfate. The anhydrous sodium sulfate was filtering out and the dichloromethane solution of 3-ethoxyacrylic acid ethyl prepared earlier was added to the filtrate. The mixture was stirred at room temperature for 1 hour. The solvent was evaporated under reduced pressure and the residue was subjected to silica gel column chromatography (n-hexane/ethyl acetate 5 to 40% gradient) to obtain 0.685 g of the title compound at E/Z=2/1.

$^1$H-NMR (CDCl$_3$): δ 0.90 (1H, t, J=7.0 Hz), 1.03 (2H, t, J=7.0 Hz), 1.89 (0.33H, t, J=5.5 Hz), 2.03 (0.67H, t, J=5.5 Hz), 2.18 (3H, d, J=2.0 Hz), 2.20 (3H, m), 3.82 (3H, s), 3.87 (2H, s), 3.89 (1H, s), 4.02-4.08 (2H, m), 4.36 (2H, d, J=5.5 Hz), 4.53-4.57 (1H, m), 4.65-4.71 (2H, m), 6.47-6.52 (1H, m), 6.51-6.53 (1H, m), 6.72 (0.67H, d, J=7.5 Hz), 6.74 (0.33H, d, J=7.5 Hz), 6.88 (0.33H, d, J=11.0 Hz), 6.94 (0.67H, d, J=11.0 Hz), 7.20 (0.67H, d, J=8.5 Hz), 7.22 (0.33H, d, J=8.5 Hz), 8.51 (0.67H, d, J=13.0 Hz), 8.61 (0.33H, d, J=14.5 Hz), 11.75 (0.33H, brd, J=14.5 Hz), 13.17 (0.67H, brd, J=13.0 Hz)

Reference Example 29

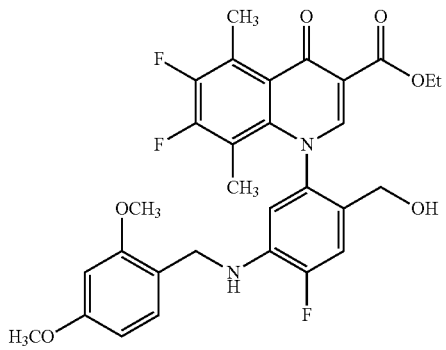 [SMILES: CCOC(=O)c1cn(-c2cc(NCc3ccc(OC)cc3OC)c(F)cc2CO)c2c(C)c(F)c(F)c(C)c2c1=O]

Ethyl 6,7-difluoro-1-[5-(2,4-dimethoxybenzyl)amino-4-fluoro-2-(hydroxymethyl)phenyl]-5,8-dimethyl-4-oxo-1,4-dihydroquinoline-3-carboxylate 0.685 g of ethyl 3-[5-(2,4-dimethoxybenzyl)amino-4-fluoro-2-(hydroxymethyl)phenyl]amino-2-(3,6-dimethyl-2,4,5-trifluorobenzoyl)acrylate was dissolved in 5.8 mL of N-methylpyrrolidin-2-one and 0.194 g of 1,8-diazabicyclo[5.4.0]undec-7-ene and 98 mg of lithium chloride were added at room temperature. The mixture was stirred at 50° C. for 3.5 hours. The mixture was cooled to room temperature and then water was added. Precipitates were collected by filtration to obtain 0.652 g of the title compound.

$^1$H-NMR (DMSO-d$_6$): δ 1.23 (3H, t, J=7.0 Hz), 1.37 (3H, d, J=2.0 Hz), 2.71 (3H, d, J=2.0 Hz), 3.56 (3H, s), 3.71 (3H, s), 4.11-4.21 (6H, m), 5.10 (1H, t, J=5.5 Hz), 6.35-6.37 (1H, m), 6.39-6.42 (2H, m), 6.55 (1H, d, J=8.0 Hz), 7.07 (1H, d, J=8.0 Hz), 7.18 (1H, d, J=12.5 Hz), 8.17 (1H, s)

Reference Example 30

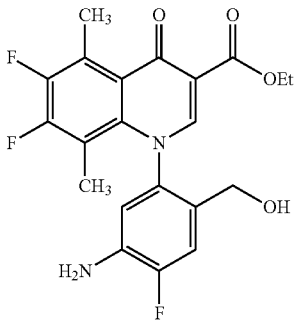 [SMILES: CCOC(=O)c1cn(-c2cc(N)c(F)cc2CO)c2c(C)c(F)c(F)c(C)c2c1=O]

Ethyl 1-[5-amino-4-fluoro-2-(hydroxymethyl)phenyl]-6,7-difluoro-5,8-dimethyl-4-oxo-1,4-dihydroquinoline-3-carboxylate 0.652 g of ethyl 6,7-difluoro-1-[5-(2,4-dimethoxybenzyl)amino-4-fluoro-2-(hydroxymethyl)phenyl]-5,8-dimethyl-4-oxo-1,4-dihydroquinoline-3-carboxylate was suspended in 25 mL of dichloromethane and 0.51 mL of anisole and 1.5 mL of trifluoroacetic acid were added. The mixture was stirred at room temperature for 15 minutes. 50 mL of a saturated aqueous solution of sodium hydrogen carbonate was added to the reaction solution and the mixture was stirred. The resulting precipitates were collected by filtration. The obtained solid was hot filtered using a hot chloroform/methanol (1/1) solution. The filtrate was concentrated and the residue was collected by filtration with water to obtain 0.327 g of the title compound.

$^1$H-NMR (DMSO-d$_6$): δ 1.24 (3H, t, J=7.0 Hz), 1.67 (3H, d, J=2.5 Hz), 2.72 (3H, d, J=2.5 Hz), 4.07 (1H, d, J=13.0 Hz), 4.10 (1H, d, J=13.0 Hz), 4.18 (2H, q, J=7.0 Hz), 5.09 (1H, brs), 5.52 (2H, s), 6.77 (1H, d, J=8.0 Hz), 7.17 (1H, d, J=11.5 Hz), 8.22 (1H, s)

Reference Example 31

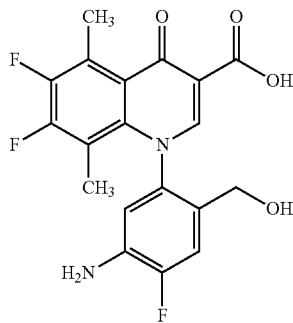 [SMILES: Cc1c(F)c(F)c(C)c2c1c(=O)c(C(=O)O)cn2-c1cc(N)c(F)cc1CO]

1-[5-Amino-4-fluoro-2-(hydroxymethyl)phenyl]-6,7-difluoro-5,8-dimethyl-4-oxo-1,4-dihydroquinoline-3-carboxylic acid 3.8 mL of ethanol and 0.571 mL of a 1 mol/L aqueous solution of sodium hydroxide were added to 80 mg of ethyl 1-[5-amino-4-fluoro-2-(hydroxymethyl)phenyl]-6,7-difluoro-5,8-dimethyl-4-oxo-1,4-dihydroquinoline-3-carboxylate and the mixture was stirred at 55° C. for 3 hours. 0.571 mL of 1 mol/L hydrochloric acid was added under ice cooling and precipitates were collected by filtration to obtain 72 mg of the title compound.

$^1$H-NMR (DMSO-d$_6$): δ 1.73 (3H, d, J=2.5 Hz), 2.83 (3H, d, J=2.0 Hz), 4.02 (1H, dd, J=5.5 Hz, 13.0 Hz), 4.08 (1H, dd, J=4.5 Hz, 13.0 Hz), 5.04 (1H, t, J=5.0 Hz), 5.61 (2H, s), 6.87 (1H, d, J=8.0 Hz), 7.19 (1H, d, J=12.0 Hz), 8.49 (1H, s)

Example 98

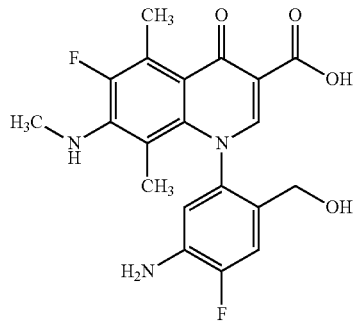 [SMILES: CNc1c(F)c(C)c2c(=O)c(C(=O)O)cn(-c3cc(N)c(F)cc3CO)c2c1C]

1-[5-Amino-4-fluoro-2-(hydroxymethyl)phenyl]-5,8-dimethyl-6-fluoro-7-methylamino-4-oxo-1,4-dihydroquinoline-3-carboxylic acid 72 mg of 1-[5-amino-4-fluoro-2-(hydroxymethyl)phenyl]-6,7-difluoro-5,8-dimethyl-4-oxo-1,4-dihydroquinoline-5-carboxylic acid was dissolved in 0.92 mL of dimethylsulfoxide and 0.087 mL of a 33% methylamine ethanol solution was added at room temperature. The mixture was stirred in a sealed tube at 50° C. for 2 days. The reaction solution was suspended in diethyl ether and then the suspension was left to stand. Removal of supernatant by decantation was repeated five times and water was added to the resulting residue to obtain a suspension. The suspension was adjusted to pH 4 with a 10% aqueous solution of citric acid and the resulting precipitates were collected by filtration to obtain 44 mg of the title compound.

$^1$H-NMR (DMSO-d$_6$): δ1.58 (3H, s), 2.75 (3H, d, J=3.0 Hz), 2.96 (3H, t, J=5.5 Hz), 4.00 (1H, dd, J=5.5 Hz, 13.0 Hz), 4.07 (1H, dd, J=5.0 Hz, 13.0 Hz), 5.10 (1H, t, J=5.0 Hz), 5.50 (2H, s), 5.90 (1H, brm), 6.72 (1H, d, J=8.5 Hz), 7.18 (1H, d, J=12.0 Hz), 8.43 (1H, s)

Example 99

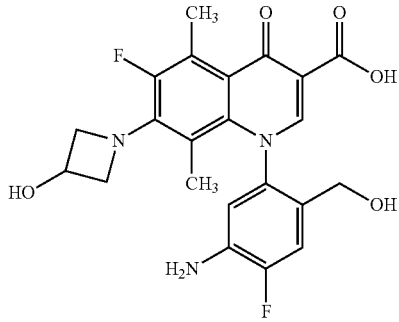

1-[5-Amino-4-fluoro-2-(hydroxymethyl)phenyl]-5,8-dimethyl-6-fluoro-7-(3-hydroxyazetidin-1-yl)-4-oxo-1,4-dihydroquinoline-3-carboxylic acid 78 mg of 1-[5-amino-4-fluoro-2-(hydroxymethyl)phenyl]-6,7-difluoro-5,8-dimethyl-4-oxo-1,4-dihydroquinoline-3-carboxylic acid was suspended in 1 mL of dimethylsulfoxide and 89 mg of 3-hydroxyazetidine tartrate, 17 mg of lithium chloride, and 0.115 g of 1,1,3,3-tetramethylguanidine were added at room temperature. The mixture was stirred in a sealed tube at 50° C. for 24 hours. The reaction solution was suspended in diethyl ether and then the suspension was left to stand. Removal of supernatant by decantation was repeated 6 times and water was added to the resulting residue to obtain a suspension. The suspension was adjusted to pH 4 with a 10% aqueous solution of citric acid and the resulting precipitates were collected by filtration. The obtained solid was recrystallized using hot ethanol to obtain 41 mg of the title compound.

$^1$H-NMR (DMSO-d$_6$): δ 1.51 (3H, s), 2.72 (3H, d, J=3.0 Hz), 3.86 (1H, b rm), 3.91 (1H, brm), 3.97 (1H, dd, J=5.5 Hz, 13.0 Hz), 4.08 (1H, dd, J=5.0 Hz, 13.0 Hz), 4.42 (3H, brm), 5.07 (1H, t, J=5.0 Hz), 5.52 (2H, s), 5.64 (1H, d, J=5.0 Hz), 6.84 (1H, d, J=8.5 Hz), 7.17 (1H, d, J=12.0 Hz), 8.43 (1H, s)

Example 100

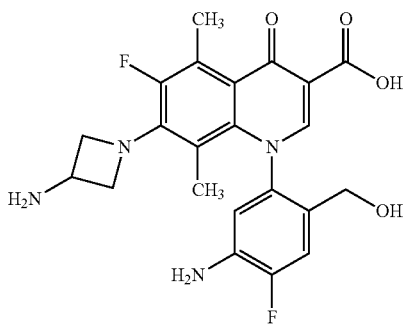 [SMILES: Cc1c(F)c(N2CC(N)C2)c(C)c2c1c(=O)c(C(=O)O)cn2-c1cc(N)c(F)cc1CO]

7-(3-Aminoazetidin-1-yl)-1-[5-amino-4-fluoro-2-(hydroxymethyl)phenyl]-5,8-dimethyl-6-fluoro-4-oxo-1,4-dihydroquinoline-3-carboxylic acid 78 mg of 1-[5-amino-4-fluoro-2-(hydroxymethyl)phenyl]-6,7-difluoro-5,8-dimethyl-4-oxo-1,4-dihydroquinoline-3-carboxylic acid was suspended in 1 mL of dimethylsulfoxide and 58 mg of 3-aminoazetidine dihydrochloride, 17 mg of lithium chloride, and 0.115 g of 1,1,3,3-tetramethylguanidine were added at room temperature. The mixture was stirred in a sealed tube at 50° C. for 2 days. The reaction solution was suspended in diethyl ether and then the suspension was left to stand. Removal of supernatant by decantation was repeated 6 times and water was added to the resulting residue to obtain a suspension. The suspension was adjusted to pH 4 with a 10% aqueous solution of citric acid and the resulting precipitates were collected by filtration. The obtained solid was recrystallized using hot ethanol to obtain 23 mg of the title compound.

$^1$H-NMR (DMSO-$d_6$): δ 1.51 (3H, s), 2.72 (3H, d, J=3.0 Hz), 3.77-3.84 (2H, m), 3.91 (1H, dd, J=5.0 Hz, 12.5 Hz), 3.91-3.97 (1H, m), 4.05 (1H, dd, J=4.5 Hz, 13.0 Hz), 4.37-4.42 (2H, m), 5.02 (1H, t, J=5.5 Hz), 5.53 (2H, s), 6.87 (1H, d, J=8.0 Hz), 7.16 (1H, d, J=12.0 Hz), 8.41 (1H, s)

Example 101

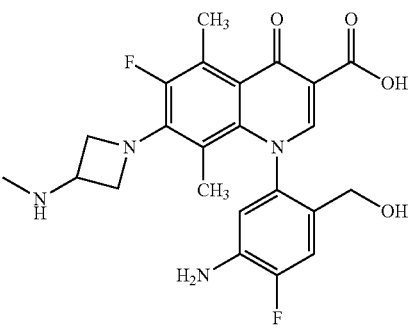

1-[5-Amino-4-fluoro-2-(hydroxymethyl)phenyl]-5,8-dimethyl-6-fluoro-7-(3-methylaminoazetidin-1-yl)-4-oxo-1,4-dihydroquinoline-3-carboxylic acid 0.486 g of 3-methylaminoazetidine dihydrochloride was suspended in 6 mL of 2-propanol and 1.02 mL of a 6 mol/L aqueous solution of sodium hydroxide was added under ice cooling, and the mixture was stirred. Insoluble matter was filtered off and then the solvent was evaporated under reduced pressure. 6 mL of 2-propanol was added again and insoluble matter was filtered off. Then, the solvent was evaporated under reduced pressure and the obtained free 3-methylaminoazetidine was used in the following reaction.

200 mg of 1-[5-amino-4-fluoro-2-(hydroxymethyl)phenyl]-6,7-difluoro-5,8-dimethyl-4-oxo-1,4-dihydroquinoline-3-carboxylic acid was suspended in 2.5 mL of dimethylsulfoxide and half the amount of 3-methylaminoazetidine prepared as described above, 43 mg of lithium chloride, and 0.117 g of 1,1,3,3-tetramethylguanidine were added at room temperature. The mixture was stirred at 50° C. for 1 day. The other half of 3-methylaminoazetidine was dissolved in 0.5 mL of dimethylsulfoxide and added to the mixture. The mixture was again stirred at 50° C. for 1 day. The reaction solution was subjected to reverse phase flash column chromatography (a 0.1% aqueous solution of heptafluorobutyric acid: 0.1% heptafluorobutyric acid/acetonitrile=10 to 80% gradient) and the fraction containing the desired product was freeze-dried. The resulting powder was suspended in 2 mL of water and 0.083 mL of a 6 mol/L aqueous solution of sodium hydroxide was added. The mixture was stirred and the resulting precipitates were collected by filtration to obtain 0.152 g of the title compound.

$^1$H-NMR (DMSO-$d_6$): δ 1.52 (3H, s), 2.20 (3H, s), 2.72 (3H, d, J=2.5 Hz), 3.44 (1H, brm), 3.81 (1H, brm), 3.90 (1H, brm), 3.94 (1H, dd, J=5.5 Hz, 13.0 Hz), 4.07 (1H, dd, J=5.0 Hz, 13.0 Hz), 4.31-4.37 (2H, m), 5.04 (1H, t, J=5.0 Hz), 5.51 (2H, s), 6.85 (1H, d, J=8.0 Hz), 7.16 (1H, d, J=12.0 Hz), 8.41 (1H, s)

Example 102

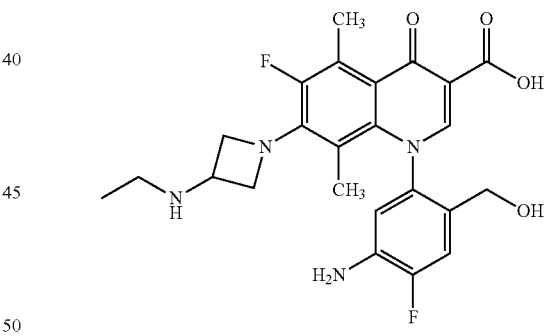

1-[5-Amino-4-fluoro-2-(hydroxymethyl)phenyl]-5,8-dimethyl-7-(3-ethylaminoazetidin-1-yl)-6-fluoro-4-oxo-1,4-dihydroquinoline-3-carboxylic acid heptafluorobutyrate 78 mg of 1-[5-amino-4-fluoro-2-(hydroxymethyl)phenyl]-6,7-difluoro-5,8-dimethyl-4-oxo-1,4-dihydroquinoline-3-carboxylic acid was suspended in 1 mL of dimethylsulfoxide and 69 mg of 3-ethylaminoazetidine dihydrochloride, 17 mg of lithium chloride, and 0.115 g of 1,1,3,3-tetramethylguanidine were added at room temperature. The mixture was stirred in a sealed tube at 50° C. for 2 days. The reaction solution was suspended in diethyl ether and then the suspension was left to stand. Removal of supernatant by decantation was repeated 6 times and water was added to the resulting residue to obtain a suspension. The suspension was adjusted to pH 4 with a 10% aqueous solution of citric acid and the resulting precipitates were removed by filtration. The filtrate was subjected to reverse phase flash column chromatography (a 0.1% heptafluorobutyric acid aqueous solution: 0.1% heptafluorobutyric acid/acetonitrile=20 to 80% gradient). The fraction containing the desired product was freeze-dried to obtain 63 mg of the title compound.

$^1$H-NMR (DMSO-$d_6$): δ 1.16 (1H, d, J=12.5 Hz), 1.55 (3H, s), 2.74 (3H, d, J=3.0 Hz), 2.94-2.98 (2H, m), 3.87 (1H, d, J=12.5 Hz), 4.01 (1H, d, J=12.5 Hz), 4.00-4.05 (1H, m), 4.13-4.17 (1H, m), 4.29-4.33 (1H, m), 4.40-4.45 (1H, m), 4.47-4.51 (1H, m), 5.56 (2H, brm), 6.92 (1H, d, J=8.0 Hz), 7.16 (1H, d, J=12.0 Hz), 8.42 (1H, s), 8.95 (2H, m)

Reference Example 32

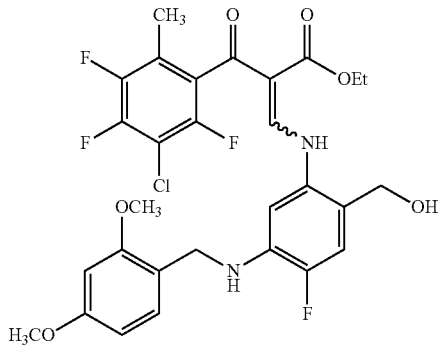 [SMILES: CCOC(=O)C(=CNc1cc(NCc2ccc(OC)cc2OC)c(F)cc1CO)C(=O)c1c(C)c(F)c(F)c(Cl)c1F]

Ethyl 2-(3-chloro-6-methyl-2,4,5-trifluorobenzoyl)-3-[5-(2,4-dimethoxybenzyl)amino-4-fluoro-2-hydroxymethylphenyl]aminoacrylate 2.49 g of ethyl 2-(3-chloro-6-methyl-2,4,5-trifluorobenzoyl)acetate was dissolved in 2.4 mL of acetic anhydride and 2.1 mL of ethyl orthoformate and the mixture was stirred at 130° C. for 18 hours. The solvent was evaporated under reduced pressure and then the residue was subjected to azeotropic distillation with toluene. The resulting ethyl 2-(3-chloro-6-methyl-2,4,5-trifluoro)benzoyl-3-ethoxyacrylate (a cis/trans mixture) was dissolved in 1 mL of dichloromethane for use in the following reaction.

0.668 g of methyl 2-amino-4-(2,4-dimethoxybenzyl) amino-5-fluorobenzoate was suspended in 20 mL of toluene and 5 mL of tetrahydrofuran and 87 mg of lithium borohydride was added. The mixture was stirred at 80° C. for 2 hours. 87 mg of lithium borohydride was added to the reaction solution and the mixture was stirred at 80° C. for 1.5 hours again. The reaction solution was cooled to room temperature and then water was added. The mixture was extracted with ethyl acetate and the extract was dried over anhydrous sodium sulfate. The anhydrous sodium sulfate was filtered off and then the aforementioned dichloromethane solution was added to the filtrate. The mixture was stirred at room temperature for 1 hour. The solvent was evaporated under reduced pressure and the residue was subjected to silica gel column chromatography (n-hexane: ethyl acetate=20 to 50% gradient) to obtain 1.03 g of the title compound at E/Z=2/1.

$^1$H-NMR (DMSO-$d_6$): δ 0.85 (1H, t, J=7.0 Hz), 0.95 (2H, t, J=7.0 Hz), 2.11 (2H, d, J=3.0 Hz), 2.14 (1H, d, J=3.0 Hz), 3.72 (3H, s), 3.82 (2H, s), 3.83 (1H, s), 3.93-3.99 (2H, m), 4.29-4.31 (2H, m), 4.41 (0.67H, d, J=4.0 Hz), 4.43 (1.33H, d, J=4.0 Hz), 5.45 (0.67H, t, J=4.5 Hz), 5.48 (0.33H, t, J=4.5 Hz), 6.14 (0.67H, t, J=5.5 Hz), 6.20 (0.33H, t, J=5.5 Hz), 6.47 (0.67H, dd, J=2.5 Hz, 8.5 Hz), 6.48 (0.33H, dd, J=2.5 Hz, 8.5 Hz), 6.56 (0.67H, d, J=2.5 Hz), 6.57 (0.33H, d, J=2.5 Hz), 6.72 (0.33H, d, J=8.5 Hz), 6.77 (0.67H, d, J=8.5 Hz), 7.02 (0.33H, d, J=12.0 Hz), 7.06 (0.67H, d, J=12.0 Hz), 7.18 (0.67H, d, J=8.0 Hz), 7.22 (0.33H, d, J=8.0 Hz), 8.36 (0.67H, d, J=14.5 Hz), 8.44 (0.33H, d, J=14.5 Hz), 11.66 (0.33H, d, J=14.5 Hz), 12.88 (0.67H, d, J=14.5 Hz)

Reference Example 33

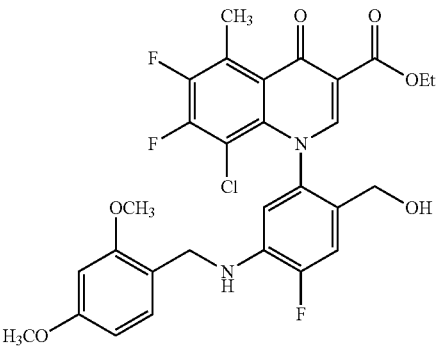 [SMILES: CCOC(=O)c1cn(-c2cc(NCc3ccc(OC)cc3OC)c(F)cc2CO)c2c(Cl)c(F)c(F)c(C)c2c1=O]

Ethyl 8-chloro-6,7-difluoro-1-[5-(2,4-dimethoxybenzyl)amino-4-fluoro-2-(hydroxymethyl)phenyl]-5-methyl-4-oxo-1,4-dihydroquinoline-3-carboxylate 1.03 g of ethyl 2-(3-chloro-6-methyl-2,4,5-trifluorobenzoyl)-3-[5-(2,4-dimethoxybenzylamino)-4-fluoro-2-hydroxymethylphenyl]aminoacrylate was dissolved in N-methylpyrrolidin-2-one and 0.286 g of 1,8-diazabicyclo[5.4.0]undec-7-ene and 0.143 g of lithium chloride were added at room temperature. The mixture was stirred at 60° C. for 2 hours. The mixture was cooled to room temperature and then water was added. Precipitates were collected by filtration. The resulting solid was recrystallized from chloroform-isopropyl ether to obtain 0.851 g of the title compound.

$^2$H-NMR (DMSO-$d_6$): δ 1.23 (3H, t, J=7.0 Hz), 2.72 (3H, d, J=3.0 Hz), 3.64 (3H, s), 3.70 (3H, s), 4.12 (2H, d, J=5.5 Hz), 4.15 (2H, d, J=6.0 Hz), 4.19 (2H, q, J=7.0 Hz), 5.06 (1H, t, J=5.5 Hz), 6.19 (1H, t, J=6.0 Hz), 6.39 (1H, dd, J=2.0 Hz, 8.0 Hz), 6.43 (1H, d, J=2.0 Hz), 6.61 (1H, d, J=8.0 Hz), 7.06 (1H, d, J=9.0 Hz), 7.16 (1H, d, J=12.5 Hz), 8.19 (1H, s)

Reference Example 34

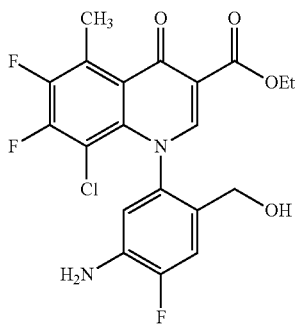 [SMILES: CCOC(=O)c1cn(-c2cc(N)c(F)cc2CO)c2c(Cl)c(F)c(F)c(C)c2c1=O]

Ethyl 1-[5-amino-4-fluoro-2-(hydroxymethyl)phenyl]-8-chloro-6,7-difluoro-5-methyl-4-oxo-1,4-dihydroquinoline-3-carboxylate 4.0 g of ethyl 8-chloro-6,7-difluoro-1-[5-(2,4-dimethoxybenzylamino)-4-fluoro-2-(hydroxymethyl)phenyl]-5-methyl-4-oxo-1,4-dihydroquinoline-3-carboxylate was dissolved in 134 mL of dichloromethane and 3.0 mL of anisole and 8.8 mL of trifluoroacetic acid were added. The mixture was stirred at room temperature for 10 minutes. A saturated aqueous solution of sodium hydrogen carbonate was added to the reaction solution to make the solution alkaline and then insoluble matter was collected by filtration with water. The resulting crystalline residue was suspended in 240 mL of chloroform and 240 mL of methanol at 60° C. and insoluble matter was filtered off. The filtrate was evaporated under reduced pressure and the resulting residue was dispersed in water, collected by filtration, and dried to obtain 1.8 g of the title compound.

$^1$H-NMR (DMSO-$d_6$): δ 1.25 (3H, q, J=7.0 Hz), 2.74 (3H, d, J=2.5 Hz), 4.12 (2H, d, J=4.5 Hz), 4.20 (2H, q, J=7.0 Hz), 5.06 (1H, t, J=4.5 Hz), 5.46 (2H, s), 6.76 (1H, d, J=8.2 Hz), 7.15 (1H, d, J=12.0 Hz), 8.24 (1H, s).

Example 103

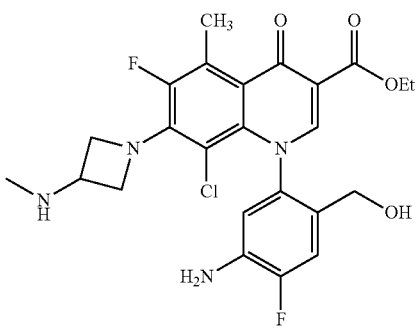 [SMILES: CCOC(=O)c1cn(-c2cc(N)c(F)cc2CO)c2c(Cl)c(N3CC(NC)C3)c(F)c(C)c2c1=O]

Ethyl 1-[5-amino-4-fluoro-2-(hydroxymethyl)phenyl]-8-chloro-6-fluoro-5-methyl-7-(3-methylaminoazetidin-1-yl)-4-oxo-1,4-dihydroquinoline-3-carboxylate 50 mg of ethyl 1-[5-amino-4-fluoro-2-(hydroxymethyl)phenyl]-8-chloro-6,7-difluoro-5-methyl-4-oxo-1,4-dihydroquinoline-3-carboxylate was dissolved in 0.57 mL of dimethylsulfoxide and 27 mg of 3-methylaminoazetidine dihydrochloride and 48 mg of N-methylpyrrolidine were added at room temperature. The mixture was stirred at 60° C. for 7 hours. The mixture was cooled to room temperature and then water was added. Precipitates were collected by filtration to obtain 48 mg of the title compound.

$^1$H-NMR (DMSO-$d_6$): δ 1.22 (3H, t, J=7.0 Hz), 2.18 (3H, s), 2.61 (3H, d, J=3.5 Hz), 3.36-3.41 (1H, m), 3.92-4.00 (2H, m), 4.14-4.18 (2H, m), 4.44-4.52 (2H, m), 5.11 (1H, t, J=5.0 Hz), 5.35 (2H, s), 6.57 (1H, d, J=8.0 Hz), 7.12 (1H, d, J=12.0 Hz), 8.14 (1H, s)

Example 104

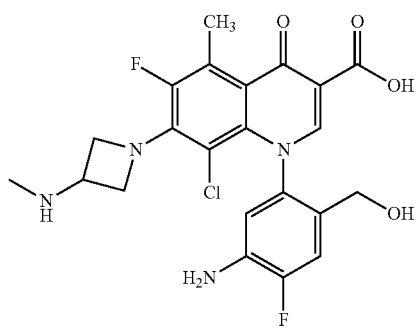 [SMILES: CNC1CN(c2c(F)c(C)c3c(=O)c(C(=O)O)cn(-c4cc(N)c(F)cc4CO)c3c2Cl)C1]

1-[5-Amino-4-fluoro-2-(hydroxymethyl)phenyl]-8-chloro-6-fluoro-5-methyl-7-(3-methylaminoazetidin-1-yl)-4-oxo-1,4-dihydroquinoline-3-carboxylic acid 0.5 mL of ethanol and 0.284 mL of a 1 mol/L aqueous solution of sodium hydroxide were added to 48 mg of ethyl 1-[5-amino-4-fluoro-2-(hydroxymethyl)phenyl]-8-chloro-6-fluoro-5-methyl-7-(3-methylaminoazetidin-1-yl)-4-oxo-1,4-dihydroquinoline-3-carboxylate and the mixture was stirred at 50° C. for 15 minutes. 0.284 mL of 1 mol/L hydrochloric acid was added and then ethanol was evaporated under reduced pressure. Precipitates were collected by filtration to obtain 32 mg of the title compound.

$^1$H-NMR (DMSO-$d_6$): δ 2.41 (3H, s), 2.72 (3H, d, J=3.5 Hz), 3.75 (1H, brm), 4.05 (1H, dd, J=5.5 Hz, 13.0 Hz), 4.12 (1H, dd, J=5.5 Hz, 13.0 Hz), 4.29-4.34 (2H, m), 4.61-4.66 (2H, m), 5.05 (1H, t, J=5.0 Hz), 5.46 (2H, s), 6.72 (1H, d, J=8.5 Hz), 7.14 (1H, d, J=12.0 Hz), 8.39 (1H, s)

Example 105

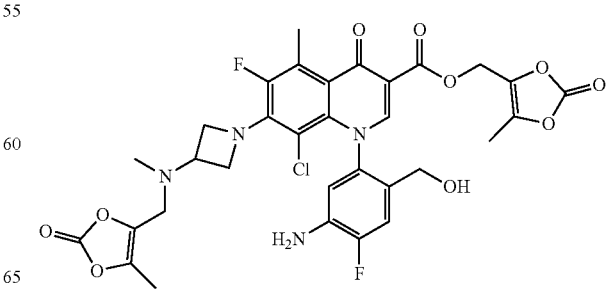

1-[5-Amino-4-fluoro-2-(hydroxymethyl)phenyl]-8-chloro-6-fluoro-5-methyl-7-(3-[N-methyl-N-[(5-methyl-2-oxo-1,3-dioxol-4-yl)methyl]amino]azetidin-1-yl)-4-oxo-1,4-dihydroquinoline-3-carboxylic acid (5-methyl-2-oxo-1,3-dioxol-4-yl)methyl ester 48 mg of 1-[5-amino-4-fluoro-2-(hydroxymethyl)phenyl]-8-chloro-6-fluoro-5-methyl-7-[3-(methylamino)azetidin-1-yl]-4-oxo-1,4-dihydroquinoline-3-carboxylic acid was suspended in 1.2 mL of N,N-dimethylformamide and 13.8 mg of potassium carbonate, 3.3 mg of potassium iodide, and 12.1 µL of 4-chloromethyl-5-methyl-1,3-dioxol-2-one were added. The mixture was stirred at 45° C. for 1 hour. 10 mL of ethyl acetate was added to the reaction solution and 10 mL of a saturated aqueous solution of sodium hydrogen carbonate was added. The mixture was extracted with ethyl acetate. The solvent was evaporated under reduced pressure and the residue was subjected to silica gel column chromatography (chloroform:methanol=0 to 5% gradient). The solvent was evaporated. Precipitates were collected by filtration to obtain 14.9 mg of the title compound.
$^1$H-NMR (500 MHz, CDCl$_3$) δ 2.11 (3H, s), 2.18 (3H, s), 2.22 (3H, s), 2.75 (3H, d, J=3.4 Hz), 3.27 (2H, s), 3.35-3.29 (1H, m), 3.91 (2H, s), 4.21-4.10 (2H, m), 4.46-4.37 (2H, m), 4.55-4.48 (2H, m), 5.00 (2H, d, J=2.5 Hz), 6.57 (1H, d, J=7.8 Hz), 7.22 (1H, d, J=11.3 Hz), 8.25 (1H, s).

Example 106

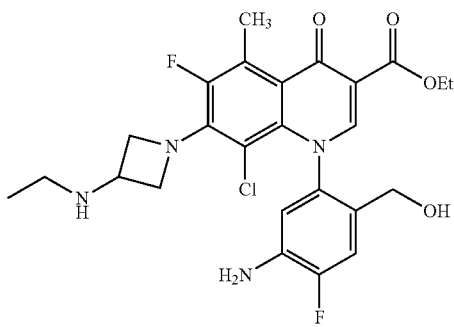 [SMILES: CCNC1CN(c2c(F)c(C)c3c(=O)c(C(=O)OCC)cn(-c4cc(N)c(F)cc4CO)c3c2Cl)C1]

Ethyl 1-[5-amino-4-fluoro-2-(hydroxymethyl)phenyl]-8-chloro-7-(3-ethylaminoazetidin-1-yl)-6-fluoro-5-methyl-4-oxo-1,4-dihydroquinoline-3-carboxylate 80 mg of ethyl 1-[5-amino-4-fluoro-2-(hydroxymethyl)phenyl]-8-chloro-6,7-difluoro-5-methyl-4-oxo-1,4-dihydroquinoline-3-carboxylate was dissolved in 0.57 mL of dimethylsulfoxide and 47 mg of 3-ethylaminoazetidine dihydrochloride and 77 mg of N-methylpyrrolidine were added at room temperature. The mixture was stirred at 40° C. for 24 hours. The mixture was cooled to room temperature and then water was added. Precipitates were collected by filtration to obtain 25 mg of the title compound.
$^1$H-NMR (DMSO-d$_6$): δ 0.96 (3H, t, J=7.0 Hz), 1.22 (3H, t, J=7.0 Hz), 2.44 (2H, q, J=7.0 Hz), 2.61 (3H, d, J=3.5 Hz), 3.45-3.50 (1H, m), 3.91-3.99 (2H, m), 4.14-4.18 (4H, m), 4.46-4.54 (2H, m), 5.11 (1H, t, J=5.0 Hz), 5.35 (2H, s), 6.57 (1H, d, J=8.0 Hz), 7.12 (1H, d, J=12.0 Hz), 8.14 (1H, s)

Example 107

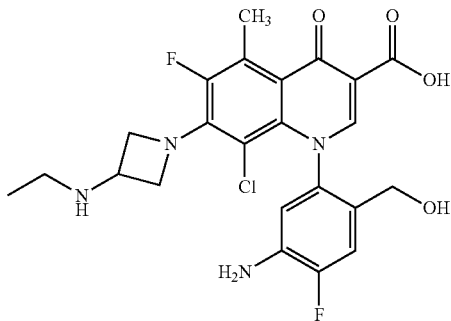 [SMILES: CCNC1CN(c2c(F)c(C)c3c(=O)c(C(=O)O)cn(-c4cc(N)c(F)cc4CO)c3c2Cl)C1]

1-[5-Amino-4-fluoro-2-(hydroxymethyl)phenyl]-8-chloro-7-(3-ethylaminoazetidin-1-yl)-6-fluoro-5-methyl-4-oxo-1,4-dihydroquinoline-3-carboxylic acid 1.9 mL of ethanol and 0.374 mL of a 1 mol/L aqueous solution of sodium hydroxide were added to 25 mg of ethyl 1-[5-amino-4-fluoro-2-(hydroxymethyl)phenyl]-8-chloro-7-(3-ethylaminoazetidin-1-yl)-6-fluoro-5-methyl-4-oxo-1,4-dihydroquinoline-3-carboxylate and the mixture was stirred at 60° C. for 1 hour. 0.284 mL of 1 mol/L hydrochloric acid was added and then ethanol was evaporated under reduced pressure. Precipitates were collected by filtration to obtain 40 mg of the title compound.
$^1$H-NMR (DMSO-d$_6$): δ 1.16 (3H, t, J=7.0 Hz), 2.73 (3H, d, J=3.5 Hz), 2.92 (2H, q, J=7.0 Hz), 4.02 (1H, brm), 4.04 (1H, dd, J=6.0 Hz, 13.0 Hz), 4.11 (1H, dd, J=4.5 Hz, 13.0 Hz), 4.47-4.54 (2H, m), 4.66-4.72 (2H, m), 5.06 (1H, t, J=5.5 Hz), 5.48 (2H, s), 6.74 (1H, d, J=8.0 Hz), 7.14 (1H, d, J=12.0 Hz), 8.40 (1H, s), 9.33 (2H, brs)

Example 108

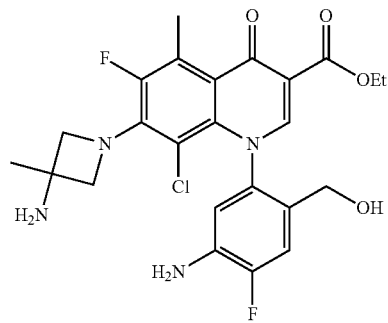 [SMILES: CCOC(=O)c1cn(-c2cc(N)c(F)cc2CO)c2c(Cl)c(N3CC(C)(N)C3)c(F)c(C)c2c1=O]

Ethyl 1-[5-amino-4-fluoro-2-(hydroxymethyl)phenyl]-7-(3-amino-3-methylazetidin-1-yl)-8-chloro-6-fluoro-5-methyl-4-oxo-1,4-dihydroquinoline-3-carboxylate 100 mg of ethyl 1-[5-amino-4-fluoro-2-(hydroxymethyl)phenyl]-8-chloro-6,7-difluoro-5-methyl-4-oxo-1,4-dihydroquinoline-3-carboxylate was dissolved in 2.0 mL of dimethylsulfoxide and 0.21 mL of N-methylpyrrolidine and 56 mg of 3-amino-3-methylazetidine diacetate were added at room temperature. The mixture was stirred at 50° C. for 1 day. Water was added to the reaction solution and then precipitates were filtered off with water. A saturated aqueous solution of sodium hydrogen carbonate was added to the filtrate to make pH of the solution neutral. Precipitates were collected by filtration with water to obtain 71 mg of the title compound.

$^1$H-NMR (DMSO-d$_6$): δ 1.23 (3H, t, J=7.1 Hz), 1.31 (3H, s), 2.62 (3H, d, J=3.5 Hz), 3.96-4.02 (2H, m), 4.12-4.19 (6H, m), 5.12 (1H, brs), 5.36 (2H, s), 6.57 (1H, d, J=8.1 Hz), 7.13 (1H, d, J=12.0 Hz), 8.15 (1H, s).

Example 109

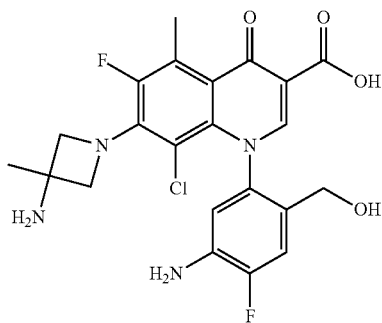

1-[5-Amino-4-fluoro-2-(hydroxymethyl)phenyl]-7-(3-amino-3-methylazetidin-1-yl)-8-chloro-6-fluoro-5-methyl-4-oxo-1,4-dihydroquinoline-3-carboxylic acid 71 mg of ethyl 1-[5-amino-4-fluoro-2-(hydroxymethyl)phenyl]-7-(3-amino-3-methylazetidin-1-yl)-8-chloro-6-fluoro-5-methyl-4-oxo-1,4-dihydroquinoline-3-carboxylate was suspended in 1.4 mL of ethanol and 0.16 mL of a 1 mol/L aqueous solution of sodium hydroxide was added at room temperature. The mixture was stirred at 40° C. for 1.5 hours. The mixture was returned to room temperature and then neutralized with hydrochloric acid. Precipitates were collected by filtration with water to obtain 46 mg of the title compound.

$^1$H-NMR (DMSO-d$_6$): δ 1.32 (3H, s), 2.71 (3H, d, J=3.2 Hz), 4.07-4.15 (4H, m), 4.22-4.26 (2H, m), 5.07 (1H, t, J=6.0 Hz), 5.44 (2H, s), 6.59 (1H, d, J=8.2 Hz), 7.14 (1H, d, J=12.0 Hz), 8.37 (1H, s).

Example 110

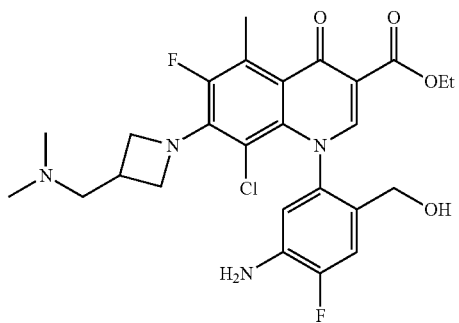 [SMILES: CCOC(=O)c1cn(-c2cc(N)c(F)cc2CO)c2c(Cl)c(N3CC(CN(C)C)C3)c(F)c(C)c2c1=O]

Ethyl 1-[5-amino-4-fluoro-2-(hydroxymethyl)phenyl]-8-chloro-7-[3-(dimethylaminomethyl)azetidin-1-yl]-6-fluoro-5-methyl-4-oxo-1,4-dihydroquinoline-3-carboxylate 100 mg of ethyl 1-[5-amino-4-fluoro-2-(hydroxymethyl)phenyl]-8-chloro-6,7-difluoro-5-methyl-4-oxo-1,4-dihydroquinoline-3-carboxylate was dissolved in 2.0 mL of dimethylsulfoxide and 0.13 mL of N-methylpyrrolidine and 66 mg of 3-(dimethylamino)methylazetidine dihydrochloride were added at room temperature. The mixture was stirred at 50° C. for 1 day. Water was added to the reaction solution and then precipitates were collected by filtration with water to obtain 110 mg of the title compound.

$^1$H-NMR (DMSO-d$_6$): δ 1.23 (3H, t, J=7.1 Hz), 2.17 (6H, brs), 2.62 (3H, d, J=3.5 Hz), 2.74-2.78 (1H, m), 3.93-3.96 (1H, m), 3.98-4.02 (1H, m), 4.15-4.19 (4H, m), 4.39-4.50 (2H, m), 5.12 (1H, t, J=5.5 Hz), 5.36 (2H, s), 6.57 (1H, d, J=8.2 Hz), 7.13 (1H, d, J=12.1 Hz), 8.15 (1H, s).

Example 111

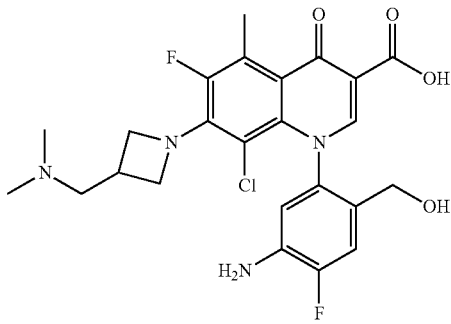 [SMILES: Cc1c(F)c(N2CC(CN(C)C)C2)c(Cl)c2c1c(=O)c(C(=O)O)cn2-c1cc(N)c(F)cc1CO]

1-[5-Amino-4-fluoro-2-(hydroxymethyl)phenyl]-8-chloro-7-[3-(dimethylaminomethyl)azetidin-1-yl]-6-fluoro-5-methyl-4-oxo-1,4-dihydroquinoline-3-carboxylic acid 110 mg of ethyl 1-[5-amino-4-fluoro-2-(hydroxymethyl)phenyl]-8-chloro-7-[3-(dimethylaminomethyl)azetidin-1-yl]-6-fluoro-5-methyl-4-oxo-1,4-dihydroquinoline-3-carboxylate was suspended in 2.1 mL of ethanol and 0.63 mL of a 1 mol/L aqueous solution of sodium hydroxide was added at room temperature. The mixture was stirred at 50° C. for 1.5 hours. The reaction solution was neutralized with 1 mol/L hydrochloric acid. Precipitates were collected by filtration with water to obtain 83 mg of the title compound.

$^1$H-NMR (MeOH-d4): δ 2.78 (3H, d, J=3.5 Hz), 2.85 (6H, s), 3.08-3.13 (1H, m), 3.42 (2H, d, J=7.1 Hz), 4.23 (2H, d, J=1.8 Hz), 4.27-4.31 (2H, m), 4.69-4.86 (2H, m), 6.73 (1H, d, J=7.9 Hz), 7.15 (1H, d, J=11.7 Hz), 8.53 (1H, s).

Example 112

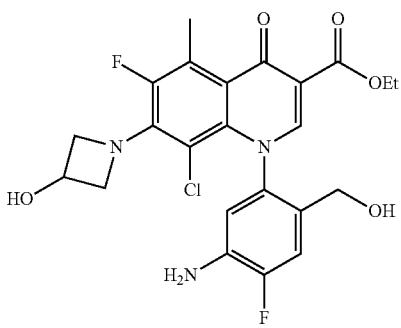 [SMILES: CCOC(=O)c1cn(-c2cc(N)c(F)cc2CO)c2c(Cl)c(N3CC(O)C3)c(F)c(C)c2c1=O]

Ethyl 1-[5-amino-4-fluoro-2-(hydroxymethyl)phenyl]-8-chloro-6-fluoro-7-(3-hydroxyazetidin-1-yl)-5-methyl-4-oxo-1,4-dihydroquinoline-3-carboxylate 100 mg of ethyl 1-[5-amino-4-fluoro-2-(hydroxymethyl)phenyl]-8-chloro-6,7-difluoro-5-methyl-4-oxo-1,4-dihydroquinoline-3-carboxylate was dissolved in 2.0 mL of dimethylsulfoxide and 0.13 mL of N-methylpyrrolidine and 78 mg of 3-hydroxyazetidine tartrate were added at room temperature. The mixture was stirred at 50° C. for 1 day. Water was added to the reaction solution and then precipitates were collected by filtration with water to obtain 96 mg of the title compound.

$^1$H-NMR (DMSO-$d_6$): δ 1.23 (3H, q, J=7.0 Hz), 2.62 (3H, d, J=3.3 Hz), 3.96-4.00 (1H, m), 4.02-4.06 (1H, m), 4.15-4.19 (4H, m), 4.37-4.43 (1H, m), 4.52-4.65 (2H, m), 5.13 (1H, t, J=5.5 Hz), 5.36 (2H, s), 5.63 (1H, d, J=5.5 Hz), 6.58 (1H, d, J=8.1 Hz), 7.13 (1H, d, J=11.9 Hz), 8.16 (1H, s).

Example 113

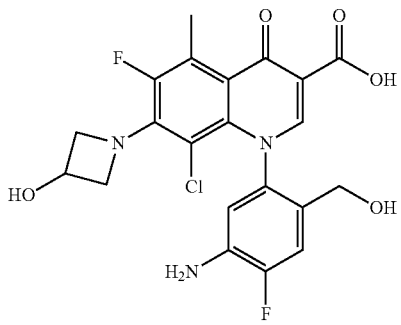

1-[5-Amino-4-fluoro-2-(hydroxymethyl)phenyl]-8-chloro-6-fluoro-7-(3-hydroxyazetidin-1-yl)-5-methyl-4-oxo-1,4-dihydroquinoline-3-carboxylic acid 96 mg of ethyl 1-[5-amino-4-fluoro-2-(hydroxymethyl)phenyl]-8-chloro-6-fluoro-7-(3-hydroxyazetidin-1-yl)-5-methyl-4-oxo-1,4-dihydroquinoline-3-carboxylate was suspended in 2.0 mL of ethanol and 0.57 mL of a 1 mol/L aqueous solution of sodium hydroxide was added at room temperature. The mixture was stirred at 50° C. for 1 hour. The reaction solution was neutralized with 1 mol/L hydrochloric acid. Precipitates were collected by filtration with water to obtain 66 mg of the title compound.

$^1$H-NMR (DMSO-$d_6$): δ 2.71 (3H, d, J=3.0 Hz), 4.06-4.15 (4H, m), 4.39-4.45 (1H, m), 4.62-4.67 (2H, m), 5.09 (1H, t, J=5.5 Hz), 5.44 (2H, s), 5.68 (1H, d, J=5.5 Hz), 6.69 (1H, d, J=8.1 Hz), 7.14 (1H, d, J=11.9 Hz), 8.38 (1H, s).

Example 114

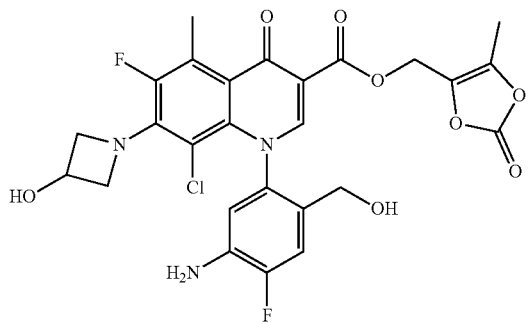 [SMILES: Cc1oc(=O)oc1COC(=O)c1cn(-c2cc(N)c(F)cc2CO)c2c(Cl)c(N3CC(O)C3)c(F)c(C)c2c1=O]

1-[5-Amino-4-fluoro-2-(hydroxymethyl)phenyl]-8-chloro-6-fluoro-7-(3-hydroxyazetidin-1-yl)-5-methyl-4-oxo-1,4-dihydroquinoline-3-carboxylic acid (5-methyl-2-oxo-1,3-dioxol-4-yl)methyl ester 47 mg of 1-[5-amino-4-fluoro-2-(hydroxymethyl)phenyl]-8-chloro-6-fluoro-7-(3-hydroxyazetidin-1-yl)-5-methyl-4-oxo-1,4-dihydroquinoline-3-carboxylic acid, 15 mg of potassium carbonate, and 8 mg of potassium iodide were added to 1.2 mL of dimethylformamide. 16 mg of 4-chloromethyl-5-methyl-1,3-dioxol-2-one was added to the mixture, which was stirred at 40° C. for 2.5 hours. The mixture was cooled and then 40 mL of ethyl acetate was added to the reaction solution. The mixture was washed three times with 30 mL of a 1% aqueous solution of citric acid. The organic layer was dried and then concentrated under reduced pressure. Hexane was added and precipitates were collected by filtration to obtain 35 mg of the title compound as pale yellow powder.

$^1$H-NMR (DMSO-$d_6$): δ 2.17 (3H, s), 2.71 (3H, d, J=3.4 Hz), 3.96-4.05 (2H, m), 4.12-4.16 (2H, m), 4.38-4.42 (1H, m), 4.52-4.68 (2H, m), 5.05 (2H, s), 5.10 (1H, t, J=5.5 Hz), 5.36 (2H, s), 5.61 (1H, d, J=5.9 Hz), 6.59 (1H, d, J=8.0 Hz), 7.12 (1H, d, J=12.0 Hz), 8.20 (1H, s).

Example 115

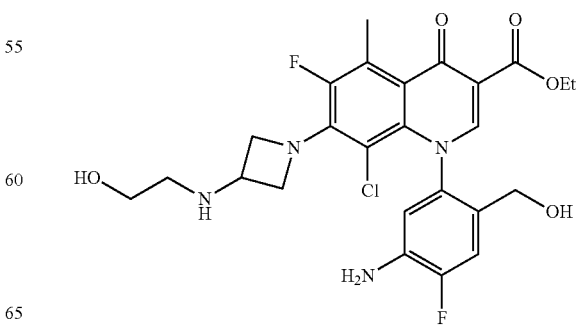

Ethyl 1-[5-amino-4-fluoro-2-(hydroxymethyl)phenyl]-8-chloro-6-fluoro-7-[3-(2-hydroxyethyl)aminoazetidin-1-yl]-5-methyl-4-oxo-1,4-dihydroquinoline-3-carboxylate 88 mg of ethyl 1-[5-amino-4-fluoro-2-(hydroxymethyl)phenyl]-8-chloro-6,7-difluoro-5-methyl-4-oxo-1,4-dihydroquinoline-3-carboxylate was dissolved in 1.7 mL of dimethylsulfoxide and 0.11 mL of N-methylpyrrolidine and 57 mg of 3-(2-hydroxyethyl)aminoazetidine dihydrochloride were added at room temperature. The mixture was stirred at 50° C. for 1 day. Diethyl ether was added to the reaction solution and they were mixed. The mixture was left to stand. Supernatant was removed by decantation and this procedure was repeated four times. Water was added to the residue and then the residue was neutralized with a saturated aqueous solution of sodium hydrogen carbonate. Precipitates were collected by filtration with water to obtain 80 mg of the title compound.

$^1$H-NMR (DMSO-d$_6$): δ 1.22 (3H, t, J=7.1 Hz), 2.62 (3H, d, J=3.4 Hz), 2.74-2.78 (1H, m), 3.38 (2H, dt, J=11.2, 5.5 Hz), 3.47-3.53 (1H, m), 3.92-4.00 (2H, m), 4.14-4.19 (4H, m), 4.45-4.54 (3H, m), 5.12 (1H, t, J=5.5 Hz), 5.36 (2H, s), 6.57 (1H, d, J=8.1 Hz), 7.13 (1H, d, J=12.1 Hz), 8.15 (1H, s).

Example 116

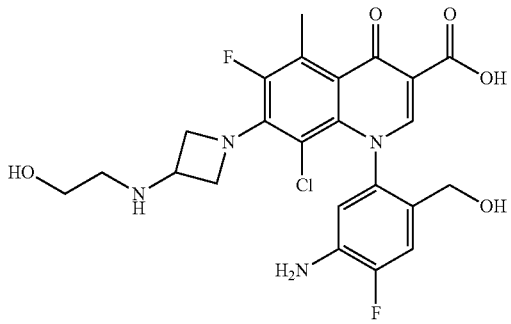 [SMILES: Cc1c(F)c(N2CC(NCCO)C2)c(Cl)c2c1c(=O)c(C(=O)O)cn2-c1cc(N)c(F)cc1CO]

1-[5-Amino-4-fluoro-2-(hydroxymethyl)phenyl]-8-chloro-6-fluoro-7-[3-(2-hydroxyethyl)aminoazetidin-1-yl]-5-methyl-4-oxo-1,4-dihydroquinoline-3-carboxylic acid 80 mg of ethyl 1-[5-amino-4-fluoro-2-(hydroxymethyl)phenyl]-8-chloro-6-fluoro-7-[3-(2-hydroxyethyl)aminoazetidin-1-yl]-5-methyl-4-oxo-1,4-dihydroquinoline-3-carboxylate was suspended in 1.5 mL of ethanol and 0.45 mL of a 1 mol/L aqueous solution of sodium hydroxide was added at room temperature. The mixture was stirred at 50° C. for 1 hour. The reaction solution was neutralized with 1 mol/L hydrochloric acid. Precipitates were collected by filtration with water to obtain 58 mg of the title compound.

$^1$H-NMR (MeOH-d4): δ 2.67 (2H, t, J=5.5 Hz), 2.77 (3H, d, J=3.4 Hz), 3.60-3.65 (3H, m), 4.17-4.22 (2H, m), 4.25 (2H, s), 4.65-4.71 (2H, m), 6.70 (1H, d, J=8.0 Hz), 7.15 (1H, d, J=11.7 Hz), 8.46 (1H, s).

Example 117

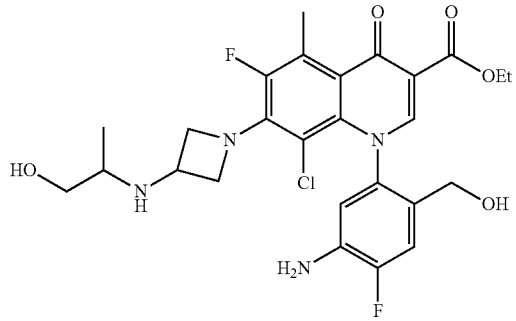 [SMILES: CCOC(=O)c1cn(-c2cc(N)c(F)cc2CO)c2c(Cl)c(N3CC(NC(C)CO)C3)c(F)c(C)c2c1=O]

Ethyl 1-[5-amino-4-fluoro-2-(hydroxymethyl)phenyl]-8-chloro-6-fluoro-7-[3-(1-hydroxypropan-2-yl)aminoazetidin-1-yl]-5-methyl-4-oxo-1,4-dihydroquinoline-3-carboxylate 88 mg of ethyl 1-[5-amino-4-fluoro-2-(hydroxymethyl)phenyl]-8-chloro-6,7-difluoro-5-methyl-4-oxo-1,4-dihydroquinoline-3-carboxylate was dissolved in 1.7 mL of dimethylsulfoxide and 0.11 mL of N-methylpyrrolidine and 57 mg of 3-(1-hydroxypropan-2-yl)aminoazetidine dihydrochloride were added at room temperature. The mixture was stirred at 50° C. for 1 day. Diethyl ether was added to the reaction solution and they were mixed, and the mixture was left to stand. Supernatant was removed by decantation and this procedure was repeated four times. Water was added to the residue and then the residue was neutralized with a saturated aqueous solution of sodium hydrogen carbonate. Precipitates were collected by filtration with water to obtain 57 mg of the title compound.

$^1$H-NMR (DMSO-d$_6$): δ 0.86-0.88 (3H, m), 1.23 (3H, t, J=7.2 Hz), 2.62 (3H, d, J=3.5 Hz), 3.19 (1H, t, J=5.6 Hz), 3.59-3.62 (1H, m), 3.88-3.98 (2H, m), 4.14-4.19 (4H, m), 4.48-4.56 (3H, m), 5.12 (1H, t, J=5.6 Hz), 5.36 (2H, s), 6.56-6.58 (1H, m), 7.13 (1H, d, J=11.9 Hz), 8.14 (0.5H, s), 8.15 (0.5H, s).

Example 118

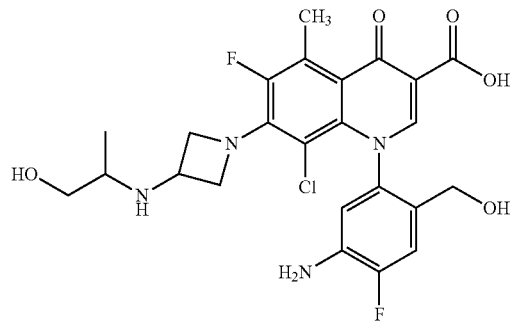 [SMILES: Cc1c(F)c(N2CC(NC(C)CO)C2)c(Cl)c2c1c(=O)c(C(=O)O)cn2-c1cc(N)c(F)cc1CO]

1-[5-Amino-4-fluoro-2-(hydroxymethyl)phenyl]-8-chloro-6-fluoro-7-[3-(1-hydroxypropan-2-yl)aminoazetidin-1-yl]-5-methyl-4-oxo-1,4-dihydroquinoline-3-carboxylic acid 57 mg of ethyl 1-[5-amino-4-fluoro-2-(hydroxymethyl)phenyl]-8-chloro-6-fluoro-7-[3-(1-hydroxypropan-2-yl)

aminoazetidin-1-yl]-5-methyl-4-oxo-1,4-dihydroquinoline-3-carboxylate was suspended in 1.0 mL of ethanol and 0.30 mL of a 1 mol/L aqueous solution of sodium hydroxide was added at room temperature. The mixture was stirred at 40° C. for 1.5 hours. The reaction solution was neutralized with 1 mol/L hydrochloric acid. Precipitates were collected by filtration with water to obtain 16 mg of the title compound.

$^1$H-NMR (DMSO-d$_6$): δ 0.87-0.88 (3H, m), 2.55-2.59 (1H, m), 2.71 (3H, d, J=3.4 Hz), 3.19 (1H, t, J=5.7 Hz), 3.61-3.66 (1H, m), 4.02-4.15 (4H, m), 4.49-4.52 (1H, m), 4.58-4.65 (2H, m), 5.07 (1H, t, J=5.0 Hz), 5.44 (2H, brs), 6.68-6.70 (1H, m), 7.14 (1H, d, J=12.1 Hz), 8.38 (1H, s).

Example 119

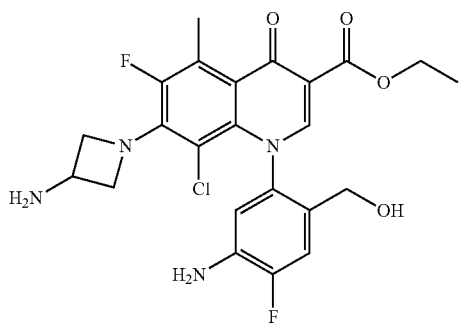 [SMILES: CCOC(=O)c1cn(-c2cc(N)c(F)cc2CO)c2c(Cl)c(N3CC(N)C3)c(F)c(C)c2c1=O]

Ethyl 1-[5-amino-4-fluoro-2-(hydroxymethyl)phenyl]-7-(3-aminoazetidin-1-yl)-8-chloro-6-fluoro-5-methyl-4-oxo-1,4-dihydroquinoline-3-carboxylate 89 mg of ethyl 1-[5-amino-4-fluoro-2-(hydroxymethyl)phenyl]-8-chloro-6,7-difluoro-5-methyl-4-oxo-1,4-dihydroquinoline-3-carboxylate was dissolved in 1 mL of dimethylsulfoxide and 44 mg of 3-aminoazetidine hydrochloride and 0.14 mL of N-methylpyrrolidine were added. The mixture was stirred at 50° C. for 15 hours. 2 mL of water was added to the reaction solution. The resulting precipitates were collected by filtration to obtain 58 mg of the title compound.

$^1$H-NMR (DMSO-d$_6$): δ 1.22 (3H, t, J=7.1 Hz), 2.61 (3H, d, J=3.1 Hz), 3.61-3.66 (1H, m), 3.85-3.92 (2H, m), 4.10-4.20 (4H, m), 4.49-4.57 (2H, m), 5.09-5.15 (1H, m), 5.36 (2H, brs), 6.57 (1H, d, J=8.1 Hz), 7.13 (1H, d, J=11.9 Hz), 8.15 (1H, s).

Example 120

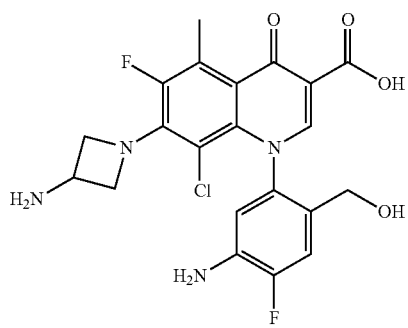

1-[5-Amino-4-fluoro-2-(hydroxymethyl)phenyl]-7-(3-aminoazetidin-1-yl)-8-chloro-6-fluoro-5-methyl-4-oxo-1,4-dihydroquinoline-3-carboxylic acid 58 mg of ethyl 1-[5-amino-4-fluoro-2-(hydroxymethyl)phenyl]-7-(3-aminoazetidin-1-yl)-8-chloro-6-fluoro-5-methyl-4-oxo-1,4-dihydroquinoline-3-carboxylate was dissolved in 1.0 mL of ethanol and 0.5 mL of a 3 mol/L aqueous solution of sodium hydroxide was added. The mixture was stirred at 50° C. for 30 minutes. 1 mol/1 hydrochloric acid was added to the reaction solution to neutralize the solution. Precipitates were collected by filtration with water to obtain 47 mg of the title compound.

$^1$H-NMR (DMSO-d$_6$): δ 2.71 (3H, d, J=3.1 Hz), 3.65-3.71 (1H, m), 3.98-4.04 (2H, m), 4.07 (1H, d, J=11.8 Hz), 4.13 (1H, d, J=11.8 Hz), 4.59-4.65 (2H, m), 5.07 (1H, brs), 5.45 (2H, brs), 6.70 (1H, d, J=8.0 Hz), 7.14 (1H, d, J=11.8 Hz), 8.38 (1H, s).

Example 121

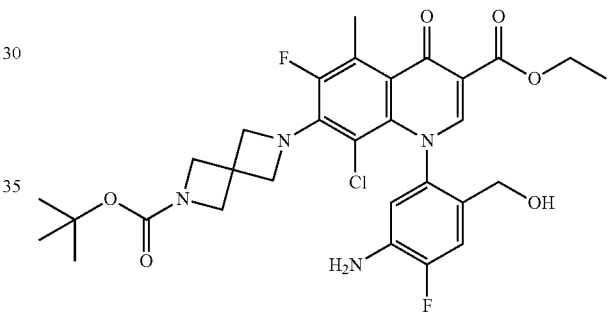

Ethyl 1-[5-amino-4-fluoro-2-(hydroxymethyl)phenyl]-7-[6-(t-butoxycarbonyl)-2,6-diazaspiro[3.3]heptan-2-yl]-8-chloro-6-fluoro-5-methyl-4-oxo-1,4-dihydroquinoline-3-carboxylate 265 mg of ethyl 1-[5-amino-4-fluoro-2-(hydroxymethyl)phenyl]-8-chloro-6,7-difluoro-5-methyl-4-oxo-1,4-dihydroquinoline-3-carboxylate was dissolved in 2.5 mL of dimethylsulfoxide and 219 mg of 2,6-diazaspiro[3.3]heptane-2-carboxylic acid tert-butyl ester half oxalate and 255 mg of N-methylpyrrolidine were added at room temperature. The mixture was stirred at 60° C. for 23 hours. The mixture was cooled and then 60 mL of ethyl acetate was added. The mixture was washed with 60 mL of a 1% aqueous solution of citric acid. The organic layer was dried and then concentrated under reduced pressure. Hexane was added and precipitates were collected by filtration to obtain 365 mg of the title compound as a pale yellow powder.

$^1$H-NMR (CDCl$_3$): δ 1.36 (3H, t, J=7.1 Hz), 1.44 (9H, s), 2.75 (3H, d, J=3.4 Hz), 4.04 (4H, s), 4.32-4.52 (8H, m), 6.55 (1H, d, J=7.8 Hz), 7.21 (1H, d, J=11.2 Hz), 8.19 (1H, s).

Example 122

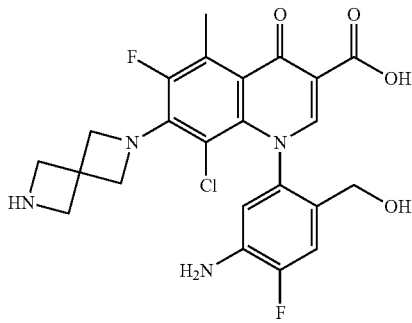 [SMILES: Cc1c(F)c(N2CC3(CNC3)C2)c(Cl)c2c1c(=O)c(C(=O)O)cn2-c1cc(N)c(F)cc1CO]

1-[5-Amino-4-fluoro-2-(hydroxymethyl)phenyl]-8-chloro-7-(2,6-diazaspiro[3.3]heptan-2-yl)-6-fluoro-5-methyl-4-oxo-1,4-dihydroquinoline-3-carboxylic acid trifluoroacetate 62 mg of ethyl 1-[5-amino-4-fluoro-2-(hydroxymethyl)phenyl]-7-[6-(tert-butoxycarbonyl)-2,6-diazaspiro[3.3]heptan-2-yl]-8-chloro-6-fluoro-5-methyl-4-oxo-1,4-dihydroquinoline-3-carboxylate was added to 3 mL of ethanol and 0.4 mL of a 1 mol/L aqueous solution of sodium hydroxide were added. The mixture was stirred at 60° C. for one hour. The mixture was cooled and then 20 mL of a 5% aqueous solution of citric acid was added and the mixture was extracted with 30 mL of dichloromethane. The organic layer was dried and then concentrated. 5 mL of dichloromethane and 1 mL of trifluoroacetic acid were added to the residue and the mixture was stirred at room temperature for 30 minutes. The mixture was concentrated under reduced pressure. Diethyl ether was added and precipitates were collected by filtration to obtain 42 mg of the title compound as a pale yellow powder.

$^1$H-NMR (DMSO-$d_6$): δ 2.72 (3H, d, J=3.2 Hz), 4.03-4.16 (6H, m), 4.56.64 (4H, m), 5.06 (1H, brs), 5.46 (2H, brs), 6.70 (1H, d, J=8.0 Hz), 7.14 (1H, d, J=11.7 Hz), 8.39 (1H, s), 8.42 (2H, brs).

Example 123

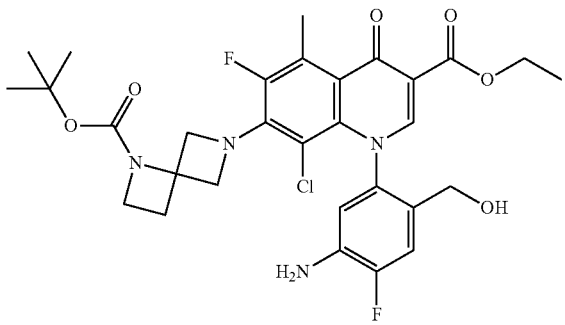 [SMILES: CCOC(=O)c1cn(-c2cc(N)c(F)cc2CO)c2c(Cl)c(N3CC4(CCN4C(=O)OC(C)(C)C)C3)c(F)c(C)c2c1=O]

Ethyl 1-[5-amino-4-fluoro-2-(hydroxymethyl)phenyl]-7-[1-(tert-butoxycarbonyl)-1,6-diazaspiro[3.3]heptan-6-yl]-8-chloro-6-fluoro-5-methyl-4-oxo-1,4-dihydroquinoline-3-carboxylate 265 mg of ethyl 1-[5-amino-4-fluoro-2-(hydroxymethyl)phenyl]-8-chloro-6,7-difluoro-5-methyl-4-oxo-1,4-dihydroquinoline-3-carboxylate was dissolved in 2.5 mL of dimethylsulfoxide and 219 mg of 1,6-diazaspiro[3.3]heptane-1-carboxylic acid tert-butyl ester half oxalate and 255 mg of N-methylpyrrolidine were added at room temperature. The mixture was stirred at 60° C. for 23 hours. The mixture was cooled and then 60 mL of ethyl acetate was added. The mixture was washed with 60 mL of a 1% aqueous solution of citric acid. The organic layer was dried and then concentrated under reduced pressure. Hexane was added and precipitates were collected by filtration to obtain 333 mg of the title compound as a pale yellow powder.

$^1$H-NMR (CDCl$_3$): δ 1.36 (3H, t, J=7.1 Hz), 1.55 (9H, s), 2.43 (2H, s), 2.76 (3H, d, J=3.04 Hz), 3.77 (2H, t, J=7.6 Hz), 4.35-4.52 (6H, m), 4.82 and 4.98 (total 2H, brs), 6.53 and 6.61 (total 1H, brs), 7.23 and 7.25 (total 1H, d, J=11.5 Hz), 8.19 (1H, s).

Example 124

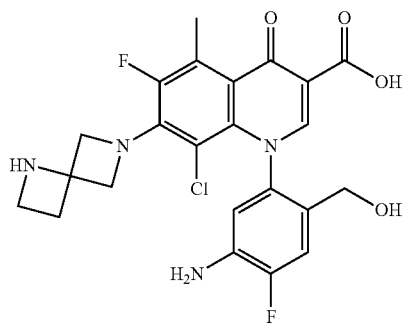 [SMILES: Cc1c(F)c(N2CC3(CCN3)C2)c(Cl)c2c1c(=O)c(C(=O)O)cn2-c1cc(N)c(F)cc1CO]

1-[5-Amino-4-fluoro-2-(hydroxymethyl)phenyl]-8-chloro-7-(1,6-diazaspiro[3.3]heptan-6-yl)-6-fluoro-5-methyl-4-oxo-1,4-dihydroquinoline-3-carboxylic acid trifluoroacetate 62 mg of ethyl 1-[5-amino-4-fluoro-2-(hydroxymethyl)phenyl]-7-[1-(tert-butoxycarbonyl)-1,6-diazaspiro[3.3]heptan-6-yl]-8-chloro-6-fluoro-5-methyl-4-oxo-1,4-dihydroquinoline-3-carboxylate was added to 3 mL of ethanol and 0.4 mL of a 1 mol/L aqueous solution of sodium hydroxide were added. The mixture was stirred at 60° C. for 1 hour. The mixture was cooled and then 20 mL of a 5% aqueous solution of citric acid was added and the mixture was extracted with 30 mL of dichloromethane. The organic layer was dried and then concentrated. 5 mL of dichloromethane and 1 mL of trifluoroacetic acid were added to the residue and the mixture was stirred at room temperature for 30 minutes. The mixture was concentrated under reduced pressure. Diethyl ether was added and precipitates were collected by filtration to obtain 41 mg of the title compound as a pale yellow powder.

$^1$H-NMR (DMSO-$d_6$): δ 2.62-2.68 (2H, m), 2.72 (3H, d, J=3.2 Hz), 3.74 (2H, s), 4.02-4.12 (2H, m), 4.62-4.68 (2H, m), 4.78-4.88 (2H, m), 5.03 (1H, brs), 5.47 (2H, brs), 6.72 (1H, d, J=8.0 Hz), 7.13 (1H, d, J=12.0 Hz), 8.39 (1H, s), 9.15 (2H, brs).

Example 125

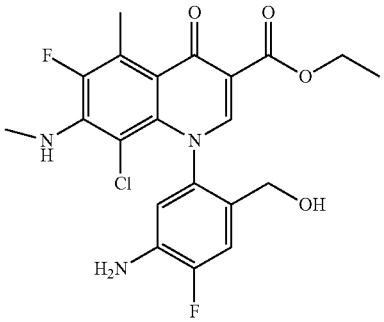 [SMILES: CCOC(=O)c1cn(-c2cc(N)c(F)cc2CO)c2c(Cl)c(NC)c(F)c(C)c2c1=O]

Ethyl 1-[5-amino-4-fluoro-2-(hydroxymethyl)phenyl]-8-chloro-6-fluoro-5-methyl-7-(methylamino)-4-oxo-1,4-dihydroquinoline-3-carboxylate 89 mg of ethyl 1-[5-amino-4-fluoro-2-(hydroxymethyl)phenyl]-8-chloro-6,7-difluoro-5-methyl-4-oxo-1,4-dihydroquinoline-3-carboxylate was dissolved in 1.0 mL of dimethylsulfoxide and 0.14 mL of N-methylpyrrolidine and 40 mg of methylamine hydrochloride were added. The mixture was stirred at 50° C. for 16 hours. 2 mL of water was added to the reaction solution. The resulting precipitates were collected by filtration to obtain 76 mg of the title compound.

$^1$H-NMR (DMSO-$d_6$) δ 1.23 (3H, t, J=7.1 Hz), 2.66 (3H, d, J=3.4 Hz), 3.04 (3H, dd, J=5.2 Hz, J=7.3 Hz), 4.11-4.20 (4H, m), 5.14 (1H, t, J=5.3 Hz), 5.36 (2H, brs), 5.97-6.03 (1H, m), 6.55 (1H, d, J=8.1 Hz), 7.14 (1H, d, J=11.9 Hz), 8.13 (1H, s).

Example 126

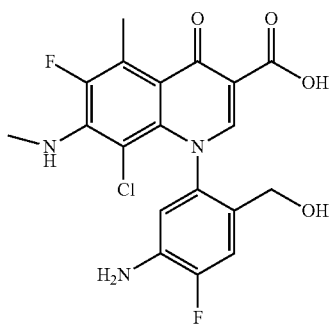 [SMILES: CNc1c(F)c(C)c2c(=O)c(C(=O)O)cn(-c3cc(N)c(F)cc3CO)c2c1Cl]

1-[5-Amino-4-fluoro-2-(hydroxymethyl)phenyl]-8-chloro-6-fluoro-5-methyl-7-(methylamino)-4-oxo-1,4-dihydroquinoline-3-carboxylic acid 66 mg of ethyl 1-[5-amino-4-fluoro-2-(hydroxymethyl)phenyl]-8-chloro-6-fluoro-5-methyl-7-(methylamino)-4-oxo-1,4-dihydroquinoline-3-carboxylate was dissolved in 1.0 mL of ethanol and 0.5 mL of a 3 mol/L aqueous solution of sodium hydroxide was added. The mixture was stirred at 50° C. for 15 minutes. 1 mol/L hydrochloric acid was added to the reaction solution to neutralize the solution. The resulting precipitates were collected by filtration with water to obtain 28 mg of the title compound.

$^1$H-NMR (DMSO-$d_6$) δ 2.76 (3H, d, J=3.2 Hz), 3.10 (3H, dd, J=5.1 Hz, J=7.8 Hz), 4.09 (1H, d, J=4.7 Hz), 4.10 (1H, d, J=4.7 Hz), 5.09 (1H, dd, J=4.9 Hz, J=5.8 Hz), 5.45 (2H, brs), 6.44 (1H, brs), 6.68 (1H, d, J=8.1 Hz), 7.15 (1H, d, J=11.9 Hz), 8.37 (1H, s).

Example 127

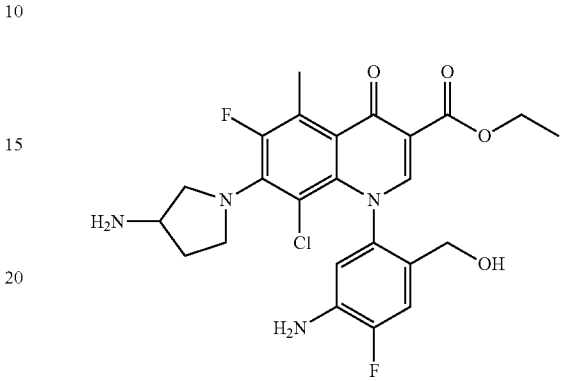

Ethyl 1-[5-amino-4-fluoro-2-(hydroxymethyl)phenyl]-7-(3-aminopyrrolidin-1-yl)-8-chloro-6-fluoro-5-methyl-4-oxo-1,4-dihydroquinoline-3-carboxylate 89 mg of ethyl 1-[5-amino-4-fluoro-2-(hydroxymethyl)phenyl]-8-chloro-6,7-difluoro-5-methyl-4-oxo-1,4-dihydroquinoline-3-carboxylate was dissolved in 1.0 mL of dimethylsulfoxide and 0.14 mL of N-methylpyrrolidine and 26 μL of 3-aminopyrrolidine were added. The mixture was stirred at 50° C. for 20 hours. 2 mL of water was added to the reaction solution. The resulting precipitates were collected by filtration to obtain 42 mg of the title compound.

$^1$H-NMR (DMSO-$d_6$) δ 1.24 (3H, t, J=7.1 Hz), 1.87-1.84 (2H, m), 2.67-2.71 (3H, m), 2.84 (2H, brm), 3.10 (2H, brm), 4.09-4.24 (5H, m), 5.085.14 (1H, m), 5.39 (2H, brs), 6.62 (1H, d, J=8.1 Hz), 7.14 (1H, d, J=11.7 Hz), 8.25 (1H, s).

Example 128

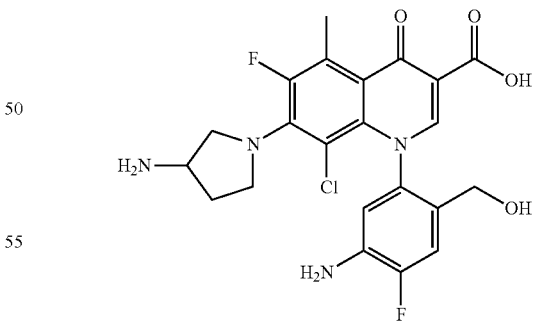

1-[5-Amino-4-fluoro-2-(hydroxymethyl)phenyl]-7-(3-aminopyrrolidin-1-yl)-8-chloro-6-fluoro-5-methyl-4-oxo-1,4-dihydroquinoline-3-carboxylic acid 82 mg of ethyl 1-[5-amino-4-fluoro-2-(hydroxymethyl)phenyl]-7-(3-aminopyrrolidin-1-yl)-8-chloro-6-fluoro-5- methyl-4-oxo-1,4-dihydroquinoline-3-carboxylate was dissolved in 1.0 mL of ethanol and 0.5 mL of a 1 mol/L aqueous solution of sodium hydroxide was added. The mixture was stirred at 50° C. for 20 minutes. 1 mol/L hydrochloric acid was added to the reaction solution to neutralize the solution. The resulting precipitates were collected by filtration with water to obtain 37 mg of the title compound.

$^1$H-NMR (DMSO-$d_6$) δ 1.82-1.89 (2H, m), 2.76-2.82 (4H, m), 2.90-2.95 (1H, m), 3.19-3.22 (1H, m), 3.48-3.54 (1H, m), 4.00-4.13 (3H, m), 5.08 (1H, t, J=5.3 Hz), 5.44 (2H, brs), 6.71 (1H, d, J=8.1 Hz), 7.16 (1H, d, J=11.7 Hz), 8.50 (1H, s).

Example 129

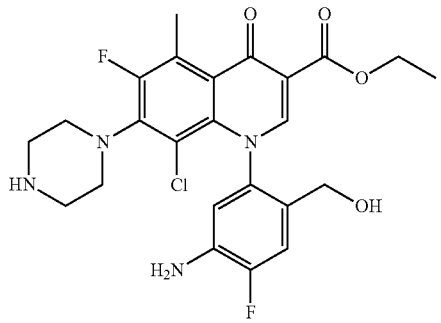 [SMILES: CCOC(=O)c1cn(-c2cc(N)c(F)cc2CO)c2c(Cl)c(N3CCNCC3)c(F)c(C)c2c1=O]

Ethyl 1-[5-amino-4-fluoro-2-(hydroxymethyl)phenyl]-8-chloro-6-fluoro-5-methyl-4-oxo-7-(piperazin-1-yl)-1,4-dihydroquinoline-3-carboxylate 89 mg of ethyl 1-[5-amino-4-fluoro-2-(hydroxymethyl)phenyl]-8-chloro-6,7-difluoro-5-methyl-4-oxo-1,4-dihydroquinoline-3-carboxylate was dissolved in 1.0 mL of dimethylsulfoxide and 0.14 mL of N-methylpyrrolidine and 26 mg of piperazine were added. The mixture was stirred at 60° C. for 31 hours. 2 mL of water was added to the reaction solution. The resulting precipitates were collected by filtration to obtain 84 mg of the title compound.

$^1$H-NMR (DMSO-$d_6$): δ 1.24 (3H, t, J=7.1 Hz), 2.59-2.63 (6H, m), 2.72-2.78 (2H, m), 3.0-3.07 (2H, m), 4.09-4.16 (2H, m), 4.17 (1H, d, J=7.1 Hz), 4.20 (1H, d, J=7.1 Hz), 5.09 (1H, t, J=5.1 Hz), 5.38 (2H, brs), 6.60 (1H, d, J=8.1 Hz), 7.13 (1H, d, J=11.9 Hz), 8.25 (1H, s).

Example 130

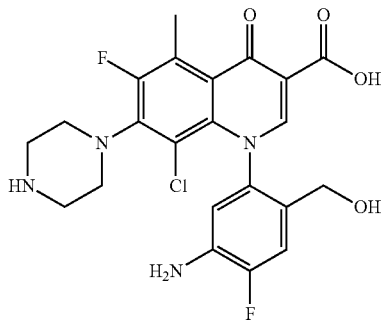

1-[5-Amino-4-fluoro-2-(hydroxymethyl)phenyl]-8-chloro-6-fluoro-5-methyl-4-oxo-7-(piperazin-1-yl)-1,4-dihydroquinoline-3-carboxylic acid 58 mg of ethyl 1-[5-amino-4-fluoro-2-(hydroxymethyl)phenyl]-8-chloro-6-fluoro-5-methyl-4-oxo-7-(piperazin-1-yl)-1,4-dihydroquinoline-3-carboxylate was dissolved in 1.0 mL of ethanol and 0.5 mL of a 1 mol/L aqueous solution of sodium hydroxide was added. The mixture was stirred at 50° C. for 30 minutes. 1 mol/L hydrochloric acid, was added to the reaction solution to neutralize the solution. Precipitates were filtered with water and the filtrate was left to stand. Precipitates were then collected by filtration with water to obtain 13 mg of the title compound.

$^1$H-NMR (CD$_3$OD): δ 1.99 (3H, d, J=3.1 Hz), 2.31-2.37 (4H, m), 2.52-2.58 (4H, m), 3.27 (1H, d, J=12.9 Hz), 3.32 (1H, d, J=12.9 Hz), 5.89 (1H, d, J=8.0 Hz), 6.26 (1H, d, J=11.6 Hz), 7.75 (1H, s).

Reference Example 35

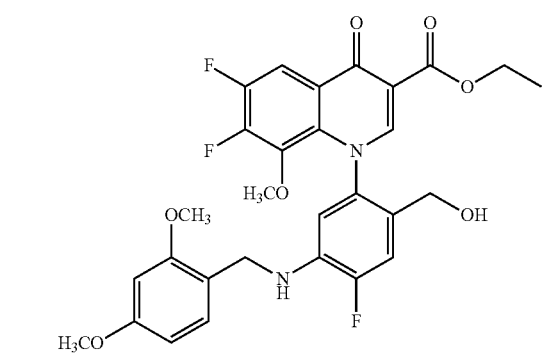 [SMILES: CCOC(=O)c1cn(-c2cc(NCc3ccc(OC)cc3OC)c(F)cc2CO)c2c(OC)c(F)c(F)cc2c1=O]

Ethyl 6,7-difluoro-1-[5-(2,4-dimethoxybenzyl)amino-4-fluoro-2-(hydroxymethyl)phenyl]-8-methoxy-4-oxo-1,4-dihydroquinoline-3-carboxylate 334 mg of methyl 2-amino-4-(2,4-dimethoxybenzyl)amino-5-fluorobenzoate and 50 mg of lithium borohydride were added to mixed solution of 5 mL of tetrahydrofuran and 20 mL of toluene and heated to reflux for 5 hours. 25 mL of ethyl acetate was added to the reaction solution and the mixture was washed three times with a saturated aqueous solution of sodium hydrogen carbonate. The organic layer was dried over anhydrous magnesium sulfate and then filtered to yield a solution of a crude product of [2-amino-4-(2,4-dimethoxybenzyl)amino-5-fluorophenyl]methanol.

To this solution (5 mmol) was added dropwise a 1 mol/L solution of ethyl 3-ethoxy-2-(2,4,5-trifluoro-3-methoxybenzoyl)acrylate in dichloromethane (5 mL) and the mixture was stirred at room temperature overnight. The solvent was evaporated under reduced pressure. The resulting ethyl 3-[5-(2,4-dimethoxybenzyl)amino-4-fluoro-2-(hydroxymethyl)phenylamino]-2-(2,4,5-trifluoro-3-methoxybenzoyl)acrylate was dissolved in 9 mL of N-methylpyrrolidin-2-one and 400 mg of lithium chloride and 680 mg of 1,8-diazabicyclo[5.4.0]undec-7-ene were added. The mixture was stirred at room temperature overnight. 50 mL of water was added to the reaction solution and precipitated crystals were collected by filtration and dried. The crystals were purified through a silica gel column (0 to 8% methanol/chloroform) to obtain 1.40 g of the title compound.

$^1$H-NMR (CDCl$_3$): δ 1.38 (3H, t, J=7 Hz), 2.22 (1H, t, J=5 Hz), 3.22 (3H, d, J=1 Hz), 3.76 (3H, s), 3.79 (3H, s), 4.23-4.39 (6H, m), 4.65-4.68 (1H, m), 6.38-6.43 (2H, m), 6.61 (1H, d, J=8 Hz), 7.11 (1H, d, J=8 Hz), 7.20 (1H, d, J=12 Hz), 8.03 (1H, dd, J=10 Hz, 8 Hz), 8.27 (1H, s)

Reference Example 36

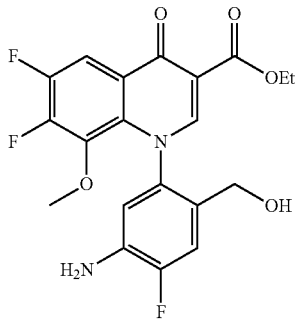 [SMILES: CCOC(=O)c1cn(-c2cc(N)c(F)cc2CO)c2c(OC)c(F)c(F)cc2c1=O]

Ethyl 1-[5-amino-4-fluoro-2-(hydroxymethyl)phenyl]-6,7-difluoro-8-methoxy-4-oxo-1,4-dihydroquinoline-3-carboxylate 5.0 mL of dichloromethane, 54 µL of anisole, and 0.10 mL of trifluoroacetic acid were added to 0.28 g of ethyl 6,7-difluoro-1-[5-(2,4-dimethoxybenzyl)amino-4-fluoro-2-hydroxymethylphenyl]-8-methoxy-4-oxo-1,4-dihydroquinoline-3-carboxylate and the mixture was stirred at room temperature for 30 minutes. 15 mL of a saturated aqueous solution of sodium bicarbonate was added to the reaction solution and the mixture was extracted with 10 mL of dichloromethane. The extract was washed with 20 mL of saturated brine and then dried over anhydrous sodium sulfate. The solvent was evaporated under reduced pressure to obtain 0.17 g of the title compound.

$^1$H-NMR (DMSO-d$_6$): δ 1.26 (3H, t, J=7.1 Hz), 3.38 (3H, s), 4.04-4.14 (2H, m), 4.17-4.25 (2H, m), 5.01 (1H, t, J=5.0 Hz), 5.44 (2H, brs), 6.86 (1H, d, J=8.2 Hz), 7.16 (1H, d, J=11.9 Hz), 7.94 (1H, t, J=8.6 Hz), 8.20 (1H, s).

Example 131

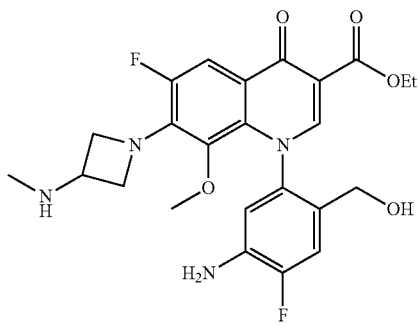 [SMILES: CCOC(=O)c1cn(-c2cc(N)c(F)cc2CO)c2c(OC)c(N3CC(NC)C3)c(F)cc2c1=O]

Ethyl 1-[5-amino-4-fluoro-2-(hydroxymethyl)phenyl]-6-fluoro-8-methoxy-7-(3-methylaminoazetidin-1-yl)-4-oxo-1,4-dihydroquinoline-3-carboxylate 1.0 mL of dimethylsulfoxide, 95 mg of 3-methylaminoazetidine hydrochloride, 0.30 mL of 1,1,3,3-tetramethylguanidine were added to 84 mg of ethyl 1-[5-amino-4-fluoro-2-(hydroxymethyl)phenyl]-6,7-difluoro-8-methoxy-4-oxo-1,4-dihydroquinoline-3-carboxylate and the mixture was stirred at room temperature overnight. 5.0 mL of isopropyl ether was added to the reaction solution and the mixture was sonicated, dispersed, and then left to stand. Supernatant was removed by decantation. This procedure was repeated three times and then 2.0 mL of water was added to the residue. Precipitates were collected by filtration to obtain 39 mg of the title compound.

$^1$H-NMR (DMSO-d$_6$): δ 1.24 (3H, t, J=7.1 Hz), 2.20 (3H, brs), 3.02 (3H, s), 4.00 (1H, dd, J=5.4 Hz, 12.9 Hz), 4.10 (1H, dd, J=4.8 Hz, 13.1 Hz), 4.12-4.20 (4H, m), 4.23-4.30 (2H, m), 4.99 (1H, t, J=5.2 Hz), 5.37 (2H, brs), 6.89 (1H, d, J=8.2 Hz), 7.10 (1H, d, J=12.0 Hz), 7.63 (1H, d, J=13.5 Hz), 8.07 (1H, s).

Example 132

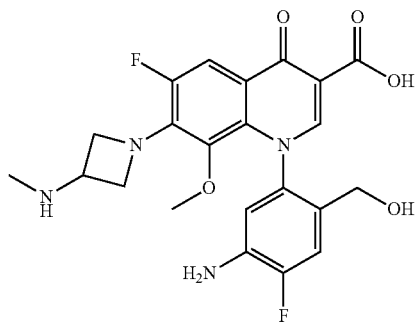 [SMILES: CNC1CN(c2c(F)cc3c(=O)c(C(=O)O)cn(-c4cc(N)c(F)cc4CO)c3c2OC)C1]

1-[5-Amino-4-fluoro-2-(hydroxymethyl)phenyl]-6-fluoro-8-methoxy-7-(3-methylaminoazetidin-1-yl)-4-oxo-1,4-dihydroquinoline-3-carboxylic acid 0.50 mL of ethanol, 0.10 mL of a 10 mol/L aqueous solution of sodium hydroxide, and 0.50 mL of water were added to 39 mg of ethyl 1-[5-amino-4-fluoro-2-(hydroxymethyl)phenyl]-6-fluoro-8-methoxy-7-(3-methylamino)azetidin-1-yl-4-oxo-1,4-dihydroquinoline-3-carboxylate and the mixture was stirred at 50° C. for 6 hours. 1 mol/L hydrochloric acid was added to make the solution acidic (pH 6 to 7). Precipitates were collected by filtration to obtain 33 mg of the title compound.

$^1$H-NMR (DMSO-d$_6$): δ 2.31 (3H, s), 3.12 (3H, s), 4.03 (1H, dd, J=5.3 Hz, 13.0 Hz), 4.20 (1H, dd, J=5.1 Hz, 13.1 Hz), 4.16-4.22 (2H, m), 5.02 (1H, t, J=5.3 Hz), 4.30-4.34 (2H, m), 5.50 (2H, brs), 6.94 (1H, d, J=8.2 Hz), 7.22 (1H, d, J=11.9 Hz), 7.71 (1H, d, J=10.9 Hz), 8.12 (1H, s).

Example 133

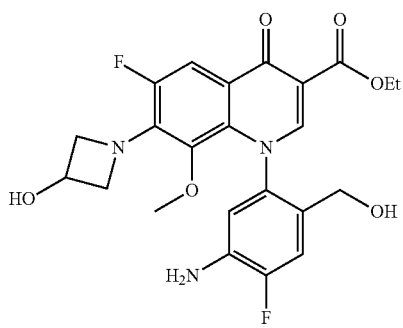 [SMILES: CCOC(=O)c1cn(-c2cc(N)c(F)cc2CO)c2c(OC)c(N3CC(O)C3)c(F)cc2c1=O]

Ethyl 1-[5-amino-4-fluoro-2-(hydroxymethyl)phenyl]-6-fluoro-7-[3-hydroxyazetidin-1-yl]-8-methoxy-4-oxo-1,4-dihydroquinoline-3-carboxylate 1.0 mL of dimethylsulfoxide, 31 mg of 3-hydroxyazetidine tartrate, and 0.11 mL of 1,1,3,3-tetramethylguanidine were added to 40 mg of ethyl 1-[5-amino-4-fluoro-2-(hydroxymethyl)phenyl]-6,7-difluoro-8-methoxy-4-oxo-1,4-dihydroquinoline-3-carboxylate and the mixture was stirred at 50° C. for 3 days. 5.0 mL of isopropyl ether was added to the reaction solution and the mixture was stirred. Supernatant was removed by decantation. This procedure was repeated three times and then 2.0 mL of water was added to the residue. Precipitates were collected by filtration to obtain 23 mg of the title compound.

$^1$H-NMR (DMSO-$d_6$): δ 1.24 (3H, t, J=7.1 Hz), 3.14 (3H, s), 3.99-4.01 (1H, m), 4.03-4.05 (1H, m), 4.08-4.10 (4H, m), 4.18-4.20 (1H, m), 4.50-4.60 (2H, m), 5.05 (1H, t, J=5.2 Hz), 5.38 (2H, brs), 5.65 (1H, d, J=5.8 Hz), 6.85 (1H, d, J=8.1 Hz), 7.10 (1H, d, J=11.9 Hz), 7.73 (1H, d, J=13.3 Hz), 8.09 (1H, s).

Example 134

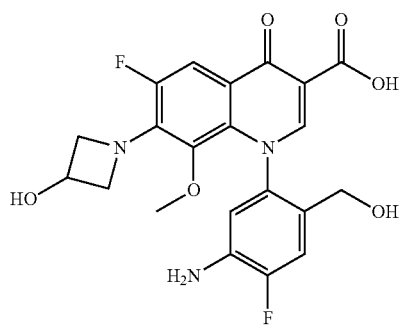 [SMILES: COc1c(N2CC(O)C2)c(F)cc2c(=O)c(C(=O)O)cn(-c3cc(N)c(F)cc3CO)c12]

1-[5-Amino-4-fluoro-2-(hydroxymethyl)phenyl]-6-fluoro-7-(3-hydroxyazetidin-1-yl)-8-methoxy-4-oxo-1,4-dihydroquinoline-3-carboxylic acid 1.0 mL of ethanol, 0.10 mL of a 10 mol/L aqueous solution of sodium hydroxide, and 1.0 mL of water were added to 23 mg of ethyl 1-[5-amino-4-fluoro-2-(hydroxymethyl)phenyl]-6-fluoro-7-[3-hydroxyazetidin-1-yl]-8-methoxy-4-oxo-1,4-dihydroquinoline-3-carboxylate and the mixture was stirred at 50° C. overnight. Ethanol was evaporated under reduced pressure and then 1 mol/L hydrochloric acid was added to make the solution acidic (pH 6 to 7). Precipitates were collected by filtration to obtain 12 mg of the title compound.

$^1$H-NMR (DMSO-$d_6$): δ 3.12 (3H, s), 4.05-4.18 (4H, m), 4.20-4.22 (1H, m), 4.60-4.66 (2H, m), 5.02 (1H, t, J=5.3 Hz), 5.50 (2H, brs), 5.68 (1H, d, J=5.7 Hz), 6.94. (1H, d, J=8.2 Hz), 7.14 (1H, d, J=11.9 Hz), 7.71 (1H, d, J=13.3 Hz), 8.18 (1H, s).

Example 135

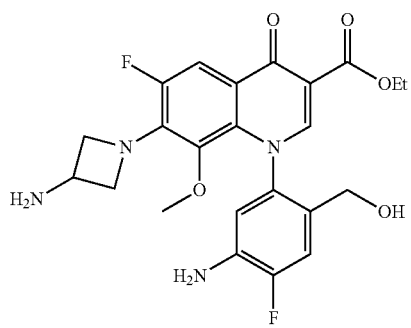 [SMILES: CCOC(=O)c1cn(-c2cc(N)c(F)cc2CO)c2c(OC)c(N3CC(N)C3)c(F)cc2c1=O]

Ethyl 7-(3-aminoazetidin-1-yl)-1-[5-amino-4-fluoro-2-(hydroxymethyl)phenyl]-6-fluoro-8-methoxy-4-oxo-1,4-dihydroquinoline-3-carboxylate 0.60 mL of dimethylsulfoxide, 31 mg of 3-aminoazetidine dihydrochloride, and 0.10 mL of 1,1,3,3-tetramethylguanidine were added to 30 mg of ethyl 1-[5-amino-4-fluoro-2-(hydroxymethyl)phenyl]-6,7-difluoro-8-methoxy-4-oxo-1,4-dihydroquinoline-3-carboxylate and the mixture was stirred at room temperature overnight. The reaction solution was filtered and 5.0 mL of isopropyl ether was added to the filtrate. The mixture was stirred and the supernatant was removed by decantation. This procedure was repeated five times and then 1.0 mL of water was added to the residue. Precipitates were collected by filtration to obtain 7.3 mg of the title compound.

$^1$H-NMR (DMSO-$d_6$): δ 1.24 (3H, t, J=7.1 Hz), 3.05 (3H, s), 3.96-4.14 (4H, m), 4.20 (2H, q, J=7.1 Hz), 4.33-4.40 (2H, m), 5.42 (2H, brs), 6.92 (1H, d, J=8.2 Hz), 7.11 (1H, d, J=11.9 Hz), 7.69 (1H, d, J=13.5 Hz), 8.53 (1H, s).

Example 136

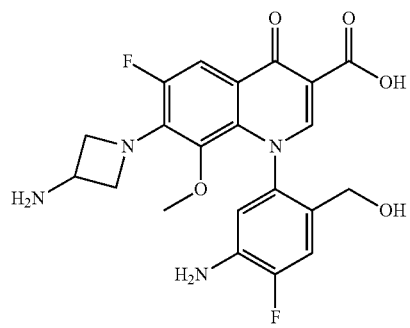 [SMILES: COc1c(N2CC(N)C2)c(F)cc2c(=O)c(C(=O)O)cn(-c3cc(N)c(F)cc3CO)c12]

7-(3-Aminoazetidin-1-yl)-1-[5-amino-4-fluoro-2-(hydroxymethyl)phenyl]-6-fluoro-8-methoxy-4-oxo-1,4-dihydroquinoline-3-carboxylic acid 0.50 mL of ethanol, 5.0 µL of a 10 mol/L aqueous solution of sodium hydroxide, and 0.20 mL of water were added to 7.3 mg of ethyl 7-(3-aminoazetidin-1-yl)-1-[5-amino-4-fluoro-2-(hydroxymethyl)phenyl]-6-fluoro-8-methoxy-4-oxo-1,4-dihydroquinoline-3-carboxylate and the mixture was stirred at 50° C. for 3 hours. Ethanol was evaporated under reduced pressure and then a 5% aqueous solution of citric acid was added to make the solution acidic (pH 5 to 6). The resulting precipitates were collected by filtration to obtain 3.5 mg of the title compound.

$^1$H-NMR (DMSO-$d_6$): δ 3.07 (3H, s), 3.37-3.40 (1H, m), 3.91-4.14 (4H, m), 4.38-4.45 (2H, m), 4.94 (1H, t, J=5.5 Hz), 5.45 (2H, brs), 6.98 (1H, d, J=8.1 Hz), 7.12 (1H, d, J=11.9 Hz), 7.82 (1H, d, J=13.2 Hz), 8.28 (1H, s).

Reference Example 37

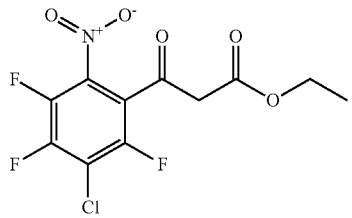 [SMILES: CCOC(=O)CC(=O)c1c(F)c(Cl)c(F)c(F)c1[N+](=O)[O-]]

Ethyl 2-(3-chloro-6-nitro-2,4,5-trifluorobenzoyl)acetate 6.31 g of 3-chloro-2,4,5-trifluorobenzoic acid was dissolved in 35 mL of sulfuric acid and 9.10 g of potassium nitrate was added to the mixture over 90 minutes under ice cooling. The mixture was stirred for 1 hour at room temperature and further for 15 hours at 40° C. The reaction solution was cooled and then poured onto 600 mL of ice. The mixture was extracted with 700 mL of diethyl ether. The extract was washed with 200 mL of water and then dried over anhydrous sodium sulfate. The solvent was evaporated under reduced pressure. Hexane was added to the residue and precipitates were collected by filtration to obtain 4.91 g of 3-chloro-6-nitro-2,4,5-trifluorobenzoic acid.

70 mL of acetonitrile, 4.01 g of magnesium chloride, and 4.25 g of triethylamine were added to 6.11 g of potassium monoethyl malonate under ice cooling. The mixture was stirred at room temperature for 24 hours to yield a suspension. 25 mL of dichloromethane, 300 µL of DMF, and 7.62 g of oxalyl chloride were added to 7.67 g of 3-chloro-6-nitro-2,4,5-trifluorobenzoic acid and the mixture was stirred at room temperature for 18 hours. The solvent was evaporated under reduced pressure and the residue was suspended in 40 mL of tetrahydrofuran, which was added to the suspension prepared before at room temperature and the mixture was stirred as it is overnight. 180 mL of 1 mol/L hydrochloric acid was added and then the resulting solution was extracted with ethyl acetate. The extract was dried over anhydrous sodium sulfate. The solvent was evaporated under reduced pressure and the residue was subjected to silica gel column chromatography (n-hexane:dichloromethane=50 to 80% gradient) to obtain 7.12 g of the title compound.

$^1$H-NMR (CDCl$_3$): δ 1.27 (1.8H, t, J=7.1 Hz), 1.35 (1.2H, t, J=7.1 Hz), 3.92 (1.2H, d, J=2.0 Hz), 4.20 (1.2H, q, J=7.1 Hz), 4.29 (0.8H, q, J=7.1 Hz), 5.30 (0.4H, s), 12.40 (0.4H, s)

Reference Example 38

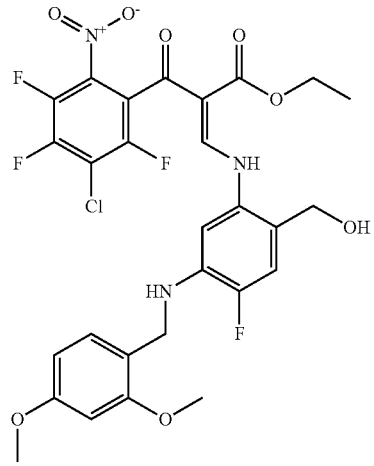 [SMILES: CCOC(=O)/C(=C\Nc1cc(NCc2ccc(OC)cc2OC)c(F)cc1CO)C(=O)c1c(F)c(Cl)c(F)c(F)c1[N+](=O)[O-]]

Ethyl 2-(3-Chloro-6-nitro-2,4,5-trifluorobenzoyl)-3-[5-(2,4-dimethoxybenzylamino)-4-fluoro-2-(hydroxymethyl)phenyl]aminoacrylate 6.50 g of ethyl 2-(3-chloro-6-nitro-2,4,5-trifluoro benzoyl)acetate, 5.67 mL of acetic anhydride, and 4.99 mL of triethyl orthoformate were stirred at 120° C. for 17 hours. The solvent was then evaporated under reduced pressure. The residue was subjected to azeotropic distillation with toluene to obtain ethyl 2-(3-chloro-6-nitro-2,4,5-trifluoro benzoyl)-3-ethoxyacrylate.

3.44 g of ethyl 2-amino-4-(2,4-dimethoxybenzylamino)-5-fluorobenzoate was added to 100 mL of toluene and 25 mL of tetrahydrofuran. 897 mg of lithium borohydride was added and the mixture was stirred at 100° C. for 90 minutes. 100 mL of water was added under ice cooling and the mixture was stirred for 20 minutes. The aqueous solution was extracted with 100 mL of ethyl acetate. The organic layer was dried over anhydrous sodium sulfate. Ethyl 2-(3-chloro-6-nitro-2,4,5-trifluorobenzoyl)-3-ethoxyacrylate was added to this organic layer and the mixture was stirred at room temperature for 3 hours. The reaction solution was concentrated under reduced pressure. The residue was subjected to silica gel column chromatography (dichloromethane:ethyl acetate=10 to 30% gradient) to obtain 1.19 g of the title compound.

$^1$H-NMR (CDCl$_3$): δ 1.17 and 1.00 (total 3H, t, J=7.1 Hz), 3.81 (3H, s), 3.87 (3H, s), 4.10-4.18 (2H, m), 4.37 (2H, d, J=5.8 Hz), 4.56-4.71 (3H, m), 6.47-6.53 (2H, m), 6.75 and 6.70 (total, 1H d, J=7.5 Hz), 6.93 and 6.89 (total 1H, d, J=11.3 Hz), 7.23 and 7.20 (total 1H, d, J=8.0 Hz), 8.63 and 8.48 (total 1H, d, J=14.0 Hz), 12.8 and 11.8 (total 1H, d, J=3.5 Hz).

Reference Example 39

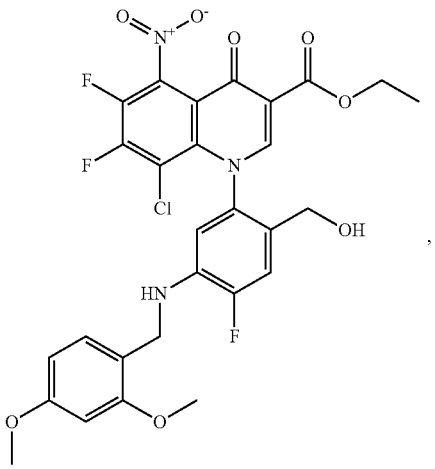 [SMILES: CCOC(=O)c1cn(-c2cc(NCc3ccc(OC)cc3OC)c(F)cc2CO)c2c(Cl)c(F)c(F)c([N+](=O)[O-])c2c1=O]

Ethyl 8-chloro-6,7-difluoro-1-[5-(2,4-dimethoxybenzyl)amino-4-fluoro-2-(hydroxymethyl)phenyl]-5-nitro-4-oxo-1,4-dihydroquinoline-3-carboxylate 4.99 g of ethyl 2-(3-chloro-6-nitro-2,4,5-trifluorobenzoyl)-3-[5-(2,4-dimethoxybenzylamino)-4-fluoro-2-(hydroxymethyl)phenyl]aminoacrylate, 661 mg of lithium chloride, 1.28 mL of 1,8-diazabicyclo[5.4.0]undec-7-ene to 40 mL of N-methyl-2-pyrrolidone and the mixture was stirred at 55° C. for 6 hours. The reaction solution was cooled and then 250 mL of ethyl acetate was added to the reaction solution. The mixture was washed three times with 200 mL of a 1% aqueous solution of citric acid. The organic layer was dried over anhydrous sodium sulfate. The solvent was evaporated under reduced pressure and the residue was subjected to silica gel column chromatography (dichloromethane:ethyl acetate=0 to 30% gradient) to obtain 2.51 g of the title compound.

$^1$H-NMR (DMSO-$d_6$): δ 1.23 (3H, t, J=7.1 Hz), 3.69 (3H, s), 3.70 (3H, s), 4.15-4.21 (6H, m), 5.07 (1H, t, J=5.1 Hz), 6.20 (1H, t, J=4.1 Hz), 6.40 (1H, dd, J=8.3, 3.4 Hz), 6.47 (1H, d, J=3.4 Hz), 6.80 (1H, d, J=8.0 Hz), 7.06 (1H, d, J=8.3 Hz), 7.19 (1H, d, J=12.2 Hz), 8.32 (1H, s).

Reference Example 40

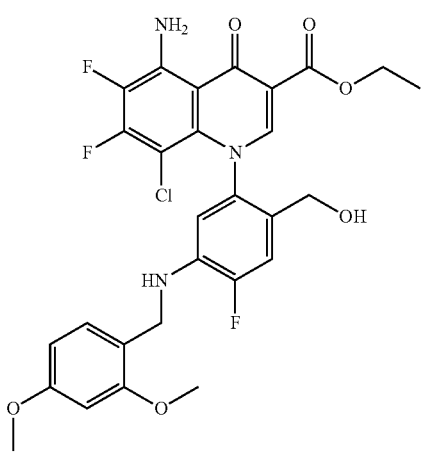 [SMILES: CCOC(=O)c1cn(-c2cc(NCc3ccc(OC)cc3OC)c(F)cc2CO)c2c(Cl)c(F)c(F)c(N)c2c1=O]

Ethyl 5-amino-8-chloro-1-[5-(2,4-dimethoxybenzylamino)-4-fluoro-2-hydroxymethylphenyl]-6,7-difluoro-4-oxo-1,4-dihydroquinoline-3-carboxylate 0.5 mL of concentrated hydrochloric acid was added to a mixture of 1.68 g of iron powder, 5 mL of water, and 10 mL of ethanol and the mixture was stirred at 60° C. for 20 minutes. A solution of 1.24 g of ethyl 8-chloro-1-[5-(2,4-dimethoxybenzylamino)-4-fluoro-2-(hydroxymethyl)phenyl]-6,7-difluoro-5-nitro-4-oxo-1,4-dihydroquinoline-3-carboxylate dissolved in 30 mL of tetrahydrofuran was added and the mixture was stirred at 70° C. for 2 hours. Insoluble matter was filtered with Celite. Celite was washed three times with 30 mL of dichloromethane. The filtrates were pooled and concentrated under reduced pressure. 70 mL of water was added to the residue and the mixture was extracted with 200 mL of dichloromethane. The organic layer was dried over anhydrous sodium sulfate. Hexane was added to the residue and precipitates were collected by filtration to obtain 1.12 g of the title compound as a pale yellow solid.

$^1$H-NMR (DMSO-$d_6$): δ 1.23 (3H, t, J=7.1 Hz), 3.67 (3H, s), 3.70 (3H, s), 4.08-4.20 (6H, m), 5.06 (1H, t, J=5.1 Hz), 6.16 (1H, t, J=5.9 Hz), 6.39 (1H, dd, J=8.3, 2.2 Hz), 6.44 (1H, d, J=2.2 Hz), 6.63 (1H, d, J=8.0 Hz), 7.06 (1H, d, J=8.3 Hz), 7.13 (1H, d, J=12.2 Hz), 7.80-7.30 (2H, br), 8.08 (1H, s).

Reference Example 41

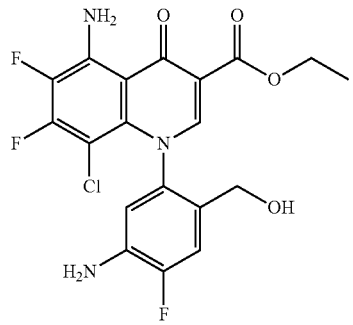 [SMILES: CCOC(=O)c1cn(-c2cc(N)c(F)cc2CO)c2c(Cl)c(F)c(F)c(N)c2c1=O]

Ethyl 5-amino-1-(5-amino-4-fluoro-2-(hydroxymethyl)phenyl)-8-chloro-6,7-difluoro-4-oxo-1,4-dihydroquinoline-3-carboxylate 1.18 g of ethyl 5-amino-8-chloro-1-[5-(2,4-dimethoxybenzylamino)-4-fluoro-2-(hydroxymethyl)phenyl]-6,7-difluoro-4-oxo-1,4-dihydroquinoline-3-carboxylate was dissolved in 40 mL of dichloromethane and 0.87 mL of anisole and then 2.60 mL of trifluoroacetic acid were added at room temperature. The mixture was stirred for 10 minutes. 100 mL of a saturated aqueous solution of sodium hydrogen carbonate was added and the mixture was stirred for 20 minutes. The resulting solid was collected by filtration and washed with water. This solid was added to a mixture of 225 mL of chloroform and 225 mL of methanol and the mixture was stirred and heated to reflux for 30 minutes. Insoluble matter was filtered off and the filtrate was concentrated under reduced pressure. Isopropyl ether was added to the residue and precipitates were collected by filtration to obtain 660 mg of the title compound.

¹H-NMR (DMSO-d₆): δ 1.23 (3H, t, J=7.0 Hz), 4.09 (2H, dd, J=4.9, 2.0 Hz), 4.17 (2H, q, J=7.0 Hz), 5.05 (1H, t, J=4.9 Hz), 5.43 (2H, s), 6.75 (1H, d, J=8.0 Hz), 7.12 (1H, d, J=12.0 Hz), 8.14 (1H, s).

Example 137

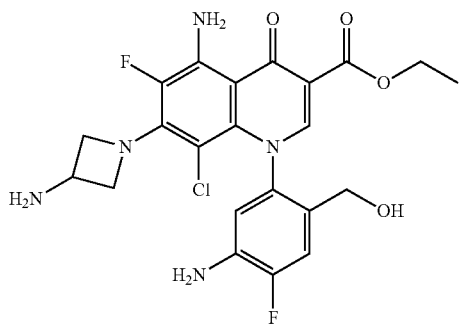 [SMILES: CCOC(=O)c1cn(-c2cc(N)c(F)cc2CO)c2c(Cl)c(N3CC(N)C3)c(F)c(N)c2c1=O]

Ethyl 5-amino-1-[5-amino-4-fluoro-2-(hydroxymethyl)phenyl]-7-(3-aminoazetidin-1-yl)-8-chloro-6-fluoro-4-oxo-1,4-dihydroquinoline-3-carboxylate 88 mg of ethyl 5-amino-1-[5-amino-4-fluoro-2-(hydroxymethyl)phenyl]-8-chloro-6,7-difluoro-4-oxo-1,4-dihydroquinoline-3-carboxylate, 85 mg of N-methylpyrrolidine, 44 mg of 3-aminoazetidine dihydrochloride were added to 0.7 mL of dimethylsulfoxide and the mixture was stirred at 50° C. for 28 hours. 10 mL of diethyl ether was added. The mixture was stirred and then supernatant was removed by decantation. 3 mL of water was added to the residue and the mixture was adjusted to pH 8 with a saturated aqueous solution of sodium hydrogen carbonate. The resulting solid was collected by filtration to obtain 69 mg of the title compound.

¹H-NMR (DMSO-d₆): δ 1.22 (3H, t, J=7.1 Hz), 3.60-3.64 (1H, m), 3.81-3.84 (2H, m), 4.10-4.18 (4H, m), 4.40-4.49 (2H, m), 5.11 (1H, brs), 5.35 (2H, s), 6.62 (1H, d, J=8.0 Hz), 7.11 (1H, d, J=12.0 Hz), 8.06 (1H, s).

Example 138

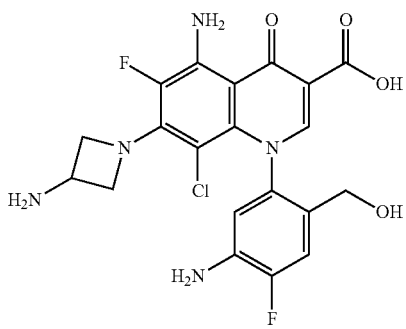 [SMILES: Nc1cc(-n2cc(C(=O)O)c(=O)c3c(N)c(F)c(N4CC(N)C4)c(Cl)c32)c(CO)cc1F]

5-Amino-7-(3-aminoazetidin-1-yl)-1-[5-amino-4-fluoro-2-(hydroxymethyl)phenyl]-8-chloro-6-fluoro-4-oxo-1,4-dihydroquinoline-3-carboxylic acid 3 mL of ethanol and 0.4 mL of a 1 mol/L aqueous solution of sodium hydroxide were added to 65 mg of ethyl 5-amino-1-[5-amino-4-fluoro-2-(hydroxymethyl)phenyl]-7-(3-aminoazetidin-1-yl)-8-chloro-6-fluoro-4-oxo-1,4-dihydroquinoline-3-carboxylate and the mixture was stirred at 60° C. for two hours. Ethanol was evaporated under reduced pressure. The residue was adjusted to pH 5 with 1 mol/L hydrochloric acid and precipitates were collected by filtration to obtain 51 mg of the title compound.

¹H-NMR (DMSO-d₆): δ 3.64-3.72 (1H, m), 3.90-4.00 (2H, m), 4.04-4.18 (2H, m), 4.55 (2H, brs), 5.06 (1H, brs), 5.43 (2H, s), 6.71 (1H, d, J=8.0 Hz), 7.12 (1H, d, J=12.0 Hz), 7.48 (2H, brs), 8.25 (1H, s).

Example 139

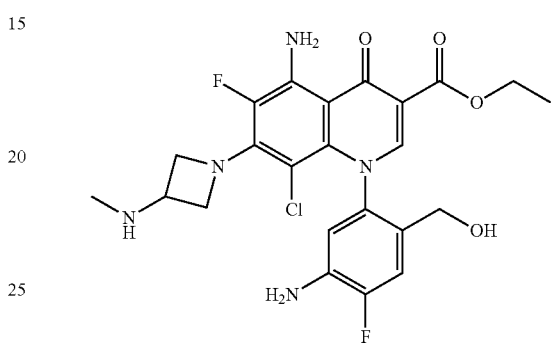

Ethyl 5-amino-1-[5-amino-4-fluoro-2-(hydroxymethyl)phenyl]-8-chloro-6-fluoro-7-(3-methylaminoazetidin-1-yl)-4-oxo-1,4-dihydroquinoline-3-carboxylate 86 mg of ethyl 5-amino-1-[5-amino-4-fluoro-2-(hydroxymethyl)phenyl]-8-chloro-6,7-difluoro-4-oxo-1,4-dihydroquinoline-3-carboxylate, 85 mg of N-methylpyrrolidine, 48 mg of 3-methylaminoazetidine dihydrochloride were added to 0.7 mL of dimethylsulfoxide and the mixture was stirred at 50° C. for 28 hours. 10 mL of diethyl ether was added. The mixture was stirred and then supernatant was removed by decantation. 3 mL of water was added to the residue and the mixture was adjusted to pH 9 with a saturated aqueous solution of sodium hydrogen carbonate. The resulting solid was collected by filtration to obtain 50 mg of the title compound.

¹H-NMR (DMSO-d₆): δ 1.22 (3H, t, J=7.1 Hz), 2.18 (3H, s), 3.26-3.40 (1H, m), 3.90-3.94 (2H, m), 4.10-4.18 (4H, m), 4.40-4.45 (2H, m), 5.11 (1H, brs), 5.35 (2H, s), 6.61 (1H, d, J=8.0 Hz), 7.11 (1H, d, J=12.0 Hz), 8.06 (1H, 8).

Example 140

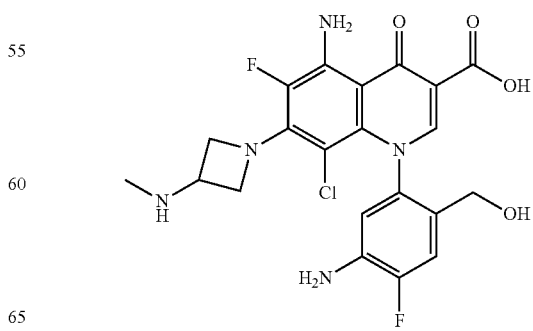

5-Amino-1-[5-amino-4-fluoro-2-(hydroxymethyl)
phenyl]-8-chloro-6-fluoro-7-(3-methylaminoazeti-
din-1-yl)-4-oxo-1,4-dihydroquinoline-3-carboxylic
acid 3 mL of ethanol and 0.4 mL of a 1 mol/L aqueous solution of sodium hydroxide were added to 45 mg of ethyl 5-amino-1-[5-amino-4-fluoro-2-(hydroxymethyl)phenyl]-8-chloro-6-fluoro-7-(3-methylaminoazetidin-1-yl)-4-oxo-1,4-dihydroquinoline-3-carboxylate and the mixture was stirred at 60° C. for 2 hours. Ethanol was evaporated under reduced pressure. The residue was adjusted to pH 5 with 1 mol/L hydrochloric acid and precipitates were collected by filtration to obtain 31 mg of the title compound.

$^1$H-NMR (DMSO-$d_6$): δ 2.24 (3H, s), 3.47 (1H, brs), 4.00-4.14 (4H, m), 4.51 (2H, brs), 5.06 (1H, brs), 5.42 (2H, s), 6.70 (1H, d, J=8.0 Hz), 7.11 (1H, d, J=12.0 Hz), 7.48 (2H, brs), 8.25 (1H, s).

Example 141

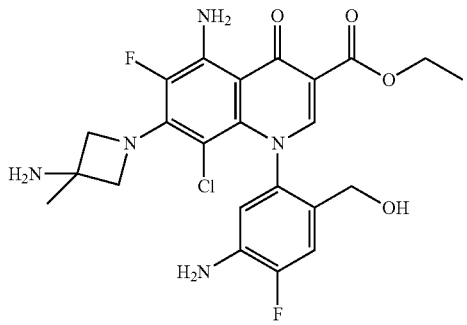 [SMILES: CCOC(=O)c1cn(-c2cc(N)c(F)cc2CO)c2c(Cl)c(N3CC(C)(N)C3)c(F)c(N)c2c1=O]

Ethyl 5-amino-1-[5-amino-4-fluoro-2-(hydroxym-
ethyl)phenyl]-7-(3-amino-3-methylazetidin-1-yl)-8-
chloro-6-fluoro-4-oxo-1,4-dihydroquinoline-3-car-
boxylate 88 mg of ethyl 5-amino-1-[5-amino-4-fluoro-2-(hydroxymethyl)phenyl]-8-chloro-6,7-difluoro-4-oxo-1,4-dihydroquinoline-3-carboxylate, 85 mg of N-methylpyrrolidine, 48 mg of 3-amino-3-methylazetidine dihydrochloride were added to 0.7 mL of dimethylsulfoxide and the mixture was stirred at 50° C. for 28 hours. 10 mL of diethyl ether was added. The mixture was stirred and then supernatant was removed by decantation. 3 mL of water was added to the residue and the mixture was adjusted to pH 9 with a saturated aqueous solution of sodium hydrogen carbonate. The resulting solid was collected by filtration to obtain 80 mg of the title compound.

$^1$H-NMR (DMSO-$d_6$): δ 1.22 (3H, t, J=7.1 Hz), 1.31 (3H, s), 3.32-3.40 (2H, m), 4.07-4.17 (6H, m), 5.10 (1H, brs), 5.35 (2H, s), 6.60 (1H, d, J=8.0 Hz), 7.11 (1H, d, J=12.0 Hz), 8.06 (1H, s).

Example 142

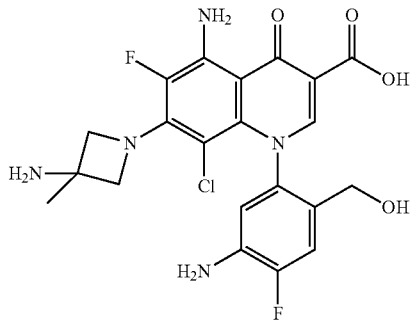 [SMILES: CC1(N)CN(c2c(F)c(N)c3c(=O)c(C(=O)O)cn(-c4cc(N)c(F)cc4CO)c3c2Cl)C1]

5-Amino-1-[5-amino-4-fluoro-2-(hydroxymethyl)
phenyl]-7-(3-amino-3-methylazetidin-1-yl)-8-chloro-
6-fluoro-4-oxo-1,4-dihydroquinoline-3-carboxylic
acid 3 mL of ethanol and 0.4 mL of a 1 mol/L aqueous solution of sodium hydroxide were added to 53 mg of ethyl 5-amino-1-[5-amino-4-fluoro-2-(hydroxymethyl)phenyl]-7-(3-amino-3-methylazetidin-1-yl)-8-chloro-6-fluoro-4-oxo-1,4-dihydroquinoline-3-carboxylate. The mixture was stirred at 60° C. for 2 hours. Ethanol was evaporated under reduced pressure. The residue was adjusted to pH 5 with 1 mol/L hydrochloric acid and precipitates were collected by filtration to obtain 51 mg of the title compound.

$^1$H-NMR (DMSO-$d_6$): δ 1.32 (3H, s), 4.02-4.20 (6H, m), 5.06 (1H, brs), 5.42 (2H, s), 6.69 (1H, d, J=7.5 Hz), 7.11 (1H, d, J=11.5 Hz), 7.51 (2H, brs), 8.24 (1H, s).

Example 143

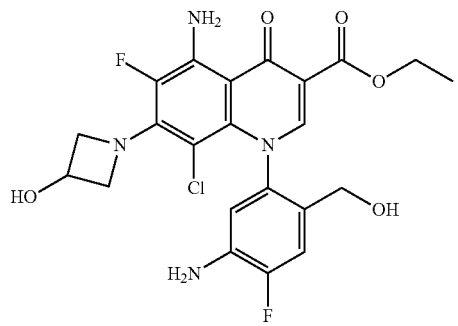 [SMILES: CCOC(=O)c1cn(-c2cc(N)c(F)cc2CO)c2c(Cl)c(N3CC(O)C3)c(F)c(N)c2c1=O]

Ethyl 5-amino-1-[5-amino-4-fluoro-2-(hydroxym-
ethyl)phenyl]-8-chloro-6-fluoro-7-[3-hydroxyazeti-
din-1-yl]-4-oxo-1,4-dihydroquinoline-3-carboxylate 88 mg of ethyl 5-amino-1-[5-amino-4-fluoro-2-(hydroxymethyl)phenyl]-8-chloro-6,7-difluoro-4-oxo-1,4-dihydroquinoline-3-carboxylate, 119 mg of N-methylpyrrolidine, and 67 mg of 3-hydroxyazetidine tartrate were added to 0.7 mL of dimethylsulfoxide and the mixture was stirred at 50° C. for 28 hours. 10 mL of diethyl ether was added. The mixture was stirred and then supernatant was removed by decantation. 3 mL of water was added to the residue and pH of the mixture was adjusted to 8 with a saturated aqueous solution of sodium hydrogen carbonate. The resulting solid was collected by filtration to obtain 80 mg of the title compound.

$^1$H-NMR (DMSO-$d_6$): δ 1.22 (3H, t, J=7.1 Hz), 3.93-3.99 (2H, m), 4.10-4.19 (4H, m), 4.39 (1H, brs), 4.47-4.54 (2H, m), 5.11 (1H, t, J=5.2 Hz), 5.35 (2H, s), 5.58 (1H, d, J=5.8 Hz), 6.61 (1H, d, J=8.3 Hz), 7.11 (1H, d, J=12.2 Hz), 8.08 (1H, s).

Example 144

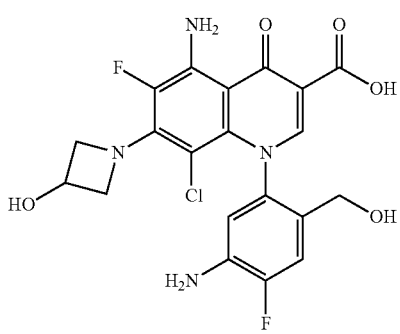 [SMILES: Nc1cc(-n2cc(C(=O)O)c(=O)c3c(N)c(F)c(N4CC(O)C4)c(Cl)c32)c(CO)cc1F]

5-Amino-1-[5-amino-4-fluoro-2-(hydroxymethyl)phenyl]-8-chloro-6-fluoro-7-[3-hydroxyazetidin-1-yl]-4-oxo-1,4-dihydroquinoline-3-carboxylic acid 3 mL of ethanol and 0.4 mL of a 1 mol/L aqueous solution of sodium hydroxide were added to 75 mg of ethyl 5-amino-1-[5-amino-4-fluoro-2-(hydroxymethyl)phenyl]-8-chloro-6-fluoro-7-[3-hydroxyazetidin-1-yl]-4-oxo-1,4-dihydroquinoline-3-carboxylate. The mixture was stirred at 60° C. for 2 hours. Ethanol was evaporated under reduced pressure. The residue was adjusted to pH 5 with 1 mol/L hydrochloric acid and precipitates were collected by filtration to obtain 53 mg of the title compound.

$^1$H-NMR (DMSO-$d_6$): δ 4.02-4.15 (4H, m), 4.39 (1H, brs), 4.39 (1H, brs), 4.58 (2H, brs), 5.06 (1H, t, J=5.1 Hz), 5.42 (2H, s), 5.62 (1H, d, J=5.9 Hz), 6.71 (1H, d, J=8.1 Hz), 7.11 (1H, d, J=11.7 Hz), 7.49 (2H, brs), 8.26 (1H, s).

Example 145

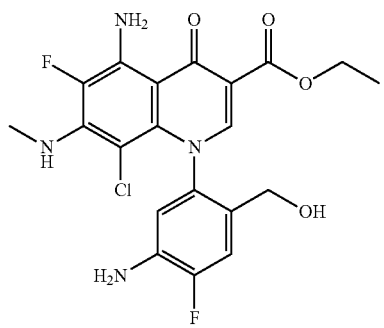 [SMILES: CCOC(=O)c1cn(-c2cc(N)c(F)cc2CO)c2c(Cl)c(NC)c(F)c(N)c2c1=O]

Ethyl 5-amino-1-[5-amino-4-fluoro-2-(hydroxymethyl)phenyl]-8-chloro-6-fluoro-7-methylamino-4-oxo-1,4-dihydroquinoline-3-carboxylate 88 mg of ethyl 5-amino-1-[5-amino-4-fluoro-2-(hydroxymethyl)phenyl]-8-chloro-6,7-difluoro-4-oxo-1,4-dihydroquinoline-3-carboxylate, 170 mg of N-methylpyrrolidine, 77 mg of methylamine hydrochloride were added to 0.7 mL of dimethylsulfoxide and the mixture was stirred at 60° C. for 18 hours. 10 mL of diethyl ether was added. The mixture was stirred and then supernatant was removed by decantation. 3 mL of water was added to the residue and the mixture was adjusted to pH 7 with a saturated aqueous solution of sodium hydrogen carbonate. The resulting solid was collected by filtration to obtain 75 mg of the title compound.

$^1$H-NMR (DMSO-$d_6$): δ 1.22 (3H, t, J=7.1 Hz), 3.02 (3H, dd, J=5.1, 7.1 Hz), 4.10-4.19 (4H, m), 5.11 (1H, t, J=5.3 Hz), 5.35 (2H, s), 5.73 (1H, brs), 6.59 (1H, d, J=8.3 Hz), 7.10 (1H, d, J=12.0 Hz), 8.03 (1H, s).

Example 146

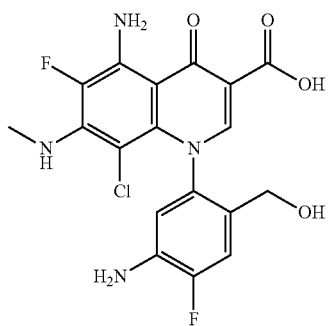 [SMILES: CNc1c(F)c(N)c2c(=O)c(C(=O)O)cn(-c3cc(N)c(F)cc3CO)c2c1Cl]

5-Amino-1-[5-amino-4-fluoro-2-(hydroxymethyl)phenyl]-8-chloro-6-fluoro-7-methylamino-4-oxo-1,4-dihydroquinoline-3-carboxylic acid 3 mL of ethanol and 0.4 mL of a 1 mol/L aqueous solution of sodium hydroxide were added to 70 mg of ethyl 5-amino-1-[5-amino-4-fluoro-2-(hydroxymethyl)phenyl]-8-chloro-6-fluoro-7-methylamino-4-oxo-1,4-dihydroquinoline-3-carboxylate. The mixture was stirred at 60° C. for 2 hours. Ethanol was evaporated under reduced pressure. The residue was adjusted to pH 5 with 1 mol/L hydrochloric acid and precipitates were collected by filtration to obtain 57 mg of the title compound.

$^1$H-NMR (DMSO-$d_6$): δ 3.02 (3H, dd, J=5.1, 7.1 Hz), 4.04-4.14 (2H, m), 5.07 (1H, t, J=5.0 Hz), 5.42 (2H, brs), 6.10-6.15 (1H, m), 6.68 (1H, d, J=8.3 Hz), 7.11 (1H, d, J=12.0 Hz), 7.55 (2H, s), 8.21 (1H, s).

Reference Example 42

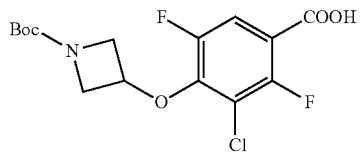 [SMILES: CC(C)(C)OC(=O)N1CC(Oc2c(F)cc(C(=O)O)c(F)c2Cl)C1]

4-[1-(tert-Butoxycarbonyl)azetidin-3-yl]oxy-3-chloro-2,5-difluorobenzoic acid Sodium hydride (55% in oil) was suspended to 1 mL of N,N-dimethylformamide and 1 mL of N,N-dimethylformamide solution of 0.520 g of tert-butyl 3-hydroxyazetidin-1-ylcarboxylate was'added under ice cooling in a nitrogen atmosphere. The mixture was stirred at room temperature for 10 minutes. 1 mL of a N,N-dimethylformamide solution of 0.210 g of 3-chloro-2,4,5-trifluorobenzoic acid was added under ice cooling and the mixture was stirred at room temperature for 30 minutes. 30 mL of a 10% aqueous solution of citric acid was added and then the mixture was extracted with ethyl acetate. The extract was washed with water and dried over anhydrous sodium sulfate and then the solvent was evaporated under reduced pressure. The residue was subjected to silica gel column chromatography (chloroform:methanol=3 to 30% gradient and hexane:ethyl acetate 40% isocratic) to obtain 0.189 g of the title compound.

$^1$H-NMR (DMSO-$d_6$): δ 1.45 (9H, s), 4.17 (2H, dd, J=4.0 Hz, 10.0 Hz), 4.32 (2H, dd, J=6.5 Hz, 10.0 Hz), 5.08-5.13 (1H, m), 7.65-7.69 (1H, m), 10.47 (1H, brs)

Reference Example 43

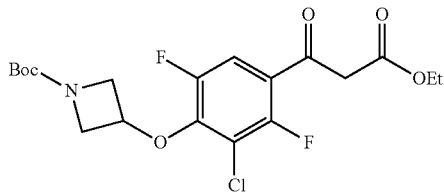 [SMILES: CCOC(=O)CC(=O)c1cc(F)c(OC2CN(C(=O)OC(C)(C)C)C2)c(Cl)c1F]

Ethyl 2-[4-[1-(tert-butoxycarbonyl)azetidin-3-yloxy]-3-chloro-2,5-difluorobenzoyl]acetate 1.1 mL of acetonitrile, 69 mg of magnesium chloride, and 0.105 g of triethylamine were added to 0.106 g of potassium monoethyl malonate under ice cooling and the mixture was stirred at room temperature for 18 hours to yield a suspension. 1.9 mL of tetrahydrofuran and 0.120 g of carbonyldiimidazole were added to 0.189 g of 4-[1-(tert-butoxycarbonyl)azetidin-3-yl]oxy-3-chloro-2,5-difluorobenzoic acid. The mixture was stirred at room temperature for 18 hours and then 25 mg of carbonyldiimidazole was added. The mixture was stirred at room temperature for 30 minutes and this solution was added to the earlier-prepared suspension under ice cooling. The mixture was stirred at room temperature for 5 hours. 20 mL of a 10% aqueous solution of citric acid was added and then the mixture was extracted with ethyl acetate. The extract was washed with saturated brine and dried over anhydrous sodium sulfate. The solvent was evaporated under reduced pressure and the residue was subjected to silica gel column chromatography (n-hexane/ethyl acetate=10 to 40% gradient) to obtain 0.123 g of the title compound.

$^1$H-NMR (CDCl$_3$, keto/enol=65/35): δ 1.28 (1.95H, t, J=7.0 Hz), 1.34 (1.35H, t, J=7.0 Hz), 1.47 (9H, s), 3.96 (1.3H, d, J=4.0 Hz), 4.14-4.18 (2H, m), 4.27-4.31 (2H, m), 5.04-5.09 (0.35H, m), 5.11-5.16 (0.65H, m), 5.85 (0.35H, s), 7.59 (0.35H, dd, J=7.0 Hz, 12.5 Hz), 7.66 (0.65H, dd, J=6.0 Hz, 12.0 Hz), 12.73 (0.35H, s)

Reference Example 44

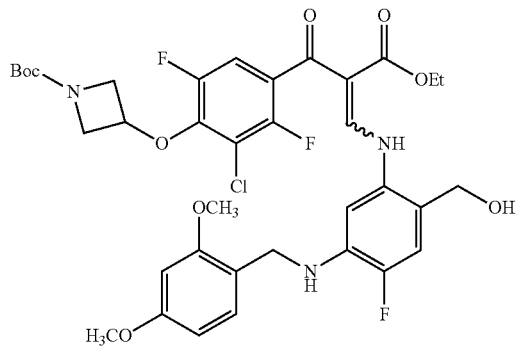 [SMILES: CCOC(=O)C(=CNc1cc(NCc2ccc(OC)cc2OC)c(F)cc1CO)C(=O)c1cc(F)c(OC2CN(C(=O)OC(C)(C)C)C2)c(Cl)c1F]

Ethyl 2-[4-[1-(tert-butoxycarbonyl)azetidin-3-yloxy]-3-chloro-2,5-difluorobenzoyl]-3-[5-(2,4-dimethoxybenzyl)amino-4-fluoro-2-hydroxymethyl-phenyl]aminoacrylate 0.123 g of ethyl 2-[4-[1-(tert-butoxycarbonyl)azetidin-3-yloxy]-3-chloro-2,5-difluorobenzoyl]acetate was dissolved in 1.5 mL of toluene and 0.169 g of N,N-dimethylformamide dimethyl acetal was added. The mixture was stirred at 100° C. for 40 minutes. The solvent was evaporated under reduced pressure and then the residue was subjected to an azeotropic distillation with toluene. The resulting residue was dissolved in 1 mL of dichloromethane for use in the following reaction. 0.100 g of methyl 2-amino-4-(2,4-dimethoxybenzyl)amino-5-fluorobenzoate was suspended to 4 mL of toluene and 1 mL of tetrahydrofuran and 26 mg of lithium borohydride was added. The mixture was stirred at 80° C. for 2 hours. The reaction solution was cooled to room temperature and then water was added. The mixture was extracted with ethyl acetate and the extract was dried over anhydrous sodium sulfate. The anhydrous sodium sulfate was filtered off and then the aforementioned dichloromethane solution was added to the filtrate. The mixture was stirred at room temperature for 2 days. The solvent was evaporated under reduced pressure and the residue was subjected to silica gel column chromatography (n-hexane/ethyl acetate=10 to 40% gradient) to obtain 0.147 g of the title compound (E/Z=2/1).

$^1$H-NMR (CDCl$_3$): δ 0.97 (1H, t, J=7.0 Hz), 1.09 (2H, t, J=7.0 Hz), 1.47 (9H, s), 2.15 (0.33H, brm), 2.24 (0.67H, brm), 2.18 (3H, d, J=2.0 Hz), 3.80 (1H, s), 3.81 (2H, s), 3.86 (1H, s), 3.87 (2H, s), 4.08-4.15 (2H, m), 4.16-4.18 (2H, m), 4.24-4.28 (2H, m), 4.34-4.35 (2H, m), 4.55 (1H, brs), 4.64-4.65 (0.67H, m), 4.66-4.67 (1.34H, m), 4.99-5.05 (1H, m), 6.47-6.51 (2H, m), 6.71 (1H, d, J=7.0 Hz), 6.87 (0.33H, d, J=11.0 Hz), 6.91 (0.67H, d, J=11.5 Hz), 7.16-7.26 (2H, m), 8.41 (0.33H, d, J=14.5 Hz), 8.45 (0.67H, d, J=13.5 Hz), 11.60 (0.33H, d, J=14.5 Hz), 12.80 (0.67H, d, J=13.5 Hz)

Reference Example 45

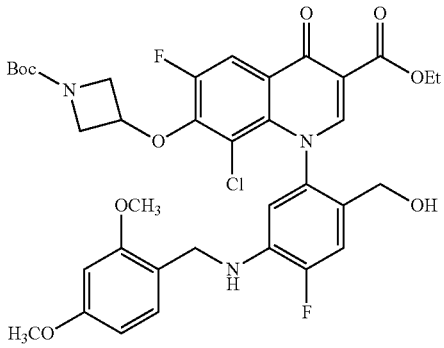 [SMILES: CCOC(=O)c1cn(-c2cc(NCc3ccc(OC)cc3OC)c(F)cc2CO)c2c(Cl)c(OC3CN(C(=O)OC(C)(C)C)C3)c(F)cc2c1=O]

Ethyl 7-[1-(tert-butoxycarbonyl)azetidin-3-yloxy]-8-chloro-1-[5-(2,4-dimethoxybenzyl)amino-4-fluoro-2-hydroxymethylphenyl]-6-fluoro-4-oxo-1,4-dihydroquinoline-3-carboxylate 0.147 g of ethyl 2-[4-[1-(tert-butoxycarbonyl)azetidin-3-yloxy]-3-chloro-2,5-difluorobenzoyl]-3-[5-(2,4-dimethoxybenzyl)amino-4-fluoro-2-hydroxymethylphenyl]aminoacrylate was dissolved in 1 mL of N-methylpyrrolidin-2-one and 33 mg of 1,8-diazabicyclo[5.4.0]undec-7-ene and 17 mg of lithium chloride were added at room temperature and the mixture was stirred at room temperature for 20 minutes. Iced water was added to the reaction solution and precipitates were collected by filtration to obtain 0.125 g of the title compound.

$^1$H-NMR (DMSO-d$_6$): δ 1.24 (3H, t, J=7.5 Hz), 1.37 (9H, s), 3.64 (3H, s), 3.70 (3H, s), 3.89-3.95 (2H, brm), 4.04 (1H, dd, J=5.5 Hz, 13.0 Hz), 4.07 (1H, dd, J=5.0 Hz, 13.0 Hz), 4.14-4.22 (6H, m), 4.96-5.00 (1H, m), 5.02 (1H, t, J=5.0 Hz), 6.17 (dt, J=2.0 Hz, 6.5 Hz), 6.42 (1H, dd, J=2.5 Hz, 8.5 Hz), 6.46 (1H, d, J=2.0 Hz), 6.73 (1H, d, J=8.0 Hz), 7.09 (1H, d, J=8.5 Hz), 7.15 (1H, d, J=12.0 Hz), 8.05 (1H, d, J=11.0 Hz), 8.23 (1H, s)

Example 147

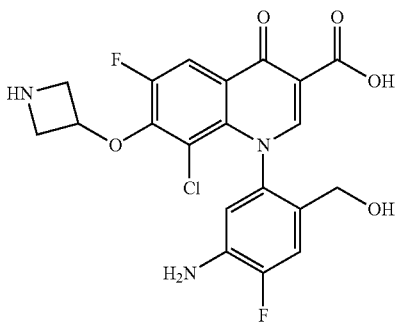 [SMILES: Nc1cc(-n2cc(C(=O)O)c(=O)c3cc(F)c(OC4CNC4)c(Cl)c32)c(CO)cc1F]

1-[5-Amino-4-fluoro-2-(hydroxymethyl)phenyl]-7-(azetidin-3-yloxy)-8-chloro-6-fluoro-4-oxo-1,4-dihydroquinoline-3-carboxylic acid acetate 0.115 g of ethyl 7-[1-(tert-butoxycarbonyl)azetidin-3-yloxy]-8-chloro-1-[5-(2,4-dimethoxybenzyl)amino-4-fluoro-2-hydroxymethylphenyl]-6-fluoro-4-oxo-1,4-dihydroquinoline-3-carboxylate was suspended in 2.3 mL of dichloromethane and 0.115 mL of anisole and 2.3 mL of trifluoroacetic acid were added. The mixture was stirred at room temperature for 30 minutes. 5 mL of a saturated aqueous solution of sodium hydrogen carbonate was added to the reaction solution and then ethyl acetate and water were added for the distribution. The resulting precipitates were filtered off. The filtrate was extracted with ethyl acetate. The extract was dried over anhydrous sodium sulfate and then the solvent was evaporated. Diisopropyl ether was added to the residue. The mixture was stirred and then supernatant was removed by decantation. The resulting residue was used for the following reaction.

The residue was dissolved in 2 mL of ethanol and 0.157 mL of a 1 mol/L aqueous solution of sodium hydroxide was added. The mixture was stirred at 60° C. for 2 hours and then 0.03 mL of a 1 mol/L aqueous solution of sodium hydroxide was added. The mixture was stirred at 60° C. for 20 minutes. Insoluble matter was filtered off and then the solution was adjusted to pH 5 with 1 mol/L hydrochloric acid and insoluble matter was filtered off. Ethanol in the filtrate was evaporated under reduced pressure and a very small amount of DMSO was added. Insoluble matter was dissolved and the solution was subjected to reverse phase flash column chromatography (1% acetic acid in water:1% acetic acid/acetonitrile=10 to 80% gradient). The fraction containing the desired product was freeze-dried to obtain the title compound as 15 mg of its acetate.

$^1$H-NMR (DMSO-d$_6$): δ 1.89 (3H, s, AcOH), 3.67 (4H, brm), 3.96-4.07 (2H, m), 5.03 (2H, brm), 5.51 (2H, s), 6.81 (1H, d, J=7.5 Hz), 7.15 (1H, d, J=12.0 Hz), 8.16 (1H, brm), 8.51 (1H, s)

Reference Example 46

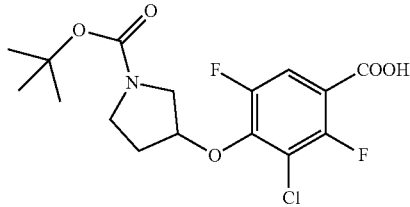 [SMILES: CC(C)(C)OC(=O)N1CCC(Oc2c(F)cc(C(=O)O)c(F)c2Cl)C1]

4-[1-(tert-Butoxycarbonyl)pyrrolidin-3-yl]oxy-3-chloro-2,5-difluorobenzoic acid 1.3 g of sodium hydride was suspended in 2.0 mL of dimethylformamide in a nitrogen atmosphere and then a solution of 3.9 g of tert-butyl 3-hydroxypyrrolidinecarboxylate dissolved in 5.0 mL of dimethylformamide was added at 0° C. The mixture was stirred at room temperature for 30 minutes. 5 mL of dimethylformamide was further added to the reaction solution. The mixture was stirred at room temperature for 10 minutes and then a solution of 1.5 g of 3-chloro-2,4,5-trifluorobenzoic acid dissolved in 5.0 mL of dimethylformamide was added at 0° C. The mixture was stirred at room temperature for 1 hour. 50 mL of a 10% aqueous solution of citric acid was added to the reaction solution. The mixture was extracted with ethyl acetate and the extract was dried over anhydrous sodium sulfate. The solvent was evaporated under reduced pressure and the residue was subjected to silica gel column chromatography (n-hexane/ethyl acetate=10 to 40% gradient) to obtain 0.28 g of the title compound.

¹H NMR DMSO-d₆): δ 1.41 (9H, d, J=14.4 Hz), 2.12 (2H, brm), 3.40-3.51 (4H, m), 5.14 (1H, m), 7.77 (1H, dd, J=6.7 Hz, 11.0 Hz)

Reference Example 47

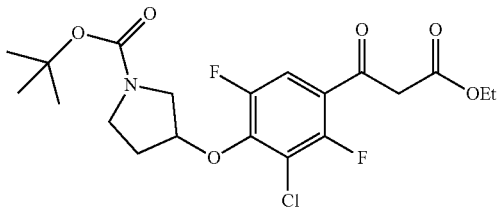 [SMILES: CCOC(=O)CC(=O)c1cc(F)c(OC2CCN(C(=O)OC(C)(C)C)C2)c(Cl)c1F]

Ethyl 2-[4-[1-(tert-butoxycarbonyl)pyrrolidin-3-yloxy]-3-chloro-2,5-difluorobenzoyl]acetate 1.5 mL of acetonitrile, 99 mg of magnesium chloride, and 0.21 mL of triethylamine were added to 0.15 g of potassium monoethyl malonate. The mixture was stirred at room temperature overnight to yield a suspension. Meanwhile, 2.5 mL of THF and 0.18 g of carbonyldiimidazole were added to 0.28 g of 4-[1-(tert-butoxycarbonyl)pyrrolidin-3-yl]oxy-3-chloro-2,5-difluorobenzoic acid and the mixture was stirred at room temperature overnight. This solution was added at room temperature to the suspension prepared earlier and the mixture was stirred overnight. 20 mL of a 10% aqueous solution of citric acid was added and then the solution was extracted with ethyl acetate. The extract was dried over anhydrous sodium sulfate. The solvent was evaporated under reduced pressure and the residue was subjected to silica gel column chromatography (n-hexane/ethyl acetate=10 to 40% gradient) to obtain 0.25 g of the title compound.

¹H NMR (CDCl₃): δ 1.28 (2.4H, t, J=7.1 Hz), 1.34 (0.6H, t, J=7.1 Hz), 2.00-2.12 (1H, m), 2.22-2.29 (1H, m), 3.48-3.72 (4H, m), 3.95 (1.6H, d, J=3.8 Hz), 4.25 (1.6H, q, J=7.1 Hz), 4.29 (0.4H, q, J=7.1 Hz), 5.10-5.21 (1H, m), 5.84 (0.2H, brs), 7.55-7.70 (1H, m), 12.7 (0.2H, s).

Reference Example 48

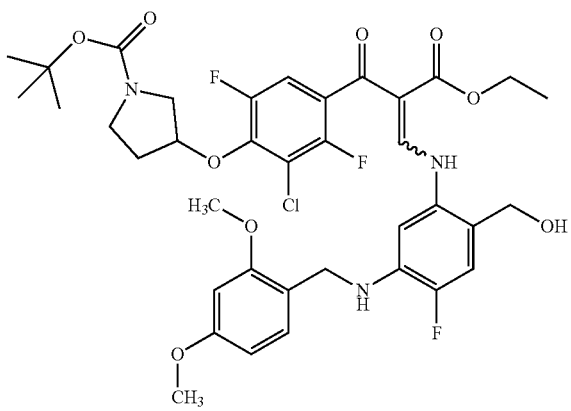 [SMILES: CCOC(=O)C(=CNc1cc(NCc2ccc(OC)cc2OC)c(F)cc1CO)C(=O)c1cc(F)c(OC2CCN(C(=O)OC(C)(C)C)C2)c(Cl)c1F]

Ethyl 2-[4-[1-(tert-butoxycarbonyl)pyrrolidin-3-yl]oxy-3-chloro-2,5-difluorobenzoyl]-3-[5-(2,4-dimethoxybenzyl)amino-4-fluoro-2-hydroxymethylphenyl]aminoacrylate 2.0 mL of tetrahydrofuran, 8.0 mL of toluene, and 37 mg of lithium borohydride were added to 0.19 g of methyl 2-amino-4-(2,4-dimethoxybenzyl)amino-5-fluorobenzoate and the mixture was heated to reflux for 3 hours. The reaction solution was cooled to room temperature and then washed with water. The resultant was dried over anhydrous sodium sulfate, and filtrated. Meanwhile, 1.0 mL of toluene and 0.38 mL of N,N-dimethylformamide dimethyl acetal were added to 0.25 g of ethyl 2-[4-[1-(tert-butoxycarbonyl)pyrrolidin-3-yloxy]-3-chloro-2,5-difluorobenzoyl]acetate. The mixture was stirred at room temperature for 1 hour and then stirred at 90° C. for 1 hour. The solution was concentrated. 1 mL of dichloromethane was added to the residue and then the mixture was added at room temperature to the filtrate prepared earlier. The mixture was stirred at 30° C. for 3 days. The solvent was evaporated under reduced pressure and the residue was subjected to silica gel column chromatography (n-hexane/ethyl acetate=0 to 15% gradient) to obtain 0.24 g of the title compound.

¹H NMR (CDCl₃): δ 0.94-1.00 (1H, m), 1.08 (2H, t, J=7.1 Hz), 1.44-1.49 (9H, m), 2.00-2.08 (1H, m), 2.20-2.29 (1H, m), 3.40-3.66 (4H, m), 3.802-3.808 (3H, m), 3.863-3.868 (3H, m), 4.08-4.14 (2H, m), 4.32-4.36 (2H, m), 4.66-4.68 (2H, m), 5.04-5.11 (1H, m), 6.46-6.51 (2H, m), 6.70-6.72 (1H, m), 6.86 (0.33H, d, J=11.3 Hz), 6.92 (0.66H, J=11.3 Hz), 7.19-7.21 (1H, m), 8.40-8.46 (1H, m).

Reference Example 49

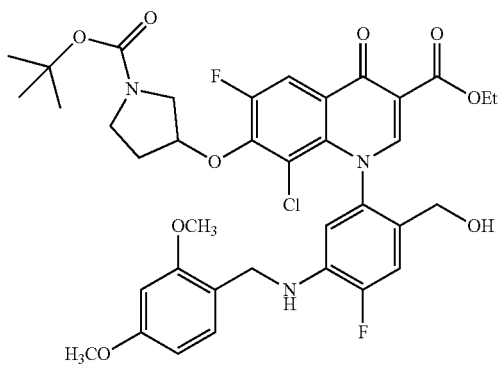 [SMILES: CCOC(=O)c1cn(-c2cc(NCc3ccc(OC)cc3OC)c(F)cc2CO)c2c(Cl)c(OC3CCN(C(=O)OC(C)(C)C)C3)c(F)cc2c1=O]

Ethyl 7-[1-(tert-butoxycarbonyl)pyrrolidin-3-yloxy]-8-chloro-1-[5-(2,4-dimethoxybenzyl)amino-4-fluoro-2-hydroxymethylphenyl]-6-fluoro-4-oxo-1,4-dihydroquinoline-3-carboxylate 2.0 mL of N-methylpyrrolidin-2-one, 0.19 mL of 1,8-diazabicyclo[5.4.0]undec-7-ene, and 54 mg of lithium chloride were added to 0.24 g of ethyl 2-[4-[1-(tert-butoxycarbonyl)pyrrolidin-3-yl]oxy-3-chloro-2,5-difluorobenzoyl]-3-[5-(2,4-dimethoxybenzyl)amino-4-fluoro-2-hydroxymethylphenyl]aminoacrylate and the mixture was stirred at room temperature overnight. The reaction solution was added to 30 mL of water and precipitates were collected by filtration. The resulting solid was subjected to silica gel column chromatography (chloroform:ethyl acetate=0 to 50% gradient) to obtain 0.12 g of the title compound.

$^1$H NMR (CDCl$_3$): δ 1.35-1.42 (7.5H, m), 1.43 (4.5H, s), 1.96-2.24 (1.5H, m), 2.35-2.42 (0.5H, m), 3.05 (1H, dd, J=2.7 Hz, 13.4 Hz), 3.43-3.69 (3.5H, m), 3.76-3.82 (6H, m), 3.97-4.20 (0.5H, m), 4.18-4.35 (3H, m), 4.36-4.40 (2H, m), 4.51-4.56 (1H, m), 5.04-5.14 (1H, m), 6.40-6.46 (2H, m), 6.58-6.65 (0.5H, m), 6.77 (0.5H, d, J=7.7 Hz), 7.06-7.14 (1H, m), 8.24-8.26 (1H, m), 8.32 (0.5H, s), 8.37 (0.5H, s).

Example 148

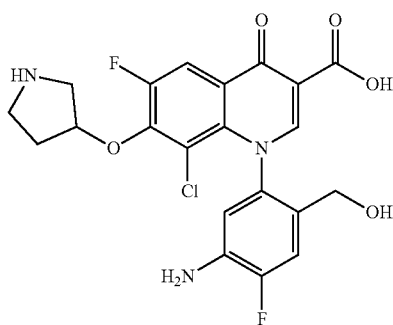 [SMILES: Nc1cc(-n2cc(C(=O)O)c(=O)c3cc(F)c(OC4CCNC4)c(Cl)c32)c(CO)cc1F]

1-[5-Amino-4-fluoro-2-(hydroxymethyl)phenyl]-8-chloro-6-fluoro-4-oxo-7-(pyrrolidin-3-yloxy)-1,4-dihydroquinoline-3-carboxylic acid 2.4 mL of dichloromethane, 70 μL of anisole, and 0.50 mL of TFA were added to 0.12 g ethyl 7-[1-(tert-butoxycarbonyl)pyrrolidin-3-yloxy]-8-chloro-1-[5-(2,4-dimethoxybenzylamino)-4-fluoro-2-hydroxymethylphenyl]-6-fluoro-4-oxo-1,4-dihydroquinoline-3-carboxylate and the mixture was stirred at room temperature for 2 hours. 12 mL of a saturated aqueous solution of sodium bicarbonate was added to the reaction solution and precipitates were collected by filtration. The resulting solid was suspended in 10 mL of a solution of chloroform:methanol=10:1 and the mixture was stirred at 60° C. for 1 hour. The solution was filtered through a membrane filter and then the resulting filtrate was concentrated.

0.50 mL of ethanol and 0.23 mL of a 1 mol/L aqueous solution of sodium hydroxide were added to 55 mg of the resulting residue and the mixture was stirred at 50° C. for 1.5 hours. Precipitates were filtrated and then 1 mol/L hydrochloric acid was added to the filtrate to make the filtrate acidic (pH 5 to 6) and then ethanol was evaporated under reduced pressure. The residue was subjected to silica gel column chromatography (a 1% aqueous solution of acetic acid:a 1% acetic acid-acetonitrile solution=10 to 80% gradient). The fraction was retrieved and then freeze-dried to obtain 7.3 mg of the title compound.

$^1$H-NMR (DMSO-d$_6$): δ 1.23 (2H, brm), 1.83 (6H, brs), 2.78 (1H, brm), 2.94 (3H, brm), 3.90-4.05 (2H, m), 4.90-5.08 (2H, m), 5.49 (2H, brs), 6.80 (1H, brm), 7.15 (1H, d, J=11.7 Hz), 8.08 (1H, brm), 8.53 (1H, brm).

$^1$H-NMR (CD$_3$OD): δ 1.24-1.35 (1H, m), 1.38-1.46 (1H, m), 2.66-2.70 (1H, m), 3.24-3.28 (2H, m), 4.36 (1H, brm), 5.99 (1H, brm), 6.28 (1H, d, J=11.8 Hz), 7.55 (1H, d, J=11.7 Hz), 7.85 (1H, brs).

Reference Example 50

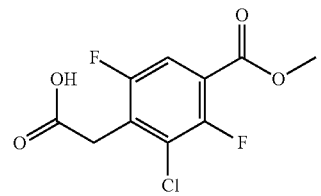 [SMILES: COC(=O)c1cc(F)c(CC(=O)O)c(Cl)c1F]

2-Chloro-3,6-difluoro-4-methoxycarbonylphenylacetic acid 2.28 g of sodium hydride was dissolved in 80 mL of N,N-dimethylformamide. 12.8 mL of malonic acid di-tert-butyl ester was added dropwise to the solution under ice cooling and the mixture was further stirred at room temperature for 90 minutes. 6.40 g of ethyl 3-chloro-2,4,5-trifluorobenzoate was added to the mixture and the resulting mixture was stirred for 2 hours. 300 mL of diethyl ether was added to the reaction solution and the mixture was washed twice with 300 mL of a 5% aqueous solution of citric acid. The organic layer was dried over anhydrous sodium sulfate and concentrated under reduced pressure. 20 mL of trifluoroacetic acid was added to the oily residue and the mixture was stirred at room temperature for 17 hours. Trifluoroacetic acid was evaporated under reduced pressure. 100 mL of diethyl ether was added to the residue and the mixture was washed with 100 mL of water. The organic layer was dried over anhydrous sodium sulfate and concentrated under reduced pressure. 50 mL of toluene was added to the residue and the mixture was stirred at 110° C. for 3 hours. The solvent was evaporated under reduced pressure and 50 mL of hexane was added. The solid was collected by filtration to obtain 6.39 g of the title compound.

$^1$H-NMR (CDCl$_3$): δ 3.95 (2H, d, J=1.0 Hz), 3.96 (3H, s), 7.62 (1H, dd, J=9.1, 5.3 Hz).

Reference Example 51

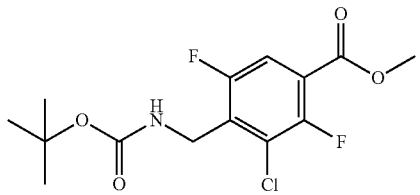 [SMILES: COC(=O)c1cc(F)c(CNC(=O)OC(C)(C)C)c(Cl)c1F]

Methyl 4-(tert-butoxycarbonylaminomethyl)-3-chloro-2,5-difluorobenzoate 2.64 g of 2-chloro-3,6-difluoro-4-methoxycarbonylphenylacetic acid, 2.59 mL of diphenylphosphoryl azide, and 1.82 mL of triethylamine were dissolved in 40 mL of toluene. The mixture was stirred at room temperature for 3 hours and then at 100° C. for 30 minutes. 100 mL of tert-butyl alcohol was added to the mixture and the resulting mixture was further stirred for 15 hours. 100 mL of ethyl acetate was added and the mixture was washed with 60 mL of a 1% aqueous solution of potassium carbonate, 60 mL of a 5% aqueous solution of citric acid, and 50 mL of saturated brine, in order. The organic layer was dried over anhydrous sodium sulfate and concentrated under reduced pressure. The residue was subjected to silica gel column chromatography (dichloromethane:ethyl acetate=0 to 5% gradient) to obtain 2.16 g of the title compound.

$^1$H-NMR (CDCl$_3$): δ 1.43 (9H, s), 3.95 (3H, s), 4.52 (2H, brs), 4.98 (1H, s), 7.57 (1H, dd, J=9.2, 5.4 Hz).

Reference Example 52

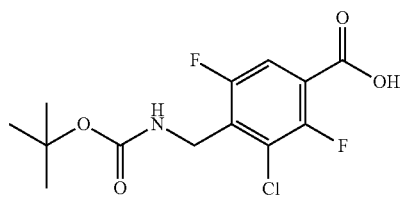 [SMILES: CC(C)(C)OC(=O)NCc1c(F)cc(C(=O)O)c(F)c1Cl]

4-(tert-Butoxycarbonylaminomethyl)-3-chloro-2,5-difluorobenzoic acid 3.96 g of methyl 4-(tert-butoxycarbonylaminomethyl)-3-chloro-2,5-difluorobenzoate was dissolved in 15 mL of 1,4-dioxane and 19 mL of ethanol and 23 mL of a 1 mol/L aqueous solution of sodium hydroxide was added. The mixture was stirred at room temperature for 1 hour. The organic solvent was evaporated under reduced pressure and then 50 mL of a 5% aqueous solution of citric acid was added to the residue. The mixture was extracted with 60 mL of ethyl acetate. The organic layer was dried over anhydrous sodium sulfate and concentrated under reduced pressure. Hexane was added to the residue and the resulting solid was collected by filtration to obtain 3.55 g of the title compound.

$^1$H-NMR (DMSO-d$_6$): δ 1.36 (9H, s), 4.29 (2H, dd, J=4.9 Hz), 7.33 (1H, s), 7.60 (1H, dd, J=5.9, 9.5 Hz), 13.8 (1H, brs).

Reference Example 53

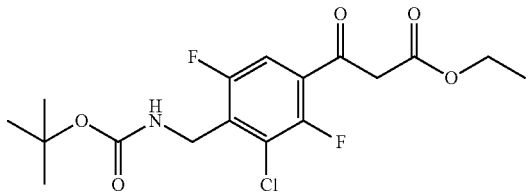 [SMILES: CCOC(=O)CC(=O)c1cc(F)c(CNC(=O)OC(C)(C)C)c(Cl)c1F]

Ethyl 3-[4-(tert-butoxycarbonylaminomethyl)-3-chloro-2,5-difluorophenyl]-3-oxopropionate 15 mL of acetonitrile, 0.93 g of magnesium chloride, and 1.42 g of triethylamine were added to 1.43 g of potassium monoethyl malonate under ice cooling. The mixture was stirred at room temperature for 24 hours to yield a suspension. 2.25 g of 4-(tert-butoxycarbonylaminomethyl)-3-chloro-2,5-difluorobenzoic acid and 1.62 g of carbonyldiimidazole were dissolved in 25 mL of tetrahydrofuran and the mixture was stirred at room temperature for 20 hours. This solution was added at room temperature to the suspension prepared earlier and the mixture was stirred overnight. The solvent was evaporated and 50 mL of dichloromethane and 50 mL of a 5% aqueous solution of citric acid was added to the residue. The mixture was stirred at room temperature for 1 hour. The organic layer was dried over anhydrous sodium sulfate. The residue was subjected to silica gel column chromatography (dichloromethane:ethyl acetate=0 to 10% gradient) to obtain 2.53 g of the title compound.

$^1$H-NMR (CDCl$_3$): δ 1.27 (1.8H, t, J=7.0 Hz), 1.35 (1.2H, t, J=7.0 Hz), 1.44 (s, 9H), 3.97 (1.2H, d, J=3.5 Hz), 4.24 (1.2H, q, J=7.0 Hz), 4.30 (0.8H, q, J=7.0 Hz), 4.54 (2H, s), 4.98 (1H, brs), 5.87 (0.4H, s), 7.52-7.59 (1H, m), 12.67 (0.4H, s)

Reference Example 54

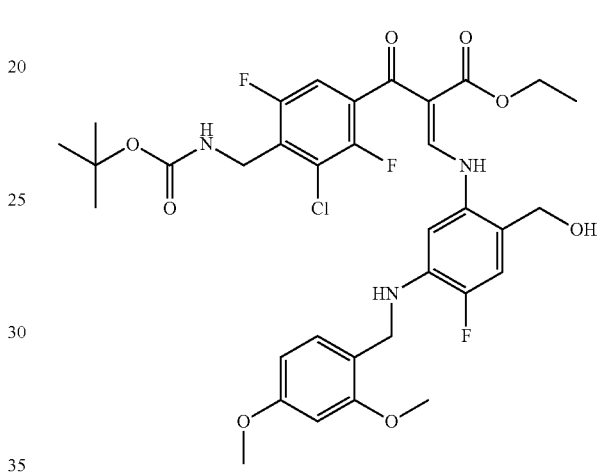

Ethyl 2-[4-(tert-butoxycarbonylaminomethyl)-3-chloro-2,5-difluorobenzoyl]-3-[5-(2,4-dimethoxybenzylamino)-4-fluoro-2-hydroxymethylphenyl]aminoacrylate 1.96 g of ethyl 3-[4-(tert-butoxycarbonylaminomethyl)-3-chloro-2,5-difluorophenyl]-3-oxopropionate and 2.66 mL of dimethylformamide dimethyl acetal were added to 20 mL of toluene and the mixture was stirred at 90° C. for 15 hours. The reaction solution was concentrated under reduced pressure to obtain an oily substance.

1.77 g of methyl 2-amino-4-(2,4-dimethoxybenzylamino)-5-fluorobenzoate was added to 50 mL of toluene and 15 mL of tetrahydrofuran. 462 mg of lithium borohydride was added and the mixture was stirred at 100° C. for 1.5 hours. 75 mL of water was added under ice cooling and the mixture was stirred for 20 minutes. The aqueous solution was extracted with 100 mL of ethyl acetate. The organic layer was dried over anhydrous sodium sulfate.

The oily substance prepared earlier was added to this organic layer and the mixture was stirred at room temperature for 24 hours. The reaction solution was concentrated under reduced pressure. The residue was subjected to silica gel column chromatography (dichloromethane:ethyl acetate=0 to 40% gradient) to obtain 2.56 g of the title compound.

$^1$H NMR (CDCl$_3$): δ 0.93 and 1.06 (total 3H, t, J=7.1 Hz), 1.45 (9H, s), 3.81 (3H, s), 3.87 (3H, s), 4.06-4.16 (4H, m), 4.35 (2H, d, J=5.8 Hz), 4.54 (2H, brs), 4.65 and 4.68 (total 2H, d, J=4.6 Hz), 4.96 (1H, brs), 6.47-6.52 (2H, m), 6.71 and 6.72 (total 1H, d, J=7.6 Hz), 6.88 and 6.91 (total 1H, d, J=11.2 Hz), 7.10 and 7.16 (total 1H, dd, J=8.8, 5.1 Hz), 7.21 and 7.22 (total 1H, d, J=8.3 Hz), 8.46 (1H, d, J=13.5 Hz), 11.7 and 12.9 (total 1H, d, J=13.5 Hz).

Reference Example 55

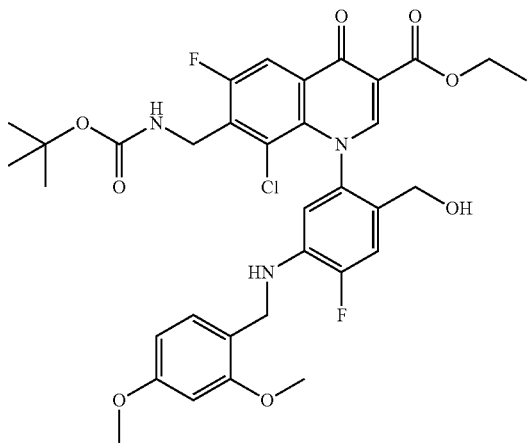 [SMILES: CCOC(=O)c1cn(-c2cc(NCc3ccc(OC)cc3OC)c(F)cc2CO)c2c(Cl)c(CNC(=O)OC(C)(C)C)c(F)cc2c1=O]

Ethyl 7-(tert-butoxycarbonylaminomethyl)-8-chloro-1-[5-(2,4-dimethoxybenzylamino)-4-fluoro-2-hydroxymethylphenyl]-6-fluoro-4-oxo-1,4-dihydroquinoline-3-carboxylate 2.56 g of ethyl 2-[4-(tert-butoxycarbonylaminomethyl)-3-chloro-2,5-difluorobenzoyl]-3-[5-(2,4-dimethoxybenzylamino)-4-fluoro-2-hydroxymethylphenyl]aminoacrylate, 307 mg of lithium chloride, and 594 μL of 1,8-diazabicyclo[5.4.0]undec-7-ene were added to 15 mL of N-methyl-2-pyrrolidone and the mixture was stirred at 60° C. for 5 hours. The mixture was cooled and then the reaction solution was extracted with 150 mL of ethyl acetate. The organic layer was dried over anhydrous sodium sulfate. The solvent was evaporated under reduced pressure and the residue was subjected to silica gel column chromatography (dichloromethane:ethyl acetate=0 to 60's gradient) to obtain 1.30 g of the title compound.

$^1$H NMR (CDCl$_3$): δ 1.39 (3H, t, J=7.1 Hz), 1.41 (9H, s), 3.78 (3H, s), 3.80 (3H, s), 4.21-4.33 (4H, m), 4.38 (2H, q, J=7.1 Hz), 4.46-4.62 (3H, m), 4.97 (1H, brs), 6.40-6.45 (2H, m), 6.61 (1H, d, J=8.6 Hz), 7.12 (1H, d, J=8.1 Hz), 7.16 (1H, d, J=11.7 Hz), 8.22 (1H, d, J=9.3 Hz), 8.42 (1H, s).

Example 149

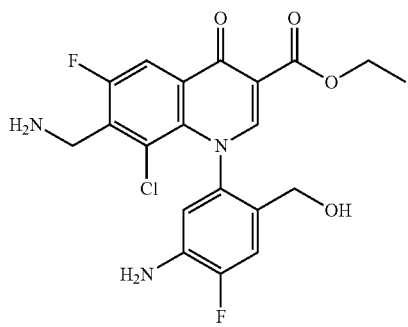 [SMILES: CCOC(=O)c1cn(-c2cc(N)c(F)cc2CO)c2c(Cl)c(CN)c(F)cc2c1=O]

Ethyl 1-[5-amino-4-fluoro-2-(hydroxymethyl)phenyl]-7-aminomethyl-8-chloro-6-fluoro-4-oxo-1,4-dihydroquinoline-3-carboxylate 688 mg of ethyl 7-(tert-butoxycarbonylaminomethyl)-8-chloro-1-[5-(2,4-dimethoxybenzylamino)-4-fluoro-2-(hydroxymethyl)phenyl]-6-fluoro-4-oxo-1,4-dihydroquinoline-3-carboxylate was dissolved in 15 mL of dichloromethane and 0.435 mL of anisole and then 3.0 mL of trifluoroacetic acid were added at room temperature. The mixture was stirred for 40 minutes. 45 mL of a saturated aqueous solution of sodium hydrogen carbonate was added and the mixture was stirred for 20 minutes. The resulting solid was collected by filtration and washed with water. This solid was added to a mixture of 100 mL of chloroform and 100 mL of methanol and the mixture was heated to reflux for 20 minutes. Insoluble matter was filtered off and the filtrate was concentrated under reduced pressure. 10 mL of water was added to the residue and precipitates were collected by filtration to obtain 400 mg of the title compound.

$^1$H NMR (DMSO-d$_6$): δ 1.25 (3H, t, J=7.1 Hz), 3.83 (2H, s), 4.06-4.13 (2H, m), 4.21 (2H, t, J=7.1 Hz), 5.06 (1H, brs), 5.46 (2H, s), 6.76 (1H, d, J=8.1 Hz), 7.15 (1H, d, J=12.0 Hz), 7.9.7 (1H, d, J=9.5 Hz), 8.32 (1H, s).

Example 150

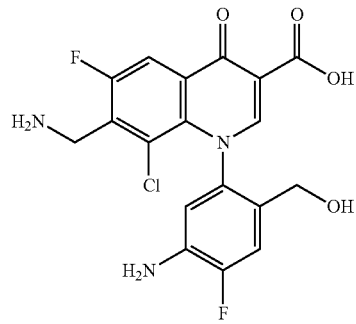 [SMILES: NCc1c(F)cc2c(=O)c(C(=O)O)cn(-c3cc(N)c(F)cc3CO)c2c1Cl]

1-[5-Amino-4-fluoro-2-(hydroxymethyl)phenyl]-7-aminomethyl-8-chloro-6-fluoro-4-oxo-1,4-dihydroquinoline-3-carboxylic acid 7 mL of ethanol and 2.6 mL of a 1 mol/L aqueous solution of sodium hydroxide were added to 400 mg of ethyl 1-[5-amino-4-fluoro-2-(hydroxymethyl)phenyl]-7-aminomethyl-8-chloro-6-fluoro-4-oxo-1,4-dihydroquinoline-3-carboxylate. The mixture was stirred at 60° C. for 2 hours. Ethanol was evaporated under reduced pressure. The residue was adjusted to pH 5 with 1 mol/L hydrochloric acid and precipitates were collected by filtration to obtain 22 mg of the title compound.

$^1$H NMR (DMSO-d$_6$): δ 3.90 (2H, d, J=2.0 Hz), 4.02-4.13 (2H, m), 5.01 (1H, t, J=4.6 Hz), 5.53 (2H, brs), 6.85 (1H d, J=8.1 Hz), 7.17 (1H, d, J=11.8 Hz), 8.14 (1H, d, J=9.0 Hz), 8.53 (1H, s).

Reference Example 56

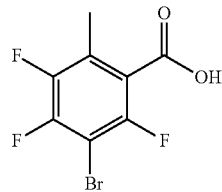

3-Bromo-6-methyl-2,4,5-trifluorobenzoic acid 2.51 g of 2-methyl-3,4,6-trifluorobenzoic acid was dissolved in 15 mL of concentrated sulfuric acid and 3.77 g of 1,3-dibromo-5,5-dimethyl-2,4-imidazolinedione was added. The mixture was stirred at room temperature for 3 days. The reaction solution was added to iced water and the mixture was extracted with diethyl ether. The extract was dried over anhydrous magnesium sulfate and then concentrated. The residue was subjected to silica gel column chromatography (chloroform:methanol=4:1) to obtain 3.0 g of the title compound as a black solid.
$^1$H-NMR (DMSO-d$_6$); δ 2.27 (3H, d, J=2.5 Hz).

Reference Example 57

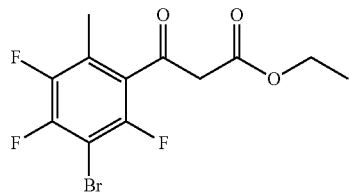 [SMILES: CCOC(=O)CC(=O)c1c(C)c(F)c(F)c(Br)c1F]

Ethyl 2-(3-bromo-6-methyl-2,4,5-trifluorobenzoyl)acetate 3.0 g of 3-bromo-6-methyl-2,4,5-trifluorobenzoic acid was dissolved in 55 mL of methylene chloride and 1.5 mL of oxalyl chloride and 30 µL of N,N-dimethylformamide were added. The mixture was stirred at room temperature for 3 hours. The reaction solution was concentrated and dissolved in 25 mL of tetrahydrofuran. 2.29 g of potassium ethyl malonate was suspended to 55 mL of acetonitrile and 1.49 g of magnesium chloride was added. 3.1 mL of triethylamine was added at 0° C. and the mixture was stirred at 0° C. for 15 minutes and at room temperature for 3.5 hours. The tetrahydrofuran solution prepared earlier was added dropwise to the mixture at 0° C. and the resulting mixture was stirred at room temperature for 18 hours. 2 mol/L hydrochloric acid was added to the reaction solution and extracted with ethyl acetate. The organic layer was washed with water and a saturated aqueous solution of sodium chloride. The extract was dried over anhydrous magnesium sulfate and then concentrated. The residue was subjected to silica gel column chromatography (n-hexane/ethyl acetate=20:1) to obtain 2.03 g of the title compound as a light brown solid.
$^1$H-NMR (CDCl$_3$); δ 1.24 (1.2H, t, J=7.0 Hz), 1.34 (1.8H, t, J=7.0 Hz), 2.30 (1.2H, d, J=2.0 Hz), 2.31 (1.8H, d, J=2.0 Hz), 3.88 (0.8H, s), 4.18 (0.8H, q, J=7.0 Hz), 4.29 (1.2H, q, J=7.0 Hz), 5.25 (0.6H, s), 12.34 (0.6H, s).

Reference Example 58

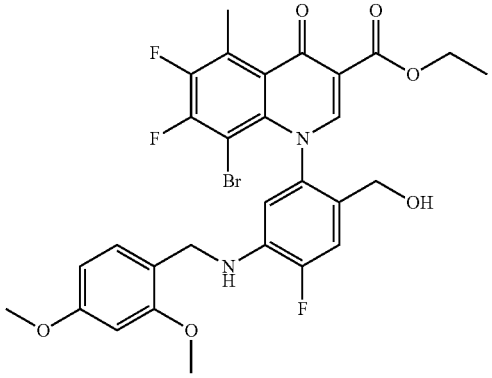 [SMILES: CCOC(=O)c1cn(-c2cc(NCc3ccc(OC)cc3OC)c(F)cc2CO)c2c(Br)c(F)c(F)c(C)c2c1=O]

Ethyl 8-bromo-6,7-difluoro-1-[5-(2,4-dimethoxybenzylamino)-4-fluoro-2-(hydroxymethyl)phenyl]-5-methyl-4-oxo-1,4-dihydroquinoline-3-carboxylate 2.03 g of ethyl 2-(3-bromo-6-methyl-2,4,5-trifluorobenzoyl)acetate was dissolved in 1.7 mL of acetic anhydride and 1.5 mL of triethyl orthoformate. The mixture was stirred at 120° C. for 7 hours. The solvent was evaporated under reduced pressure and then the residue was subjected to azeotropic distillation with toluene. The resulting ethyl 2-(3-bromo-6-methyl-2,4,5-trifluorobenzoyl)-3-ethoxyacrylate (a cis/trans mixture) was dissolved in 10 mL of methylene chloride for use in the following reaction.

2.01 g of methyl 2-amino-4-(2,4-dimethoxybenzyl)amino)-5-fluorobenzoate was suspended in 50 mL of toluene and 15 mL of tetrahydrofuran and 0.26 g of lithium borohydride was added. The mixture was heated to reflux for 1 hour. The reaction solution was added to iced water and the mixture was extracted with ethyl acetate. The extract was dried over anhydrous magnesium sulfate. The anhydrous magnesium sulfate was filtered off and then the methylene chloride solution prepared earlier was added to the filtrate. The mixture was stirred at room temperature for 20 hours. The solvent was evaporated under reduced pressure and the resulting residue was subjected to silica gel column chromatography (hexane:ethyl acetate=4:1) to obtain a yellow amorphous solid.

The resulting amorphous solid was dissolved in 30 mL of N-methylpyrrolidin-2-one and 0.99 mL of 1,8-diazabicyclo[5.4.0]undec-7-ene and 0.51 g of lithium chloride were added at room temperature. The mixture was stirred at 60° C. for 1 hour. The reaction solution was cooled to room temperature and then water was added thereto. Precipitates were collected by filtration. The resulting solid was subjected to silica gel column chromatography (methylene chloride:methanol=50:1) to obtain 1.68 g of the title compound as a yellow powder.
$^1$H-NMR (DMSO-d$_6$); δ 1.24 (3H, t, J=7.0 Hz), 2.71 (3H, t, J=2.0 Hz), 3.63 (3H, s), 3.71 (3H, s), 4.11 (2H, d, J=2.0 Hz), 4.13-4.16 (2H, m), 4.19 (2H, q, J=7.0 Hz), 5.08 (1H, brs), 6.23 (1H, brs), 6.39 (1H, dd, J=8.5 Hz, 2.5 Hz), 6.42 (1H, d, J=2.5 Hz), 6.52 (1H, d, J=8.5 Hz), 7.06 (1H, d, J=8.5 Hz), 7.17 (1H, d, J=12.5 Hz), 8.25 (1H, s).

Reference Example 59

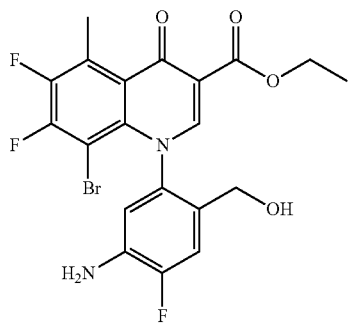 [SMILES: CCOC(=O)c1cn(-c2cc(N)c(F)cc2CO)c2c(Br)c(F)c(F)c(C)c2c1=O]

Ethyl 1-[5-amino-4-fluoro-2-(hydroxymethyl)phenyl]-8-bromo-6,7-difluoro-5-methyl-4-oxo-1,4-dihydroquinoline-3-carboxylate 1.68 g of ethyl 8-bromo-6,7-difluoro-1-[5-(2,4-dimethoxybenzylamino)-4-fluoro-2-(hydroxymethyl)phenyl]-5-methyl-4-oxo-1,4-dihydroquinoline-3-carboxylate was suspended in 25 mL of methylene chloride and 1.2 mL of anisole and 3.5 mL of trifluoroacetic acid were added. The mixture was stirred at room temperature for 20 minutes. A saturated aqueous solution of sodium hydrogen carbonate was added to the reaction solution to make pH of the solution alkaline and then insoluble matter was collected by filtration with water. The resulting crystalline residue was suspended in a chloroform/methanol mixture (1:1) and then the suspension was stirred at 60° C. for 20 minutes. Insoluble matter was filtered off. The filtrate was evaporated under reduced pressure and then the residue was washed with chloroform to obtain 0.8 g the title compound as a colorless powder.

$^1$H-NMR (DMSO-$d_6$); δ 1.24 (3H, t, J=7.0 Hz), 2.72 (3H, d, J=3.0 Hz), 4.12 (2H, t, J=5.0 Hz), 4.20 (2H, q, J=7.0 Hz), 5.09 (1H, t, J=5.0 Hz), 5.45 (2H, s), 6.70 (1H, d, J=8.0 Hz), 7.15 (1H, d, J=12 Hz), 8.30 (1H, s).

Example 151

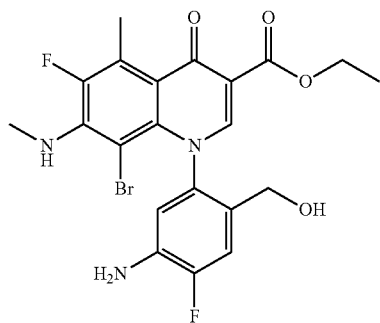 [SMILES: CCOC(=O)c1cn(-c2cc(N)c(F)cc2CO)c2c(Br)c(NC)c(F)c(C)c2c1=O]

Ethyl 1-[5-amino-4-fluoro-2-(hydroxymethyl)phenyl]-8-bromo-6-fluoro-5-methyl-7-(methylamino)-4-oxo-1,4-dihydroquinoline-3-carboxylate 73 mg of ethyl 1-[5-amino-4-fluoro-2-(hydroxymethyl)phenyl]-8-bromo-6,7-difluoro-5-methyl-4-oxo-1,4-dihydroquinoline-3-carboxylate was dissolved in 1 mL of dimethylsulfoxide and 96 μL of N-methylpyrrolidine and 21 mg of methylamine hydrochloride were added. The mixture was stirred at 50° C. for 19 hours. The reaction solution was cooled to room temperature. The resulting precipitates were collected by filtration to obtain 70 mg of the title compound as a colorless powder.

$^1$H-NMR (DMSO-$d_6$); δ 1.23 (3H, t, J=7.0 Hz), 2.65 (3H, d, J=3.0 Hz), 3.04 (3H, dd, J=7.5 Hz, 5.0 Hz), 4.17 (2H, q, J=7.0 Hz), 4.20-4.23 (2H, m), 5.16 (1H, brs), 5.34 (2H, s), 5.84-5.88 (1H, m), 6.46 (1H, d, J=8.0 Hz), 7.15 (1H, d, J=12 Hz), 8.21 (1H, s).

Example 152

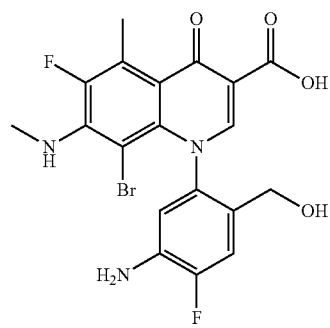 [SMILES: CNc1c(F)c(C)c2c(=O)c(C(=O)O)cn(-c3cc(N)c(F)cc3CO)c2c1Br]

1-[5-Amino-4-fluoro-2-(hydroxymethyl)phenyl]-8-bromo-6-fluoro-5-methyl-7-(methylamino)-4-oxo-1,4-dihydroquinoline-3-carboxylic acid 70 mg of ethyl 1-[5-amino-4-fluoro-2-(hydroxymethyl)phenyl]-8-bromo-6-fluoro-5-methyl-7-(methylamino)-4-oxo-1,4-dihydroquinoline-3-carboxylate was suspended in 2 mL of ethanol and 0.42 mL of a 1 mol/L aqueous solution of sodium hydroxide was added. The mixture was stirred at 50° C. for 1 hour. 0.42 mL of a 1 mol/L aqueous solution of sodium hydroxide was added to the reaction solution and the mixture was further stirred for 20 minutes. 1 mol/L hydrochloric acid was added to the reaction solution and pH was adjusted to approximately 5. The resulting precipitates were collected by filtration with water to obtain 6 mg of the title compound as a light brown powder.

$^1$H-NMR (DMSO-$d_6$); δ 2.74 (3H, d, J=3.5 Hz), 3.11 (3H, dd, J=8.0 Hz, 5.5 Hz), 4.11 (1H, dd, J=13 Hz, 4.5 Hz), 4.15 (1H, dd, J=13 Hz, 4.5 Hz), 5.12 (1H, dd, J=6.0 Hz, 4.5 Hz), 5.43 (2H, s), 6.59 (1H, d, J=8.0 Hz), 7.16 (1H, d, J=12 Hz), 8.45 (1H, s), 15.34 (1H, s).

Example 153

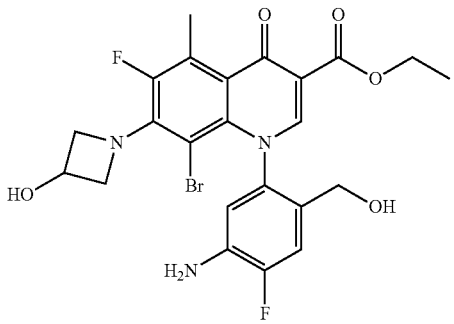 [SMILES: CCOC(=O)c1cn(-c2cc(N)c(F)cc2CO)c2c(Br)c(N3CC(O)C3)c(F)c(C)c2c1=O]

Ethyl 1-[5-amino-4-fluoro-2-(hydroxymethyl)phenyl]-8-bromo-6-fluoro-7-[3-hydroxyazetidin-1-yl]-5-methyl-4-oxo-1,4-dihydroquinoline-3-carboxylate 73 mg of ethyl 1-[5-amino-4-fluoro-2-(hydroxymethyl)phenyl]-8-bromo-6,7-difluoro-5-methyl-4-oxo-1,4-dihydroquinoline-3-carboxylate was dissolved in 1 mL of dimethylsulfoxide and 48 μL of N-methylpyrrolidine and 50 mg of 3-hydroxyazetidine tartrate were added. The mixture was stirred at 50° C. for 19 hours. 48 μL of N-methylpyrrolidine and 50 mg of 3-hydroxyazetidine tartrate were added to the reaction solution and the mixture was further stirred at 50° C. for 9 hours. The reaction solution was cooled to room temperature. The resulting precipitates were collected by filtration to obtain 53 mg of the title compound as a colorless powder.

$^1$H-NMR (DMSO-d$_6$); δ 1.23 (3H, t, J=7.0 Hz), 2.60 (3H, d, J=3.0 Hz), 3.85-3.94 (1H, m), 4.04-4.08 (1H, m), 4.17 (2H, q, J=7.0 Hz), 4.20-4.22 (2H, m), 4.36-4.43 (1H, m), 4.47-4.52 (1H, m), 4.60-4.66 (1H, m), 5.14 (1H, t, J=5.0 Hz), 5.34 (2H, s), 5.64 (1H, d, J=5.5 Hz), 6.51 (1H, d, J=8.0 Hz), 7.15 (1H, d, J=12 Hz), 8.25 (1H, s).

Example 154

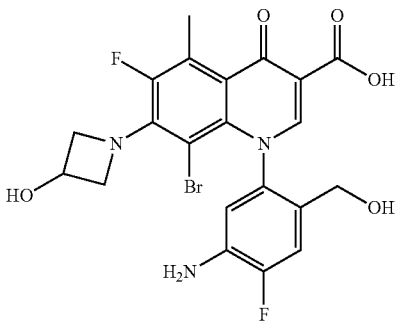 [SMILES: Cc1c(F)c(N2CC(O)C2)c(Br)c2c1c(=O)c(C(=O)O)cn2-c1cc(N)c(F)cc1CO]

1-[5-Amino-4-fluoro-2-(hydroxymethyl)phenyl]-8-bromo-6-fluoro-7-(3-hydroxyazetidin-1-yl)-5-methyl-4-oxo-1,4-dihydroquinoline-3-carboxylic acid 53 mg of ethyl 1-[5-amino-4-fluoro-2-(hydroxymethyl)phenyl]-8-bromo-6-fluoro-7-(3-hydroxyazetidin-1-yl)-5-methyl-4-oxo-1,4-dihydroquinoline-3-carboxylate was suspended in 2.5 mL of ethanol and 0.3 mL of a 1 mol/L aqueous solution of sodium hydroxide was added. The mixture was stirred at 50° C. for 15 minutes. 1 mol/L hydrochloric acid was added to the reaction solution to adjust pH to approximately 5 and the solvent was evaporated under reduced pressure. The resulting precipitates were collected by filtration with water to obtain 51 mg of the title compound as a yellowish-brown powder.

$^1$H-NMR (DMSO-d$_6$); δ 2.69 (3H, brs), 4.02-4.08 (1H, m), 4.09-4.15 (2H, m), 4.17 (1H, dd, J=13 Hz, 4.5 Hz), 4.39-4.45 (1H, m), 4.58-4.64 (1H, m), 4.64-4.70 (1H, m), 5.11 (1H, dd, J=6.0 Hz, 4.5 Hz). 5.42 (2H, s), 5.69 (1H, d, J=5.5 Hz), 6.64 (1H, d, J=8.0 Hz), 7.16 (1H, d, J=12 Hz), 8.47 (1H, s), 15.28 (1H, s).

Example 155

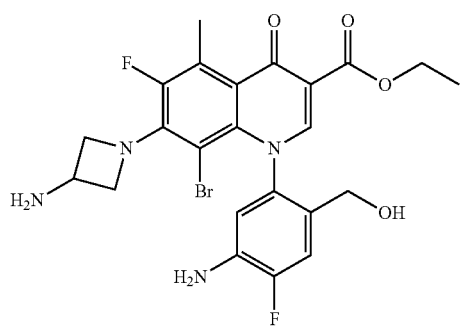 [SMILES: CCOC(=O)c1cn(-c2cc(N)c(F)cc2CO)c2c(Br)c(N3CC(N)C3)c(F)c(C)c2c1=O]

Ethyl 7-(3-aminoazetidin-1-yl)-1-[5-amino-4-fluoro-2-(hydroxymethyl)phenyl]-8-bromo-6-fluoro-5-methyl-4-oxo-1,4-dihydroquinoline-3-carboxylate 73 mg of ethyl 1-[5-amino-4-fluoro-2-(hydroxymethyl)phenyl]-8-bromo-6,7-difluoro-5-methyl-4-oxo-1,4-dihydroquinoline-3-carboxylate was dissolved in 1 mL of dimethylsulfoxide and 48 μL of N-methylpyrrolidine and 33 mg of 3-aminoazetidine hydrochloride were added. The mixture was stirred at 50° C. for 19 hours. 48 μL of N-methylpyrrolidine and 33 mg of 3-aminoazetidine hydrochloride were added to the reaction solution and the mixture was further stirred at 50° C. for 9 hours. The reaction solution was cooled to room temperature and then water was added. The resulting precipitates were collected by filtration with diisopropyl ether to obtain 31 mg of the title compound as a pale yellow powder.

$^1$H-NMR (DMSO-d$_6$); δ 1.23 (3H, t, J=7.0 Hz), 2.60 (3H, d, J=3.0 Hz), 3.59-3.66 (1H, m), 3.75-3.80 (1H, m), 3.87-3.92 (1H, m), 4.14-4.23 (4H, m), 4.45-4.51 (1H, m), 4.56-4.62 (1H, m), 5.13 (1H, t, J=5.0 Hz), 5.34 (2H, s), 6.51 (1H, d, J=8.0 Hz), 7.15 (1H, d, J=12 Hz), 8.23 (1H, s).

Example 156

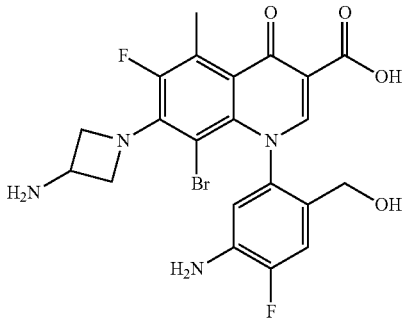 [SMILES: Cc1c(F)c(N2CC(N)C2)c(Br)c2c1c(=O)c(C(=O)O)cn2-c1cc(N)c(F)cc1CO]

7-(3-Aminoazetidin-1-yl)-1-[5-amino-4-fluoro-2-(hydroxymethyl)phenyl]-8-bromo-6-fluoro-5-methyl-4-oxo-1,4-dihydroquinoline-3-carboxylic acid 31 mg of ethyl 7-(3-aminoazetidin-1-yl)-1-[5-amino-4-fluoro-2-(hydroxymethyl)phenyl]-8-bromo-6-fluoro-5-methyl-4-oxo-1,4-dihydroquinoline-3-carboxylate was suspended in 2 mL of ethanol and 0.18 mL of a 1 mol/L aqueous solution of sodium hydroxide was added. The mixture was stirred at 50° C. for 15 minutes. 1 mol/L hydrochloric acid was added to the reaction solution to adjust pH to approximately 5 and the solvent was evaporated under reduced pressure. The resulting precipitates were collected by filtration with water to obtain 51 mg of the title compound as a light brown powder.

$^1$H-NMR (DMSO-$d_6$); δ 2.70 (3H, d, J=3.0 Hz), 3.63-3.69 (1H, m), 3.90-3.98 (2H, m), 4.09 (1H, dd, J=8.0 Hz, 6.0 Hz), 4.16 (1H, dd, J=13 Hz, 4.5 Hz), 4.56-4.66 (2H, m), 5.09 (1H, dd, J=6.0 Hz, 4.5 Hz), 5.43 (2H, s), 6.65 (1H, d, J=8.0 Hz), 7.16 (1H, d, J=12 Hz), 8.47 (1H, s).

Example 157

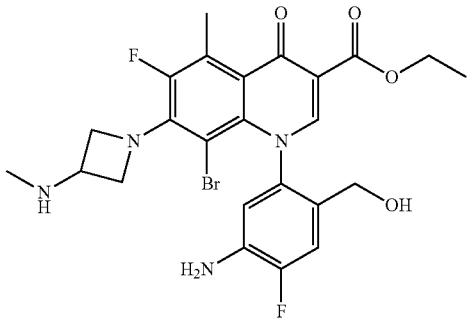 [SMILES: CCOC(=O)c1cn(-c2cc(N)c(F)cc2CO)c2c(Br)c(N3CC(NC)C3)c(F)c(C)c2c1=O]

Ethyl 1-[5-amino-4-fluoro-2-(hydroxymethyl)phenyl]-8-bromo-6-fluoro-5-methyl-7-(3-methylaminoazetidin-1-yl)-4-oxo-1,4-dihydroquinoline-3-carboxylate 73 mg of ethyl 1-[5-amino-4-fluoro-2-(hydroxymethyl)phenyl]-8-bromo-6,7-difluoro-5-methyl-4-oxo-1,4-dihydroquinoline-3-carboxylate was dissolved in 1 mL of dimethylsulfoxide and 48 μL of N-methylpyrrolidine and 37 mg of 3-methylaminoazetidine hydrochloride were added. The mixture was stirred at 50° C. for 6 hours. 48 L of N-methylpyrrolidine and 37 mg of 3-methylaminoazetidine hydrochloride were added to the reaction solution and the mixture was further stirred at 50° C. for 3 hours. The reaction solution was cooled to room temperature and then water was added. The resulting precipitates were collected by filtration with diisopropyl ether to obtain 55 mg of the title compound as a pale yellow powder.

$^1$H-NMR (DMSO-$d_6$); δ 1.23 (3H, t, J=7.0 Hz), 2.19 (3H, s), 2.60 (3H, d, J=3.5 Hz), 3.85-3.90 (1H, m), 3.98-4.03 (1H, m), 4.14-4.24 (4H, m), 4.39-4.44 (1H, m), 4.52-4.57 (1H, m), 5.14 (1H, dd, J=5.5 Hz, 5.0 Hz), 5.34 (2H, s), 6.51 (1H, d, J=8.0 Hz), 7.15 (1H, d, J=12 Hz), 8.24 (1H, s).

Example 158

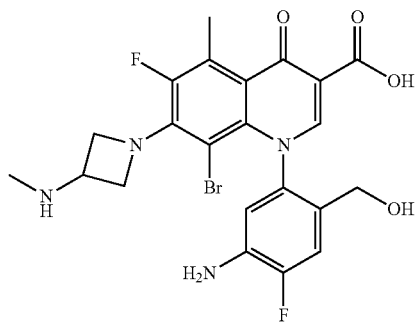 [SMILES: CNC1CN(c2c(F)c(C)c3c(=O)c(C(=O)O)cn(-c4cc(N)c(F)cc4CO)c3c2Br)C1]

1-[5-Amino-4-fluoro-2-(hydroxymethyl)phenyl]-8-bromo-6-fluoro-5-methyl-7-(3-methylaminoazetidin-1-yl)-4-oxo-1,4-dihydroquinoline-3-carboxylic acid 54 mg of ethyl 1-[5-amino-4-fluoro-2-(hydroxymethyl)phenyl]-8-bromo-6-fluoro-5-methyl-7-(3-methylaminoazetidin-1-yl)-4-oxo-1,4-dihydroquinoline-3-carboxylate was suspended in 2 mL of ethanol and 0.3 mL of a 1 mol/L aqueous solution of sodium hydroxide was added. The mixture was stirred at 50° C. for 30 minutes. 0.15 mL of a 1 mol/L aqueous solution of sodium hydroxide was added to the reaction solution and the mixture was further stirred for 30 minutes. 1 mol/L hydrochloric acid was added to the reaction solution to adjust pH to approximately 5 and the solvent was evaporated under reduced pressure. The resulting precipitates were collected by filtration with water to obtain 39 mg of the title compound as a light brown powder.

$^1$H-NMR (DMSO-$d_6$); δ 2.20 (3H, s), 2.70 (3H, d, J=3.0 Hz), 3.99-4.04 (1H, m), 4.04-4.13 (2H, m), 4.17 (1H, dd, J=13 Hz, 4.5 Hz), 4.50-4.56 (1H, m), 4.56-4.62 (1H, m), 5.10 (1H, dd, J=6.0 Hz, 4.5 Hz), 5.43 (2H, s), 6.65 (1H, d, J=8.0 Hz), 7.16 (1H, d, J=12 Hz), 8.47 (1H, s).

Reference Example 60

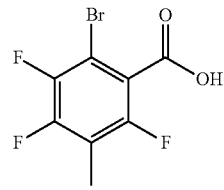

2-Bromo-5-methyl-3,4,6-trifluorobenzoic acid 24 mL of anhydrous tetrahydrofuran was added to 4.8 mL of diisopropylamine and the mixture was stirred in a nitrogen atmosphere at −78° C. 22 mL of a 1.6 mol/L n-butyllithium solution in n-hexane was added dropwise to the mixture over 45 minutes at −78° C. and the mixture was stirred at the same temperature for 10 minutes. A solution of 3-bromo-2,4,5-trifluorobenzoic acid (4.1 g) in 24 mL of anhydrous tetrahydrofuran was added dropwise to the reaction solution over 20 minutes at −78° C. and the mixture was stirred at the same temperature for 45 minutes. 1.5 mL of iodomethane was added to the reaction solution and the mixture was stirred at room temperature for 3 hours. 100 mL of 1 mol/L hydrochloric acid was added to the reaction solution to adjust pH to approximately 5 and then the mixture was extracted three times with 100 mL of ethyl acetate. The extract was washed with 100 mL of 1 mol/L hydrochloric acid and 100 mL of saturated brine and then dried over anhydrous sodium sulfate. The anhydrous sodium sulfate was filtered off and then the solvent was evaporated under reduced pressure. The resulting crystalline residue was collected by filtration with toluene to obtain 2.1 g of the title compound as a light brown solid.

$^1$H-NMR (DMSO-$d_6$); δ 2.19 (3H, t, J=1.9 Hz).

Reference Example 61

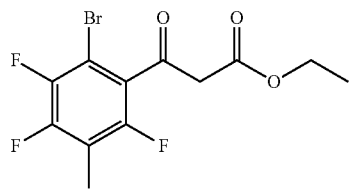 [SMILES: CCOC(=O)CC(=O)c1c(F)c(C)c(F)c(F)c1Br]

Ethyl 2-(2-bromo-5-methyl-3,4,6-trifluorobenzoyl)acetate 2.94 g of 2-bromo-5-methyl-3,4,6-trifluorobenzoic acid was dissolved in 55 mL of methylene chloride and 1.4 mL of oxalyl chloride and 31 μL of N,N-dimethylformamide were added. The reaction solution was concentrated and dissolved in 24 mL of tetrahydrofuran. 2.23 g of potassium ethyl malonate was suspended in 55 mL of acetonitrile and 1.45 g of magnesium chloride was added. 3 mL of triethylamine was added at 0° C. and the mixture was stirred at room temperature for 4 hours. The tetrahydrofuran solution prepared earlier was added dropwise to the mixture at 0° C. and the resulting mixture was stirred at room temperature for 19 hours. 2 mol/L hydrochloric acid was added to the reaction solution and the mixture was extracted with ethyl acetate. The organic layer was washed with water and a saturated aqueous solution of sodium chloride, and then dried over anhydrous magnesium sulfate and concentrated. The residue was subjected to silica gel column chromatography (hexane/ethyl acetate=20:1) to obtain 2.71 g of the title compound as a light brown oily substance.

$^1$H-NMR (CDCl$_3$); δ 1.25 (1.5H, t, J=7.0 Hz), 1.34 (1.5H, t, J=7.0 Hz), 2.23 (1.5H, d, J=2.0 Hz), 2.24 (1.5H, d, J=2.0 Hz), 3.89 (1H, d, J=1.5 Hz), 4.19 (1H, q, J=7.0 Hz), 4.29 (1H, q, J=7.0 Hz), 5.25 (0.5H, s), 12.26 (0.5H, s).

Reference Example 62

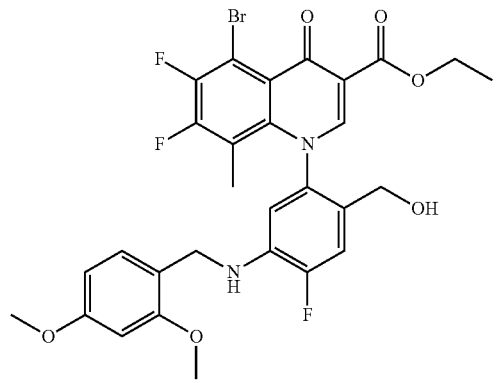 [SMILES: CCOC(=O)c1cn(-c2cc(NCc3ccc(OC)cc3OC)c(F)cc2CO)c2c(C)c(F)c(F)c(Br)c2c1=O]

Ethyl 5-bromo-6,7-difluoro-1-[5-(2,4-dimethoxybenzylamino)-4-fluoro-2-(hydroxymethyl)phenyl]-8-methyl-4-oxo-1,4-dihydroquinoline-3-carboxylate 2.3 mL of acetic anhydride and 2 mL of triethyl orthoformate were added to 2.71 g of ethyl 2-(2-bromo-5-methyl-3,4,6-trifluorobenzoyl)acetate and the mixture was stirred at 120° C. for 5.5 hours. The reaction solution was concentrated and was subjected to azeotropic distillation with toluene three times to obtain ethyl 2-(2-bromo-5-methyl-3,4,6-trifluorobenzoyl)-3-ethoxyacrylate as a brown oily substance.

2.67 g of ethyl 2-amino-4-(2,4-dimethoxybenzylamino)-5-fluorobenzoate was suspended in 20 mL of tetrahydrofuran and 80 mL of toluene and 0.35 g of lithium borohydride was added. The mixture was refluxed for 5 hours. 0.17 g of lithium borohydride was added and further refluxed for 1 hour. The reaction solution was added to iced water and the mixture was extracted with ethyl acetate. The extract was dried over anhydrous magnesium sulfate. 8 mL of the earlier-prepared methylene chloride solution of ethyl 2-(2-bromo-5-methyl-3,4,6-trifluorobenzoyl)-3-ethoxyacrylate was added to the filtrate and the mixture was stirred at room temperature for 40 hours. The reaction solution was concentrated and the residue was subjected to silica gel column chromatography (hexane:ethyl acetate=3:1) to obtain a yellow amorphous solid.

The resulting amorphous was dissolved in 40 mL of N-methyl-2-pyrrolidone and 0.68 g of lithium chloride and 1.32 mL of 1,8-diazabicyclo[5.4.0]undec-7-ene were added. The mixture was stirred at 60° C. for two hours. The reaction solution was added to water and precipitates were collected by filtration. The resulting precipitates were subjected to silica gel column chromatography (methylene chloride:methanol=25:1) to obtain 1.95 g of the title compound as a colorless powder.

$^1$H-NMR (DMSO-$d_6$); δ 1.24 (3H, t, J=7.0 Hz), 1.39 (3H, d, J=2.5 Hz), 3.60 (3H, s), 3.72 (3H, s), 4.13-4.22 (6H, m), 5.10 (1H, t, J=5.0 Hz), 6.36 (1H, t, J=5.0 Hz), 6.39-6.43 (2H, m), 6.60 (1H, d, J=8.0 Hz), 7.06 (1H, d, J=9.0 Hz), 7.20 (1H, d, J=12.5 Hz), 8.22 (1H, s).

Reference Example 63

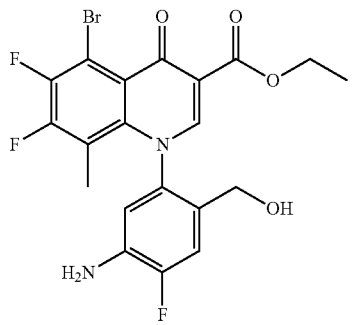 [SMILES: CCOC(=O)c1cn(-c2cc(N)c(F)cc2CO)c2c(C)c(F)c(F)c(Br)c2c1=O]

Ethyl 1-[5-amino-4-fluoro-2-(hydroxymethyl)phenyl]-5-bromo-6,7-difluoro-8-methyl-4-oxo-1,4-dihydroquinoline-3-carboxylate 1.94 g of ethyl 5-bromo-6,7-difluoro-1-[5-(2,4-dimethoxybenzylamino)-4-fluoro-2-(hydroxymethyl)phenyl]-8-methyl-4-oxo-1,4-dihydroquinoline-3-carboxylate was suspended in 25 mL of methylene chloride and 1.4 mL of anisole and 4 mL of trifluoroacetic acid were added. The mixture was stirred at room temperature for 20 minutes. A saturated aqueous solution of sodium hydrogen carbonate was added to the reaction solution and precipitates were collected by filtration. A chloroform/methanol mixture (1:1) was added to the resulting precipitates and the mixture was stirred at 60° C. for 20 minutes and hot-filtered. The filtrate was concentrated and washed with chloroform to obtain 1.16 g of the title compound as a colorless powder.

$^1$H-NMR (DMSO-$d_6$); δ 1.25 (3H, t, J=7.0 Hz), 1.68 (3H, d, J=3.0 Hz), 4.07 (1H, dd, J=13 Hz, 5.0 Hz), 4.11 (1H, dd, J=13 Hz, 5.0 Hz), 4.21 (2H, q, J=7.0 Hz), 5.07 (1H, t, J=5.0 Hz), 5.55 (2H, s), 6.83 (1H, d, J=8.0 Hz), 7.18 (1H, d, J=12 Hz), 8.26 (1H, s).

Example 159

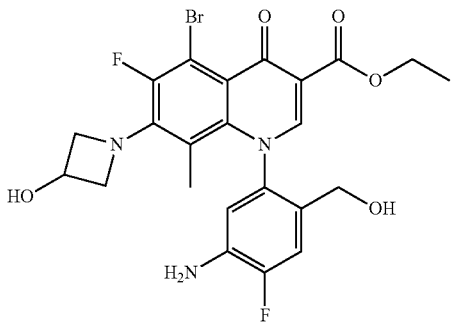 [SMILES: CCOC(=O)c1cn(-c2cc(N)c(F)cc2CO)c2c(C)c(N3CC(O)C3)c(F)c(Br)c2c1=O]

Ethyl 1-[5-amino-4-fluoro-2-(hydroxymethyl)phenyl]-5-bromo-6-fluoro-7-[3-hydroxyazetidin-1-yl]-8-methyl-4-oxo-1,4-dihydroquinoline-3-carboxylate 0.1 g of ethyl 1-[5-amino-4-fluoro-2-(hydroxymethyl)phenyl]-5-bromo-6,7-difluoro-8-methyl-4-oxo-1,4-dihydroquinoline-3-carboxylate, 70 mg of 3-hydroxyazetidine tartrate, and 67 μL of N-methylpyrrolidine were added to 2 mL of dimethylsulfoxide and the mixture was stirred at 50° C. for 1 day and at 70° C. for 3.5 hours. 70 mg of 3-hydroxyazetidine tartrate and 67 μL of N-methylpyrrolidine were added and the mixture was further stirred at 70° C. for 4 days. 140 mg of 3-hydroxyazetidine tartrate and 155 μL of N-methylpyrrolidine were added and the mixture was further stirred at 70° C. for 16 hours. Water was added to the reaction solution and the mixture was extracted with ethyl acetate. The resulting extract was dried over anhydrous magnesium sulfate and then concentrated. The residue was subjected to silica gel column chromatography (chloroform:methanol=50:1 to 10:1) to obtain 43 mg of the title compound as a brown powder.

$^1$H-NMR (DMSO-$d_6$); δ 1.24 (3H, t, J=7.0 Hz), 1.45 (3H, s), 3.79-3.85 (1H, m), 4.02-4.14 (2H, m), 4.34-4.40 (2H, m), 4.40-4.45 (1H, m), 5.12 (1H, brs), 5.46 (2H, s), 5.63 (1H, d, J=5.5 Hz), 6.76 (1H, d, J=8.0 Hz), 7.15 (1H, d, J=12 Hz), 8.24 (1H, s).

Example 160

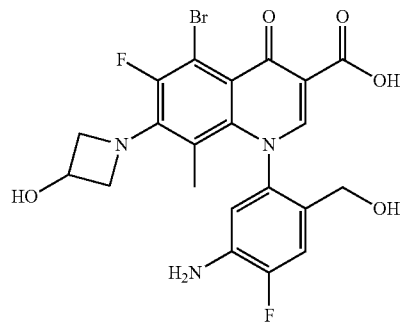

1-[5-Amino-4-fluoro-2-(hydroxymethyl)phenyl]-5-bromo-6-fluoro-7-(3-hydroxyazetidin-1-yl)-8-methyl-4-oxo-1,4-dihydroquinoline-3-carboxylic acid 43 mg of ethyl 1-[5-amino-4-fluoro-2-(hydroxymethyl)phenyl]-5-bromo-6-fluoro-7-(3-hydroxyazetidin-1-yl)-8-methyl-4-oxo-1,4-dihydroquinoline-3-carboxylate was suspended in 2 mL of ethanol and 80 μL of a 1 mol/L aqueous solution of sodium hydroxide was added. The mixture was stirred at 50° C. for 1 hour. 160 μL of a 1 mol/L aqueous solution of sodium hydroxide was added and the mixture was stirred at 50° C. for 30 minutes. 120 μL of 2 mol/L hydrochloric acid and water were added to the reaction solution and the mixture was concentrated. Precipitates were collected by filtration and washed with water to obtain 20 mg of the title compound as a brown powder.

$^1$H-NMR (DMSO-$d_6$); δ 1.52 (3H, s), 3.88-3.93 (1H, m), 3.93-4.02 (2H, m), 4.08 (1H, dd, J=13 Hz, 5.0 Hz), 4.41-4.49 (3H, m), 5.06 (1H, t, J=5.0 Hz), 5.53 (2H, s), 5.68 (1H, d, J=4.0 Hz), 6.87 (1H, d, J=8.5 Hz), 7.17 (1H, d, J=12 Hz), 8.46 (1H, s), 15.20 (1H, s).

Reference Example 64

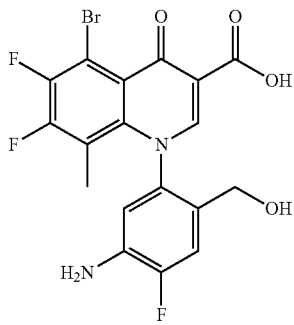 [SMILES: Cc1c(F)c(F)c(Br)c2c(=O)c(C(=O)O)cn(-c3cc(N)c(F)cc3CO)c12]

1-[5-Amino-4-fluoro-2-(hydroxymethyl)phenyl]-5-bromo-6,7-difluoro-8-methyl-4-oxo-1,4-dihydroquinoline-3-carboxylic acid 0.1 g of ethyl 1-[5-amino-4-fluoro-2-(hydroxymethyl)phenyl]-5-bromo-6,7-difluoro-8-methyl-4-oxo-1,4-dihydroquinoline-3-carboxylate was suspended in 5 mL of ethanol and 0.63 mL of a 1 mol/L aqueous solution of sodium hydroxide was added. The mixture was stirred at 50° C. for 30 minutes. 2 mol/L hydrochloric acid was added to the reaction solution to make the solution acidic. Precipitates were collected by filtration and washed with water to obtain 81 mg of the title compound as a pale yellow powder.

$^1$H-NMR (DMSO-$d_6$); δ 1.74 (3H, d, J=2.5 Hz), 4.05 (1H, dd, J=13 Hz, 5.0 Hz), 4.10 (1H, dd, J=13 Hz, 5.0 Hz), 5.04 (1H, t, J=5.0 Hz), 5.63 (2H, s), 6.90 (1H, d, J=8.5 Hz), 7.20 (1H, d, J=12 Hz), 8.52 (1H, s), 14.53 (1H, s).

Reference Example 65

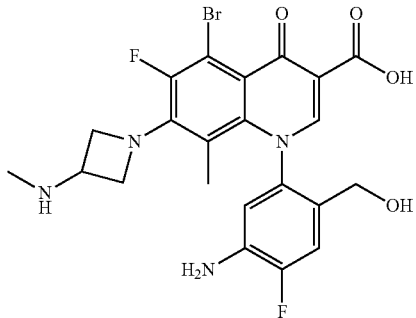 [SMILES: CNC1CN(c2c(F)c(Br)c3c(=O)c(C(=O)O)cn(-c4cc(N)c(F)cc4CO)c3c2C)C1]

1-[5-Amino-4-fluoro-2-(hydroxymethyl)phenyl]-5-bromo-6-fluoro-8-methyl-7-(3-methylaminoazetidin-1-yl)-4-oxo-1,4-dihydroquinoline-3-carboxylic acid 81 mg of 1-[5-amino-4-fluoro-2-(hydroxymethyl)phenyl]-5-bromo-6,7-difluoro-8-methyl-4-oxo-1,4-dihydroquinoline-3-carboxylic acid, 29 mg of 3-methylaminoazetidine dihydrochioride, 90 μL of 1,1,3,3-tetramethylguanidine, and 61 mg of lithium chloride were added to 1 mL of dimethylsulfoxide and the mixture was stirred at 50° C. for 31 hours. Diethyl ether was added to the reaction solution and the upper layer was removed. Water was added and pH was adjusted to approximately 4 with a 5% aqueous solution of citric acid. Precipitates were collected by filtration. The resulting precipitates were washed with diisopropyl ether and chloroform to obtain 65 mg of the title compound as a colorless powder.

$^1$H-NMR (DMSO-$d_6$); δ 1.53 (3H, s), 2.21 (3H, s), 3.42-3.49 (1H, m), 3.82-3.87 (1H, m), 3.92-3.99 (2H, m), 4.07 (1H, dd, J=13 Hz, 5.0 Hz), 4.34-4.42 (2H, m), 5.04 (1H, t, J=5.0 Hz), 5.54 (2H, s), 6.89 (1H, d, J=8.0 Hz), 7.17 (1H, d, J=12 Hz), 8.45 (1H, s).

Reference Example 66

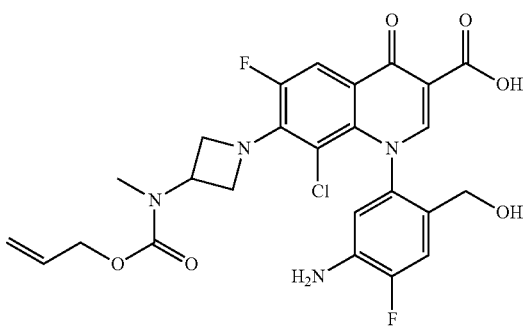

7-[3-(N-allyloxycarbonyl-N-methylamino)azetidin-1-yl]-1-[5-amino-4-fluoro-2-(hydroxymethyl)phenyl]-8-chloro-6-fluoro-4-oxo-1,4-dihydroquinoline-3-carboxylic acid 5 mL of N,N-dimethylformamide and 0.35 mL of diisopropylethylamine were added to 460 mg of 1-[5-amino-4-fluoro-2-(hydroxymethyl)phenyl]-8-chloro-6-fluoro-7-[3-methylaminoazetidin-1-yl]-4-oxo-1,4-dihydroquinoline-3-carboxylic acid and the mixture was stirred at room temperature for 15 minutes. 2 mL of an N,N-dimethylformamide solution of 0.11 mL allyl chloroformate was added to the mixture and the resulting mixture was stirred at room temperature for 2 hours. 20 mL of a 1% aqueous solution of acetic acid was added to the reaction solution and the mixture was extracted three times with 20 mL of ethyl acetate. The extract was washed six times with 50 mL of water, with 50 mL of a 1% aqueous solution of acetic acid, and with 50 mL of saturated brine and then dried over anhydrous sodium sulfate. The anhydrous sodium sulfate was filtered off and then the solvent was evaporated under reduced pressure to obtain 440 mg of the title compound as a pale yellow solid.

$^1$H-NMR (DMSO-$d_6$); δ 2.94 (3H, s), 4.02-4.12 (2H, m), 4.45-4.54 (4H, m), 4.62-4.70 (2H, m), 4.73-4.83 (1H, m), 5.03 (1H, t, J=4.8 Hz), 5.17 (1H, d, J=10.6 Hz), 5.25 (1H, d, J=17.4 Hz), 5.50 (2H, brs), 5.85-5.96 (1H, m), 6.78 (1H, d, J=8.2 Hz), 7.13 (1H, d, J=12.0 Hz), 7.89 (1H, d, J=13.8 Hz), 8.38 (1H, s).

Reference Example 67

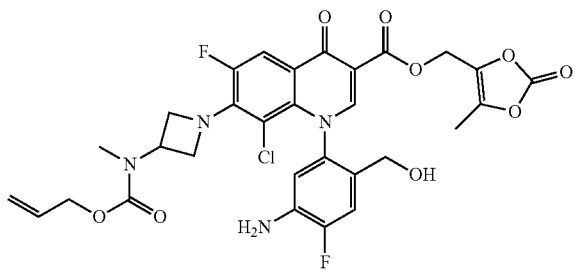 [SMILES: C=CCOC(=O)N(C)C1CN(c2c(F)cc3c(=O)c(C(=O)OCc4oc(=O)oc4C)cn(-c4cc(N)c(F)cc4CO)c3c2Cl)C1]

7-[3-(N-Allyloxycarbonyl-N-methyl)aminoazetidin-1-yl]-1-[5-amino-4-fluoro-2-(hydroxymethyl)phenyl]-8-chloro-6-fluoro-4-oxo-1,4-dihydroquinoline-3-carboxylic acid (5-methyl-2-oxo-1,3-dioxol-4-yl)methyl ester 5 mL of N,N-dimethylformamide and 110 mg of potassium carbonate were added to 220 mg of 7-[3-(N-allyloxycarbonyl-N-methylamino)azetidin-1-yl]-1-[5-amino-4-fluoro-2-(hydroxymethyl)phenyl]-8-chloro-6-fluoro-4-oxo-1,4-dihydroquinoline-3-carboxylic acid and the mixture was stirred at 40° C. for 15 minutes. 66 mg of potassium iodide and 70 mg of 4-chloromethyl-5-methyl-1,3-dioxol-2-one were added to the mixture and the resulting mixture was stirred at 40° C. overnight. The mixture was cooled and then 50 mL of water was added to the reaction solution. Precipitates were collected by filtration. The resulting solid was subjected to silica gel column chromatography (methanol:methylene chloride=0:100 to 7:93 gradient) to obtain 150 mg of the title compound as a pale yellow solid.

$^1$H-NMR (DMSO-$d_6$); δ 2.18 (3H, s), 2.93 (3H, s), 4.05-4.15 (2H, m), 4.34-4.41 (2H, m), 4.49-4.53 (2H, m), 4.55-4.62 (2H, m), 4.70-4.78 (1H, m), 5.081-5.087 (3H, m), 5.16 (1H, d, J=10.6 Hz), 5.25 (1H, d, J=18.2 Hz), 5.44 (2H, brs), 5.84-5.95 (1H, m), 6.71 (1H, d, J=8.1 Hz), 7.12 (1H, d, J=12.0 Hz), 7.76 (1H, d, J=14.1 Hz), 8.23 (1H, s).

Example 161

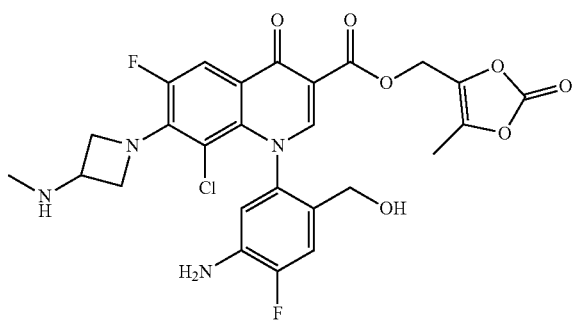 [SMILES: CNC1CN(c2c(F)cc3c(=O)c(C(=O)OCc4oc(=O)oc4C)cn(-c4cc(N)c(F)cc4CO)c3c2Cl)C1]

1-[5-Amino-4-fluoro-2-(hydroxymethyl)phenyl]-8-chloro-6-fluoro-7-(3-methylaminoazetidin-1-yl)-4-oxo-1,4-dihydroquinoline-3-carboxylic acid (5-methyl-2-oxo-1,3-dioxol-4-yl)methyl ester 60 mg of 7-[3-(N-allyloxycarbonyl-N-methylamino)azetidin-1-yl]-1-[5-amino-4-fluoro-2-(hydroxymethyl)phenyl]-8-chloro-6-fluoro-4-oxo-1,4-dihydroquinoline-3-carboxylic acid (5-methyl-2-oxo-1,3-dioxol-4-yl)methyl ester and 42 mg of 1,3-dimethylbarbituric acid were added to 2 mL of methylene chloride. 2 mg of tetrakis(triphenylphosphine) palladium (0) was added to the mixture and the resulting mixture was stirred in a nitrogen atmosphere at 35° C. for 8 hours. Precipitates were collected by filtration, washed with methylene chloride, and then suspend in 30 mL of ethyl acetate. The suspension was washed five times with 20 mL of a saturated aqueous solution of sodium hydrogen carbonate and 30 mL of saturated brine and then dried over anhydrous sodium sulfate. The anhydrous sodium Sulfate was filtered off and then the solvent was evaporated under reduced pressure to obtain 31 mg of the title compound as a white solid.

$^1$H-NMR (DMSO-$d_6$); δ 2.18 (6H, s), 3.37-3.42 (1H, m), 3.97-4.03 (2H, m), 4.06 (1H, dd, J=6.6 Hz, 13.5 Hz), 4.11 (1H, dd, J=4.9 Hz, 13.3 Hz), 4.48-4.55 (2H, m), 5.06-5.09 (3H, m), 5.44 (2H, brs), 6.69 (1H, d, J=8.2 Hz), 7.12 (1H, d, J=12.0 Hz), 7.73 (1H, d, J=14.2 Hz), 8.23 (1H, s).

Reference Example 68

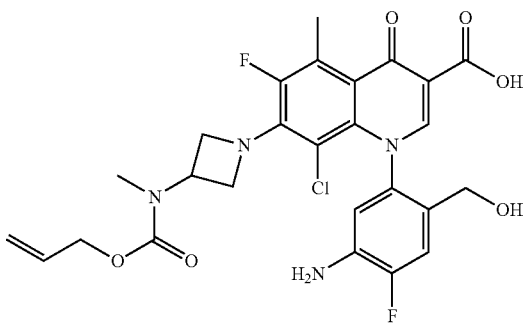 [SMILES: C=CCOC(=O)N(C)C1CN(c2c(F)c(C)c3c(=O)c(C(=O)O)cn(-c4cc(N)c(F)cc4CO)c3c2Cl)C1]

7-[3-(N-allyloxycarbonyl-N-methylamino)azetidin-1-yl]-1-[5-amino-4-fluoro-2-(hydroxymethyl)phenyl]-8-chloro-6-fluoro-5-methyl-4-oxo-1,4-dihydroquinoline-3-carboxylic acid 2 mL of N,N-dimethylformamide and 0.18 mL of diisopropylethylamine were added to 240 mg of 1-[5-amino-4-fluoro-2-(hydroxymethyl)phenyl]-8-chloro-6-fluoro-5-methyl-7-(3-methylaminoazetidin-1-yl)-4-oxo-1,4-dihydroquinoline-3-carboxylic acid and the mixture was stirred at room temperature for 15 minutes. 2 mL of an N,N-dimethylformamide solution of 0.053 mL of allyl chloroformate was added to the mixture and the resulting mixture was stirred at room temperature for 3 hours. 20 mL of a 1% aqueous solution of acetic acid was added to the reaction solution and the mixture was extracted three times with 10 mL of ethyl acetate. The extract was washed five times with 30 mL of water and with 50 mL of saturated brine and then dried over anhydrous sodium sulfate. The anhydrous sodium sulfate was filtered off and then the solvent was evaporated under reduced pressure to obtain 200 mg of the title compound as a pale yellow solid.

$^1$H-NMR (DMSO-$d_6$); δ 2.71 (3H, d, J=3.3 Hz), 2.93 (3H, s), 4.03-4.14 (2H, m), 4.37-4.54 (4H, m), 4.56-4.68 (2H, m), 4.70-4.80 (1H, m), 5.05 (1H, t, J=4.9 Hz), 5.17 (1H, d, J=10.6 Hz), 5.25 (1H, d, J=16.9 Hz), 5.45 (2H, brs), 5.83-5.96 (1H, m), 6.70 (1H, d, J=8.1 Hz), 7.12 (1H, d, J=11.9 Hz), 8.38 (1H, s).

Reference Example 69

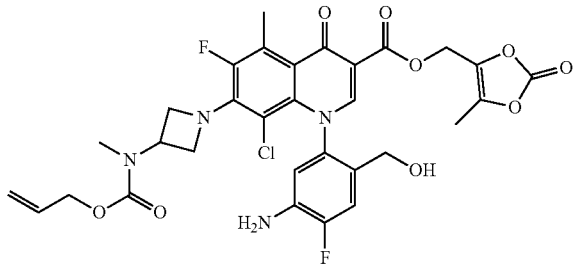 [SMILES: C=CCOC(=O)N(C)C1CN(c2c(F)c(C)c3c(=O)c(C(=O)OCc4oc(=O)oc4C)cn(-c4cc(N)c(F)cc4CO)c3c2Cl)C1]

7-[3-(N-allyloxycarbonyl-N-methylamino)azetidin-1-yl]-1-[5-amino-4-fluoro-2-(hydroxymethyl)phenyl]-8-chloro-6-fluoro-5-methyl-4-oxo-1,4-dihydroquinoline-3-carboxylic acid (5-methyl-2-oxo-1,3-dioxol-4-yl)methyl ester 1 mL of N,N-dimethylformamide and 25 mg of potassium carbonate were added to 100 mg of 7-[3-(N-allyloxycarbonyl-N-methylamino)azetidin-1-yl]-1-[5-amino-4-fluoro-2-(hydroxymethyl)phenyl]-8-chloro-6-fluoro-5-methyl-4-oxo-1,4-dihydroquinoline-3-carboxylic acid and the mixture was stirred at 45° C. for 15 minutes. 15 mg of potassium iodide and 27 mg of 4-chloromethyl-5-methyl-1,3-dioxol-2-one were added to the mixture and the resulting mixture was stirred at 45° C. overnight. The mixture was cooled and then 20 mL of water was added to the reaction solution and the mixture was extracted four times with 20 mL of ethyl acetate. The extract was washed with 50 mL of saturated brine and then dried over anhydrous sodium sulfate. The anhydrous sodium sulfate was filtered off and then the solvent was evaporated under reduced pressure. The residue was subjected to silica gel column chromatography (methanol:chloroform=0 to 5% gradient) to obtain 62 mg of the title compound.

$^1$H-NMR (DMSO-d$_6$); δ 2.17 (3H, s), 2.62 (3H, d, J=3.4 Hz), 2.92 (3H, s), 4.11-4.15 (2H, m), 4.26-4.39 (2H, m), 4.46-4.60 (4H, m), 4.68-4.77 (1H, m), 5.06 (2H, s), 5.08 (1H, t, J=5.1 Hz), 5.16 (1H, d, J=10.6 Hz), 5.25 (1H, d, J=16.1 Hz), 5.38 (2H, brs), 5.85-5.95 (1H, m), 6.60 (1H, d, J=8.1 Hz), 7.11 (1H, d, J=12.0 Hz), 8.20 (1H, s).

Example 162

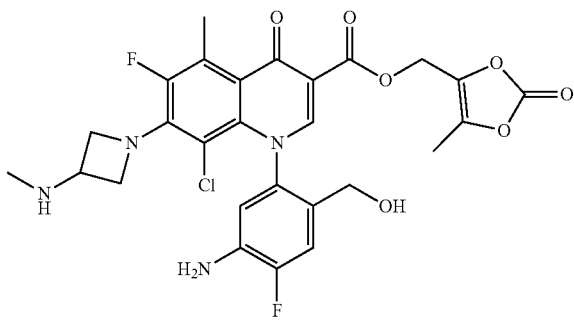 [SMILES: CNC1CN(c2c(F)c(C)c3c(=O)c(C(=O)OCc4oc(=O)oc4C)cn(-c4cc(N)c(F)cc4CO)c3c2Cl)C1]

1-[5-Amino-4-fluoro-2-(hydroxymethyl)phenyl]-8-chloro-6-fluoro-5-methyl-7-(3-methylaminoazetidin-1-yl)-4-oxo-1,4-dihydroquinoline-3-carboxylic acid (5-methyl-2-oxo-1,3-dioxol-4-yl)methyl ester 38 mg of 7-[3-(N-allyloxycarbonyl-N-methylamino)azetidin-1-yl]-1-[5-amino-4-fluoro-2-(hydroxymethyl)phenyl]-8-chloro-6-fluoro-5-methyl-4-oxo-1,4-dihydroquinoline-3-carboxylic acid (5-methyl-2-oxo-1,3-dioxol-4-yl)methyl ester and 25 mg of 1,3-dimethylbarbituric acid were added to 2 mL of methylene chloride. 1 mg of tetrakis(triphenylphosphine)palladium (0) was added to the mixture and the resulting mixture was stirred in a nitrogen atmosphere at room temperature for 2 hours. Precipitates were collected by filtration, washed with methylene chloride, and then suspend in 30 mL of ethyl acetate. The suspension was washed twice with 30 mL of a saturated aqueous solution of sodium hydrogen carbonate and washed with 30 mL of saturated brine and then dried over anhydrous sodium sulfate. The anhydrous sodium sulfate was filtered off and then the solvent was evaporated under reduced pressure and then the residue was collected by filtration with diisopropyl ether to obtain 19 mg of the title compound as a white solid.

$^1$H-NMR (DMSO-d$_6$); δ 2.17 (6H, s), 2.62 (3H, d, J=3.4 Hz), 3.39-3.45 (1H, m), 3.96-4.00 (2H, m), 4.04 (1H, dd, J=6.7 Hz, 13.5 Hz), 4.13 (1H, dd, J=4.9 Hz, 13.5 Hz), 4.50-4.55 (2H, m), 5.06 (2H, s), 5.09 (1H, t, J=5.1 Hz), 5.38 (2H, s), 6.60 (1H, d, J=8.1 Hz), 7.13 (1H, d, J=12.0 Hz), 8.19 (1H, s).

Reference Example 70

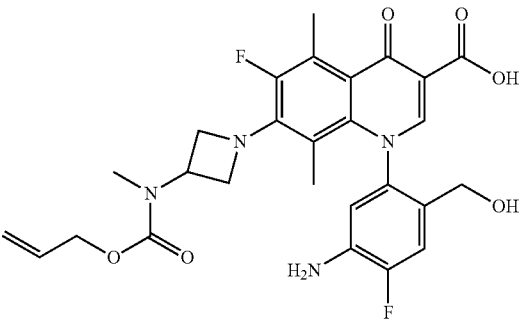

7-[3-(N-allyloxycarbonyl-N-methylamino)azetidin-1-yl]-1-[5-amino-4-fluoro-2-(hydroxymethyl)phenyl]-5,8-dimethyl-6-fluoro-4-oxo-1,4-dihydroquinoline-3-carboxylic acid 0.6 mL of N,N-dimethylformamide and 0.042 mL of diisopropylethylamine were added to 92 mg of 1-[5-amino-4-fluoro-2-(hydroxymethyl)phenyl]-5,8-dimethyl-6-fluoro-7-[3-methylaminoazetidin-1-yl]-4-oxo-1,4-dihydroquinoline-3-carboxylic acid and the mixture was stirred at room temperature for 15 minutes. 0.4 mL of an N,N-dimethylformamide solution of 0.021 mL of allyl chloroformate was added to the mixture and the resulting mixture was stirred at room temperature for 3 hours. 20 mL of a 1% aqueous solution of acetic acid was added to the reaction solution and the mixture was extracted with 10 mL of ethyl acetate three times. The extract was washed five times with 30 mL of water and with 50 mL of saturated brine and then dried over anhydrous sodium sulfate. The anhydrous sodium sulfate was filtered off and then the solvent was evaporated under reduced pressure to obtain 53 mg of the title compound as a pale yellow solid.

$^1$H-NMR (DMSO-d$_6$); δ 1.53 (3H, s), 2.72 (3H, d, J=3.1 Hz), 2.93 (3H, s), 4.10-4.18 (2H, m), 4.32-4.48 (4H, m), 4.50-4.54 (2H, m), 4.70-4.80 (1H, m), 5.03 (1H, t, J=5.3 Hz), 5.17 (1H, d, J=11.7 Hz), 5.25 (1H, d, J=15.1 Hz), 5.53 (2H, brs), 5.81-5.96 (1H, m), 6.86 (1H, d, J=8.1 Hz), 7.15 (1H, d, J=12.1 Hz), 8.43 (1H, s).

Reference Example 71

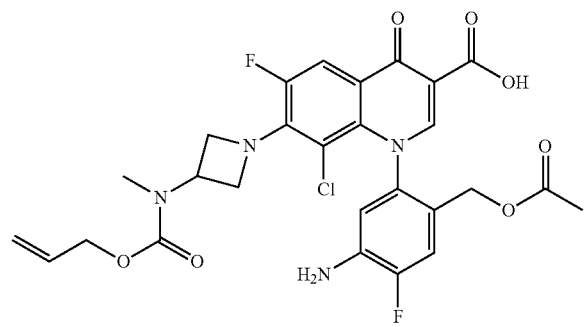 [SMILES: C=CCOC(=O)N(C)C1CN(c2c(F)cc3c(=O)c(C(=O)O)cn(-c4cc(N)c(F)cc4COC(C)=O)c3c2Cl)C1]

1-(2-Acetoxymethyl-5-amino-4-fluorophenyl)-7-[3-(N-allyloxycarbonyl-N-methylamino)azetidin-1-yl]-8-chloro-6-fluoro-4-oxo-1,4-dihydroquinoline-3-carboxylic acid 3 mL of methylene chloride, 12 mg of 4-dimethylaminopyridine, and 0.084 mL of diisopropylethylamine were added to 110 mg of 7-[3-(N-allyloxycarbonyl-N-methylamino)azetidin-1-yl]-1-[5-amino-4-fluoro-2-(hydroxymethyl)phenyl]-8-chloro-6-fluoro-4-oxo-1,4-dihydroquinoline-3-carboxylic acid and the mixture was stirred at room temperature. 0.019 mL of acetic anhydride was added to the mixture and the resulting mixture was stirred at room temperature for 1 hour. 30 mL of methylene chloride was added to the reaction solution. The mixture was washed with 30 mL of a 1% aqueous solution of acetic acid and 30 mL of saturated brine and then dried over anhydrous sodium sulfate. The anhydrous sodium sulfate was filtered off and then the solvent was evaporated under reduced pressure to obtain 54 mg of the title compound as a pale yellow solid.

$^1$H-NMR (DMSO-d$_6$); δ 1.83 (3H, s), 2.94 (3H, s), 4.39-4.56 (4H, m), 4.58-4.85 (5H, m), 5.17 (1H, d, J=10.8 Hz), 5.25 (1H, d, J=17.1 Hz), 5.76 (2H, s), 5.83-5.96 (1H, m), 6.83 (1H, d, J=8.2 Hz), 7.26 (1H, d, J=11.7 Hz), 7.89 (1H, d, J=13.8 Hz), 8.36 (1H, s).

Example 163

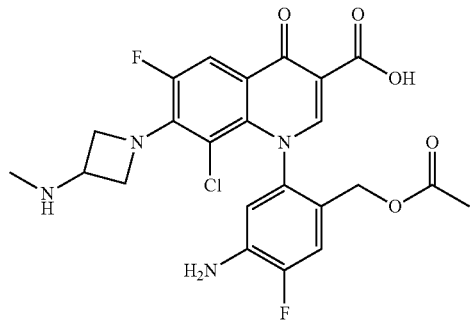 [SMILES: CNC1CN(c2c(F)cc3c(=O)c(C(=O)O)cn(-c4cc(N)c(F)cc4COC(C)=O)c3c2Cl)C1]

1-[2-(Acetoxymethyl)-5-amino-4-fluorophenyl]-8-chloro-6-fluoro-7-(3-methylaminoazetidin-1-yl)-4-oxo-1,4-dihydroquinoline-3-carboxylic acid 54 mg of 1-(2-acetoxymethyl-5-amino-4-fluorophenyl)-7-[3-(N-allyloxycarbonyl-N-methylamino)azetidin-1-yl]-8-chloro-6-fluoro-4-oxo-1,4-dihydroquinoline-3-carboxylic acid and 39 mg of 1,3-dimethylbarbituric acid were added to 2 mL of methylene chloride. 2 mg of tetrakis(triphenylphosphine)palladium (0) was added to the mixture and the resulting mixture was stirred in a nitrogen atmosphere at room temperature for 1 hour. Precipitates were collected by filtration, washed with methylene chloride, and then suspend in 30 mL of ethyl acetate. The suspension was washed five times with 20 mL of a saturated aqueous solution of sodium hydrogen carbonate and 30 mL of saturated brine and then dried over anhydrous sodium sulfate. The anhydrous sodium sulfate was filtered off and then the solvent was evaporated under reduced pressure to obtain 22 mg of the title compound as a white solid.

$^1$H-NMR (DMSO-d$_6$); δ 1.85 (3H, s), 2.18 (3H, s), 3.37-3.43 (1H, m), 4.04-4.13 (2H, m), 4.55-4.63 (2H, m), 4.66 (1H, d, J=12.5 Hz), 4.71 (1H, d, J=12.5 Hz), 5.73 (2H, brs), 6.80 (1H, d, J=8.1 Hz), 7.26 (1H, d, J=11.7 Hz), 7.84 (1H, d, J=14.0 Hz), 8.29 (1H, s).

Reference Example 72

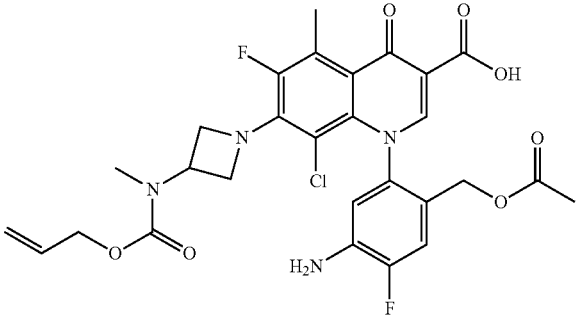 [SMILES: C=CCOC(=O)N(C)C1CN(c2c(F)c(C)c3c(=O)c(C(=O)O)cn(-c4cc(N)c(F)cc4COC(C)=O)c3c2Cl)C1]

1-[2-(Acetoxymethyl)-5-amino-4-fluorophenyl]-7-[3-(N-anyloxycarbonyl-N-methylamino)azetidin-1-yl]-8-chloro-6-fluoro-5-methyl-4-oxo-1,4-dihydroquinoline-3-carboxylic acid 1 mL of methylene chloride, a methylene chloride solution (8.8 μL) of 1 mol/L N,N-dimethylaminopyridine, and 16 μL of diisopropylethylamine were added to 25 mg of 7-[3-(N-allyloxycarbonyl-N-methylamino)azetidin-1-yl]-1-[5-amino-4-fluoro-2-(hydroxymethyl)phenyl]-8-chloro-6-fluoro-5-methyl-4-oxo-1,4-dihydroquinoline-3-carboxylic acid and the mixture was stirred at room temperature. 4.2 μL of acetic anhydride was added to the mixture and the resulting mixture was stirred at room temperature for 1 hour. The reaction solution was concentrated and then suspended in 10 mL of a 10% aqueous solution of citric acid and a solid was collected by filtration to obtain 25 mg of the title compound as a pale yellow solid.

$^1$H-NMR (DMSO-$d_6$); δ 1.89 (3H, s), 2.70 (3H, d, J=3.4 Hz), 2.93 (3H, s), 4.39-4.57 (4H, m), 4.60-4.82 (5H, m), 5.17 (1H, d, J=10.6 Hz), 5.25 (1H, d, J=18.7 Hz), 5.72 (2H, s), 5.86-5.95 (1H, m), 6.75 (1H, d, J=8.1 Hz), 7.25 (1H, d, J=11.7 Hz), 8.35 (1H, s).

Example 164

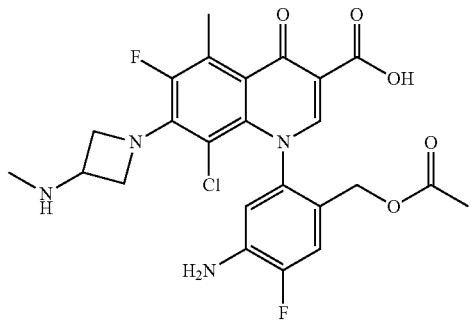 [SMILES: CNC1CN(c2c(F)c(C)c3c(=O)c(C(=O)O)cn(-c4cc(N)c(F)cc4COC(C)=O)c3c2Cl)C1]

1-[2-(Acetoxymethyl)-5-amino-4-fluorophenyl]-8-chloro-6-fluoro-5-methyl-7-(3-methylaminoazetidin-1-yl)-4-oxo-1,4-dihydroquinoline-3-carboxylic acid 25 mg of 1-[2-(acetoxymethyl)-5-amino-4-fluorophenyl]-7-[3-(N-allyloxycarbonyl-N-methylamino)azetidin-1-yl]-8-chloro-6-fluoro-5-methyl-4-oxo-1,4-dihydroquinoline-3-carboxylic acid and 16 mg of 1,3-dimethylbarbituric acid were added to 1 mL of methylene chloride. 2 mg of tetrakis(triphenylphosphine)palladium (0) was added to the mixture and the resulting mixture was stirred in a nitrogen atmosphere at room temperature for 1 hour. Precipitates were collected by filtration, washed with methylene chloride, and then suspend in 30 mL of ethyl acetate. The suspension was washed five times with 20 mL of a saturated aqueous solution of sodium hydrogen carbonate and washed with 30 mL of saturated brine and then dried over anhydrous sodium sulfate. The anhydrous sodium sulfate was filtered off and then the solvent was evaporated under reduced pressure to obtain 13 mg of the title compound as a white solid.

$^1$H-NMR (DMSO-$d_6$); δ 1.84 (3H, s), 2.19 (3H, s), 2.70 (3H, d, J=3.4 Hz), 3.38-3.45 (1H, m), 3.98-4.11 (2H, m), 4.58-4.72 (4H, m), 5.70 (2H, brs), 6.78 (1H, d, J=8.1 Hz), 7.26 (1H, d, J=11.7 Hz), 8.28 (1H, s).

Reference Example 73

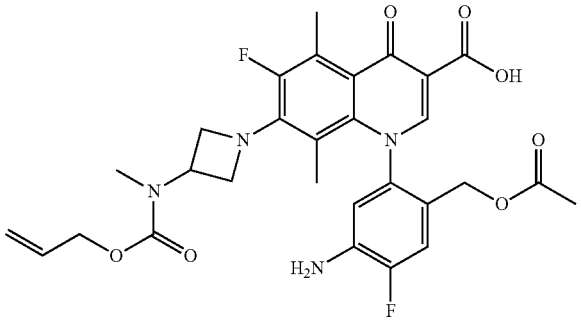 [SMILES: C=CCOC(=O)N(C)C1CN(c2c(F)c(C)c3c(=O)c(C(=O)O)cn(-c4cc(N)c(F)cc4COC(C)=O)c3c2C)C1]

1-(2-Acetoxymethyl-5-amino-4-fluorophenyl)-7-[3-(N-allyloxycarbonyl-N-methylamino)azetidin-1-yl]-8-chloro-5,8-dimethyl-6-fluoro-4-oxo-1,4-dihydroquinoline-3-carboxylic acid 1 mL of methylene chloride, a methylene chloride solution (5 μL) of 1 mol/L 4-dimethylaminopyridine, and 15 μL of diisopropylethylamine were added to 25 mg of 7-[3-(N-allyloxycarbonyl-N-methylamino)azetidin-1-yl]-1-[5-amino-4-fluoro-2-(hydroxymethyl)phenyl]-5,8-dimethyl-6-fluoro-4-oxo-1,4-dihydroquinoline-3-carboxylic acid and the mixture was stirred at room temperature. 4.5 μL of acetic anhydride was added to the mixture and the resulting mixture was stirred at room temperature for 1 hour. The reaction solution was concentrated and then suspended in 10 mL of a 10% aqueous solution of citric acid and a solid was collected by filtration to obtain 22 mg of the title compound as a pale yellow solid.

$^1$H-NMR (DMSO-$d_6$); δ 1.52 (3H, s), 1.88 (3H, s), 2.70 (3H, d, J=3.2 Hz), 2.93 (3H, s), 4.41-4.54 (4H, m), 4.59-4.81 (5H, m), 5.17 (1H, d, J=10.6 Hz), 5.25 (1H, d, J=17.2 Hz), 5.71 (2H, s), 5.85-5.95 (1H, m), 6.75 (1H, d, J=8.1 Hz), 7.25 (1H, d, J=11.7 Hz), 8.34 (1H, s).

Example 165

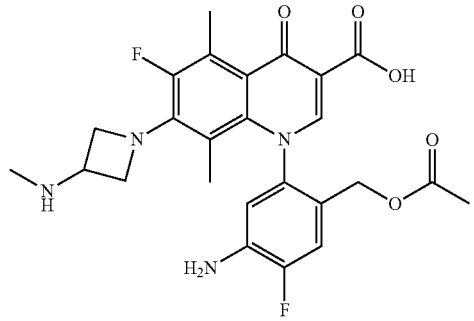 [SMILES: CNC1CN(c2c(F)c(C)c3c(=O)c(C(=O)O)cn(-c4cc(N)c(F)cc4COC(C)=O)c3c2C)C1]

1-[2-(Acetoxymethyl)-5-amino-4-fluorophenyl]-5,8-dimethyl-6-fluoro-7-(3-methylaminoazetidin-1-yl)-4-oxo-1,4-dihydroquinoline-3-carboxylic acid 22 mg of 1-[2-(acetoxymethyl)-5-amino-4-fluorophenyl]-7-[3-(N-allyloxycarbonyl-N-methylamino)azetidin-1-yl]-5, 8-dimethyl-6-fluoro-4-oxo-1,4-dihydroquinoline-3-carboxylic acid and 14 mg of 1,3-dimethylbarbituric acid were added to 1 mL of methylene chloride. 2 mg of tetrakis(triphenylphosphine)palladium (0) was added to the mixture and the resulting mixture was stirred in a nitrogen atmosphere at room temperature for 1 hour. Precipitates were collected by filtration, washed with methylene chloride, and then suspend in 30 mL of ethyl acetate. The suspension was washed five times with 20 mL of a saturated aqueous solution of sodium hydrogen carbonate and washed with 30 mL of saturated brine and then dried over anhydrous sodium sulfate. The anhydrous sodium sulfate was filtered off and then the solvent was evaporated under reduced pressure to obtain 7 mg of the title compound as a pale yellow solid.

$^1$H-NMR (DMSO-$d_6$); δ 1.53 (3H, s), 1.82 (3H, s), 2.18 (3H, s), 2.77 (3H, d, J=3.2 Hz), 3.99-4.14 (2H, m), 4.58-4.68 (4H, m), 5.70 (2H, b rs), 6.81 (1H, d, J=8.3 Hz), 7.33 (1H, d, J=11.7 Hz), 8.28 (1H, s).

Example 166

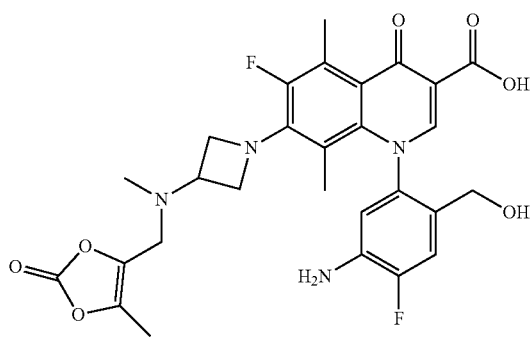 [SMILES: Cc1oc(=O)oc1CN(C)C1CN(c2c(F)c(C)c3c(=O)c(C(=O)O)cn(-c4cc(N)c(F)cc4CO)c3c2C)C1]

1-[5-Amino-4-fluoro-2-(hydroxymethyl)phenyl]-5,8-dimethyl-6-fluoro-7-[3-[N-methyl-N-(5-methyl-2-oxo-1,3-dioxol-4-yl)methylamino]azetidin-1-yl]-4-oxo-1,4-dihydroquinoline-3-carboxylic acid 1.2 mL of N,N-dimethylformamide and 14 mg of potassium carbonate were added to 46 mg of 1-[5-amino-4-fluoro-2-(hydroxymethyl)phenyl]-5,8-dimethyl-6-fluoro-7-[3-methylaminoazetidin-1-yl]-4-oxo-1,4-dihydroquinoline-3-carboxylic acid and the mixture was stirred at 45° C. for 15 minutes. 3.4 mg of potassium iodide and 11 μL of 4-chloromethyl-5-methyl-1,3-dioxol-2-one were added and the mixture was stirred at 45° C. for 3 hours. The reaction solution was cooled, then diluted with 10 mL of ethyl acetate, washed three times with 10 mL of a 5% aqueous solution of citric acid sodium hydrogen carbonate, and then dried over anhydrous sodium sulfate. The anhydrous sodium sulfate was filtered off and then the solvent was evaporated under reduced pressure to obtain 31 mg of the title compound as a light brown solid.

$^1$H-NMR (DMSO-$d_6$); δ 1.54 (3H, s), 2.10 (3H, s), 2.17 (3H, s), 2.72 (3H, d, J=3.0 Hz), 3.98-4.05 (5H, m), 4.24-4.32 (2H, m), 5.06 (1H, t, J=5.2 Hz), 5.52 (2H, s), 6.83 (1H, d, J=8.1 Hz), 7.15 (1H, d, J=11.9 Hz), 8.43 (1H, s).

$^1$H-NMR (CDCl$_3$); δ 1.59 (3H, s), 2.11 (3H, s), 2.18 (3H, s), 2.79 (3H, d, J=3.2 Hz), 3.27 (2H, s), 3.31-3.39 (1H, m), 3.91-4.08 (4H, m), 4.10-4.37 (2H, m), 4.28-4.37 (2H, m), 6.72 (1H, d, J=7.9 Hz), 8.53 (1H, s).

Example 167

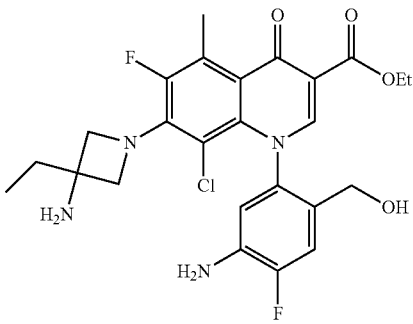 [SMILES: CCOC(=O)c1cn(-c2cc(N)c(F)cc2CO)c2c(Cl)c(N3CC(N)(CC)C3)c(F)c(C)c2c1=O]

Ethyl 7-(3-Amino-3-ethylazetidin-1-yl)-1-[5-amino-4-fluoro-2-(hydroxymethyl)phenyl]-8-chloro-6-fluoro-5-methyl-4-oxo-1,4-dihydroquinoline-3-carboxylate 44 mg of ethyl 1-[5-amino-4-fluoro-2-(hydroxymethyl)phenyl]-8-chloro-6,7-difluoro-5-methyl-4-oxo-1,4-dihydroquinoline-3-carboxylate was dissolved in 1.0 mL of dimethylsulfoxide and 0.52 mL of N-methylpyrrolidine and 26 mg of 3-amino-3-ethylazetidine dihydrochloride were added at room temperature. The mixture was stirred at 50° C. for 16 hours. 8 mL of diethyl ether was added to the reaction solution. The mixture was stirred and then the supernatant was removed by decantation. Water was added to the residue and then pH was adjusted to 9 with a saturated aqueous solution of sodium bicarbonate. Precipitates were collected by filtration to obtain 36 mg of the title compound.

$^1$H-NMR (DMSO-$d_6$): δ 0.87 (3H, t, J=7.5 Hz), 1.22 (3H, t, J=7.5 Hz), 1.59 (2H, q, J=7.5 Hz), 2.61 (3H, d, J=3.5 Hz), 3.90-3.98 (2H, m), 4.13-4.21 (6H, m), 5.12 (1H, t, J=5.0 Hz), 5.37 (2H, s), 6.56 (1H, d, J=8.5 Hz), 7.13 (1H, d, J=12.0 Hz), 8.15 (1H, s).

Example 168

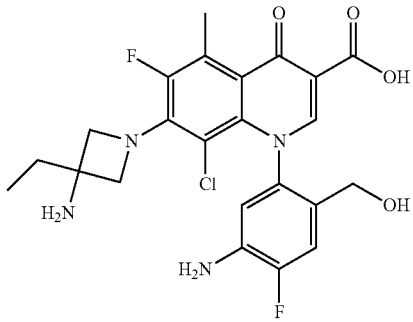 [SMILES: CCC1(N)CN(c2c(F)c(C)c3c(=O)c(C(=O)O)cn(-c4cc(N)c(F)cc4CO)c3c2Cl)C1]

7-(3-Amino-3-ethylazetidin-1-yl)-1-[5-amino-4-fluoro-2-(hydroxymethyl)phenyl]-8-chloro-6-fluoro-5-methyl-4-oxo-1,4-dihydroquinoline-3-carboxylic acid 35 mg of ethyl 7-(3-amino-3-ethylazetidin-1-yl)-1-[5-amino-4-fluoro-2-(hydroxymethyl)phenyl]-8-chloro-6- fluoro-5-methyl-4-oxo-1,4-dihydroquinoline-3-carboxylate was suspended in 1.4 mL of ethanol and 0.156 mL of a 1 mol/L aqueous solution of sodium hydroxide was added at room temperature. The mixture was stirred at 60° C. for 4 hours. The mixture was returned to room temperature and then neutralized with hydrochloric acid. Precipitates were collected by filtration with water to obtain 19 mg of the title compound.

$^1$H-NMR (DMSO-d$_6$): δ 0.89 (3H, t, J=7.5 Hz), 1.66 (2H, q, J=7.5 Hz), 2.71 (3H, d, J=3.0 Hz), 4.41-4.47 (6H, m), 5.07 (1H, s), 5.47 (2H, s), 6.70 (1H, d, J=8.0 Hz), 7.14 (1H, d, J=12.0 Hz), 8.38 (1H, s).

Example 169

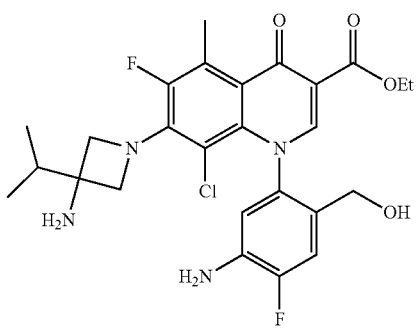 [SMILES: CCOC(=O)c1cn(-c2cc(N)c(F)cc2CO)c2c(Cl)c(N3CC(N)(C(C)C)C3)c(F)c(C)c2c1=O]

Ethyl 1-[5-amino-4-fluoro-2-(hydroxymethyl)phenyl]-7-(3-amino-3-isopropylazetidin-1-yl)-8-chloro-6-fluoro-5-methyl-4-oxo-1,4-dihydroquinoline-3-carboxylate 44 mg of ethyl 1-[5-amino-4-fluoro-2-(hydroxymethyl)phenyl]-8-chloro-6,7-difluoro-5-methyl-4-oxo-1,4-dihydroquinoline-3-carboxylate was dissolved in 1.0 mL of dimethylsulfoxide and 0.52 mL of N-methylpyrrolidine and 28 mg of 3-amino-3-isopropylazetidine dihydrochloride were added at room temperature. The mixture was stirred at 50° C. for 16 hours. 8 mL of diethyl ether was added to the reaction solution. The mixture was stirred and then the supernatant was removed by decantation. Water was added to the residue and then pH was adjusted to 9 with a saturated aqueous solution of sodium bicarbonate. Precipitates were collected by filtration to obtain 40 mg of the title compound.

$^1$H-NMR (DMSO-d$_6$): δ 0.83 (6H, d, J=7.0 Hz), 1.22 (3H, t, J=7.5 Hz), 1.82-1.88 (1H, m), 2.61 (3H, d, J=3.0 Hz), 3.89-3.97 (2H, m), 4.14-4.25 (6H, m), 5.12 (1H, t, J=5.0 Hz), 5.37 (2H, s), 6.57 (1H, d, J=8.5 Hz), 7.13 (1H, d, J=12.0 Hz), 8.14 (1H, s).

Example 170

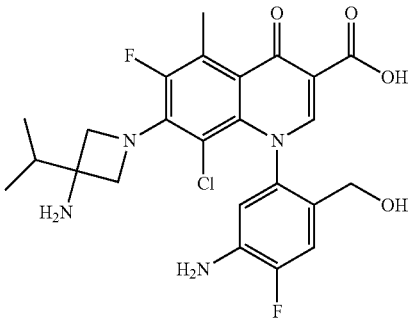 [SMILES: Cc1c(F)c(N2CC(N)(C(C)C)C2)c(Cl)c2c1c(=O)c(C(=O)O)cn2-c1cc(N)c(F)cc1CO]

1-[5-Amino-4-fluoro-2-(hydroxymethyl)phenyl]-7-(3-amino-3-isopropylazetidin-1-yl)-8-chloro-6-fluoro-5-methyl-4-oxo-1,4-dihydroquinoline-3-carboxylic acid 39 mg of ethyl 1-[5-amino-4-fluoro-2-(hydroxymethyl)phenyl]-7-(3-amino-3-isopropylazetidin-1-yl)-8-chloro-6-fluoro-5-methyl-4-oxo-1,4-dihydroquinoline-3-carboxylate was suspended in 1.0 mL of ethanol and 0.16 mL of a 1 mol/L aqueous solution of sodium hydroxide was added at room temperature. The mixture was stirred at 60° C. for 4 hours. The mixture was returned to room temperature and then neutralized with hydrochloric acid. Precipitates were collected by filtration with water to obtain 29 mg of the title compound.

$^1$H-NMR (DMSO-d$_6$): δ 0.88 (6H, d, J=7.0 Hz), 1.95-2.00 (1H, m), 2.71 (3H, d, J=3.5 Hz), 4.03-4.23 (4H, m), 4.36-4.42 (2H, m), 5.06 (1H, t, J=5.0 Hz), 5.47 (2H, s), 6.72 (1H, d, J=8.5 Hz), 7.13 (1H, d, J=12.0 Hz), 8.39 (1H, s).

Reference Example 74

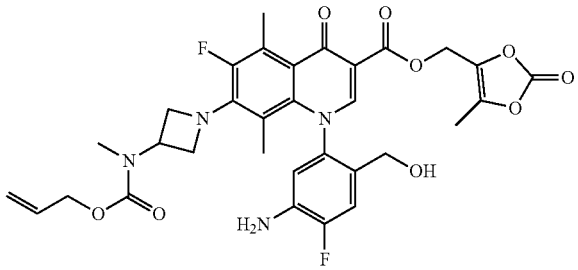 [SMILES: C=CCOC(=O)N(C)C1CN(c2c(F)c(C)c3c(=O)c(C(=O)OCc4oc(=O)oc4C)cn(-c4cc(N)c(F)cc4CO)c3c2C)C1]

7-[3-(N-allyloxycarbonyl-N-methylamino)azetidin-1-yl]-1-[5-amino-4-fluoro-2-(hydroxymethyl)phenyl]-5,8-dimethyl-6-fluoro-4-oxo-1,4-dihydroquinoline-3-carboxylic acid (5-methyl-2-oxo-1,3-dioxol-4-yl)methyl ester 2 mL of N,N-dimethylformamide and 83 mg of potassium carbonate were added to 162 mg of 7-[3-(N-allyloxycarbonyl-N-methylamino)azetidin-1-yl]-1-[5-amino-4-fluoro-2-(hydroxymethyl)phenyl]-5,8-dimethyl-6-fluoro-4-oxo-1,4-dihydroquinoline-3-carboxylic acid and the mixture was stirred at 45° C. for 30 minutes. 29 mg of potassium iodide and 39 mL of 4-chloromethyl-5-methyl-1,3-dioxol-2-one were added to the mixture and the resulting mixture was stirred at 45° C. overnight. The reaction solution was cooled and then 20 mL of water was added to the solution. Precipitates were collected by filtration. The resulting solid was subjected to silica gel column chromatography (methanol: methylene chloride=0:1 to 20:1 gradient) to obtain 122 mg of the title compound as a brown solid.

$^1$H-NMR (DMSO-$d_6$); δ 1.53 (3H, s), 2.19 (3H, s), 2.64 (3H, d, J=3.4 Hz), 2.90 (3H, s), 3.92-4.06 (2H, m), 4.15-4.24 (2H, m), 4.35-4.45 (2H, m), 4.50-4.52 (2H, m), 4.70-4.78 (1H, m), 5.06-5.09 (3H, m), 5.17 (1H, d, J=10.6 Hz), 5.26 (1H, d, J=16.1 Hz), 5.40 (2H, brs), 5.85-5.96 (1H, m), 6.84 (1H, d, J=8.1 Hz), 7.11 (1H, d, J=12.0 Hz), 8.30 (1H, s).

Example 171

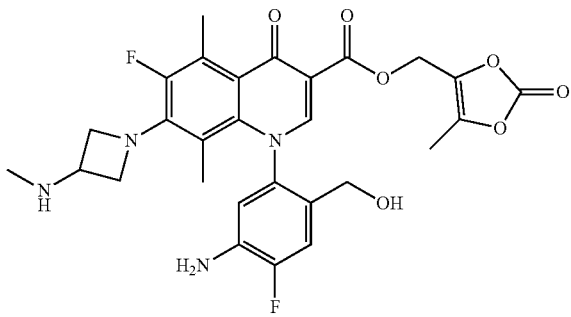 [SMILES: CNC1CN(c2c(F)c(C)c3c(=O)c(C(=O)OCc4oc(=O)oc4C)cn(-c4cc(N)c(F)cc4CO)c3c2C)C1]

(5-Methyl-2-oxo-1,3-dioxol-4-yl)methyl 1-[5-amino-4-fluoro-2-(hydroxymethyl)phenyl]-5,8-dimethyl-6-fluoro-7-(3-methylaminoazetidin-1-yl)-4-oxo-1,4-dihydroquinoline-3-carboxylate 122 mg of (5-methyl-2-oxo-1,3-dioxol-4-yl)methyl 7-[3-(N-allyloxycarbonyl-N-methylamino)azetidin-1-yl]-1-[5-amino-4-fluoro-2-(hydroxymethyl)phenyl]-5,8-dimethyl-6-fluoro-4-oxo-1,4-dihydroquinoline-3-carboxylate and 87 mg of 1,3-dimethylbarbituric acid were added to 3 mL of methylene chloride. 4 mg of tetrakis(triphenylphosphine) palladium (0) was added to the mixture and the resulting mixture was stirred in a nitrogen atmosphere at room temperature for 2 hours. Precipitates were collected by filtration, washed with methylene chloride, and then suspend in 30 mL of ethyl acetate. The suspension was washed twice with 30 mL of a saturated aqueous solution of sodium hydrogen carbonate and 30 mL of saturated brine and then dried over anhydrous sodium sulfate. The anhydrous sodium sulfate was filtered off and then the solvent was evaporated under reduced pressure and then the residue was collected by filtration with isopropyl ether to obtain 53 mg of the title compound as a light brown solid.

$^1$H-NMR (DMSO-$d_6$); δ 1.52 (3H, s), 2.16-2.19 (6H, m), 2.63 (3H, d, J=3.3 Hz), 3.38-3.44 (1H, m), 3.97-4.18 (5H, m), 4.50-4.55 (2H, m), 5.04-5.11 (3H, m), 5.43 (2H, brs), 6.83 (1H, d, J=8.2 Hz), 7.12 (1H, d, J=12.0 Hz), 8.28 (1H, s).

Test Examples

The results of tests for antimicrobial effect and for combined antibacterial effect with a drug efflux pump inhibitor of the compounds of the present invention are described in Test Examples 1 and 2. The following compounds described in International Publication No. WO96/23775 (Patent Literature 6) were used as Comparison Compounds.

Comparison Compound 1: 7-(3-Aminoazetidin-1-yl)-1-(5-amino-2,4-difluorophenyl)-8-chloro-6-fluoro-4-oxo-1,4-dihydroquinoline-3-carboxylic acid, which is the compound of Example 152 in Patent Literature 6

Comparison Compound 2: 1-(5-amino-2,4-difluorophenyl)-8-chloro-6-fluoro-7-(3-methylaminoazetidin-1-yl)-4-oxo-1,4-dihydroquinoline-3-carboxylic acid, which is the compound of Example 157 in Patent Literature 6

Test Example 1

Antibacterial Effect

The minimum inhibitory concentrations (MIC: μg/mL) of the compounds set forth in Table 1 were measured according to the standard method of Japanese Society of Chemotherapy (Japanese Journal of Chemotherapy, 56 (1), 49, 2008). The minimum inhibitory concentrations (MIC: μg/mL) of the conventional antimicrobial agents ciprofloxacin and levofloxacin were also measured similarly. *P. aeruginosa* is a clinical isolate given by Kameda Medical Center. *C. difficile* is a clinical isolate purchased from International Health Management Associates, Inc. (IHMA). The result is shown in Table 1.

TABLE 1

| Compound | MRSA9522 | MRSA9532 | P. aeruginosa 2014-16 | C. difficile 2015-12 | C. difficile 2015-13 |
|---|---|---|---|---|---|
| Compound of Example 104 | 1 | 1 | 2 | 1 | 0.5 |
| Compound of Example 113 | 1 | 1 | 4 | 0.12 | 0.06 |
| Comparative Compound 1 | 4 | 4 | 8 | 16 | 8 |
| Comparative Compound 2 | 1 | 2 | 16 | 8 | 4 |
| Ciprofloxacin | 128 | >128 | >128 | >128 | 64 |
| Levofloxacin | >128 | >128 | >128 | >128 | >128 |

MIC value: (μg/mL)

The result in Table 1 indicates that the compounds of the present invention have antibacterial activities superior to those of the conventional antimicrobial agents and Comparison Compounds.

Test Example 2

Combined Antibacterial Effect with Drug Efflux Pump Inhibitor

The combined antibacterial effects with a drug efflux pump inhibitor of the compounds set forth in Table 2 were measured. The method used was a broth microdilution method according to the standard method of the Japanese Society of Chemotherapy (Chemotherapy, 38 (1), 102, 1990). In the condition which added H-Phe-Arg-βNA, 2HCl (PAβN) (50 μg/mL) as drug efflux pump inhibitor, the minimum inhibitory concentrations (MIC: μg/mL) was measured. The minimum inhibitory concentrations (MIC: μg/mL) of the conventional antimicrobial agents levofloxacin and cefepime as a positive control compound and a negative control compound for the evaluation were also measured similarly. *P. aeruginosa* is a clinical isolate given by Kameda Medical Center. The result is shown in Table 2.

TABLE 2

| Compound | P. aeruginosa PA01 | | | P. aeruginosa 2014-17 | | | P. aeruginosa 08-05 | | |
|---|---|---|---|---|---|---|---|---|---|
| | PAβN − | PAβN + | MIC radio | PAβN − | PAβN + | MIC radio | PAβN − | PAβN + | MIC ratio |
| Compound of Example 70 | 0.25 | 0.25 | 1 | 16 | 4 | 4 | 1 | 0.25 | 4 |
| Compound of Example 100 | 0.12 | 0.016 | 8 | 2 | 0.25 | 8 | 0.5 | 0.06 | 8 |
| Compound of Example 104 | 0.12 | 0.016 | 8 | 4 | 0.25 | 16 | 0.5 | 0.06 | 8 |
| Levofloxacin | 0.5 | 0.06 | 8 | 32 | 1 | 32 | 4 | 0.12 | 32 |
| Cefepime | 1 | 0.5 | 2 | 64 | 16 | 4 | 8 | 2 | 4 |

MIC value: (μg/mL)
MIC ratio: PAβN(−) MIC/PAβN(+) MIC

The result in Table 2 indicates that the compounds of the present invention are less susceptible to drug efflux pumps than the conventional quinolone antimicrobial agents and Comparison Compounds.

The invention claimed is:

1. A pyridonecarboxylic acid derivative or a salt thereof represented by Formula (1):

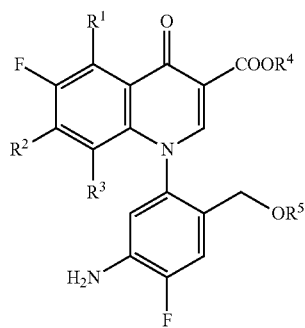

wherein
$R^1$ represents a hydrogen atom, a halogen atom, a lower alkyl group or an amino group;
$R^2$ represents:
a group —NH—$R^6$, wherein $R^6$ represents a hydrogen atom, a lower alkyl group, an amino lower alkyl group, a hydroxy lower alkyl group, a dimethylamino lower alkyl group, a lower alkoxy lower alkyl group, a morpholino lower alkyl group, or an optionally substituted aralkyl group;
a group —O—$R^7$, wherein $R^7$ represents a hydrogen atom, a lower alkyl group, an optionally substituted azetidin-3-yl group, or an optionally substituted pyrrolidin-3-yl group;
a group —$(CH_2)_m$—$R^8$, wherein $R^8$ represents an amino group, a lower alkyl amino group, a cyclic amino group, a hydroxyl group, or a lower alkoxy group and m represents an integer of 1 to 4; or
a cyclic amino group represented by Formula (2):

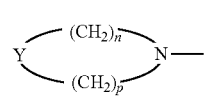

(2)

wherein
Y represents NH or C—$R^{9a}R^{9b}$, wherein $R^{9a}$ and $R^{9b}$ each independently represent a hydrogen atom, a lower alkyl group, an amino group, a lower alkyl amino group, an N-methyl-N-(5-methyl-2-oxo-1,3-dioxol-4-yl)methylamino group, a hydroxy lower alkyl amino group, a lower alkyl hydrazino group, a tetrahydropyran-4-ylamino group, a pyrazol-1-yl group, a dimethylamino lower alkyl group, or a hydroxyl group or $R^{9a}$ and $R^{9b}$ optionally form a nitrogen-containing saturated heterocyclic ring together with the adjacent carbon atom and
n and p represent an integer of 1 or 2;
$R^3$ represents a hydrogen atom, a halogen atom, a lower alkyl group, or a lower alkoxy group;
$R^4$ represents a hydrogen atom or a carboxyl group-protecting group; and
$R^5$ represents a hydrogen atom or a hydroxyl group-protecting group.

2. The pyridonecarboxylic acid derivative or a salt thereof according to claim 1, wherein $R^1$, $R^3$, $R^6$, or $R^7$ is a lower alkyl group, which is a $C_{1-4}$ alkyl group.

3. The pyridonecarboxylic acid derivative or a salt thereof according to claim 1, wherein $R^3$ is a lower alkoxy group, which is a $C_{1-4}$ alkoxy group.

4. The pyridonecarboxylic acid derivative or a salt thereof according to claim 1, wherein $R^3$ is a halogen atom, which is a fluorine atom, a chlorine atom, or a bromine atom.

5. The pyridonecarboxylic acid derivative or a salt thereof according to claim 1, wherein $R^1$ is a hydrogen atom, a methyl group, a bromine atom, or an amino group and $R^2$ is a cyclic amino group represented by the Formula (2).

6. The pyridonecarboxylic acid derivative or a salt thereof according to claim 5, wherein Y is $C-R^{9a}R^{9b}$ and n and p are 1 in the Formula (2).

7. The pyridonecarboxylic acid derivative or a salt thereof according to claim 6, wherein $R^{9a}$ is a hydrogen atom and $R^{9b}$ is a $C_{1-4}$ alkyl amino group in the $C-R^{9a}R^{9b}$.

8. The pyridonecarboxylic acid derivative or a salt thereof according to claim 1, wherein $R^4$ is a hydrogen atom or a carboxyl group-protecting group eliminated easily in a living body and $R^5$ is a hydrogen atom or a hydroxyl group-protecting group eliminated easily in a living body.

9. An antimicrobial agent, comprising the pyridonecarboxylic acid derivative or a salt thereof according to claim 1 as an active ingredient.

10. An antimicrobial composition, comprising the pyridonecarboxylic acid derivative or a salt thereof according to claim 1 and a pharmaceutically acceptable carrier.

11. A method for treating an infection, the method comprising
administering the pyridonecarboxylic acid derivative or a salt thereof according to claim 1.

* * * * *